United States Patent
Zhang et al.

(10) Patent No.: US 11,660,347 B2
(45) Date of Patent: *May 30, 2023

(54) NUCLEIC ACID, COMPOSITION AND CONJUGATE CONTAINING SAME, PREPARATION METHOD, AND USE THEREOF

(71) Applicant: SUZHOU RIBO LIFE SCIENCE CO., LTD., Suzhou (CN)

(72) Inventors: Hongyan Zhang, Suzhou (CN); Shan Gao, Suzhou (CN); Daiwu Kang, Suzhou (CN)

(73) Assignee: SUZHOU RIBO LIFE SCIENCE CO., LTD., Jiangsu (CN)

( * ) Notice: Subject to any disclaimer, the term of this patent is extended or adjusted under 35 U.S.C. 154(b) by 155 days.

This patent is subject to a terminal disclaimer.

(21) Appl. No.: 16/758,532

(22) PCT Filed: Nov. 29, 2018

(86) PCT No.: PCT/CN2018/118232
§ 371 (c)(1),
(2) Date: Apr. 23, 2020

(87) PCT Pub. No.: WO2019/105419
PCT Pub. Date: Jun. 6, 2019

(65) Prior Publication Data
US 2020/0360522 A1    Nov. 19, 2020

(30) Foreign Application Priority Data
Dec. 1, 2017 (CN) .......................... 201711249345.0
Dec. 29, 2017 (CN) .......................... 201711486999.5

(51) Int. Cl.
*A61K 47/54* (2017.01)
*A61P 3/06* (2006.01)
(Continued)

(52) U.S. Cl.
CPC .......... *A61K 47/549* (2017.08); *A61K 31/713* (2013.01); *A61P 3/06* (2018.01);
(Continued)

(58) Field of Classification Search
None
See application file for complete search history.

(56) References Cited

U.S. PATENT DOCUMENTS 8,030,474 B2   10/2011   Khvorova et al.
8,106,022 B2   1/2012    Manoharan et al.
(Continued)

FOREIGN PATENT DOCUMENTS

AU   2014208251 A1   8/2014
CA      2930393 A1   6/2009
(Continued)

OTHER PUBLICATIONS

U.S. Appl. No. 16/758,720, filed Apr. 23, 2020, Zhang, H. et al.*
(Continued)

*Primary Examiner* — Eric Olson
(74) *Attorney, Agent, or Firm* — Buchanan, Ingersoll & Rooney PC

(57) ABSTRACT

The present disclosure provides a siRNA for inhibiting the expression of apolipoprotein C3 (ApoC3) gene, and a pharmaceutical composition and a conjugate comprising the siRNA; wherein each nucleotide in the siRNA is independently a modified nucleotide, and the siRNA comprises a sense strand and an antisense strand; the sense strand comprises a nucleotide sequence A, the nucleotide sequence A having the same length as the nucleotide sequence as represented by SEQ ID NO:1 with no more than 3 nucleotide differences; the antisense strand comprises a nucleotide sequence B, the nucleotide sequence B having the same
(Continued)

length as the nucleotide sequence as represented by SEQ ID NO:2 with no more than 3 nucleotide differences.

26 Claims, 5 Drawing Sheets

Specification includes a Sequence Listing.

(51) Int. Cl.
  A61K 31/713    (2006.01)
  C12N 15/113   (2010.01)
  C07H 1/00     (2006.01)
(52) U.S. Cl.
  CPC ............. *C07H 1/00* (2013.01); *C12N 15/113* (2013.01); *C12N 2310/14* (2013.01); *C12N 2310/351* (2013.01)

(56) References Cited

U.S. PATENT DOCUMENTS

| | | |
|---|---|---|
| 8,334,372 B2 | 12/2012 | Freier et al. |
| 8,344,125 B2 | 1/2013 | Manoharan et al. |
| 9,428,751 B2 | 8/2016 | MacDonald et al. |
| 9,670,492 B2 | 6/2017 | Freier et al. |
| 10,130,651 B2 | 11/2018 | Wooddell et al. |
| 10,246,708 B2 | 4/2019 | Kasperkovitz et al. |
| 10,294,477 B2 | 5/2019 | Swayze |
| 10,370,453 B2 | 8/2019 | Sexton et al. |
| 10,934,544 B2 | 3/2021 | Akinc et al. |
| 11,084,884 B2 | 8/2021 | Sexton et al. |
| 11,414,661 B2 * | 8/2022 | Zhang .................. C12N 15/113 |
| 11,414,665 B2 | 8/2022 | Zhang et al. |
| 11,492,620 B2 | 11/2022 | Zhang et al. |
| 2003/0206887 A1 | 11/2003 | Morrissey et al. |
| 2005/0245475 A1 | 11/2005 | Khvorova et al. |
| 2005/0246794 A1 | 11/2005 | Khvorova et al. |
| 2005/0255487 A1 | 11/2005 | Khvorova et al. |
| 2008/0113351 A1 | 5/2008 | Naito et al. |
| 2008/0146788 A1 | 6/2008 | Bhat et al. |
| 2010/0063132 A1 | 3/2010 | Kim et al. |
| 2010/0137414 A1 | 6/2010 | Freier et al. |
| 2011/0015252 A1 | 1/2011 | Fitzgerald et al. |
| 2011/0039914 A1 | 2/2011 | Pavco et al. |
| 2011/0054005 A1 | 3/2011 | Naito et al. |
| 2012/0052487 A9 | 3/2012 | Khvorova et al. |
| 2012/0108803 A1 | 5/2012 | Han et al. |
| 2012/0172412 A1 | 7/2012 | Rozema et al. |
| 2012/0184595 A1 | 7/2012 | MacDonald et al. |
| 2012/0201756 A1 | 8/2012 | Sexton |
| 2012/0227119 A1 | 9/2012 | Doran et al. |
| 2013/0005793 A1 | 1/2013 | Chin et al. |
| 2013/0023579 A1 | 1/2013 | Crooke et al. |
| 2013/0041133 A1 * | 2/2013 | Aaronson ............... C07K 19/00 530/324 |
| 2013/0096288 A1 | 4/2013 | Han et al. |
| 2013/0123482 A1 | 5/2013 | Xi et al. |
| 2013/0158021 A1 | 6/2013 | Dong et al. |
| 2013/0190484 A1 | 7/2013 | Rozema et al. |
| 2014/0099666 A1 | 4/2014 | Rossomando et al. |
| 2014/0128453 A1 | 5/2014 | Mullick et al. |
| 2014/0179768 A1 | 6/2014 | Bettencourt et al. |
| 2014/0194489 A1 | 7/2014 | Bumcrot et al. |
| 2014/0343123 A1 | 11/2014 | Prakash et al. |
| 2015/0093444 A1 | 4/2015 | Zhang et al. |
| 2015/0152436 A1 | 6/2015 | Musunuru et al. |
| 2015/0174260 A1 | 6/2015 | Yang et al. |
| 2015/0191726 A1 | 7/2015 | Manoharan et al. |
| 2015/0247143 A1 | 9/2015 | Fitzgerald et al. |
| 2015/0263948 A1 | 9/2015 | Jan et al. |
| 2015/0291958 A1 | 10/2015 | Albaek et al. |
| 2015/0315584 A1 | 11/2015 | MacDonald et al. |
| 2015/0315594 A1 | 11/2015 | Prakash et al. |
| 2016/0017335 A1 | 1/2016 | Borodovsky et al. |
| 2016/0186180 A1 | 6/2016 | Bettencourt et al. |
| 2016/0237438 A1 | 8/2016 | Brown et al. |
| 2016/0283653 A1 | 9/2016 | Staudt et al. |
| 2016/0354404 A1 | 12/2016 | Hinkle et al. |
| 2017/0000815 A1 | 1/2017 | Fitzgerald et al. |
| 2017/0002094 A1 | 1/2017 | Sexton et al. |
| 2017/0114341 A1 | 4/2017 | Bradshaw et al. |
| 2018/0087054 A1 | 3/2018 | Querbes et al. |
| 2018/0148722 A1 | 5/2018 | Fitzgerald et al. |
| 2018/0216114 A1 | 8/2018 | Fitzgerald et al. |
| 2018/0245077 A1 | 8/2018 | Chiu et al. |
| 2019/0062749 A1 | 2/2019 | Zhang |
| 2019/0202855 A1 | 7/2019 | Sakamuri et al. |
| 2019/0255091 A1 | 8/2019 | Li et al. |
| 2019/0292547 A1 | 9/2019 | Li et al. |
| 2020/0199591 A1 | 6/2020 | Fitzgerald et al. |
| 2020/0338201 A1 | 10/2020 | Zhang et al. |
| 2020/0360522 A1 | 11/2020 | Zhang et al. |
| 2021/0032623 A1 | 2/2021 | Zhang et al. |
| 2021/0275564 A1 | 9/2021 | Zhang et al. |
| 2021/0277400 A1 | 9/2021 | Zhang et al. |
| 2021/0401994 A1 | 12/2021 | Zhang et al. |
| 2022/0049249 A1 * | 2/2022 | Zhang ..................... A61P 29/00 |
| 2022/0062427 A1 * | 3/2022 | Zhang .................. A61K 47/549 |
| 2022/0186221 A1 | 6/2022 | Zhang et al. |
| 2022/0235359 A1 | 7/2022 | Zhang et al. |
| 2022/0356474 A1 | 11/2022 | Zhang et al. |
| 2022/0389428 A1 | 12/2022 | Zhang et al. |
| 2022/0395526 A1 | 12/2022 | Zhang et al. |

FOREIGN PATENT DOCUMENTS

| | | |
|---|---|---|
| CN | 101603042 A | 12/2009 |
| CN | 102006890 A | 4/2011 |
| CN | 102016036 A | 4/2011 |
| CN | 102083983 A | 4/2011 |
| CN | 102124107 A | 7/2011 |
| CN | 102140459 A | 8/2011 |
| CN | 102140460 A | 8/2011 |
| CN | 102344477 A | 2/2012 |
| CN | 102439148 A | 5/2012 |
| CN | 102719434 A | 10/2012 |
| CN | 102753186 A | 10/2012 |
| CN | 102140461 B | 12/2012 |
| CN | 102869774 A | 1/2013 |
| CN | 102140458 B | 5/2013 |
| CN | 103380113 A | 10/2013 |
| CN | 105378082 A | 3/2014 |
| CN | 103890000 A | 6/2014 |
| CN | 104107437 A | 10/2014 |
| CN | 104232644 A | 12/2014 |
| CN | 104328121 A | 2/2015 |
| CN | 104717982 A | 6/2015 |
| CN | 104854242 A | 8/2015 |
| CN | 104922141 A | 9/2015 |
| CN | 105324485 A | 2/2016 |
| CN | 105392488 A | 3/2016 |
| CN | 105452465 A | 3/2016 |
| CN | 105517556 A | 4/2016 |
| CN | 105713092 A | 6/2016 |
| CN | 105814204 A | 7/2016 |
| CN | 106132442 A | 11/2016 |
| CN | 106146591 A | 11/2016 |
| CN | 106232831 A | 12/2016 |
| CN | 106255755 A | 12/2016 |
| CN | 106460025 A | 2/2017 |
| CN | 107075516 A | 8/2017 |
| CN | 107109405 A | 8/2017 |
| CN | 107250362 A | 10/2017 |
| CN | 107854478 A | 3/2018 |
| CN | 108271386 A | 3/2018 |
| CN | 108064294 A | 5/2018 |
| CN | 108064313 A | 5/2018 |
| CN | 108220293 A | 6/2018 |
| CN | 108239644 A | 7/2018 |
| CN | 108265052 A | 7/2018 |
| CN | 108348541 A | 7/2018 |
| CN | 110945131 A | 3/2020 |
| CN | 110959011 A | 4/2020 |
| CN | 111050807 A | 4/2020 |

(56) References Cited

FOREIGN PATENT DOCUMENTS

| | | |
|---|---|---|
| CN | 111973617 A | 11/2020 |
| CN | 111973618 A | 11/2020 |
| CN | 111973619 A | 11/2020 |
| CN | 111979237 A | 11/2020 |
| CN | 112423795 A | 2/2021 |
| CN | 113330117 A | 8/2021 |
| EP | 2 194 128 A1 | 6/2010 |
| EP | 2 213 738 A2 | 8/2010 |
| EP | 2 376 641 | 10/2011 |
| EP | 2669377 A2 | 12/2013 |
| EP | 2990410 A1 | 3/2016 |
| EP | 3312281 A2 | 4/2018 |
| EP | 3315608 A1 | 5/2018 |
| EP | 3 335 715 A2 | 6/2018 |
| EP | 3409780 A1 | 12/2018 |
| EP | 3 719 128 A1 | 10/2020 |
| EP | 3 862 024 A1 | 8/2021 |
| JP | 2013523149 A | 6/2013 |
| JP | 2013537423 A | 10/2013 |
| JP | 2016501195 A | 1/2016 |
| JP | 2016523087 A | 8/2016 |
| JP | 2017521045 A | 8/2017 |
| JP | 2017534290 A | 11/2017 |
| RU | 2013 134 745 A | 2/2015 |
| RU | 2 558 258 C2 | 7/2015 |
| RU | 2015 133 167 A | 3/2017 |
| TW | 201925471 A | 7/2019 |
| TW | 201929905 A | 8/2019 |
| WO | 00/27795 A1 | 5/2000 |
| WO | 2004/078181 A1 | 9/2004 |
| WO | 2005/116204 A1 | 12/2005 |
| WO | 2006/006948 A2 | 1/2006 |
| WO | 2006/096018 A1 | 9/2006 |
| WO | 2007/134161 A2 | 11/2007 |
| WO | 2008/011431 A2 | 1/2008 |
| WO | 2008/109472 A2 | 9/2008 |
| WO | 2009/073809 A2 | 6/2009 |
| WO | 2009/082607 A2 | 7/2009 |
| WO | 2009/134487 A2 | 11/2009 |
| WO | 2010/012244 A1 | 2/2010 |
| WO | 2010/045509 A2 | 4/2010 |
| WO | 2010/068978 A1 | 6/2010 |
| WO | 2010/083615 A1 | 7/2010 |
| WO | 2010/101951 A1 | 9/2010 |
| WO | 2010/121074 A1 | 10/2010 |
| WO | 2010/131916 A2 | 11/2010 |
| WO | 2010/147992 A1 | 12/2010 |
| WO | 2011/085271 A2 | 7/2011 |
| WO | 2011/104169 A1 | 9/2011 |
| WO | 2011126974 A1 | 10/2011 |
| WO | 2011/139702 A2 | 11/2011 |
| WO | 2011/154331 A1 | 12/2011 |
| WO | 2012/013127 A1 | 2/2012 |
| WO | 2012/024170 A2 | 2/2012 |
| WO | 2012024170 A2 | 2/2012 |
| WO | 2012/037254 A1 | 3/2012 |
| WO | 2012/068176 A1 | 5/2012 |
| WO | 2012/083185 A2 | 6/2012 |
| WO | 2012/089352 A1 | 7/2012 |
| WO | 2012/130086 A1 | 10/2012 |
| WO | 2012/139469 A1 | 10/2012 |
| WO | 2012/177784 A2 | 12/2012 |
| WO | 2013/060261 A1 | 5/2013 |
| WO | 2013/070771 A1 | 5/2013 |
| WO | 2013/166155 A1 | 11/2013 |
| WO | 2014/025805 A1 | 2/2014 |
| WO | 2014076195 A1 | 5/2014 |
| WO | 2014/089313 A1 | 6/2014 |
| WO | 2014/118267 A2 | 11/2014 |
| WO | 2014/179626 A2 | 11/2014 |
| WO | 2014/179627 A2 | 11/2014 |
| WO | 2014/179629 A2 | 11/2014 |
| WO | 2014205451 A1 | 12/2014 |
| WO | 2015/006498 A2 | 1/2015 |
| WO | 2015/006740 A2 | 1/2015 |
| WO | 2015/015496 A1 | 2/2015 |
| WO | 2015/031679 A2 | 3/2015 |
| WO | 2015/100394 A1 | 7/2015 |
| WO | 2015/113922 A1 | 8/2015 |
| WO | 2015/148580 A2 | 10/2015 |
| WO | 2015/168532 A2 | 11/2015 |
| WO | 2015168589 A1 | 11/2015 |
| WO | 2015/188197 A2 | 12/2015 |
| WO | 2016/011123 A1 | 1/2016 |
| WO | 2016/028649 A1 | 2/2016 |
| WO | 2016/077321 A1 | 5/2016 |
| WO | 2016/081444 A1 | 5/2016 |
| WO | 2016077349 A1 | 5/2016 |
| WO | 2016/099982 A2 | 6/2016 |
| WO | 2016/149331 A2 | 9/2016 |
| WO | 2016154127 A2 | 9/2016 |
| WO | 2016/168286 A1 | 10/2016 |
| WO | 2016/179342 A2 | 11/2016 |
| WO | 2016/188473 A1 | 12/2016 |
| WO | 2016/206626 A1 | 12/2016 |
| WO | 2017/015175 A1 | 1/2017 |
| WO | 2017/019660 A1 | 2/2017 |
| WO | 2017/019891 A2 | 2/2017 |
| WO | 2017/035340 A1 | 3/2017 |
| WO | 2017/055627 A1 | 4/2017 |
| WO | 2017/100542 A1 | 6/2017 |
| WO | 2017/120397 A1 | 7/2017 |
| WO | 2017131236 A1 | 8/2017 |
| WO | 2017/184689 A1 | 10/2017 |
| WO | 2017/189813 A1 | 11/2017 |
| WO | 2018/027106 A2 | 2/2018 |
| WO | 2018/044350 A1 | 3/2018 |
| WO | 2018/075658 A1 | 4/2018 |
| WO | 2018/140920 A1 | 8/2018 |
| WO | 2018/191278 A2 | 10/2018 |
| WO | 2018/209848 A1 | 11/2018 |
| WO | WO-2018223073 A1 * | 12/2018 ........... C12N 15/113 |
| WO | 2019/105403 A1 | 6/2019 |
| WO | 2019/105404 A1 | 6/2019 |
| WO | 2019/105419 A1 | 6/2019 |
| WO | 2019/105435 A1 | 6/2019 |
| WO | 2019/105437 A1 | 6/2019 |
| WO | 2019/128611 A1 | 7/2019 |
| WO | 2020/093053 A1 | 5/2020 |
| WO | 2020/135581 A1 | 7/2020 |
| WO | 2020/147847 A1 | 7/2020 |

OTHER PUBLICATIONS

U.S. Appl. No. 17/847,770, filed Jun. 2022, Zhang; Hongyan.*
International Search Report (PCT/ISA/210) dated Mar. 7, 2019, by the State Intellectual Property Office of P.R. China as the International Searching Authority for International Application No. PCT/CN2018/118232.
Written Opinion (PCT/ISA/237) dated Mar. 7, 2019, by the State Intellectual Property Office of P.R. China as the International Searching Authority for International Application No. PCT/CN2018/118232.
Wooddell et al.,"Hepatocyte-targeted RNAi Therapeutics for the Treatment of Chronic Hepatitis B Virus Infection" The American Society of Gene & Cell Therapy, 2013, 13 pages.
Rajeev et al., "Hepatocyte-Specific Delivery of siRNAs Conjugated to Novel Non-nucleosidic Trivalent N-Acetylgalactosamine Elicits Robust Gene Silencing in Vivo" ChemBioChem, 2015, vol. 16, pp. 903-908.
Matsuda et al., "siRNA Conjugates Carrying Sequentially Assembled Trivalent N-Acetylgalactosamine Linked Through Nucleosides Elicit Robust Gene Silencing In Vivo in Hepatocytes", ACS Chemical Biology, 2015, DOI: 10.1021/cb501028c. (7 pages).
Nair et al., "Multivalent N-Acetylgalactosamine-Conjugated siRNA Localizes in Hepatocytes and Elicits Robust RNAi-Mediated Gene Silencing", Journal of the American Chemical Society, 2014, vol. 136, pp. 16958-16961.
Khvorova et al., "The chemical evolution of oligonucleotide therapies of clinical utility", Nature Biotechnology Advance Online Publication, Feb. 27, 2017; doi:10.1038/nbt.3765, (11 pages).

(56) References Cited

OTHER PUBLICATIONS

Love et al., "Lipid-like materials for low-dose, in vivo gene silencing", Proceedings of the National Academy of Sciences, Feb. 2, 2010, vol. 107, No. 5, pp. 1864-1869. (7 pages).
Dong et al., "Lipopeptide nanoparticles for potent and selective siRNA delivery in rodents and nonhuman primates", Proceedings of the National Academy of Sciences, Feb. 2014, www.pnas.org/cgi/doi/10.1073/pnas.1322937111 (6 pages).
Beaucage et al., "Advances in the Synthesis of Oligonucleotides by the Phosphoramidite Approach", Tetrahedron, 1992, vol. 48, No. 12, pp. 2223-2311.
Greene et al., "Protection for the Hydroxyl Group, Including 1,2- and 1,3-DIOLS", Protective Groups in Organic Synthesis, Third Edition, 1999 John Wiley & Sons, Inc. pp. 17-245, (229 pages).
Ui-Tei et al., "Functional dissection of siRNA sequence by systematic DNA substitution: modified siRNA with a DNA seed arm is a powerful tool for mammalian gene silencing with significantly reduced off-target effect", Nucleic Acids Rearch, 2008, vol. 36, No. 7, pp. 2136-2151.
Watts et al., "Chemically modified siRNA: tools and applications", Drug Discovery Today, Oct. 2008, vol. 13, Nos. 19/20, pp. 842-855.
Extended European Search Report dated Sep. 17, 2021, by the European Patent Office in corresponding European Patent Application No. 18883982.3. (9 pages).
Berthold et al., "Cellular Delivery and Antisense Effects of Peptide Nucleic Acid Conjugated to Polyethyleneimine via Disulfide Linkers," Bioconjugate Chemistry, 2010, vol. 21, No. 10, pp. 1933-1938.
Paris et al., "Conjugating Phosphospermines to siRNAs for Improved Stability in Serum, Intracellular Delivery and RNAi-Mediated Gene Silencing," Molecular Pharmaceutics, 2012, vol. 9, No. 12, pp. 3464-3475.
The First Office Action dated Jan. 30, 2022, by the State Intellectual Property Office of the People's Republic of China in Chinese Patent Application No. 201880049520.8 and an English translation of the Action (11 pages).
Decision of Rejection dated Mar. 3, 2022, by the State Intellectual Property Office of the People's Republic of China in Chinese Patent Application No. 202010426194.7 and an English translation of the Action. (20 pages).
The Second Office Action dated Mar. 16, 2022, by the State Intellectual Property Office of the People's Republic of China in Chinese Patent Application No. 201980046892.X and an English translation of the Action. (24 pages).
The Second Office Action dated Mar. 21, 2022, by the State Intellectual Property Office of the People's Republic of China in Chinese Patent Application No. 201980046893.4 and an English translation of the Action. (19 pages).
The First Office Action dated May 7, 2022, by the State Intellectual Property Office of the People's Republic of China in Chinese Patent Application No. 201980010095.6 and an English translation of the Action. (27 pages).
The First Office Action dated May 7, 2022, by the State Intellectual Property Office of the People's Republic of China in Chinese Patent Application No. 201980010175.1 and an English translation of the Action. (30 pages).
The First Office Action dated May 7, 2022, by the State Intellectual Property Office of the People's Republic of China in Chinese Patent Application No. 201880049190.2 and an English translation of the Action. (31 pages).
The First Office Action dated May 7, 2022, by the State Intellectual Property Office of the People's Republic of China in Chinese Patent Application No. 201880049191.7 and an English translation of the Action. (30 pages).
The First Office Action dated May 7, 2022, by the State Intellectual Property Office of the People's Republic of China in Chinese Patent Application No. 202080007282.1 and an English translation of the Action. (33 pages).
The First Office Action dated May 7, 2022, by the State Intellectual Property Office of the People's Republic of China in Chinese Patent Application No. 201880049564.0 and an English translation of the Action. (29 pages).
The First Office Action dated May 7, 2022, by the State Intellectual Property Office of the People's Republic of China in Chinese Patent Application No. 201880049586.7 and an English translation of the Action. (33 pages).
The First Office Action dated May 7, 2022, by the State Intellectual Property Office of the People's Republic of China in Chinese Patent Application No. 201880048597.3 and an English translation of the Action. (34 pages).
The First Office Action dated May 7, 2022, by the State Intellectual Property Office of the People's Republic of China in Chinese Patent Application No. 201880048600.1 and an English translation of the Action. (34 pages).
The First Office Action dated May 7, 2022, by the State Intellectual Property Office of the People's Republic of China in Chinese Patent Application No. 202080009787.1 and an English translation of the Action. (50 pages).
The First Office Action dated May 7, 2022, by the State Intellectual Property Office of the People's Republic of China in Chinese Patent Application No. 201880048949.5 and an English translation of the Action. (33 pages).
The First Office Action dated May 20, 2021, by the State Intellectual Property Office of the People's Republic of China in Chinese Patent Application No. 202010426194.7 and an English translation of the Action. (20 pages).
The First Office Action dated Jun. 23, 2021, by the State Intellectual Property Office of the People's Republic of China in Chinese Patent Application No. 201980046892.X and an English translation of the Action. (13 pages).
The First Office Action dated Jun. 23, 2021, by the State Intellectual Property Office of the People's Republic of China in Chinese Patent Application No. 201980046893.4 and an English translation of the Action. (12 pages).
Decision of Rejection dated Jun. 29, 2022, by the State Intellectual Property Office of the People's Republic of China in Chinese Patent Application No. 201980046892.X and an English translation of the Decision. (8 pages).
Decision of Rejection dated Jun. 29, 2022, by the State Intellectual Property Office of the People's Republic of China in Chinese Patent Application No. 201980046893.4 and an English translation of the Decision. (8 pages).
The First Office Action dated Oct. 25, 2021, by the State Intellectual Property Office of the People's Republic of China in Chinese Patent Application No. 202010426196.6 and an English translation of the Action. (16 pages).
The Second Office Action dated Nov. 12, 2021, by the State Intellectual Property Office of the People's Republic of China in Chinese Patent Application No. 202010426194.7 and an English translation of the Action. (16 pages).
The Extended European Search Report dated Jun. 9, 2022, by the European Patent Office in European Patent Application Publication No. 19851738.5. (64 pages).
The Extended European Search Report and Supplementary European Search Report dated Aug. 9, 2021, by the European Patent Office in European Patent Application Publication No. 18883362.8. (9 pages).
Extended European Search Report dated Sep. 29, 2021, issued by the European Patent Office in corresponding European Application No. 18884492.2. (45 pages).
The Extended European Search Report dated Oct. 7, 2021, by the European Patent Office in European Patent Application Publication No. 18896766.5. (19 pages).
The Extended European Search Report dated Sep. 16, 2021, by the European Patent Office in European Patent Application No. 18883803.1. (10 pages).
Invitation to remedy deficiencies pursuant to Rule 30(3) EPC / Rule 163(3) EPC dated Feb. 22, 2022, by the European Patent Office in European Patent Application No. 20809029.0. (2 pages).

(56) References Cited

OTHER PUBLICATIONS

Communication pursuant to Rule 159 and Rule 58 EPC Invitation to remedy deficiencies in the application documents dated Jan. 24, 2022, by the European Patent Office in European Patent Application No. 20815633.1 (2 pages).
Supplementary European Search Report dated Jul. 27, 2022, by the European Patent Office in European Patent Application No. 18883153. (7 pages).
Notification of Substantive Examination Result issued on Dec. 2, 2021, by the Intellectual Property Office of the Republic of Indonesia in Indonesian Patent Application No. P00202003125 and an English translation of the Notification. (6 pages).
Notification of Substantive Examination Result issued on Aug. 24, 2021, by the Intellectual Property Office of the Republic of Indonesia in Indonesian Patent Application No. P00202003131 and an English translation of the Notification. (6 pages).
Examination report under sections 12 & 13 of the Patents Act, 1970 and the Patents Rules, 2003 dated Nov. 24, 2021, by the Intellectual Property Office of India in Indian Patent Application No. 202047017398 and English translation of the Report. (7 pages).
International Preliminary Report on Patentability dated Jun. 2, 2020, by the International Bureau of WIPO in International Patent Application No. PCT/CN2018/118191. (6 pages).
International Preliminary Report on Patentability dated Jun. 16, 2021, by the International Bureau of WIPO in International Patent Application No. PCT/CN2019/128686 and English translation of the Report. (16 pages).
International Preliminary Report on Patentability dated Jun. 23, 2020, by the International Bureau of WIPO in International Patent Application No. PCT/CN2018/118232 and English translation of the Report. (13 pages).
International Preliminary Report on Patentability dated Sep. 3, 2021, by the State Intellectual Property Office of the People's Republic of China in International Patent Application No. PCT/CN2020/091489 and English translation of the Report. (12 pages).
Written Opinion of the International Searching Authority and International Search Report dated Feb. 20, 2019, by the State Intellectual Property Office of the People's Republic of China in International Patent Application No. PCT/CN2018/118107 and English translation. (22 pages).
Written Opinion of the International Searching Authority and International Search Report dated Feb. 25, 2019, by the State Intellectual Property Office of the People's Republic of China in International Patent Application No. PCT/CN2018/118212 and English translation. (23 pages).
English translation of the Written Opinion of the International Searching Authority and International Search Report dated Feb. 27, 2019, by the State Intellectual Property Office of the People's Republic of China in International Patent Application No. PCT/CN2018/118224. (13 pages).
Written Opinion of the International Searching Authority and International Search Report dated Feb. 28, 2019, by the State Intellectual Property Office of the People's Republic of China in International Patent Application No. PCT/CN2018/118300 and English translation. (20 pages).
Written Opinion of the International Searching Authority and International Search Report dated Mar. 6, 2019, by the State Intellectual Property Office of the People's Republic of China in International Patent Application No. PCT/CN2018/118106 and English translation. (20 pages).
Written Opinion of the International Searching Authority and International Search Report dated Mar. 6, 2019, by the State Intellectual Property Office of the People's Republic of China in International Application No. PCT/CN2018/118191 and English translation. (17 pages).
Written Opinion of the International Searching Authority and International Search Report dated Mar. 7, 2019, by the State Intellectual Property Office of the People's Republic of China in International Patent Application No. PCT/CN2018/118303 and English translation. (22 pages).
Written Opinion of the International Searching Authority and International Search Report dated Mar. 26, 2020, by the State Intellectual Property Office of the People's Republic of China in International Patent Application No. PCT/CN2019/129016 and English translation. (27 pages).
Written Opinion of the International Searching Authority and International Search Report dated Mar. 26, 2020, by the State Intellectual Property Office of the People's Republic of China in International Patent Application No. PCT/CN2019/128686 and English translation. (27 pages).
Written Opinion of the International Searching Authority and International Search Report dated Aug. 19, 2020, by the State Intellectual Property Office of the People's Republic of China in International Patent Application No. PCT/CN2020/091489 and English translation. (26 pages).
Written Opinion of the International Searching Authority and International Search Report dated Aug. 21, 2020, by the State Intellectual Property Office of the People's Republic of China in International Patent Application No. PCT/CN2020/091484 and English translation. (29 pages).
Written Opinion of the International Searching Authority and International Search Report dated Aug. 21, 2020, by the State Intellectual Property Office of the People's Republic of China in International Patent Application No. PCT/CN2020/091614 and English translation. (24 pages).
Written Opinion of the International Searching Authority and International Search Report dated Aug. 24, 2020, by the State Intellectual Property Office of the People's Republic of China in International Patent Application No. PCT/CN2020/091624 and English translation. (26 pages).
Written Opinion of the International Searching Authority and International Search Report dated Aug. 25, 2020, by the State Intellectual Property Office of the People's Republic of China in International Patent Application No. PCT/CN2020/091485 and English translation. (30 pages).
Written Opinion of the International Searching Authority and International Search Report dated Aug. 28, 2020, by the State Intellectual Property Office of the People's Republic of China in International Patent Application No. PCT/CN2020/091649 and English translation. (25 pages).
Written Opinion of the International Searching Authority and International Search Report dated Sep. 2, 2020, by the State Intellectual Property Office of the People's Republic of China in International Patent Application No. PCT/CN2020/091606 and English translation. (22 pages).
Written Opinion of the International Searching Authority and International Search Report dated Nov. 21, 2019, by the State Intellectual Property Office of the People's Republic of China in International Patent Application No. PCT/CN2019/101653 and English translation. (23 pages).
Written Opinion of the International Searching Authority and International Search Report dated Nov. 28, 2019, by the State Intellectual Property Office of the People's Republic of China in International Patent Application No. PCT/CN2019/101656 and English translation. (21 pages).
Written Opinion of the International Searching Authority and International Search Report dated Apr. 17, 2020, by the State Intellectual Property Office of the People's Republic of China in International Patent Application No. PCT/CN2020/072813 and English translation. (32 pages).
Office Action dated Mar. 9, 2022, by the Russian Agency for Patents and Trademarks in Russian Patent Application No. 2020118025/10(030488) and English translation of the Action. (14 pages).
Office Action dated May 11, 2022, by the Russian Agency for Patents and Trademarks in Russian Patent Application No. 2020121741/04(037329) and English translation of the Action. (18 pages).
Office Action dated Mar. 11, 2022, by the U.S. Patent and Trademark Office in U.S. Appl. No. 16/758,720. (21 pages).
Notice of Allowance dated Mar. 31, 2022, by the U.S. Patent and Trademark Office in U.S. Appl. No. 16/764,307. (7 pages).
Notice of Allowance dated Apr. 5, 2022, by the U.S. Patent and Trademark Office in U.S. Appl. No. 16/763,058. (7 pages).

(56) References Cited

OTHER PUBLICATIONS

Notice of Allowance dated Jul. 25, 2022, by the U.S. Patent and Trademark Office in U.S. Appl. No. 16/758,720. (5 pages).
Office Action dated Oct. 29, 2021, by the U.S. Patent and Trademark Office in U.S. Appl. No. 16/764,307. (17 pages).
Office Action dated Nov. 16, 2021, by the U.S. Patent and Trademark Office in U.S. Appl. No. 16/763,058. (26 pages).
Office Action dated Aug. 14, 2020, by the Intellectual Property Office of Vietnam in Vietnamese Patent Application No. 1-2020-03065 and an English translation of the Action. (3 pages).
Office Action dated Aug. 28, 2020, by the Intellectual Property Office of Vietnam in Vietnamese Patent Application No. 1-2020-03777 and an English translation of the Action. (3 pages).
Payment and Certificate of Renewal issued on May 30, 2022 by the Patent Office of South Africa in South African Patent Application No. 2020/03833. (1 page).
Ahmad Dar et al., "siRNAmod: A database of experimentally validated chemically modified siRNAs," Scientific Reports, Jan. 28, 2016, vol. 6, No. 1. (8 pages).
Behlke, Mark A., "Chemical Modification of siRNAs for In Vivo Use," OLIGONUCLEOTIDES, 2008, vol. 18, pp. 305-320.
Chen et al., "Research progress on factor XI as a novel target for antithrombotic therapy," Chinese Pharmacological Bulletin, Apr. 15, 2015, vol. 31, No. 5, with English abstract, pp. 619-622.
Dai et al., "A vital role for Angpll3 in the PAN-induced podocyte loss by affecting detachment and apoptosis in vitro," BMC Nephrology, 2015, vol. 16, No. 1. (10 pages).
Ding et al., "Limited role of kininogen in the host response during gram-negative pneumonia derived sepsis," American Journal of Physiology Lung Cellular and Molecular Physiology, Nov. 9, 2017. (33 pages).
Dong et al., "A novel packaging system of recombinant AAV5/5 vector," Chinese Journal of Biotechnology, May 25, 2010, vol. 26, No. 5, pp. 679-686.
Foster et al., "Advanced siRNA Designs Further Improve In Vivo Performance of GalNAc-siRNA Conjugates," Molecular Therapy, vol. 26, No. 3, pp. 708-717.
"*Homo sapiens* Kininogen 1 (KNG1), Transcript Variant 1, mRNA" GenBank, May 2, 2018, NM 00102416.2. (8 pages).
Khaitmetova et al., "Synthesis and Study of the Properties of Polymer Complexes of Ethacizin with Carboxymethylcellulose," Chemistry of Plant Raw Materials, No. 4, with English translation. (18 pages).
Khan et al., "High-Molecular-Weight Kininogen Fragments Stimulate the Secretion of Cytokines and Chemokines Through uPAR, Mac-1, and gC1qR in Monocytes," Arteriosclerosis, Thrombosis, and Vascular Biology, Oct. 2006, vol. 26, No. 10, pp. 2260-2266.
Kim et al., "Bifunctional compounds for targeted hepatic gene delivery," Gene Therapy, 2007, vol. 14, pp. 704-708.
Liu et al., "Determination of Human Plasma Pre-Kallikrein," Journal of China Medical University, 1988, vol. 17, No. 6, with English abstract, pp. 432-436.
Liu et al., "Coagulation factor XI induces Ca2+ response and accelerates cell migration in vascular smooth muscle cells via proteinase-activated receptor 1," American Journal of Physiology, Cell Physiology, Mar. 1, 2019, vol. 316, No. 3, pp. C377-C392.
Montagne et al., "Pericyte degeneration causes white matter dysfunction in the mouse CNS," Nature Medicine, 2018, vol. 24, vol. 3, pp. 326-337.
Nakagawa et al., "The RNAi-Mediated Silencing of Xanthine Dehydrogenase Impairs Growth and Fertility and Accelerates Leaf Senescence in Transgenic *Arabidopsis* Plants," Plant & Cell Physiology, 2007, vol. 48, No. 10, pp. 1484-1495.
Norata et al., "Gene silencing approaches for the management of dyslipidaemia," Trends in Pharmacological Sciences, Apr. 13, 2013, vol. 34, No. 4, pp. 198-205.
Nordestgaard et al., "Advances in lipid-lowering therapy through gene-silencing technologies," Nature Reviews, Feb. 8, 2018, vol. 15. (12 pages).

Papulov, Yu. G., "Relationship between Properties of Compounds with Their Structures: Math Modeling," Advances in Modern Natural Sciences, 2006, with English translation, pp. 75-76.
Peña-Altamira, et al., "Release of soluble and vesicular purine nucleoside phosphorylase from rat astrocytes and microglia induced by pro-inflammatory stimulation with extracellular ATP via P2X7 receptors," Neurochemistry International, May 31, 2018, vol. 115, pp. 37-49.
Pessentheiner et al., "ANGPTL3 targeting: The power of versatile lipid-lowering," Atherosclerosis, Jan. 2018, vol. 268, pp. 185-187.
Prakash et al., "Comprehensive Structure-Activity Relationship of Triantennary N-Acetylgalactosamine Conjugated Antisense Oligonucleotides for Targeted Delivery to Hepatocytes," Journal of Medicinal Chemistry, 2016, vol. 59, pp. 2718-2733.
Ren et al., "Synthesis of bifunctional cationic compound for gene delivery," Tetrahedron Letters, 2001, vol. 42, pp. 1007-1010.
Ren et al., "Gene Expression Profile of Transgenic Mouse Kidney Reveals Pathogenesis of Hepatitis B Virus Associated Nephropathy," Journal of Medical Virology, 2006, vol. 78, pp. 551-560.
Ren et al., "Stable Inhibition of Hepatitis B Virus Expression and Replication by Expressed siRNA", Biochemical and Biophysical Research Communications, Oct. 7, 2005, vol. 335, No. 4, with English abstract, pp. 1051-1058.
Springer et al., "GalNAc-siRNA Conjugates: Leading the Way for Delivery of RNAi Therapeutics," Nucleic Acid Therapeutics, May 2018, vol. 28, No. 3, pp. 109-118.
Su et al., "Progress on the Inhibition of Hepatitis B virus by siRNA Strategy," China Biotechnology, 2014, vol. 34, No. 9, with English abstract, pp. 102-107.
Tangkijvanich et al., "Low pretreatment serum HBsAg level and viral mutations as predictors of response to PEG-interferon alpha-2b therapy in chronic hepatitis B," Journal of Clinical Virology, vol. 46, 2009, pp. 117-123.
Wu et al., "Cleaved high molecular weight kininogen inhibits tube formation of endothelial progenitor cells via suppression of matrix metalloproteinase 2," Journal of Thrombosis and Haemostasis, 2010, vol. 8, pp. 185-193.
Wu et al., "Contact pathway of coagulation and inflammation," Thrombosis Journal, 2015, pp. 13-17.
Xu et al., "Role of angiopoielin-like 3 (ANGPTL3) in regulating plasma level of low-density Tipoprotein cholesterol," Atherosclerosis, 2018, vol. 268, pp. 196-206.
Yang et al., "A critical role for plasma kallikrein in the pathogenesis of autoantibody-induced arthritis," Federation of American Societies for Experimental Biology, Nov. 2017, vol. 31, No. 12, pp. 5419-5431.
Yang et al., "An essential role of high-molecular-weight kininogen in endotoxemia," Journal of Experimental Medicine, Sep. 4, 2017, vol. 214, No. 9, pp. 2649-2670.
Extended European Search Report dated Jul. 19, 2022, by the European Patent Office in corresponding European Patent Application No. 19867686.8. (12 pages).
Nakamoto et al., "Enhanced Intercellular Delivery of cRGD-siRNA Conjugates by an Additional Oligospermine Modification," ACS Omega, 2018, vol. 3, pp. 8226-8232. (7 pages).
Nothisen et al., "Cationic siRNAs Provide Carrier-Free Gene Silencing in Animal Cells," Journal of the American Chemical Society, 2009, vol. 131, No. 29, pp. 17730-17731. (2 pages).
Common knowledge "RNAi technology," 2005, with English translation. (5 pages).
Foster et al., "Advanced siRNA Designs Further Improve In Vivo Performance of GalNAc-siRNA Conjugates," Molecular Therapy, Mar. 2018, vol. 26, No. 3, pp. 708-717.
Khaitmetova et al., "Synthesis and Study of the Properties of Polymer Complexes of Ethacizin with Carboxymethylcellulose," Chemistry of Plant Raw Materials, 2017, No. 4, with English translation. (18 pages).
Durnov, et al., "Children's Oncology", Paediatric Oncology, Second Edition, Moscow Publishing House Medicine, 2002, p. 139 and its English translation. Cited in Office Action dated Oct. 10, 2022 in Russian Application No. 2020121741). (4 pages).

(56) References Cited

OTHER PUBLICATIONS

Dysop, "Chemistry of Synthetic Drugs", Publishing House MIR, 1964, pp. 12-19 and its English translation. Cited in Office Action dated Oct. 10, 2022 in Russian Application No. 2020121741). (18 pages).

Belikov, V.G., "Pharmaceutical Chemistry", textbook, Moscow, 11th Edition, MEDpress-inform, 2007, pp. 27-29 and its English translation. (Cited in Office Action dated Oct. 10, 2022 in Russian Application No. 2020121741). (8 pages).

\* cited by examiner

SEQUENCE LISTING

```
<160> NUMBER OF SEQ ID NOS: 61

<210> SEQ ID NO 1
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (19)..(19)
<223> OTHER INFORMATION: n is Z, Z is A

<400> SEQUENCE: 1
caauaaagcu ggacaagan                                              19

<210> SEQ ID NO 2
<211> LENGTH: 19
<212> TYPE: RNA
<213> ORGANISM: Artificial Sequence
<220> FEATURE:
```

<223> OTHER INFORMATION: siRNA
<220> FEATURE:
<221> NAME/KEY: misc_feature
<222> LOCATION: (1)..(1)
<223> OTHER INFORMATION: n is Z', Z' is U

<400> SEQUENCE: 2
nucuugucca gcuuuauug                                                      19

<210> SEQ ID NO 3
<211> LENGTH: 21
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n is Z'B, Z'B is a neucleotide complementary to
      ZA, ZA is selected from A, U, G or C

<400> SEQUENCE: 3
nucuugucca gcuuuauugg g                                                   21

<210> SEQ ID NO 4
<211> LENGTH: 21
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (21)..(21)
<223> OTHER INFORMATION: n is ZA, ZA is selected from A, U, G or C

<400> SEQUENCE: 4
cccaauaaag cuggacaaga n                                                   21

<210> SEQ ID NO 5
<211> LENGTH: 23
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n is Z'B, Z'B is a neucleotide complementary to
      ZA, ZA is selected from A, U, G or C

<400> SEQUENCE: 5
nucuugucca gcuuuauugg gag                                                 23

<210> SEQ ID NO 6
<211> LENGTH: 19
<212> TYPE: RNA
<213> ORGANISM: Artificial Sequence
<220> FEATURE:
<223> OTHER INFORMATION: siRNA

<400> SEQUENCE: 6
caauaaagcu ggacaagaa                                                      19

<210> SEQ ID NO 7
<211> LENGTH: 21
<212> TYPE: RNA
<213> ORGANISM: Artificial Sequence
<220> FEATURE:
<223> OTHER INFORMATION: siRNA

```
<400> SEQUENCE: 7
uucuugucca gcuuuauugg g                                              21

<210> SEQ ID NO 8
<211> LENGTH: 21
<212> TYPE: RNA
<213> ORGANISM: Artificial Sequence
<220> FEATURE:
<223> OTHER INFORMATION: siRNA

<400> SEQUENCE: 8
cccaauaaag cuggacaaga a                                              21

<210> SEQ ID NO 9
<211> LENGTH: 23
<212> TYPE: RNA
<213> ORGANISM: Artificial Sequence
<220> FEATURE:
<223> OTHER INFORMATION: siRNA

<400> SEQUENCE: 9
uucuugucca gcuuuauugg gag                                            23

<210> SEQ ID NO 10
<211> LENGTH: 19
<212> TYPE: RNA
<213> ORGANISM: Artificial Sequence
<220> FEATURE:
<223> OTHER INFORMATION: siRNA

<400> SEQUENCE: 10
caauaaagcu ggacaagaa                                                 19

<210> SEQ ID NO 11
<211> LENGTH: 21
<212> TYPE: RNA
<213> ORGANISM: Artificial Sequence
<220> FEATURE:
<223> OTHER INFORMATION: siRNA

<400> SEQUENCE: 11
uucuugucca gcuuuauugg g                                              21

<210> SEQ ID NO 12
<211> LENGTH: 21
<212> TYPE: RNA
<213> ORGANISM: Artificial Sequence
<220> FEATURE:
<223> OTHER INFORMATION: siRNA

<400> SEQUENCE: 12
cccaauaaag cuggacaaga a                                              21

<210> SEQ ID NO 13
<211> LENGTH: 23
<212> TYPE: RNA
<213> ORGANISM: Artificial Sequence
<220> FEATURE:
<223> OTHER INFORMATION: siRNA

<400> SEQUENCE: 13
uucuugucca gcuuuauugg gag                                            23

<210> SEQ ID NO 14
```

```
<211> LENGTH: 19
<212> TYPE: RNA
<213> ORGANISM: Artificial Sequence
<220> FEATURE:
<223> OTHER INFORMATION: siRNA

<400> SEQUENCE: 14
caauaaagcu ggacaagaa                                                      19

<210> SEQ ID NO 15
<211> LENGTH: 21
<212> TYPE: RNA
<213> ORGANISM: Artificial Sequence
<220> FEATURE:
<223> OTHER INFORMATION: siRNA

<400> SEQUENCE: 15
uucuugucca gcuuuauugg g                                                   21

<210> SEQ ID NO 16
<211> LENGTH: 21
<212> TYPE: RNA
<213> ORGANISM: Artificial Sequence
<220> FEATURE:
<223> OTHER INFORMATION: siRNA

<400> SEQUENCE: 16
cccaauaaag cuggacaaga a                                                   21

<210> SEQ ID NO 17
<211> LENGTH: 23
<212> TYPE: RNA
<213> ORGANISM: Artificial Sequence
<220> FEATURE:
<223> OTHER INFORMATION: siRNA

<400> SEQUENCE: 17
uucuugucca gcuuuauugg gag                                                 23

<210> SEQ ID NO 18
<211> LENGTH: 19
<212> TYPE: RNA
<213> ORGANISM: Artificial Sequence
<220> FEATURE:
<223> OTHER INFORMATION: siRNA

<400> SEQUENCE: 18
caauaaagcu ggacaagaa                                                      19

<210> SEQ ID NO 19
<211> LENGTH: 21
<212> TYPE: RNA
<213> ORGANISM: Artificial Sequence
<220> FEATURE:
<223> OTHER INFORMATION: siRNA

<400> SEQUENCE: 19
uucuugucca gcuuuauugg g                                                   21

<210> SEQ ID NO 20
<211> LENGTH: 21
<212> TYPE: RNA
<213> ORGANISM: Artificial Sequence
<220> FEATURE:
<223> OTHER INFORMATION: siRNA
```

```
<400> SEQUENCE: 20
cccaauaaag cuggacaaga a                                              21

<210> SEQ ID NO 21
<211> LENGTH: 23
<212> TYPE: RNA
<213> ORGANISM: Artificial Sequence
<220> FEATURE:
<223> OTHER INFORMATION: siRNA

<400> SEQUENCE: 21
uucuugucca gcuuuauugg gag                                            23

<210> SEQ ID NO 22
<211> LENGTH: 19
<212> TYPE: RNA
<213> ORGANISM: Artificial Sequence
<220> FEATURE:
<223> OTHER INFORMATION: siRNA

<400> SEQUENCE: 22
caauaaagcu ggacaagaa                                                 19

<210> SEQ ID NO 23
<211> LENGTH: 21
<212> TYPE: RNA
<213> ORGANISM: Artificial Sequence
<220> FEATURE:
<223> OTHER INFORMATION: siRNA

<400> SEQUENCE: 23
uucuugucca gcuuuauugg g                                              21

<210> SEQ ID NO 24
<211> LENGTH: 21
<212> TYPE: RNA
<213> ORGANISM: Artificial Sequence
<220> FEATURE:
<223> OTHER INFORMATION: siRNA

<400> SEQUENCE: 24
cccaauaaag cuggacaaga a                                              21

<210> SEQ ID NO 25
<211> LENGTH: 23
<212> TYPE: RNA
<213> ORGANISM: Artificial Sequence
<220> FEATURE:
<223> OTHER INFORMATION: siRNA

<400> SEQUENCE: 25
uucuugucca gcuuuauugg gag                                            23

<210> SEQ ID NO 26
<211> LENGTH: 21
<212> TYPE: RNA
<213> ORGANISM: Artificial Sequence
<220> FEATURE:
<223> OTHER INFORMATION: siRNA

<400> SEQUENCE: 26
uucuugucca gcuuuauugg g                                              21

<210> SEQ ID NO 27
```

```
<211> LENGTH: 23
<212> TYPE: RNA
<213> ORGANISM: Artificial Sequence
<220> FEATURE:
<223> OTHER INFORMATION: siRNA

<400> SEQUENCE: 27
uucuugucca gcuuuauugg gag                                              23

<210> SEQ ID NO 28
<211> LENGTH: 21
<212> TYPE: RNA
<213> ORGANISM: Artificial Sequence
<220> FEATURE:
<223> OTHER INFORMATION: siRNA

<400> SEQUENCE: 28
uucuugucca gcuuuauugg g                                                21

<210> SEQ ID NO 29
<211> LENGTH: 23
<212> TYPE: RNA
<213> ORGANISM: Artificial Sequence
<220> FEATURE:
<223> OTHER INFORMATION: siRNA

<400> SEQUENCE: 29
uucuugucca gcuuuauugg gag                                              23

<210> SEQ ID NO 30
<211> LENGTH: 21
<212> TYPE: RNA
<213> ORGANISM: Artificial Sequence
<220> FEATURE:
<223> OTHER INFORMATION: siRNA

<400> SEQUENCE: 30
uucuugucca gcuuuauugg g                                                21

<210> SEQ ID NO 31
<211> LENGTH: 23
<212> TYPE: RNA
<213> ORGANISM: Artificial Sequence
<220> FEATURE:
<223> OTHER INFORMATION: siRNA

<400> SEQUENCE: 31
uucuugucca gcuuuauugg gag                                              23

<210> SEQ ID NO 32
<211> LENGTH: 21
<212> TYPE: RNA
<213> ORGANISM: Artificial Sequence
<220> FEATURE:
<223> OTHER INFORMATION: siRNA

<400> SEQUENCE: 32
uucuugucca gcuuuauugg g                                                21

<210> SEQ ID NO 33
<211> LENGTH: 23
<212> TYPE: RNA
<213> ORGANISM: Artificial Sequence
<220> FEATURE:
<223> OTHER INFORMATION: siRNA
```

```
<400> SEQUENCE: 33
uucuugucca gcuuuauugg gag                                            23

<210> SEQ ID NO 34
<211> LENGTH: 21
<212> TYPE: RNA
<213> ORGANISM: Artificial Sequence
<220> FEATURE:
<223> OTHER INFORMATION: siRNA

<400> SEQUENCE: 34
uucuugucca gcuuuauugg g                                              21

<210> SEQ ID NO 35
<211> LENGTH: 23
<212> TYPE: RNA
<213> ORGANISM: Artificial Sequence
<220> FEATURE:
<223> OTHER INFORMATION: siRNA

<400> SEQUENCE: 35
uucuugucca gcuuuauugg gag                                            23

<210> SEQ ID NO 36
<211> LENGTH: 21
<212> TYPE: RNA
<213> ORGANISM: Artificial Sequence
<220> FEATURE:
<223> OTHER INFORMATION: siRNA

<400> SEQUENCE: 36
uucuugucca gcuuuauugg g                                              21

<210> SEQ ID NO 37
<211> LENGTH: 23
<212> TYPE: RNA
<213> ORGANISM: Artificial Sequence
<220> FEATURE:
<223> OTHER INFORMATION: siRNA

<400> SEQUENCE: 37
uucuugucca gcuuuauugg gag                                            23

<210> SEQ ID NO 38
<211> LENGTH: 21
<212> TYPE: RNA
<213> ORGANISM: Artificial Sequence
<220> FEATURE:
<223> OTHER INFORMATION: siRNA

<400> SEQUENCE: 38
uucuugucca gcuuuauugg g                                              21

<210> SEQ ID NO 39
<211> LENGTH: 23
<212> TYPE: RNA
<213> ORGANISM: Artificial Sequence
<220> FEATURE:
<223> OTHER INFORMATION: siRNA

<400> SEQUENCE: 39
uucuugucca gcuuuauugg gag                                            23

<210> SEQ ID NO 40
```

```
<211> LENGTH: 21
<212> TYPE: RNA
<213> ORGANISM: Artificial Sequence
<220> FEATURE:
<223> OTHER INFORMATION: siRNA

<400> SEQUENCE: 40
uucuugucca gcuuuauugg g                                               21

<210> SEQ ID NO 41
<211> LENGTH: 23
<212> TYPE: RNA
<213> ORGANISM: Artificial Sequence
<220> FEATURE:
<223> OTHER INFORMATION: siRNA

<400> SEQUENCE: 41
uucuugucca gcuuuauugg gag                                             23

<210> SEQ ID NO 42
<211> LENGTH: 21
<212> TYPE: RNA
<213> ORGANISM: Artificial Sequence
<220> FEATURE:
<223> OTHER INFORMATION: siRNA

<400> SEQUENCE: 42
uucuugucca gcuuuauugg g                                               21

<210> SEQ ID NO 43
<211> LENGTH: 21
<212> TYPE: RNA
<213> ORGANISM: Artificial Sequence
<220> FEATURE:
<223> OTHER INFORMATION: siRNA

<400> SEQUENCE: 43
uucuugucca gcuuuauugg g                                               21

<210> SEQ ID NO 44
<211> LENGTH: 19
<212> TYPE: RNA
<213> ORGANISM: Artificial Sequence
<220> FEATURE:
<223> OTHER INFORMATION: siRNA

<400> SEQUENCE: 44
ccuugaggca uacuucaaa                                                  19

<210> SEQ ID NO 45
<211> LENGTH: 21
<212> TYPE: RNA
<213> ORGANISM: Artificial Sequence
<220> FEATURE:
<223> OTHER INFORMATION: siRNA

<400> SEQUENCE: 45
uuugaaguau gccucaaggu u                                               21

<210> SEQ ID NO 46
<211> LENGTH: 19
<212> TYPE: RNA
<213> ORGANISM: Artificial Sequence
<220> FEATURE:
<223> OTHER INFORMATION: siRNA
```

```
<400> SEQUENCE: 46
uucuccgaac gugucacgu                                                19

<210> SEQ ID NO 47
<211> LENGTH: 21
<212> TYPE: RNA
<213> ORGANISM: Artificial Sequence
<220> FEATURE:
<223> OTHER INFORMATION: siRNA

<400> SEQUENCE: 47
acgugacacg uucggagaac u                                             21

<210> SEQ ID NO 48
<211> LENGTH: 21
<212> TYPE: RNA
<213> ORGANISM: Artificial Sequence
<220> FEATURE:
<223> OTHER INFORMATION: siRNA

<400> SEQUENCE: 48
gcuuaaaagg gacaguauuc a                                             21

<210> SEQ ID NO 49
<211> LENGTH: 23
<212> TYPE: RNA
<213> ORGANISM: Artificial Sequence
<220> FEATURE:
<223> OTHER INFORMATION: siRNA

<400> SEQUENCE: 49
ugaauacugu cccuuuuaag caa                                           23

<210> SEQ ID NO 50
<211> LENGTH: 20
<212> TYPE: DNA
<213> ORGANISM: Artificial Sequence
<220> FEATURE:
<223> OTHER INFORMATION: primer

<400> SEQUENCE: 50
gtgaccgatg gcttcagttc                                               20

<210> SEQ ID NO 51
<211> LENGTH: 20
<212> TYPE: DNA
<213> ORGANISM: Artificial Sequence
<220> FEATURE:
<223> OTHER INFORMATION: primer

<400> SEQUENCE: 51
atggataggc aggtggactt                                               20

<210> SEQ ID NO 52
<211> LENGTH: 18
<212> TYPE: DNA
<213> ORGANISM: Artificial Sequence
<220> FEATURE:
<223> OTHER INFORMATION: primer

<400> SEQUENCE: 52
ccaaccgcga gaagatga                                                 18

<210> SEQ ID NO 53
```

```
<211> LENGTH: 20
<212> TYPE: DNA
<213> ORGANISM: Artificial Sequence
<220> FEATURE:
<223> OTHER INFORMATION: primer

<400> SEQUENCE: 53
ccagaggcgt acagggatag                                               20

<210> SEQ ID NO 54
<211> LENGTH: 24
<212> TYPE: DNA
<213> ORGANISM: Artificial Sequence
<220> FEATURE:
<223> OTHER INFORMATION: primer

<400> SEQUENCE: 54
agcttctttg cagctccttc gttg                                          24

<210> SEQ ID NO 55
<211> LENGTH: 24
<212> TYPE: DNA
<213> ORGANISM: Artificial Sequence
<220> FEATURE:
<223> OTHER INFORMATION: primer

<400> SEQUENCE: 55
ttctgaccca ttcccaccat caca                                          24

<210> SEQ ID NO 56
<211> LENGTH: 20
<212> TYPE: DNA
<213> ORGANISM: Artificial Sequence
<220> FEATURE:
<223> OTHER INFORMATION: primer

<400> SEQUENCE: 56
ttgaaccctg aggccaaacc                                               20

<210> SEQ ID NO 57
<211> LENGTH: 20
<212> TYPE: DNA
<213> ORGANISM: Artificial Sequence
<220> FEATURE:
<223> OTHER INFORMATION: primer

<400> SEQUENCE: 57
cggtaggagg gcactgagaa                                               20

<210> SEQ ID NO 58
<211> LENGTH: 20
<212> TYPE: DNA
<213> ORGANISM: Artificial Sequence
<220> FEATURE:
<223> OTHER INFORMATION: primer

<400> SEQUENCE: 58
gggagccaaa agggtcatca                                               20

<210> SEQ ID NO 59
<211> LENGTH: 20
<212> TYPE: DNA
<213> ORGANISM: Artificial Sequence
<220> FEATURE:
<223> OTHER INFORMATION: primer
```

```
<400> SEQUENCE: 59
cgtggactgt ggtcatgagt                                                20

<210> SEQ ID NO 60
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (19)..(19)
<223> OTHER INFORMATION: n is ZA, ZA is selected from A, U, G or C

<400> SEQUENCE: 60
caauaaagcu ggacaagan                                                 19

<210> SEQ ID NO 61
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n is Z'B, Z'B is a neucleotide complementary to
      ZA, ZA is selected from A, U, G or C

<400> SEQUENCE: 61
nucuugucca gcuuuauug                                                 19
```

NUCLEIC ACID, COMPOSITION AND CONJUGATE CONTAINING SAME, PREPARATION METHOD, AND USE THEREOF

SEQUENCE LISTING

Incorporated by reference in its entirety herein is a computer-readable sequence listing submitted via EFS-Web and identified as follows: One (11,735 Byte ASCII (Text)) file named "sequence_listing_3_16758532.txt" created on Aug. 5, 2020.

BACKGROUND ART

Dyslipidemia (hyperlipidemia) refers to a systemic disease involving a higher plasma lipid content than normal value, which is caused by abnormal metabolism and transportation of fat, and severely threatens the health of patients worldwide. The currently available medicines for treating dyslipidemia include mainly statins, cholesterol absorption inhibitor, resins, probucol, fibrates and niacins and derivatives thereof.

Apolipoprotein C3 (APOC3) plays a crucial function in lipid metabolism. People carrying APOC3 mutant gene show an expression amount of APOC3 in blood circulation reduced by 46%, and triglyceride level in plasma reduced by 39% as compared with normal population. Meanwhile, the relatively low blood lipid level can reduce the risk of heart diseases in people carrying APOC3 mutant gene by 35.1% than those not carrying said gene. Thus, silencing gene expression at genetic level to block the production of APOC3 is undoubtedly the most idealist treatment manner. Based on the mechanism of RNA interference (RNAi), small interfering RNA (siRNA) could inhibits or blocks the expression of any target gene of interest by means of sequence specificity, so as to treat diseases.

Stabilization modification of siRNA and the delivery system thereof are two crucial technolgies in the development of siRNA medicines.

SUMMARY OF THE INVENTION

In some embodiments, the present disclosure provides a modified siRNA, which has the structure represented by Formula (1):

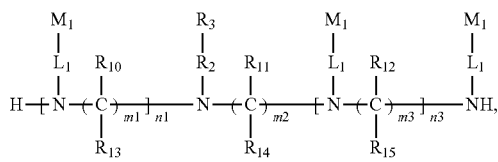

Formula (1)

wherein, n1 is an integer of 1-3, and n3 is an integer of 0-4;

m1, m2, and m3 are independently an integer of 2-10;

each of $R_{10}$, $R_{11}$, $R_{12}$, $R_{13}$, $R_{14}$ and $R_{15}$ is independently H, or selected from the group consisting of $C_1$-$C_{10}$ alkyl, $C_1$-$C_{10}$ haloalkyl, and $C_1$-$C_{10}$ alkoxy;

$R_3$ is a group having the structure represented by Formula A59:

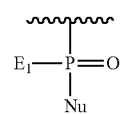

(A59)

wherein $E_1$ is OH, SH or $BH_2$, and Nu is a siRNA;

in said siRNA, each nucleotide is independently a modified or unmodified nucleotide; the siRNA comprises a sense strand and an antisense strand; the sense strand comprises a nucleotide sequence 1, and the antisense strand comprises a nucleotide sequence 2; said nucleotide sequence 1 and nucleotide sequence 2 are at least partly reverse complementary to form a double-stranded region, wherein the nucleotide sequence 1 has the same length as the nucleotide sequence represented by SEQ ID NO: 1 with no more than 3 nucleotide differences, and the nucleotide sequence 2 has the same length as the nucleotide sequence represented by SEQ ID NO:2 with no more than 3 nucleotide differences:

```
                                            (SEQ ID NO: 1)
        5'-CAAUAAAGCUGGACAAGAZ-3';

(SEQ ID NO: 2)
        5'-Z'UCUUGUCCAGCUUUAUUG-3';
``` wherein, Z is A and Z' is U, and the nucleotide sequence 1 comprises a nucleotide $Z_A$ at the corresponding position of Z, the nucleotide sequence 2 comprises a nucleotide $Z'_B$ at the corresponding position of Z', wherein $Z'_B$ is the first nucleotide at 5' terminal of the antisense strand;

$R_2$ is a linear alkylene of 1 to 20 carbon atoms in length, wherein one or more carbon atoms are optionally replaced with one or more groups selected from the group consisting of: C(O), NH, O, S, CH=N, S(O)$_2$, $C_2$-$C_{10}$ alkeylene, $C_2$-$C_{10}$ alkynylene, $C_6$-$C_{10}$ arylene, $C_3$-$C_{18}$ heterocyclylene, and $C_5$-$C_{10}$ heteroarylene, and wherein $R_2$ is optionally substituted by any one or more groups selected from the group consisting of: $C_1$-$C_{10}$ alkyl, $C_6$-$C_{10}$ aryl, $C_5$-$C_{10}$ heteroaryl, $C_1$-$C_{10}$ haloalkyl, —O$C_1$-$C_{10}$ alkyl, —O$C_1$-$C_{10}$ alkylphenyl, —$C_1$-$C_{10}$ alkyl-OH, —O$C_1$-$C_{10}$ haloalkyl, —S$C_1$-$C_{10}$ alkyl, —S$C_1$-$C_{10}$ alkylphenyl, —$C_1$-$C_{10}$ alkyl-SH, —S$C_1$-$C_{10}$ haloalkyl, halo, —OH, —SH, —NH$_2$, —$C_1$-$C_{10}$ alkyl-NH$_2$, —N($C_1$-$C_{10}$ alkyl)($C_1$-$C_{10}$ alkyl), —NH($C_1$-$C_{10}$ alkyl), cyano, nitro, —CO$_2$H, —C(O)O($C_1$-$C_{10}$ alkyl), —CON($C_1$-$C_{10}$ alkyl)($C_1$-$C_{10}$ alkyl), —CONH($C_1$-$C_{10}$ alkyl), —CONH$_2$, —NHC(O)($C_1$-$C_{10}$ alkyl), —NHC(O)(phenyl), —N($C_1$-$C_{10}$ alkyl)C(O)($C_1$-$C_{10}$ alkyl), —N($C_1$-$C_{10}$ alkyl)C(O)(phenyl), —C(O)$C_1$-$C_{10}$ alkyl, —C(O)$C_1$-$C_{10}$ alkylphenyl, —C(O)$C_1$-$C_{10}$ haloalkyl, —OC(O)$C_1$-$C_{10}$ alkyl, —SO$_2$($C_1$-$C_{10}$ alkyl), —SO$_2$(phenyl), —SO$_2$($C_1$-$C_{10}$ haloalkyl), —SO$_2$NH$_2$, —SO$_2$NH($C_1$-$C_{10}$ alkyl), —SO$_2$NH (phenyl), —NHSO$_2$($C_1$-$C_{10}$ alkyl), —NHSO$_2$(phenyl), and —NHSO$_2$($C_1$-$C_{10}$ haloalkyl);

each $L_1$ is a linear alkylene of 1 to 70 carbon atoms in length, wherein one or more carbon atoms are optionally replaced with one or more groups selected from the group consisting of: C(O), NH, O, S, CH=N, S(O)$_2$, $C_2$-$C_{10}$ alkeylene, $C_2$-$C_{10}$ alkynylene, $C_6$-$C_{10}$ arylene, $C_3$-$C_{18}$ heterocyclylene, and $C_5$-$C_{10}$ heteroarylene; and wherein $L_1$ is optionally substituted by any one or more groups selected from the group consisting of: $C_1$-$C_{10}$ alkyl, $C_6$-$C_{10}$ aryl, $C_5$-$C_{10}$ heteroaryl, $C_1$-$C_{10}$ haloalkyl, —O$C_1$-$C_{10}$ alkyl, —O$C_1$-$C_{10}$ alkylphenyl, —$C_1$-$C_{10}$ alkyl-OH, —O$C_1$-$C_{10}$ haloalkyl, —S$C_1$-$C_{10}$ alkyl, —S$C_1$-$C_{10}$ alkylphenyl, —$C_1$-

$C_{10}$ alkyl-SH, —$SC_1$-$C_{10}$ haloalkyl, halo, —OH, —SH, —$NH_2$, —$C_1$-$C_{10}$ alkyl-$NH_2$, —$N(C_1$-$C_{10}$ alkyl)($C_1$-$C_{10}$ alkyl), —$NH(C_1$-$C_{10}$ alkyl), cyano, nitro, —$CO_2H$, —C(O)O($C_1$-$C_{10}$ alkyl), —$CON(C_1$-$C_{10}$ alkyl)($C_1$-$C_{10}$ alkyl), —$CONH(C_1$-$C_{10}$ alkyl), —$CONH_2$, —$NHC(O)(C_1$-$C_{10}$ alkyl), —NHC(O)(phenyl), —$N(C_1$-$C_{10}$ alkyl)C(O)($C_1$-$C_{10}$ alkyl), —$N(C_1$-$C_{10}$ alkyl)C(O)(phenyl), —C(O)$C_1$-$C_{10}$ alkyl, —C(O)$C_1$-$C_{10}$ alkylphenyl, —C(O)$C_1$-$C_{10}$ haloalkyl, —OC(O)$C_1$-$C_{10}$ alkyl, —$SO_2$($C_1$-$C_{10}$ alkyl), —$SO_2$(phenyl), —$SO_2$($C_1$-$C_{10}$ haloalkyl), —$SO_2NH_2$, —$SO_2NH(C_1$-$C_{10}$ alkyl), —$SO_2NH$(phenyl), —$NHSO_2$($C_1$-$C_{10}$ alkyl), —$NHSO_2$(phenyl), and —$NHSO_2$($C_1$-$C_{10}$ haloalkyl).

In some embodiments, each $L_1$ is independently selected from connection combinations of one or more of the groups having Formulae A1-A26:

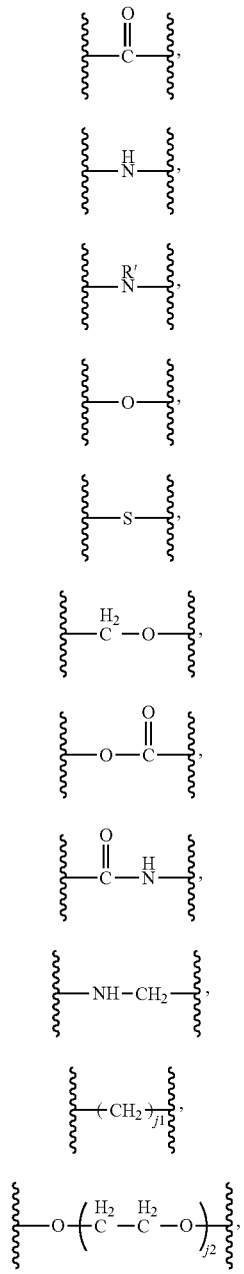

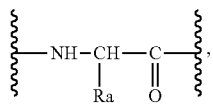

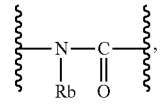

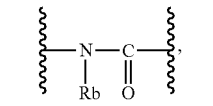

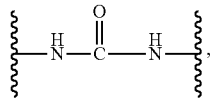

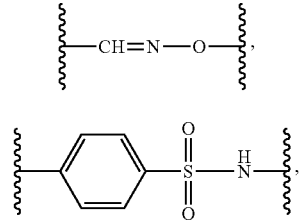

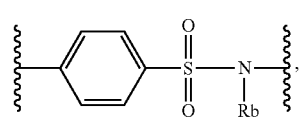

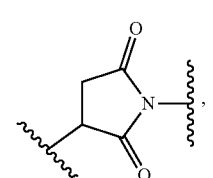

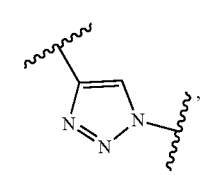

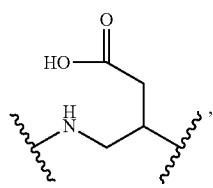

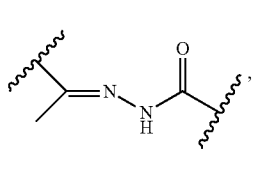

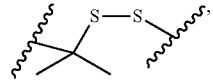

-continued
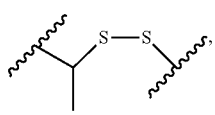
(A23)
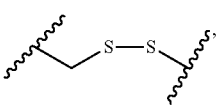
(A24)
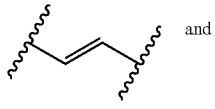 and
(A25)
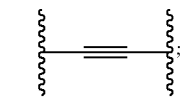
(A26)
wherein, j1 is an integer of 1-20; j2 is an integer of 1-20; R' is a $C_1$-$C_{10}$ alkyl;
Ra is selected from the group consisting of Formulae A27-A45 and any combination thereof:
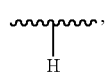
(A27)
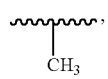
(A28)
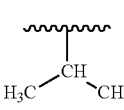
(A29)
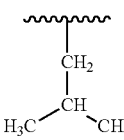
(A30)
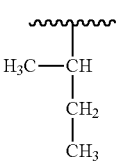
(A31)
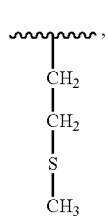
(A32)
-continued
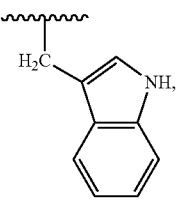
(A33)
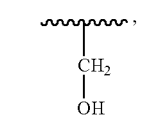
(A34)
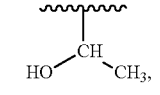
(A35)
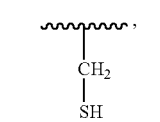
(A36)
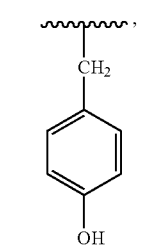
(A37)
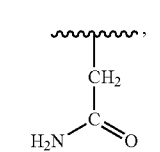
(A38)
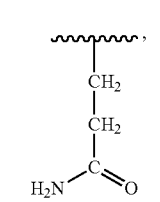
(A39)
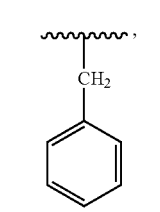
(A40)
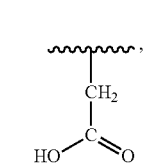
(A41)

-continued

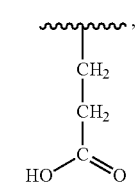
(A42)

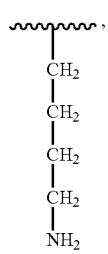
(A43)

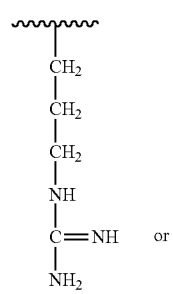
(A44)

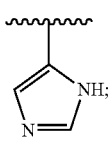 or (A45)

Rb is a $C_1$-$C_{10}$ alkyl;

~~~ represents a site where a group is attached to the rest of the molecule; and $M_1$ represents a targeting group.

In some embodiments, the present disclosure provides a method for preparing a conjugate, comprising: successively linking nucleoside monomers in 3' to 5' direction according to the nucleotide type and sequence of a sense strand and an antisense strand of siRNA, under a condition of phosphoramidite solid phase synthesis, wherein the linking of each nucleoside monomer includes a four-step reaction of deprotection, coupling, capping, and oxidation or sulfurization; isolating the sense strand and antisense strand of the siRNA; and annealing; wherein each nucleotide in the siRNA is independently a modified or unmodified nucleotide; the siRNA comprises a sense strand and an antisense strand; the sense strand comprises a nucleotide sequence 1, and the antisense strand comprises a nucleotide sequence 2; said nucleotide sequence 1 and nucleotide sequence 2 are at least partly reverse complementary to form a double-stranded region, wherein the nucleotide sequence 1 has the same length as the nucleotide sequence represented by SEQ ID NO: 1 with no more than 3 nucleotide differences, and the nucleotide sequence 2 has the same length as the nucleotide sequence represented by SEQ ID NO:2 with no more than 3 nucleotide differences:

(SEQ ID NO: 1)
5'-CAAUAAAGCUGGACAAGAZ-3';

(SEQ ID NO: 2)
5'-Z'UCUUGUCCAGCUUUAUUG-3';

wherein, Z is A and Z' is U, and the nucleotide sequence 1 comprises a nucleotide $Z_A$ at the corresponding position of Z, the nucleotide sequence 2 comprises a nucleotide $Z'_B$ at the corresponding position of Z', wherein $Z'_B$ is the first nucleotide at 5' terminal of the antisense strand;

and, wherein the method further comprises contacting the compound represented by Formula (321) with a nucleoside monomer or a nucleotide sequence linked to a solid phase support under a coupling reaction condition in the presence of a coupling reagent, thereby linking the compound represented by Formula (321) to the nucleotide sequence via a coupling reaction. In the following text, the compound represented by Formula (321) is also referred to as a conjugating molecule.

Formula (321)

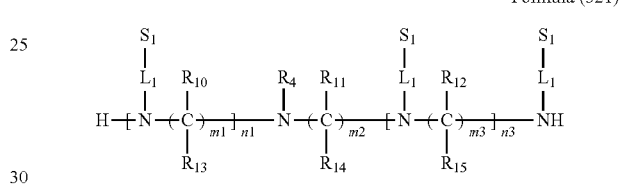

wherein:

$R_4$ is a moiety capable of binding to the siRNA represented by Nu. In some embodiments, $R_4$ is a moiety capable of binding to the siRNA represented by Nu via a covalent bond. In some embodiments, $R_4$ is a moiety capable of being conjugated to any functional group of siRNA represented by Nu via a phosphodiester bond by a reaction;

each $S_1$ is independently a group formed by replacing all the active hydroxyl groups in $M_1$ with YCOO— group, wherein each Y is independently one selected from the group consisting of methyl, trifluoromethyl, difluoromethyl, monofluoromethyl, trichloromethyl, dichloromethyl, monochloromethyl, ethyl, n-propyl, isopropyl, phenyl, halophenyl and alkylphenyl; in some embodiments, Y is methyl;

the definitions and options of n1, n3, m1, m2, m3, $R_{10}$, $R_{11}$, $R_{12}$, $R_{13}$, $R_{14}$, $R_{15}$, $L_1$, and $M_1$ are respectively described as above.

In some embodiments, the present disclosure provides a modified siRNA capable of inhibiting the expression of APOC3 gene, wherein the siRNA comprises a sense strand and an antisense strand, wherein each nucleotide in the sense strand and the antisense strand is independently a modified nucleotide, wherein the sense strand and antisense strand both comprise a fluoro modified nucleotide and a non-fluoro modified nucleotide; wherein the sense strand comprises a nucleotide sequence I and the antisense strand comprises a nucleotide sequence II, wherein the nucleotide sequence I and the nucleotide sequence II are at least partly reverse complementary to form a double-stranded region, wherein the nucleotide sequence I comprises a nucleotide sequence A, which has the same length as the nucleotide sequence represented by SEQ ID NO: 1 with no more than 3 nucleotide differences, and the nucleotide sequence II comprises a nucleotide sequence B, which has the same length as the nucleotide sequence represented by SEQ ID NO:2 with no more than 3 nucleotide differences:

5'-CAAUAAAGCUGGACAAGAZ-3'; (SEQ ID NO: 1)

5'-Z'UCUUGUCCAGCUUUAUUG-3', (SEQ ID NO: 2)

wherein, Z is A and Z' is U, the nucleotide sequence A comprises a nucleotide $Z_A$ at the corresponding position of Z, the nucleotide sequence B comprises nucleotide $Z'_B$ which is at the corresponding position of Z', wherein $Z'_B$ is the first nucleotide at the 5' terminal of the antisense strand; the fluoro modified nucleotide is present in the nucleotide sequence A and the nucleotide sequence B; and in the direction from 5' terminal to 3' terminal, the nucleotides at positions 7, 8, 9 of the nucleotide sequence A are fluoro modified nucleotides; and in the direction from 5'terminal to 3'terminal, the nucleotides at positions 2, 6, 14 and 16 of the nucleotide sequence B are fluoro modified nucleotides.

In some embodiments, the present disclosure provides use of the modified siRNA, the pharmaceutical composition and/or the siRNA conjugate of the present disclosure in the manufacture of a medicament for treating and/or preventing dyslipidemia caused by overexpression of apolipoprotein C3 (ApoC3)

In some embodiments, the present disclosure provides a method for treating dyslipidemia, which method comprises administering an effective amount of the modified siRNA, the pharmaceutical composition and/or the siRNA conjugate of the present disclosure to a subject suffering from dyslipidemia.

In some embodiments, the present disclosure provides a method for inhibiting the expression of APOC3 gene in hepatocytes, which method comprises contacting an effective amount of the modified siRNA, the pharmaceutical composition and/or the siRNA conjugate of the present disclosure with the hepatocytes.

In some embodiments, the present disclosure provides a kit, which comprises the modified siRNA, the pharmaceutical composition and/or the siRNA conjugate of the present disclosure.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BENEFICIAL EFFECTS

In some embodiments, the siRNA, the composition comprising the siRNA, or the siRNA conjugate of the present disclosure could exhibit higher stability and/or higher activity in vivo. In some embodiments, the siRNA, the composition comprising the siRNA, or the siRNA conjugate of the present disclosure exhibits an in vivo inhibition rate against target gene expression of at least 20%, 30%, 40%, 50%, 60%, 70%, 80%, 90% or 95%. In some embodiments, the siRNA, the composition comprising the siRNA, or the siRNA conjugate of the present disclosure exhibits an in vivo inhibition rate of APOC3 gene expression of at least 20%, 30%, 40%, 50%, 60%, 70%, 80%, 90%, or 95%. In some embodiments, the siRNA, the composition comprising the siRNA or, the siRNA conjugate of the present disclosure exhibits an in vivo inhibition rate of APOC3 gene expression in liver of at least 20%, 30%, 40%, 50%, 60%, 70%, 80%, 90%, or 95%. In some embodiments, the siRNA, the composition comprising the siRNA, or the siRNA conjugate of the present disclosure exhibits an in vivo inhibition rate of APOC3 gene expression in liver in an animal model of at least 20%, 30%, 40%, 50%, 60%, 70%, 80%, 90%, or 95%. In some embodiments, the siRNA, the composition comprising the siRNA, or the siRNA conjugate of the present disclosure exhibits an in vivo inhibition rate of APOC3 gene expression in liver in a human subject of at least 20%, 30%, 40%, 50%, 60%, 70%, 80%, 90%, or 95%. In some embodiments, the siRNA, the composition comprising the siRNA, or the siRNA conjugate of the present disclosure exhibits no significant off-target effect. An off-target effect may be for example inhibition on normal expression of a gene which is not the target gene. It is considered that the off-target effect is not significant if the binding/inhibition of off-target gene expression is at a level of lower than 50%, 40%, 30%, 20%, or 10% of the on-target effect.

In some embodiments, the siRNA conjugate of the present disclosure exhibits excellent performance in inhibiting the expression of APOC3 gene: inhibiting at least 88% of the expression of APOC3 gene in liver of high-fat model mice at a dose of 1 mg/kg. In particular, compared with the conjugates formed from conjugating molecules as provided in the prior art, the modified siRNA and the siRNA conjugate of the present disclosure exhibit excellent gene inhibition rate and low off-target effect. Moreover, the siRNA conjugate of the present disclosure continuously shows excellent effect of inhibiting blood lipid over a period of up to 189 days under the conditions of low dose and frequency of administration.

This indicates that the siRNA, the pharmaceutical composition and the siRNA conjugate of the present disclosure could effectively inhibit the expression of genes of target cells, and thus shows excellent delivery potentials.

Additional features and advantages of the present disclosure will be illustrated in detail in the following part of detailed description of the invention.

BRIEF DESCRIPTION OF THE DRAWINGS

In order to clarify the inventive examples and the technical solutions of the prior art more clearly, a brief introduction is made to the figures that are required to be used in the examples and the prior art in the following text. Obviously, the figures described below represent only some examples of the present invention. In view of these figures, those skilled in the art could obtain other figures without paying inventive labor.

DETAILED DESCRIPTION OF THE INVENTION

Figure 1:
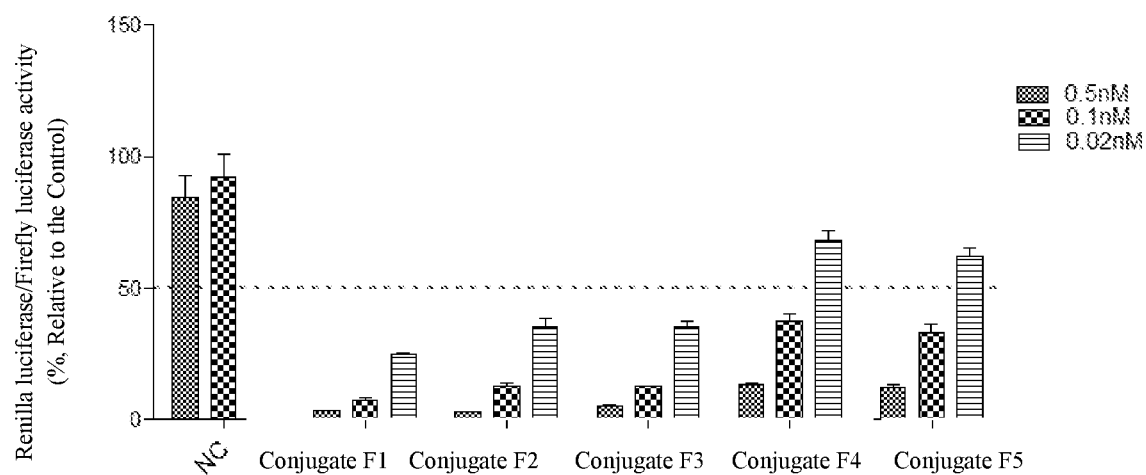
FIG. 1 shows the inhibition activity of conjugates F1-F5 in psiCHECK system in vitro.

The detailed embodiments of the present disclosure are described in detail as below. It should be understood that the detailed embodiments described herein are only used to illustrate and explain the present disclosure and are not intended to limit the present disclosure.

In the present disclosure, APOC3 gene refers to a gene having an mRNA sequence, as shown in Genbank Accession No. NM_000040.1. The target mRNA sequence is shown in Genbank Accession No. NM_000040.1.

Definitions

In the context of the present disclosure, unless otherwise specified, C, G, U, and A represent the base composition of the nucleotides; m represents that the nucleotide adjacent to the left side of the letter m is a methoxy modified nucleotide; f represents that the nucleotide adjacent to the left side of the letter f is a fluoro modified nucleotide; s represents the two nucleotides adjacent to both sides of the letter s are linked by a thiophosphate linkage; P1 represents that the nucleotide adjacent to the right side of P1 is a 5'-phosphate nucleotide or a 5'-phosphate analogue modified nucleotide; VP represents that the nucleotide adjacent to the right side of the monogram VP is a vinyl phosphate modified nucleotide; Ps represents that the nucleotide adjacent to the right side of the monogram Ps is a thiophosphate modified nucleotide; and P represents that the nucleotide adjacent to the right side of the letter P is a 5'-phosphate nucleotide.

In the context of the present disclosure, a "fluoro modified nucleotide" refers to a nucleotide formed by replacing 2'-hydroxy of the ribose group with a fluorine atom. A "non-fluoro modified nucleotide" refers to a nucleotide formed by replacing 2'-hydroxy of the ribose group with a non-fluoro group, or a nucleotide analogue. A "nucleotide analogue" refers to a group that can replace a nucleotide in the nucleic acid, while differs from an adenine ribonucleotide, a guanine ribonucleotide, a cytosine ribonucleotide, a uracil ribonucleotide or thymine deoxyribonucleotide in terms of structure, such as an isonucleotide, a bridged nucleic acid (BNA) nucleotide or a acyclic nucleotide. The "methoxy modified nucleotide" refers to a nucleotide formed by replacing 2'-hydroxy of the ribose group with a methoxy group.

In the context of the present disclosure, expressions "complementary" and "reverse complementary" are interchangeably used herein, and have a meaning well-known in the art, namely, bases in one strand are each paired in complementary with those in another strand in a double-stranded nucleic acid molecule. In DNAs, a purine base adenine (A) is always paired with a pyrimidine base thymine (T) (or a uracil (U) in RNAs); and a purine base guanine (C) is always paired with a pyrimidine base cytosine (G). Each base pair comprises a purine and a pyrimidine. While adenines in a strand are always paired with thymines (or uracils) in another strand, and guanines are always paired with cytosines, these two strands are considered as being complementary with each other; and the sequence of a strand may be deduced from the sequence of its complementary strand. Correspondingly, a "mispairing" means that the bases at corresponding positions are not present in a manner of being complementary paired in a double-stranded nucleic acid.

In the context of the present disclosure, unless otherwise specified, "basically reverse complementary" means that there are no more than 3 base mispairings between two nucleotide sequences. "Substantially reverse complementary" means that there is no more than 1 base mispairing between two nucleotide sequences. "Completely reverse complementary" means that there is no base mispairing between two nucleotide sequences.

In the context of the present disclosure, a "nucleotide difference" between a nucleotide sequence and another nucleotide sequence refers to a change in the type of the nucleotide base at the same position therebetween. For example, in the case that a nucleotide base in the later sequence is A while the nucleotide base at the same position in the former sequence is U, C, G or T, it is considered that a nucleotide difference is present at this position between these two nucleotide sequences. In some embodiments, while a nucleotide at a position is replaced with an abasic nucleotide or a nucleotide analogue, it is also considered that there is a nucleotide difference at the position.

In the context of the present disclosure, particularly in the description of the method for preparing the siRNA, the composition comprising the siRNA, or the siRNA conjugate of the present disclosure, unless otherwise specified, the "nucleoside monomer" refers to, according to the type and sequence of the nucleotides in the siRNA or siRNA conjugate to be prepared, unmodified or modified RNA phosphoramidites used in the solid phase synthesis of phosphoramidites (sometimes the RNA phosphoramidites are referred to as Nucleoside phosphoramidites). Solid phase synthesis of phosphoramidites is a method well known by those skilled in the art to be used in the synthesis of RNA. Nucleoside monomers used in the present disclosure are all commercially available.

In the context of the present disclosure, unless otherwise specified, "conjugating" refers to two or more chemical moieties each having specific function being covalently linked with each other. Correspondingly, "conjugate" refers to a compound formed by covalent linkage of individual chemical moieties. Furthermore, "siRNA conjugate" represents a compound formed by covalently attaching one or more chemical moieties each with specific functions to siRNA. In the following text, the siRNA conjugate of the present disclosure is sometimes abbreviated as "conjugate". According to the context of the present disclosure, the siRNA conjugate should be understood as the general term of siRNA conjugates, the first siRNA conjugate or the second siRNA conjugate. In the context of the present disclosure, "conjugating molecule" should be interpreted as a specific compound capable of being conjugated to a siRNA via reactions, thus finally forming the siRNA conjugate of the present disclosure.

As used herein, a dash ("-") that is not between two letters or symbols is used to indicate the position that is an attachment point for a substituent. For example, —$C_1$-$C_{10}$alkyl-$NH_2$ is attached through the $C_1$-$C_{10}$alkyl.

As used herein, "optional" or "optionally" is meant that the subsequently described event or circumstance may or may not occur, and that the description includes instances wherein the event or circumstance occurs and instances in which it does not. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically infeasible and/or inherently unstable.

As used herein, "alkyl" refers to straight chain and branched chain having the indicated number of carbon atoms, usually from 1 to 20 carbon atoms, for example 1 to 10 carbon atoms, such as 1 to 8 or 1 to 6 carbon atoms. For example $C_1$-$C_6$ alkyl encompasses both straight and branched chain alkyl of from 1 to 6 carbon atoms. When an alkyl residue having a specific number of carbons is named, all branched and straight chain forms having that number of carbons are intended to be encompassed; thus, for example, "butyl" is meant to include n-butyl, sec-butyl, isobutyl and t-butyl; "propyl" includes n-propyl and isopropyl. Alkylene is a subset of alkyl, referring to the same residues as alkyl, but having two attachment points. As used herein, "alkenyl" refers to an unsaturated branched or straight-chain alkyl group having at least one carbon-carbon double bond obtained by respectively removing one hydrogen molecule from two adjacent carbon atoms of the parent alkyl. The group may be in either the cis or trans configuration of the double bond(s). Typical alkenyl groups include, but are not limited to, ethenyl; propenyls such as prop-1-en-1-yl, prop-1-en-2-yl, prop-2-en-1-yl (allyl), prop-2-en-2-yl; butenyls such as but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl; and the like. In certain embodiments, an alkenyl group has from 2 to 20 carbon atoms and in other embodiments, from 2 to 10, 2 to 8, or 2 to 6 carbon atoms. Alkenylene is a subset of alkenyl, referring to the same residues as alkenyl, but having two attachment points.

As used herein, "alkynyl" refers to an unsaturated branched or straight-chain alkyl group having at least one carbon-carbon triple bond obtained by respectively removing two hydrogen molecules from two adjacent carbon atoms of the parent alkyl. Typical alkynyl groups include, but are not limited to, ethynyl; propynyls such as prop-1-yn-1-yl, prop-2-yn-1-yl; butynyls such as but-1-yn-1-yl, but-1-yn-3-yl, but-3-yn-1-yl; and the like. In certain embodiments, an alkynyl group has from 2 to 20 carbon atoms and in other embodiments, from 2 to 10, 2 to 8, or 2 to 6 carbon atoms. Alkynylene is a subset of alkynyl, referring to the same residues as alkynyl, but having two attachment points.

As used herein, "alkoxy" refers to an alkyl group of the indicated number of carbon atoms attached through an oxygen bridge such as, for example, methoxy, ethoxy, propoxy, isopropoxy, n-butoxy, sec-butoxy, tert-butoxy, pentyloxy, 2-pentyloxy, isopentyloxy, neopentyloxy, hexyloxy, 2-hexyloxy, 3-hexyloxy, 3-methylpentyloxy, and the like. Alkoxy groups will usually have from 1 to 10, 1 to 8, 1 to 6, or 1 to 4 carbon atoms attached through oxygen bridge.

As used herein, "aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon, including from 6 to 18 carbon atoms, where at least one ring in the ring system is fully unsaturated, i.e., it contains a cyclic, delocalized (4n+2)π-electron system in accordance with the Hückel theory. Aryl groups include, but are not limited to, groups such as phenyl, fluorenyl, and naphthyl. Arylene is a subset of aryl, referring to the same residues as aryl, but having two attachment points.

As used herein, "cycloalkyl" refers to a non-aromatic carbon ring, usually having from 3 to 7 ring carbon atoms. The ring may be saturated or have one or more carbon-carbon double bonds. Examples of cycloalkyl groups include cyclopropyl, cyclobutyl, cyclopentyl, cyclopentenyl, cyclohexyl, and cyclohexenyl, as well as bridged and caged ring groups such as norbornane.

As used herein, "halo substituent" or "halo" refers to fluoro, chloro, bromo, and iodo, and the term "halogen" includes fluorine, chlorine, bromine, and iodine.

As used herein, "haloalkyl" refers to alkyl as defined above having the specified number of carbon atoms, substituted with 1 or more halogen atoms, up to the maximum allowable number of halogen atoms. Examples of haloalkyl include, but are not limited to, trifluoromethyl, difluoromethyl, 2-fluoroethyl, and penta-fluoroethyl. "Heterocyclyl" refers to a stable 3 to 18 membered non-aromatic ring radical that comprises two to twelve carbon atoms and one to six heteroatoms selected from nitrogen, oxygen or sulfur. Unless stated otherwise specifically in the specification, the heterocyclyl is a monocyclic, bicyclic, tricyclic or tetracyclic ring system, which may include fused or bridged ring system(s). The heteroatom(s) in the heterocyclyl free radical may be optionally oxidized. One or more nitrogen atoms, if present, are optionally quaternized. The heterocyclyl radical is partially or fully saturated. The heterocyclyl may be attached to the rest of the molecule through any atom of the ring(s). Examples of such heterocyclyl include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxapiperazinyl, 2-oxapiperidinyl, 2-oxapyrimidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxathiomorpholinyl, and 1,1-dioxa thiomorpholinyl.

"Heteroaryl" refers to a radical derived from a 3 to 18 membered aromatic ring radical that comprises two to seventeen carbon atoms and one to six heteroatoms selected from nitrogen, oxygen or sulfur. As used herein, the heteroaryl radical may be a monocyclic, bicyclic, tricyclic or tetracyclic ring system, wherein at least one ring in the ring system is fully unsaturated, i.e., it contains a cyclic, delocalized (4n+2)π-electron system in accordance with the Hückel theory. Heteroaryl includes fused or bridged ring system(s). The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryl include, but are not limited to, azepinyl, acridinyl, benzimidazolyl, benzindolyl, 1,3-benzodioxazolyl, benzofuranyl, benzoxazolyl, benzo[d]thiazolyl, benzothiadiazolyl, benzo[b][1,4]dioxazoly, benzo[b][1,4]oxazolyl, 1,4-benzodioxazoyl, benzonaphthofuranyl, benzodiazolyl, benzodioxaphenyl, benzopyranyl, benzopyranonyl, benzofuranyl, benzofuranonyl, benzothienyl, benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro 5H-cyclopenta[4,5]thieno[2,3-d]pyrimidinyl, 5,6-dihydrobenzo[h]quinazolinyl, 5,6 dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10 hexahydrocycloocta[d]pyrimidinyl, 5,6,7,8,9,10-hexahydrocyclohepta[d]pyridazinyl, 5,6,7,8,9,10-hexahydrocycloocta[d]pyridinyl, isothiazolyl, indazolyl, imidazolyl, indolyl, isoindolyl, indolinyl, isoindolinyl, isoquinolyl, indolizinyl, isoxazolyl, 5,8-methano-5,6,7,8-tetrahydroquinazolinyl, naphthyridinonyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta [4,5]thieno[2,3-d]pyrimidinyl, 5,6,7, 8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3c] pridinyl and thienyl.

Various hydroxyl protecting groups may be used in the present disclosure. In general, protecting groups render chemical functionalities inert to specific reaction conditions, and may be appended to and removed from such functionalities in a molecule without substantially damaging the remainder of the molecule. Representative hydroxyl protecting groups are disclosed in Beaucage, et al., Tetrahedron 1992, 48, 2223-2311, and also in Greene and Wuts, Protective Groups in Organic Synthesis, Chapter 2, 2d ed, John Wiley & Sons, New York, 1991, each of which is hereby incorporated by reference in their entirety. In some embodiments, the protecting group is stable under basic conditions but may be removed under acidic conditions. In some embodiments, non-exclusive examples of the hydroxyl protecting groups that may be used herein include dimethoxytrityl (DMT), monomethoxytrityl, 9-phenylxanthen-9-yl (Pixyl) and 9-(p-methoxyphenyl)xanthen-9-yl (Mox). In some embodiments, non-exclusive examples of the hydroxyl protecting groups that may be used herein comprises Tr (trityl), MMTr (4-methoxytrityl), DMTr (4,4'-dimethoxytrityl), and TMTr (4,4',4"-trimethoxytrityl).

The term "subject", as used herein, refers to any animal, e.g., a mammal or marsupial. Subject of The present disclosure includes but are not limited to human, non-human primate (e.g., rhesus or other types of macaques), mouse, pig, horse, donkey, cow, sheep, rat and any kind of poultry.

As used herein, "treatment" or "treating," or "alleviating" or "ameliorating" are used interchangeably herein. These terms refers to an approach for obtaining beneficial or desired results including but not limited to therapeutic benefit. By "therapeutic benefit" is meant eradication or amelioration of the underlying disorder being treated. Also, a therapeutic benefit is achieved by eradicating or ameliorating one or more of the physiological symptoms associated with the underlying disorder such that amelioration is observed in the subject, notwithstanding that the subject may still be afflicted with the underlying disorder.

As used herein, "prevention" and "preventing" are used interchangeably. These terms refer to an approach for obtaining beneficial or desired results including but not limited to a prophylactic benefit. For "prophylactic benefit", the conjugates or compositions may be administered to a subject at risk of developing a particular disease, or to a subject reporting one or more of the physiological symptoms of a disease, even though a diagnosis of this disease may not have been made.

Modified siRNA

The siRNA of the present disclosure comprises nucleotide group as a basic structural unit. It is well known to those skilled in the art that the nucleotide group, in turn, comprises a phosphate group, a ribose group and a base. No more information would be repeated here.

The present disclosure provides a modified siRNA capable of inhibiting the expression of APOC3 gene, wherein the modified siRNA comprises a sense strand and an antisense strand, wherein each nucleotide in the sense strand and the antisense strand is independently a modified nucleotide, wherein the sense strand and antisense strand both comprise a fluoro modified nucleotide and a non-fluoro modified nucleotide; the sense strand comprises a nucleotide sequence I and the antisense strand comprises a nucleotide sequence II, the nucleotide sequence I and the nucleotide sequence II are at least partly reverse complementary to form a double-stranded region, wherein the nucleotide sequence I comprises a nucleotide sequence A, which has the same length as the nucleotide sequence represented by SEQ ID NO: 1 with no more than 3 nucleotide differences, and the nucleotide sequence II comprises a nucleotide sequence B, which has the same length as the nucleotide sequence represented by SEQ ID NO:2 with no more than 3 nucleotide differences:

```
                                        (SEQ ID NO: 1)
        5'-CAAUAAAGCUGGACAAGAZ-3';

(SEQ ID NO: 2)
        5'-Z'UCUUGUCCAGCUUUAUUG-3',
``` wherein, Z is A and Z' is U, the nucleotide sequence A comprises a nucleotide $Z_A$ at the corresponding position of Z, the nucleotide sequence B comprises a nucleotide $Z'_B$ at the corresponding position of Z', wherein $Z'_B$ is the first nucleotide at the 5' terminal of the antisense strand; and the fluoro modified nucleotide is present in the nucleotide sequence A and the nucleotide sequence B; in the direction from 5' terminal to 3' terminal, the nucleotides at positions 7, 8 and 9 of nucleotide sequence A are fluoro modified nucleotides; and in the direction from 5' terminal to 3' terminal, the nucleotides at positions 2, 6, 14 and 16 of nucleotide sequence B are fluoro modified nucleotides. In some embodiments, there is no more than 5 fluoro modified nucleotides present in the nucleotide sequence A; there is no more than 7 fluoro modified nucleotides present in the nucleotide sequence B.

In the context of the present disclosure, "corresponding position" refers to the same position in the nucleotide sequence by counting from the same terminal of the nucleotide sequence. For example, the first nucleotide at the 3' terminal of nucleotide sequence A is a nucleotide at the corresponding position of the first nucleotide at the 3' terminal of SEQ ID NO:1.

In some embodiments, the sense strand comprises only nucleotide sequence I, and the antisense strand comprises only nucleotide sequence II.

In some embodiments, there is no more than 1 nucleotide difference between the nucleotide sequence A and the nucleotide sequence represented by SEQ ID NO: 1, and/or there is no more than 1 nucleotide difference between the nucleotide sequence B and the nucleotide sequence represented by SEQ ID NO:2.

In some embodiments, the nucleotide difference between the nucleotide sequence B and the nucleotide sequence represented by SEQ ID NO:2 includes a difference at the position of $Z'_B$, wherein $Z'_B$ is selected from A, C or G. In some embodiments, the nucleotide difference is a difference at the position of $Z'_B$, wherein $Z'_B$ is selected from A, C or G. In some embodiments, $Z_A$ is a nucleotide complementary to $Z'_B$. These nucleotide differences will not significantly reduce the ability of the siRNA conjugates to inhibit the target gene, and thus these siRNA conjugates comprising the nucleotide differences are within the scope of the present disclosure.

In some embodiments, the nucleotide sequence A is basically reverse complementary, substantially reverse complementary, or completely reverse complementary with the nucleotide sequence B; "basically reverse complementary" means that there is no more than 3 base mispairings between two nucleotide sequences; "substantially reverse complementary" means that there is no more than 1 base mispairing between two nucleotide sequences; "completely reverse complementary" means that there is no mispairing between two nucleotide sequences.

In some embodiments, the nucleotide sequence A is a nucleotide sequence represented by SEQ ID NO:60, and the nucleotide sequence B is a nucleotide sequence represented by SEQ ID NO: 61:

```
                                    (SEQ ID NO: 60)
    5'-CAAUAAAGCUGGACAAGAZ_A-3';

(SEQ ID NO: 61)
    5'-Z'_BUCUUGUCCAGCUUUAUUG-3',
``` wherein, $Z'_B$ is the first nucleotide at the 5' terminal of the antisense strand, $Z_A$ is selected from A, U, G, or C, and $Z'_B$ is a nucleotide complementary to $Z_A$; and in the direction from 5' terminal to 3' terminal, the nucleotides at positions 7, 8 and 9 of the nucleotide sequence A are fluoro modified nucleotides; in the direction from 5' terminal to 3' terminal, the nucleotides at positions 2, 6, 14 and 16 of the nucleotide sequence B are fluoro modified nucleotides.

In some embodiments, the siRNA comprises a sense strand and an antisense strand, wherein the sense strand comprises a nucleotide sequence I and the antisense strand comprises a nucleotide sequence II, the nucleotide sequence I and the nucleotide sequence II are reverse complementary to form a double-stranded region, wherein nucleotide sequence I comprises the nucleotide sequence represented by SEQ ID NO: 60, and the nucleotide sequence II comprises the nucleotide sequence represented by SEQ ID NO:61:

```
                                    (SEQ ID NO: 60)
    5'-CAAUAAAGCUGGACAAGAZ_A-3';

(SEQ ID NO: 61)
    5'-Z'_BUCUUGUCCAGCUUUAUUG-3',
``` wherein, $Z'_B$ is the first nucleotide at the 5' terminal of the antisense strand, $Z_A$ is selected from A, U, G, or C, and $Z'_B$ is a nucleotide complementary to $Z_A$; in some embodiments, $Z_A$ is A, and $Z'_B$ is U;

and in the direction from 5' terminal to 3' terminal, the nucleotides at positions 7, 8 and 9 of SEQ ID NO: 60 in the sense strand of the siRNA are fluoro modified nucleotides, and the nucleotides at the other positions in the sense strand of siRNA are non-fluoro modified nucleotides; and in the direction from 5' terminal to 3' terminal, the nucleotides at positions 2, 6, 14 and 16 of SEQ ID NO:61 in the antisense strand of the siRNA are fluoro modified nucleotides, and the nucleotides at the other positions in the antisense strand of siRNA are non-fluoro modified nucleotides. The sense strand and the antisense strand have the same or different length, wherein the sense strand has a length of 19 to 23 nucleotides, and the antisense strand has a length of 19 to 26 nucleotides. Thus, the sense strand and antisense strand of the siRNA of the present disclosure may have a length ratio of 19/19, 19/20, 19/21, 19/22, 19/23, 19/24, 19/25, 19/26, 20/20, 20/21, 20/22, 20/23, 20/24, 20/25, 20/26, 21/20, 21/21, 21/22, 21/23, 21/24, 21/25, 21/26, 22/20, 22/21, 22/22, 22/23, 22/24, 22/25, 22/26, 23/20, 23/21, 23/22, 23/23, 23/24, 23/25 or 23/26. In some embodiments, the sense strand and the antisense strand of the siRNA have a length ratio of 19/21, 21/23 or 23/25.

In some embodiments, the sense strand and the antisense strand have the same length, wherein the nucleotide sequence I further comprises nucleotide sequence III, the nucleotide sequence II further comprises nucleotide sequence IV, and the nucleotide sequence III and the nucleotide sequence IV each independently have a length of 1 to 4 nucleotides; the nucleotide sequence III is linked to the 5' terminal of the nucleotide sequence A, the nucleotide sequence IV is linked to the 3' terminal of the nucleotide sequence B; and the nucleotide sequence III and the nucleotide sequence IV have the same length.

The nucleotide sequence III and the nucleotide sequence IV may be complementary or non-complementary. In order to enhance the stability of siRNA, in some embodiments, the nucleotide sequence III and the nucleotide sequence IV are at least partially complementary; in some embodiments, the nucleotide sequence III is complementary to more than 80% or 90% of the bases in the nucleotide sequence IV; in some embodiments, the nucleotide sequence III and the nucleotide sequence IV are substantially reverse complementary or completely reverse complementary. "Substantially reverse complementary" means that there is no more than 1 base mispairing between two nucleotide sequences. "Completely reverse complementary" means that there is no pairing between two nucleotide sequences. In some embodiments, the nucleotide sequence III and the nucleotide sequence IV are completely reverse complementary. In this case, the sense strand and the antisense strand of the siRNA have the same length, and have a length ratio of 20/20, 21/21, 22/22 or 23/23. In some embodiments, the sense strand and the antisense strand of the siRNA have a length ratio of 21/21 or 23/23.

In some embodiments, the nucleotide sequence III and the nucleotide sequence IV both have a length of one nucleotide, and the base of the nucleotide sequence III is C, and the base of the nucleotide sequence IV is G; in this case, the length ratio of the sense strand and the antisense strand thereof is 20/20; or, the nucleotide sequence III and the nucleotide sequence IV both have a length of 2 nucleotides, and in the direction from 5' terminal to 3' terminal, the bases of the nucleotide sequence III are sequentially C and C, and the bases of the nucleotide sequence IV are sequentially G and G; in this case, the length ratio of the sense strand and the antisense strand thereof is 21/21; or, the nucleotide sequence III and the nucleotide sequence IV both have a length of 3 nucleotides, and in the direction from 5' terminal to 3' terminal, the bases of the nucleotide sequence III are sequentially U, C and C, and the bases of the nucleotide sequence IV are sequentially G, G and A; in this case, the length ratio of the sense strand and the antisense strand thereof is 22/22; or, the nucleotide sequence III and the nucleotide sequence IV both have a length of 4 nucleotides, and in the direction from 5' terminal to 3' terminal, the bases of the nucleotide sequence III are sequentially C, U, C and C, and the bases of the nucleotide sequence IV are sequentially G, G, A and G; in this case, the length ratio of the sense strand and the antisense strand thereof is 23/23. In some embodiments, the nucleotide sequence III and the nucleotide sequence IV have a length of 2 nucleotides, and in the direction from 5' terminal to 3' terminal, the bases of the nucleotide sequence III are sequentially C and C, and the bases of the nucleotide sequence IV are sequentially G and G; in this case, the length ratio of the sense strand and the antisense strand thereof is 21/21.

In some embodiments, the nucleotide sequence III and the nucleotide sequence IV have the same length, and are completely reverse complementary. Hence, where the base(s) of nucleotide III is(are) provided, the base(s) of nucleotide IV is(are) determined.

In some embodiments, the sense strand and the antisense strand have different lengths. The nucleotide sequence II comprises nucleotide sequence V. The nucleotide sequence V has a length of 1 to 3 nucleotides and is linked to the 3' terminal of the antisense strand, thereby forming a 3' overhang terminal of the antisense strand. In this case, the length ratio of the sense strand and the antisense strand of the siRNA of the present disclosure is 19/20, 19/21, 19/22, 20/21, 20/22, 20/23, 21/22, 21/23, 21/24, 22/23, 22/24, 22/25, 23/24, 23/25 or 23/26. In some embodiments, the nucleotide sequence V has a length of two nucleotides. In this case, the length ratio of the sense strand and the antisense strand of the siRNA of the present disclosure is 19/21, 21/23 or 23/25.

Each nucleotide in the nucleotide sequence V may be any nucleotide. In order to facilitate the synthesis and to save synthesis cost, the nucleotide sequence V is 2 continuous thymine deoxyribonucleotides (TT) or 2 continuous uridine ribonucleotides (UU); in order to enhance the affinity of the antisense strand of the siRNA to the target mRNA, the nucleotide sequence V is complementary to the nucleotides at the corresponding positions of the target mRNA.

In some embodiments, the sense strand comprises nucleotide sequence represented by SEQ ID NO:60, and the antisense strand comprises the nucleotide sequence represented by SEQ ID NO:3:

```
                                       (SEQ ID No: 60)
         5'-CAAUAAAGCUGGACAAGAZ_A-3'

(SEQ ID No: 3)
         5'-Z'_BUCUUGUCCAGCUUUAUUG-3'
``` or, the sense strand comprises nucleotide sequence represented by SEQ ID NO:4, and the antisense strand comprises the nucleotide sequence represented by SEQ ID NO:5:

```
                                       (SEQ ID No: 4)
         5'-CCCAAUAAAGCUGGACAAGAZ_A-3'

(SEQ ID No: 5)
         5'-Z'_BUCUUGUCCAGCUUUAUUGGGAG-3'
``` wherein, $Z'_B$ is the first nucleotide at the 5' terminal of the antisense strand, $Z_A$ is selected from A, U, G or C, and $Z'_B$ is a nucleotide complementary to $Z_A$.

In some embodiments, the siRNA of the present disclosure is siAP1 or siAP2:

```
siAP1
sense strand:
                                       (SEQ ID No: 6)
5'-CAAUAAAGCUGGACAAGAA-3' antisense strand:
                                       (SEQ ID No: 7)
5'-UUCUUGUCCAGCUUUAUUGGG-3' siAP2
sense strand:
                                       (SEQ ID No: 8)
5'-CCCAAUAAAGCUGGACAAGAA-3' antisense strand:
                                       (SEQ ID No: 9)
5'-UUCUUGUCCAGCUUUAUUGGGAG-3'.
```

In some embodiments, in the direction from 5' terminal to 3' terminal, the nucleotides at positions 7, 8 and 9 or at positions 5, 7, 8 and 9 of the nucleotide sequence A in the sense strand are fluoro modified nucleotides, and the nucleotides at the other positions in the sense strand are non-fluoro modified nucleotides; in the direction from 5' terminal to 3' terminal, the nucleotides at positions 2, 6, 14 and 16 or at positions 2, 6, 8, 9, 14 and 16 of the nucleotide sequence B in the antisense strand are fluoro modified nucleotides, and the nucleotides at the other positions in the antisense strand are non-fluoro modified nucleotides.

Fluoro modified nucleotide refers to a nucleotide formed by replacing 2'-hydroxy of the ribose group with fluoro, and has the structures represented by the following Formula (107). A non-fluoro modified nucleotide refers to a nucleotide formed by replacing 2'-hydroxy of the ribose group with a non-fluoro group, or a nucleotide analogue. In some embodiments, each non-fluoro modified nucleotide is independently selected from a nucleotide formed by replacing 2'-hydroxy of the ribose group thereof with a non-fluoro group, or a nucleotide analogue.

A nucleotide formed by replacing 2'-hydroxy of the ribose group with a non-fluoro group is well-known in the art, such as one selected from the group consisting of 2'-alkoxy modified nucleotides, 2'-substituted alkoxy modified nucleotides, 2'-alkyl modified nucleotides, 2'-substituted alkyl modified nucleotides, 2'-amino modified nucleotides, 2'-substituted amino modified nucleotides and 2'-deoxy nucleotides. In some embodiments, the 2'-alkoxy modified nucleotide is a methoxy modified nucleotide (2'-OMe), represented by Formula (108). In some embodiments, the 2'-substituted alkoxy modified nucleotide is for example a 2'-O-methoxyethyl modified nucleotide (2'-MOE), represented by Formula (109). In some embodiments, the 2'-amino modified nucleotide (2'-NH$_2$) is represented by Formula (110). In some embodiments, the 2'-deoxy nucleotide (DNA) is represented by Formula (111).

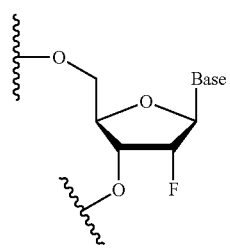

Formula (107)

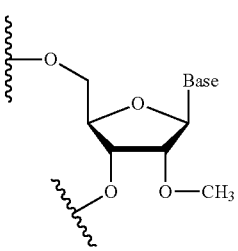

Formula (108)

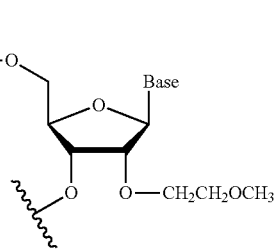

Formula (109)

Formula (110)

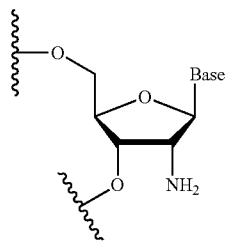

Formula (111)

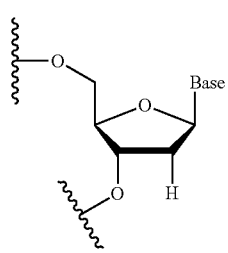

A nucleotide analogue refers to a group that can replace a nucleotide in the nucleic acid, while differs from an adenine ribonucleotide, a guanine ribonucleotide, a cytosine ribonucleotide, a uracil ribonucleotide or thymine deoxyribonucleotide in terms of structure. In some embodiments, the nucleotide analogue may be an isonucleotide, a bridged nucleic acid (BNA) nucleotide or an acyclic nucleotide.

A BNA nucleotide is a nucleotide that is constrained or inaccessible. BNA can contain a 5-, 6-membered or even a 7-membered ring bridged structure with a "fixed" C3'-endo sugar puckering. The bridge is typically incorporated at the 2'- and 4'-position of the ribose to afford a 2', 4'-BNA nucleotide. In some embodiments, BNA may be LNA, ENA and cET BNA which is represented by Formulae (112), (113) and (114), respectively.

Formula (112)

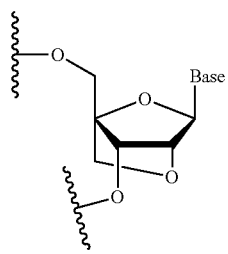

Formula (113)

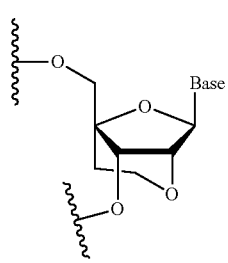

Formula (114)

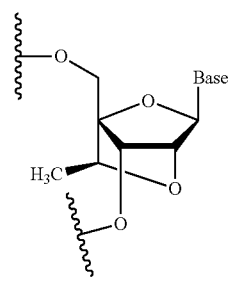

An acyclic nucleotide is a category of nucleotides in which the ribose ring is opened. In some embodiments, the acrylic nucleotide is an unlocked nucleic acid (UNA) and a glycerol nucleic acid (GNA), which are represented by Formulae (115) and (116), respectively.

Formula (115)

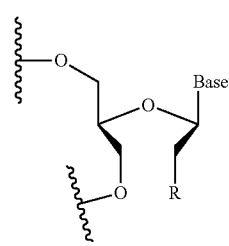

Formula (116)

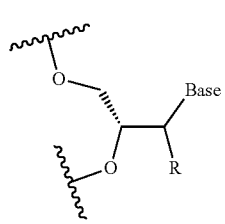

In the above Formulae (115) and (116), R is selected from H, OH or alkoxy (O-alkyl). An isonucleotide is a compound in which the position of the base on the ribose ring in the nucleotide is changed. In some embodiments, the isonucleotide is a compound formed by transposing the base from position-1' to position-2' or position-3' on the ribose ring, as represented by Formula (117) or (118), respectively.

Formula (117)

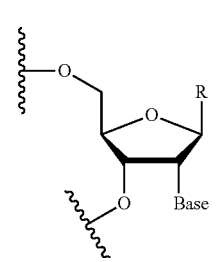

-continued

Formula (118)

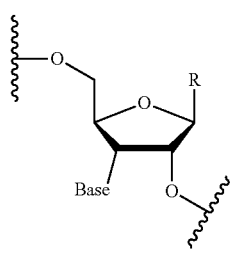

In the compounds of formulae (117)-(118), "Base" represents a base, such as A, U, G, C or T; R is selected from H, OH, F or a non-fluoro group described above.

In some embodiments, a nucleotide analogue is one selected from isonucleotide, LNA, ENA, cET, UNA or GNA. In some embodiments, each non-fluoro modified nucleotide is a methoxy modified nucleotide. In the context of the present disclosure, the methoxy modified nucleotide refers to a nucleotide formed by replacing 2'-hydroxy of the ribose group with a methoxy group.

In the context of the disclosure, a "fluoro modified nucleotide", a "2'-fluoro modified nucleotide", a "nucleotide in which 2'-hydroxy of a ribose group is replaced with fluoro" and a "2'-fluororibosyl" have the same meaning, referring to a compound in which 2'-hydroxy of the nucleotide is replaced with fluoro, having a structure represented by Formula (107). A "methoxy modified nucleotide", a "2'-methoxy modified nucleotide", a "nucleotide in which 2'-hydroxy of a ribose group is replaced with methoxy" and a "2'-methoxyribosyl" have the same meaning, referring to a compound in which 2'-hydroxy of the ribose group in the nucleotide is replaced with methoxy, having a structure represented by Formula (108).

In some embodiments, the siRNA of the present disclosure is a siRNA with the following modifications: in the direction from 5' terminal to 3' terminal, the nucleotides at positions 7, 8 and 9 or at positions 5, 7, 8 and 9 of the nucleotide sequence A in the sense strand are fluoro modified nucleotides, and the nucleotides at the other positions in the sense strand are methoxy modified nucleotides; the nucleotides at positions 2, 6, 14 and 16 or at positions 2, 6, 8, 9, 14 and 16 of the nucleotide sequence B in the antisense strand are fluoro modified nucleotides, and the nucleotides at the other positions in the antisense strand are methoxy modified nucleotides.

In some embodiments, the siRNA of the present disclosure is a siRNA with the following modifications: in the direction from 5' terminal to 3' terminal, the nucleotides at positions 5, 7, 8 and 9 of the nucleotide sequence A in the sense strand of the siRNA are fluoro modified nucleotides, and the nucleotides at the other positions of the sense strand of the siRNA are methoxy modified nucleotides; and in the direction from 5' terminal to 3' terminal, the nucleotides at positions 2, 6, 8, 9, 14 and 16 of the nucleotide sequence B in the antisense strand of the siRNA are fluoro modified nucleotides, and the nucleotides at the other positions in the antisense strand are methoxy modified nucleotides;

or, in the direction from 5' terminal to 3' terminal, the nucleotides at positions 7, 8 and 9 of the nucleotide sequence A in the sense strand of the siRNA are fluoro modified nucleotides, and the nucleotides at the other positions in the sense strand of the siRNA are methoxy modified nucleotides; and in the direction from 5' terminal to 3' terminal, the nucleotides at positions 2, 6, 14 and 16 of the nucleotide sequence B in the antisense strand of the siRNA are fluoro modified nucleotides, and the nucleotides at the other positions in the antisense strand of the siRNA are methoxy modified nucleotides.

In other words, the ribose groups in phosphate-ribose backbone of the siRNA respectively have the following modifying groups: in the direction from 5' terminal to 3' terminal, the ribose groups at positions 5, 7, 8 and 9 of the nucleotide sequence A in the sense strand of the siRNA is 2'-fluororibosyl, and the ribose groups of the nucleotides at the other positions in the sense strand of the siRNA is 2'-methoxyribosyl; and in the direction from 5' terminal to 3' terminal, the ribose groups at positions 2, 6, 8, 9, 14 and 16 of the nucleotide sequence B in the antisense strand of the siRNA is 2'-fluororibosyl, and the ribose groups of the nucleotides at the other positions in the antisense strand of the siRNA is 2'-methoxyribosyl; or, in the direction from 5' terminal to 3' terminal, the ribose groups at positions 7, 8 and 9 of the nucleotide sequence A in the sense strand of the siRNA is 2'-fluororibosyl, and the ribose groups of the nucleotides at the other positions in the sense strand of the siRNA is 2'-methoxyribosyl; and in the direction from 5' terminal to 3' terminal, the ribose groups at positions 2, 6, 14 and 16 of the nucleotide sequence B in the antisense strand of the siRNA is 2'-fluororibosyl, and the ribose groups of the nucleotides at the other positions in the antisense strand of the siRNA is 2'-methoxyribosyl.

In some embodiments, the siRNA molecule is any one selected from siAP1-M1, siAP2-M1, siAP1-M2, or siAP2-M2:

siAP1-M1
sense strand:
(SEQ ID NO: 10)
5'-CmAmAmUmAfAmAfGfCfUmGmGmAmCmAmAmGmAmAm-3' antisense strand:
(SEQ ID NO: 11)
5'-UmUfCmUmUmGfUmCfCfAmGmCmUmUfUmAfUmUmGmGmGm-3' siAP2-M1
sense strand:
(SEQ ID NO: 12)
5'-CmCmCmAmAmUmAfAmAfGfCfUmGmGmAmCmAmAmGmAmAm-3' antisense strand:
(SEQ ID NO: 13)
5'-UmUfCmUmUmGfUmCfCfAmGmCmUmUfUmAfUmUmGmGmGmAmGm-3' siAP1-M2
sense strand:
(SEQ ID NO: 14)
5'-CmAmAmUmAmAmAfGfCfUmGmGmAmCmAmAmGmAmAm-3' antisense strand:
(SEQ ID NO: 15)
5'-UmUfCmUmUmGfUmCmCmAmGmCmUmUfUmAfUmUmGmGmGm-3' siAP2-M2
sense strand:
(SEQ ID NO: 16)
5'-CmCmCmAmAmUmAmAmAfGfCfUmGmGmAmCmAmAmGmAmAm-3' antisense strand:
(SEQ ID NO: 17)
5'-UmUfCmUmUmGfUmCmCmAmGmCmUmUfUmAfUmUmGmGmGmAmGm-3'.

In some embodiments, at least a portion of the phosphoester groups in phosphate-ribose backbone of at least one single strand in the sense strand and the antisense strand of the siRNA of the present disclosure is phosphoester group(s) with modified group(s). In some embodiments, the phosphoester group with modified group(s) is a phosphorothioate groups formed by replacing at least one oxygen atom in a phosphodiester bond in the phosphate groups with a sulfur atom. In some embodiments, the phosphoester group with modified group(s) is a phosphorothioate group having a structure represented by Formula (101):

Formula (101)

This modification stabilizes the double-strand structure of the siRNA and maintains high specificity and high affinity for base pairing.

In some embodiments, in the siRNA of the present disclosure, a phosphorothioate linkage is present at at least one position selected from the group consisting of the following positions: the position between the first and the second nucleotides at either terminal of the sense or antisense strand, the position between the second and the third nucleotides at either terminal of the sense strand or antisense strand, or any combination thereof. In some embodiments, a phosphorothioate linkage is present at all the above positions except for 5' terminal of the sense strand. In some embodiments, a phosphorothioate linkage is present at all the above positions except for 3' terminal of the sense strand. In some embodiments, a phosphorothioate linkage is present at at least one of the following positions:

the position between the first and second nucleotides at 5' terminal of the sense strand;
the position between the second and third nucleotides at 5' terminal of the sense strand;
the position between the first and second nucleotides at 3' terminal of the sense strand;
the position between the second and third nucleotides at 3' terminal of the sense strand;
the position between the first and second nucleotides at 5' terminal of the antisense strand;
the position between the second and third nucleotides at 5' terminal of the antisense strand;
the position between the first and second nucleotides at 3' terminal of the antisense strand; and
the position between the second and third nucleotides at 3' terminal of the antisense strand.

In some embodiments, the siRNA is any one of siAP1-M1S, siAP2-M1S, siAP1-M2S, and siAP2-M2S:

siAP1-M1S
sense strand:
(SEQ ID NO: 18)
5'-CmsAmsAmUmAfAmAfGfCfUmGmGmAmCmAmAmGmAmAm-3' anti sense strand:
(SEQ ID NO: 19)
5'-UmsUfsCmUmUmGfUmCfCfAmGmCmUmUfUmAfUmUmGmsGmsGm-3' siAP2-M1S
sense strand:
(SEQ ID NO: 20)
5'-CmsCmsCmAmAmUmAfAmAfGfCfUmGmGmAmCmAmAmGmAmAm-3' antisense strand:
(SEQ ID NO: 21)
5'-UmsUfsCmUmUmGfUmCfCfAmGmCmUmUfUmAfUmUmGmGms AmsGm-3' siAP1-M2S
sense strand:
(SEQ ID NO: 22)
5'-CmsAmsAmUmAmAmAfGfCfUmGmGmAmCmAmAmGmAmAm-3' antisense strand:
(SEQ ID NO: 23)
5'-UmsUfsCmUmUmGfUmCmCmAmGmCmUmUfUmAfUmUmGmsGmsGm-3' siAP2-M2S
sense strand:
(SEQ ID NO: 24)
5'-CmsCmsCmAmAmUmAmAmAfGfCfUmGmGmAmCmAmAmGmAmAm-3' antisense strand:
(SEQ ID NO: 25)
5'-UmsUfsCmUmUmGfUmCmCmAmGmCmUmUfUmAfUmUmGmGmsAmsGm-3'.

In some embodiments, the nucleotide at 5' terminal of the antisense strand of the siRNA is a 5'-phosphate nucleotide or a 5'-phosphate analogue modified nucleotide. Common 5'-phosphate nucleotides or the 5'-phosphate analogue modified nucleotides are well known to those skilled in the art, for example, 5'-phosphate nucleotide may have the following structure:

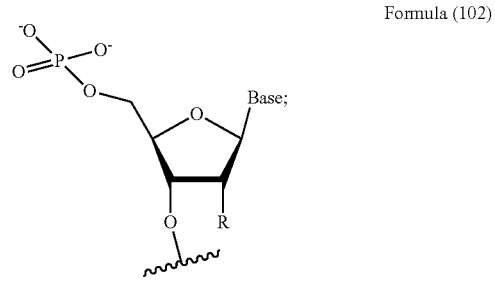

Formula (102)

as another example, the following four 5'-phosphate analogue modified nucleotides are disclosed in Anastasia Khvorova and Jonathan K. Watts, The chemical evolution of oligonucleotide therapies of clinical utility. Nature Biotechnology, 2017, 35(3): 238-48:

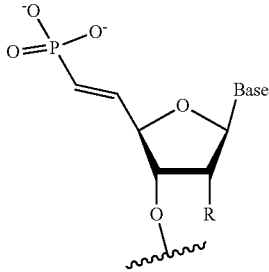

Formula (103)

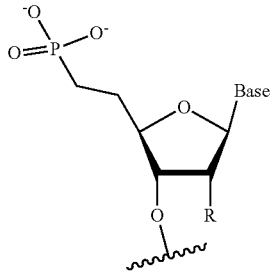

Formula (104)

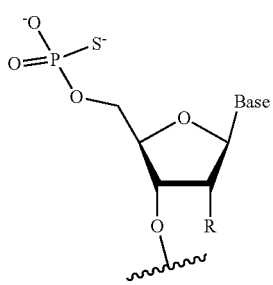

Formula (105)

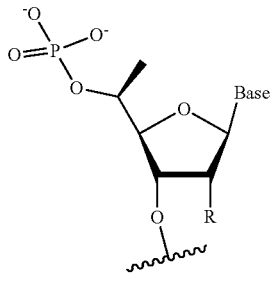

Formula (106)

wherein, R represents a group selected from the group consisting of H, OH, methoxy, and F; "Base" represents a base selected from A, U, C, G, or T.

In some embodiments, 5'-phosphate nucleotide is 5'-phosphate modified nucleotide represented by Formula (102), the 5'-phosphate analogue modified nucleotide is a nucleotide modified with a vinyl phosphate (5'-(E)-vinylphosphonate, E-VP) as represented by Formula (103), or phosphorothioate modified nucleotide represented by Formula (105).

In some embodiments, the siRNA of the present disclosure is any one of siAP1-M1P1, siAP2-M1P1, siAP1-M2P1, siAP2-M2P1, siAP1-M1SP1, siAP2-M1SP1, siAP1-M2SP1, and siAP2-M2SP1:

siAP1-M1P1
sense strand:
(SEQ ID NO: 10)
5'-CmAmAmUmAfAmAfGfCfUmGmGmAmCmAmAmGmAmAm-3' antisense strand:
(SEQ ID NO: 26)
5'-P1-UmUfCmUmUmGfUmCfCfAmGmCmUmUfUmAfUmUmGmGmGm-3' siAP2-M1P1
sense strand:
(SEQ ID NO: 12)
5'-CmCmCmAmAmUmAfAmAfGfCfUmGmGmAmCmAmAmGmAmAm-3' antisense strand:
(SEQ ID NO: 27)
5'-P1-UmUfCmUmUmGfUmCfCfAmGmCmUmUfUmAfUmUmGmGmGmAm
Gm-3' siAP1-M2P1
sense strand:
(SEQ ID NO: 14)
5'-CmAmAmUmAmAmAfGfCfUmGmGmAmCmAmAmGmAmAm-3' antisense strand:
(SEQ ID NO: 28)
5'-P1-UmUfCmUmUmGfUmCmCmAmGmCmUmUfUmAfUmUmGmGmGm-3' siAP2-M2P1
sense strand:
(SEQ ID NO: 16)
5'-CmCmCmAmAmUmAmAmAfGfCfUmGmGmAmCmAmAmGmAmAm-3' antisense strand:
(SEQ ID NO: 29)
5'-P1-UmUfCmUmUmGfUmCmCmAmGmCmUmUfUmAfUmUmGmGmGm
AmGm-3' siAP1-M1SP1
sense strand:
(SEQ ID NO: 18)
5'-CmsAmsAmUmAfAmAfGfCfUmGmGmAmCmAmAmGmAmAm-3' antisense strand:
(SEQ ID NO: 30)
5'-P1-UmsUfsCmUmUmGfUmCfCfAmGmCmUmUfUmAfUmUmGmsGms
Gm-3' siAP2-M1SP1
sense strand:
(SEQ ID NO: 20)
5'-CmsCmsCmAmAmUmAfAmAfGfCfUmGmGmAmCmAmAmGmAmAm-3' antisense strand:
(SEQ ID NO: 31)
5'-P1-UmsUfsCmUmUmGfUmCfCfAmGmCmUmUfUmAfUmUmGmGmGms
AmsGm-3' siAP1-M2SP1
sense strand:
(SEQ ID NO: 22)
5'-CmsAmsAmUmAmAmAfGfCfUmGmGmAmCmAmAmGmAmAm-3' antisense strand:
(SEQ ID NO: 32)
5'-P1-UmsUfsCmUmUmGfUmCmCmAmGmCmUmUfUmAfUmUmGms
GmsGm-3' siAP2-M2SP1
sense strand:
(SEQ ID NO: 24)
5'-CmsCmsCmAmAmUmAmAmAfGfCfUmGmGmAmCmAmAmGmAmAm-3' antisense strand:
(SEQ ID NO: 33)
5'-P1-UmsUfsCmUmUmGfUmCmCmAmGmCmUmUfUmAfUmUmGmGmGms
AmsGm-3'.

The inventors of the present disclosure have unexpectedly discovered that the siRNA of the present disclosure not only have significantly enhanced stability in plasma and lysosome, and reduced off-target effect, but also maintain very high activity of suppressing gene.

The siRNAs of the present disclosure may be obtained by conventional processes for preparing nucleic acid in the art, such as solid phase synthesis process and liquid phase synthesis process. Among them, commercial customized services have already been available for solid phase synthesis. A modified nucleotide group can be introduced into the siRNA of the present disclosure by using the nucleoside monomer with corresponding modification. The process for preparing the nucleotide monomer with corresponding modification and the process for introducing the modified nucleotide group into the siRNA are also well known to those skilled in the art.

Pharmaceutical Composition

The present disclosure provides a pharmaceutical composition comprising the modified siRNA described above as an active ingredient and a pharmaceutically acceptable carrier.

The pharmaceutically acceptable carrier may be a carrier conventionally used in the field of siRNA administration, for example, but not limited to, one or more of magnetic nanoparticles, such as $Fe_3O_4$ or $Fe_2O_3$-based nanoparticles, carbon nanotubes, mesoporous silicon, calcium phosphate nanoparticles, polyethylenimine (PEI), polyamidoamine (PAMAM) dendrimer, poly(L-lysine) (PLL), chitosan, 1,2-dioleoyl-3-trimethylammonium-propane (DOTAP), poly(D&L-lactic/glycolic acid)copolymer (PLGA), poly(2-aminoethyl ethylene phosphate) (PPEEA), and poly(2-dimethylaminoethyl methacrylate) (PDMAEMA), and derivatives thereof. In some embodiments, in the pharmaceutical composition, there are no special requirements for the contents of the siRNA and the pharmaceutically acceptable carrier. In some embodiments, the weight ratio of the siRNA and the pharmaceutically acceptable carrier is 1: (1-500). In some embodiments, the weight ratio is 1: (1-50).

In some embodiments, the pharmaceutical composition further contains other pharmaceutically acceptable excipients, which may be one or more of various formulations or compounds conventionally employed in the art. For example, said other pharmaceutically acceptable excipients may include at least one of a pH buffer, a protective agent and an osmotic pressure regulator.

The pH buffer may be tris(hydroxymethyl) aminomethane hydrochloride buffer solution with a pH of 7.5-8.5, and/or phosphate buffer solution with a pH of 5.5-8.5, for example phosphate buffer solution with a pH of 5.5-8.5.

The protective agent may be at least one of inositol, sorbitol, sucrose, trehalose, mannose, maltose, lactose and glucose. The content of the protective agent may be from 0.01 wt % to 30 wt % on the basis of the total weight of the pharmaceutical composition.

The osmotic pressure regulator may be sodium chloride and/or potassium chloride. The content of the osmotic pressure regulator allows the osmotic pressure of the pharmaceutical composition to be 200-700 mOsm/kg. Depending on the desired osmotic pressure, those skilled in the art can readily determine the content of the osmotic pressure regulator.

In some embodiments, the pharmaceutical composition may be a liquid formulation, for example, an injection solution; or a lyophilized powder for injection, which is mixed with a liquid excipient to form a liquid formulation upon administration. The liquid formulation may be administered by, but is not limited to, subcutaneous, intramuscular or intravenous injection, and also may be administrated to, but is not limited to, lung by spray, or to other organ tissues (such as liver) via lung by spray. In some embodiments, the pharmaceutical composition is administered by intravenous injection.

In some embodiments, the pharmaceutical composition may be in the form of a liposome formulation. In some embodiments, the pharmaceutically acceptable carrier used in the liposome formulation comprises an amine-containing transfection compound (hereinafter also referred to as an amine-containing compound), a helper lipid and/or a PEGylated lipid. Among others, the organic amine, the helper lipid and the PEGylated lipid may be respectively selected from one or more of the amine-containing transfection compounds or pharmaceutically acceptable salts or derivatives thereof, the helper lipids and the PEGylated lipids described in CN103380113A, which is incorporated herein by reference in its entirety.

In some embodiments, the organic amine is a compound represented by Formula (201) or a pharmaceutically acceptable salt thereof described in CN103380113A:

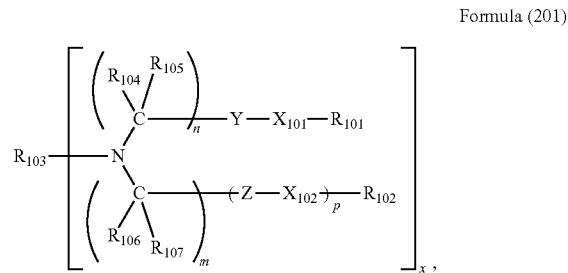

Formula (201)

wherein:

each of $X_{101}$ and $X_{102}$ is independently selected from O, S, N-A or C-A, wherein A is hydrogen or a $C_1$-$C_{20}$ hydrocarbon chain;

each of Y and Z is independently selected from C=O, C=S, S=O, CH—OH or $SO_2$; each of $R_{101}$, $R_{102}$, $R_{103}$, $R_{104}$, $R_{105}$, $R_{106}$ and $R_{107}$ is independently selected from hydrogen; a cyclic or an acyclic, substituted or unsubstituted, branched or linear aliphatic group; a cyclic or an acyclic, substituted or unsubstituted, branched or linear heteroaliphatic group; a substituted or unsubstituted, branched or linear acyl group; a substituted or unsubstituted, branched or linear aryl group; a substituted or unsubstituted, branched or linear heteroaryl group;

x is an integer of 1-10;

n is an integer of 1-3, m is an integer of 0-20, p is an integer of 0 or 1; wherein if m=p=0, then $R_{102}$ is hydrogen;

and if at least one of n or m is 2, then $R_{103}$ and nitrogen in Formula (201) form a structure as represented by Formula (202) or Formula (203):

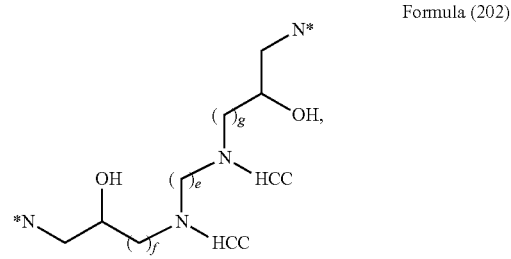

Formula (202)

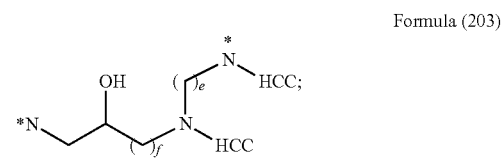

Formula (203)

wherein, each of g, e and f is independently an integer of 1-6, "HCC" represents a hydrocarbon chain, and each *N represents nitrogen atom in Formula (201).

In some embodiments, $R_{103}$ is polyamine. In other embodiments, $R_{103}$ is ketal. In some embodiments, each of $R_{101}$ and $R_{102}$ in Formula (201) is independently any substituted or unsubstituted, branched or linear alkyl or alkenyl, wherein the alkyl or alkenyl has 3 to about 20 carbon atoms, such as 8 to about 18 carbon atoms, and 0 to 4 double bonds, such as 0 to 2 double bonds.

In some embodiments, if each of n and m is independently a value of 1 or 3, $R_{103}$ may be any one of the following formulae (204) to (213):

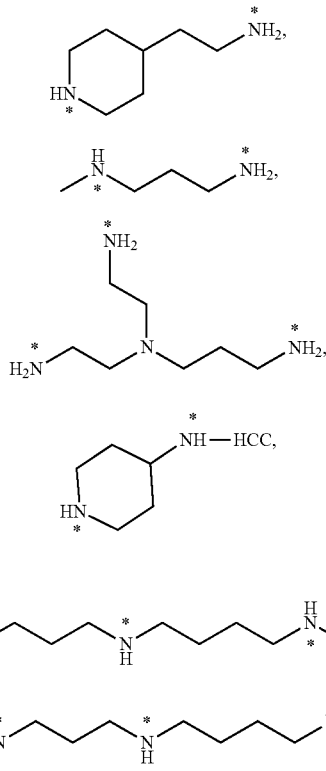

Formula(204)

formula(205)

Formula(206)

Formula(207)

Formula (208)

Formula (209)

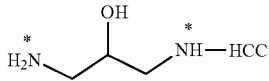

Formula(210)

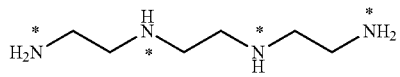

Formula (211)

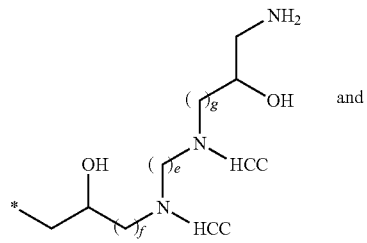

Formula (212)

and

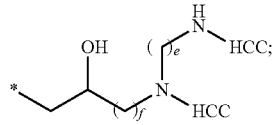

Formula (213)

wherein, in formulae (204) to (213), each of g, e and f is independently an integer of 1-6, each "HCC" represents a hydrocarbon chain, and each * represents a possible attachment point of $R_{103}$ to the nitrogen atom in Formula (201), wherein each H at any * position may be replaced to achieve the attachment to the nitrogen atom in Formula (201).

The compound represented by Formula (201) may be prepared according to the description of CN103380113A.

In some embodiments, the organic amine is the organic amine represented by Formula (214) and/or the organic amine represented by Formula (215):

Formula (214)
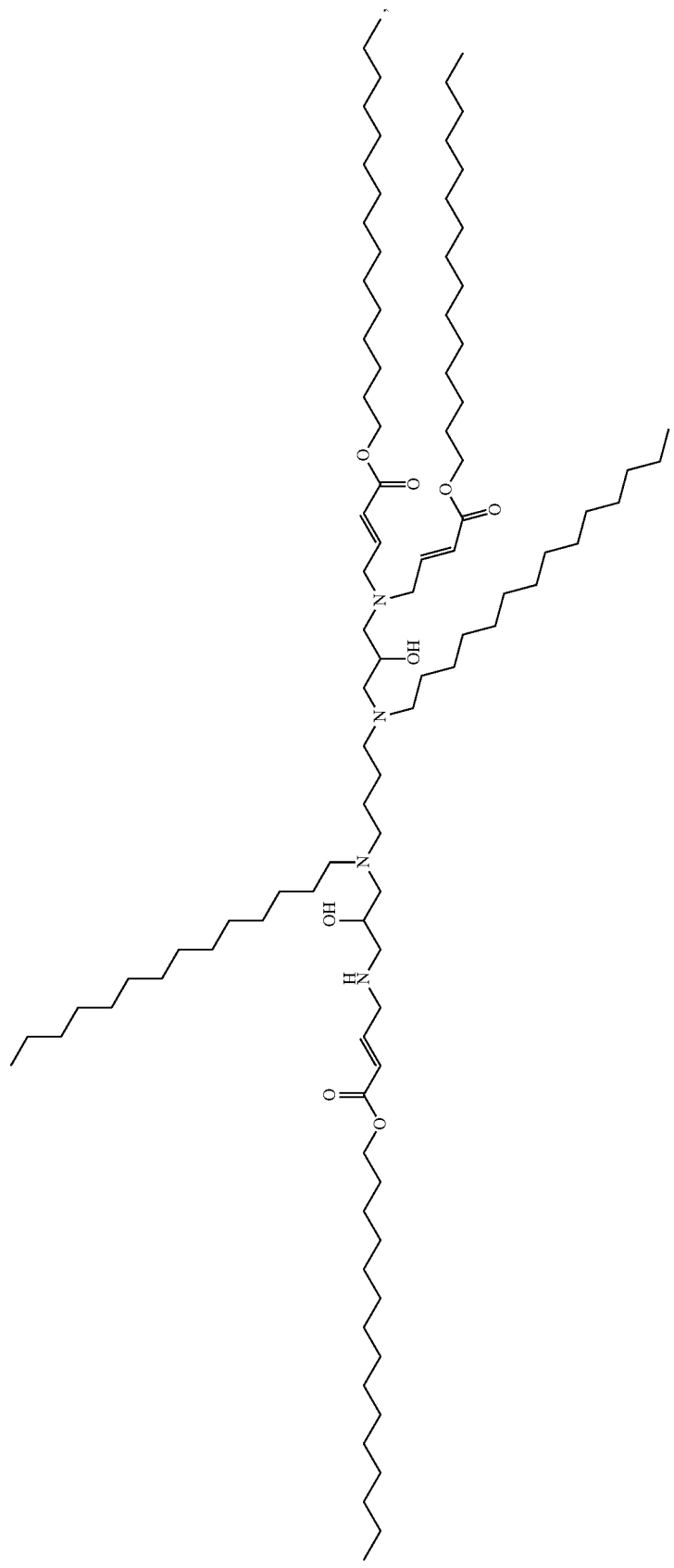

-continued
Formula (215)
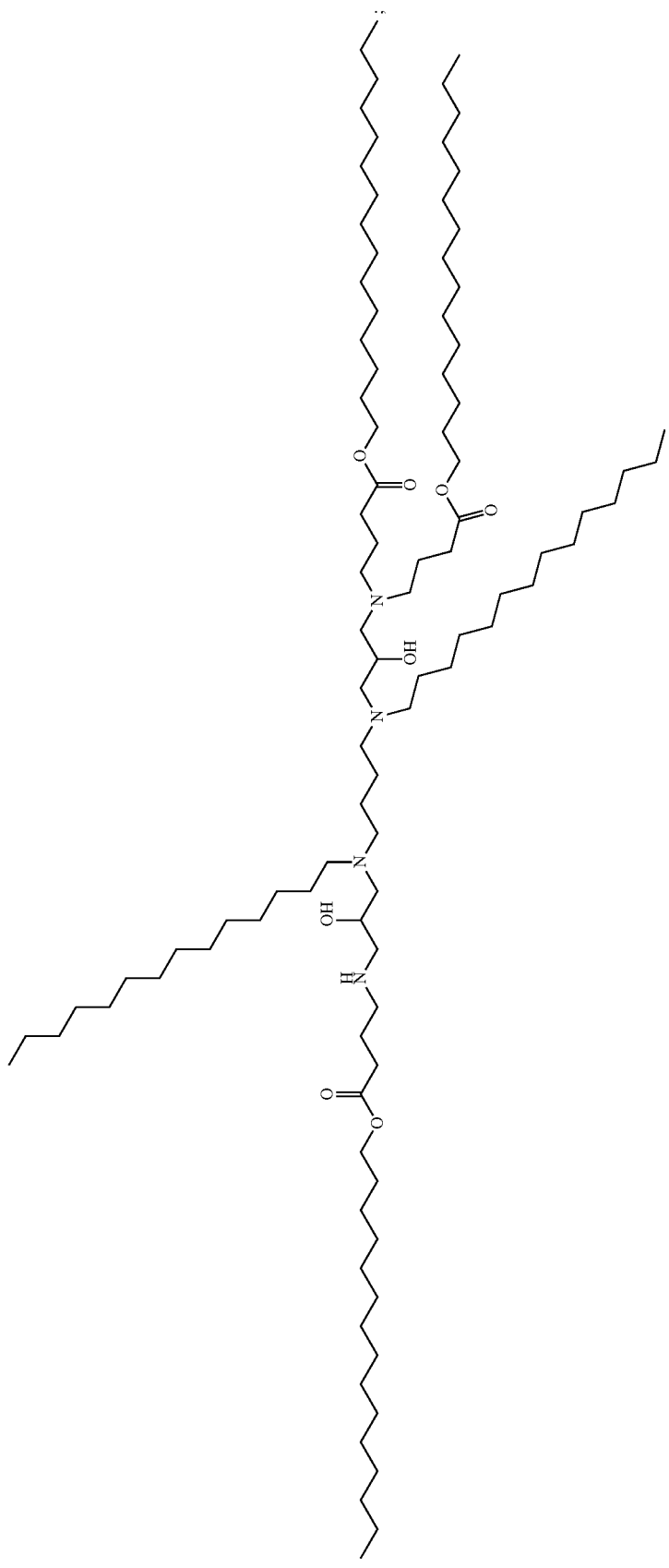

the helper lipid is cholesterol, cholesterol analogues and/or cholesterol derivatives;

the PEGylated lipid is 1,2-dipalmitoyl-sn-glycero-3-phosphatidylethanolamine-N-[methoxy(polyethylene glycol)-2000].

In some embodiments, the molar ratio of the organic amine, the helper lipid and the PEGylated lipid in the pharmaceutical compositions is (19.7-80): (19.7-80): (0.3-50), for example (50-70): (20-40): (3-20).

In some embodiments, the particles of the pharmaceutical composition formed by the siRNA of the present disclosure and the above amine-containing transfection agent have an average diameter from about 30 nm to about 200 nm, typically from about 40 nm to about 135 nm, and more typically, the average diameter of the liposome particles is from about 50 nm to about 120 nm, from about 50 nm to about 100 nm, from about 60 nm to about 90 nm, or from about 70 nm to about 90 nm, for example, the average diameter of the liposome particles is about 30, 40, 50, 60, 70, 75, 80, 85, 90, 100, 110, 120, 130, 140, 150 or 160 nm.

In some embodiments, in the pharmaceutical composition formed by the siRNA of the present disclosure and the above amine-containing transfection agent, the weight ratio (weight/weight ratio) of the siRNA to total lipids, e.g., the organic amines, the helper lipids and/or the PEGylated lipids, ranges from about 1:1 to about 1:50, from about 1:1 to about 1:30, from about 1:3 to about 1:20, from about 1:4 to about 1:18, from about 1:5 to about 1:17, from about 1:5 to about 1:15, from about 1:5 to about 1:12, from about 1:6 to about 1:12, or from about 1:6 to about 1:10, for example, the weight ratio of the siRNA of the present disclosure to total lipids is about 1:5, 1:6, 1:7, 1:8, 1:9, 1:10, 1:11, 1:12, 1:13, 1:14, 1:15, 1:16, 1:17 or 1:18.

In some embodiments, the pharmaceutical compositions may be marketed with each component being separate, and used in the form of liquid formulation. In some embodiments, the pharmaceutical composition formed by the siRNA of the present disclosure and the above pharmaceutically acceptable carrier may be prepared according to various known processes, except replacing the existing siRNA with the siRNA of the present disclosure. In some embodiments, it may be prepared according to the following process:

the organic amines, the helper lipids and the PEGylated lipids in the molar ratio as described above are suspended in alcohol and mixed uniformly to afford a lipid solution; the alcohol is used in such an amount that the afforded lipid solution has a total mass concentration of 2 to 25 mg/mL, for example, 8 to 18 mg/mL. The alcohol is selected from a pharmaceutically acceptable alcohol, for example an alcohol that is in liquid form at about room temperature, such as one or more of ethanol, propylene glycol, benzyl alcohol, glycerol, polyethylene glycol 200, polyethylene glycol 300, and polyethylene glycol 400, e.g. ethanol.

The siRNA of the present disclosure is dissolved in a buffer salt solution to produce a siRNA aqueous solution. The buffer salt solution is in a concentration of 0.05 to 0.5 M, for example 0.1 to 0.2 M. The pH of the buffer salt solution is adjusted to 4.0 to 5.5, for example 5.0 to 5.2. The buffer salt solution is used in an amount to make the concentration of siRNA no more than 0.6 mg/ml, for example 0.2 to 0.4 mg/mL. The buffer salt solution may be one or more selected from the group consisting of soluble acetate and soluble citrate, for example sodium acetate and/or potassium acetate.

The lipid solution and the siRNA aqueous solution are mixed. The obtained mixture is incubated at a temperature of 40 to 60° C. for at least 2 minutes, for example 5 to 30 minutes, to produce a incubated liposome formulation. The lipid solution and the aqueous solution of the siRNA is in a volume ratio of 1: (2-5), for example 1:4.

The incubated liposome formulation is concentrated or diluted, and then subjected to impurity removal and sterilization to obtain the pharmaceutical composition of the present disclosure, of which the physical and chemical parameters are as follows: a pH of 6.5 to 8, an encapsulation percentage of not lower than 80%, a particle size of 40 to 200 nm, a polydispersity index of no greater than 0.30, and an osmotic pressure of 250 to 400 mOsm/kg; for example, the physical and chemical parameters may be as follows: a pH of 7.2 to 7.6, an encapsulation percentage of not lower than 90%, a particle size of 60 to 100 nm, a polydispersity index of no greater than 0.20, and an osmotic pressure of 300 to 400 mOsm/kg.

In particular, concentration or dilution may be performed before, after or simultaneously with the step of removing impurities. The methods for removing impurities may be various existing methods, for example, ultrafiltration under 100K Da using a hollow fiber column, a phosphate buffer (PBS) at pH 7.4 as ultrafiltration exchange solution, and a cross flow system. The methods for sterilization may be various existing methods, such as filtration sterilization on a 0.22 μm filter.

First siRNA Conjugate

The present disclosure provides a siRNA conjugate, this first siRNA conjugate comprises the siRNA and a conjugating group linked to the siRNA by conjugation. Generally speaking, the conjugating group comprises at least one pharmaceutically acceptable targeting group and an optional linker. Moreover, the siRNA, the linker and the targeting group are sequentially linked. In some embodiments, the number of the targeting group is 1 to 6. In some embodiments, the number of target groups is 2 to 4. The siRNA molecule may be non-covalently or covalently conjugated to the conjugating group, for example the siRNA molecule may be covalently conjugated to the conjugating group. The conjugating site between the siRNA and the conjugating group can be at the 3' terminal or 5' terminal of the sense strand of the siRNA, or at the 5' terminal of the antisense strand, and can be within the internal sequence of the siRNA. In some embodiments, the conjugating site between the siRNA and the conjugating group is at the 3' terminal of the sense strand of the siRNA.

In some embodiments, the conjugating group may be linked to a phosphate group, 2'-hydroxy or a base in the nucleotide. In some embodiments, the conjugating group may be linked to 3'-hydroxyl when the nucleotides are linked via 2'-5' phosphoramidite bond. Where the conjugating group is linked to a terminal of the siRNA strand, the conjugating group is usually linked to a phosphate group of the nucleotide. Where the conjugating group is linked to an internal sequence of the siRNA, the conjugating group is usually linked to a ribose ring or a base. For various linking manners, reference shall be made to the document: Muthiah Manoharan et. al. siRNA conjugates carrying sequentially assembled trivalent N-acetylgalactosamine linked through nucleosides elicit robust gene silencing in vivo in hepatocytes. ACS Chemical biology, 2015, 10 (5): 1181-7.

In some embodiments, the siRNA and the conjugating group may be linked through acid-unstable or reducible chemical bonds, and these chemical bonds may be degraded under acidic environment of cell inclusions, thereby rendering the siRNA to be in free state. With respect to undegradable conjugating manner, the conjugating group may be linked to the sense strand of siRNA, thereby reducing the influence of conjugation on the siRNA activity as low as possible.

In some embodiments, the pharmaceutically acceptable targeting group may be a ligand conventionally used in the field of siRNA administration, for example, all the ligands described in WO 2009082607A2, which is incorporated herein by reference in its entirety.

In some embodiments, the pharmaceutically acceptable targeting group may be selected from one or more of the ligands formed by the following targeting molecules or derivatives thereof: lipophilic molecules, such as cholesterol, bile acids, vitamins such as vitamin E, lipid molecules of different chain lengths; polymers, such as polyethylene glycol; polypeptides, such as cell-penetrating peptide; aptamers; antibodies; quantum dots; saccharides, such as lactose, polylactose, mannose, galactose, N-acetylgalactosamine (GalNAc); folate; or receptor ligands expressed in hepatic parenchymal cells, such as asialoglycoprotein, asialo-sugar residue, lipoproteins (such as high density lipoprotein, low density lipoprotein and the like), glucagon, neurotransmitters (such as adrenaline), growth factors, transferrin and the like.

In some embodiments, each ligand is independently selected from a ligand capable of binding to a cell surface receptor. In some embodiments, at least one ligand is a ligand capable of binding to a receptor on the surface of a hepatocyte. In some embodiments, at least one ligand is a ligand capable of binding to a surface receptor on the surface of a mammalian cell. In some embodiments, at least one ligand is a ligand capable of binding to a surface receptor on the surface of a human hepatocyte. In some embodiments, at least one ligand is a ligand capable of binding to an asialoglycoprotein receptor (ASGPR) on the surface of liver. The kinds of these ligands are well-known to those skilled in the art, and they generally serve the function of binding to specific receptor on the surface of the target cells, thereby mediating the delivery of the siRNA linked to the ligands into target cells.

In some embodiments, the pharmaceutically acceptable targeting group may be any ligand that binds to the ASGPR on the surface of mammalian hepatocytes. In some embodiments, each ligand is independently an asialoglycoprotein, such as asialoorosomucoid (ASOR) or asialofetuin (ASF). In some embodiments, the ligand is a saccharide or derivatives thereof.

In some embodiments, at least one ligand is a saccharide. In some embodiments, each ligand is a saccharide. In some embodiments, at least one ligand is a monosaccharide, polysaccharide, modified saccharide, modified polysaccharide or saccharide derivatives. In some embodiments, at least one ligand is a monosaccharide, disaccharide or trisaccharide. In some embodiments, at least one ligand is a modified saccharide. In some embodiments, each ligand is a modified saccharide. In some embodiments, each ligand is independently selected from polysaccharides, modified polysaccharides, monosaccharides, modified monosaccharides, polysaccharide derivatives or monosaccharide derivatives. In some embodiments, each or at least one ligand is selected from a group consisting of glucose and its derivatives, mannose and its derivatives, galactose and its derivatives, xylose and its derivatives, ribose and its derivatives, fucose and its derivatives, lactose and its derivatives, maltose and its derivatives, arabinose and its derivatives, fructose and its derivatives, and sialic acid. In some embodiments, each ligand may be independently selected from the group consisting of D-mannopyranose, L-mannopyranose, D-arabinose, D-xylofuranose, L-xylofuranose, D-glucose, L-glucose, D-galactose, L-galactose, α-D-mannofuranose, β-D-mannofuranose, α-D-mannopyranose, β-D-mannopyranose, α-D-glucopyranose, β-D-glucopyranose, α-D-glucofuranose, β-D-glucofuranose, α-D-fructofuranose, α-D-fructopyranose, α-D-galactopyranose, β-D-galactopyranose, α-D-galactofuranose, β-D-galactofuranose, glucosamine, sialic acid, galactosamine, N-acetylgalactosamine, N-trifluoroacetylgalactosamine, N-propionylgalactosamine, N-n-butyrylgalactosamine, N-isobutyrylgalactosamine, 2-amino-3-O—[(R)-1-carboxyethyl]-2-deoxy-β-D-glucopyranose, 2-deoxy-2-methylamino-L-glucopyranose, 4,6-dideoxy-4-formamido-2,3-di-O-methyl-D-mannopyranose, 2-deoxy-2-sulfoamino-D-glucopyranose, N-glycolyl-α-neuraminic acid, 5-thio-β-D-glucopyranose, methyl 2,3,4-tris-O-acetyl-1-thio-6-O-trityl-α-D-glucopyranoside, 4-thio-β-D-galactopyranose, ethyl 3,4,6,7-tetra-O-acetyl-2-deoxy-1,5-dithio-α-D-glucoheptopyranoside, 2,5-anhydro-D-allononitrile, ribose, D-ribose, D-4-thioribose, L-ribose, and L-4-thioribose. Other selections of the ligand may be found, for example, in the disclosure of CN105378082A, which is incorporated herein by reference in its entirety.

In some embodiments, the pharmaceutically acceptable targeting group in the first siRNA conjugate may be galactose or N-acetylgalactosamine, which may be of monovalence, divalence, trivalence or tetravalence. It should be understood that the monovalence, divalence, trivalence and tetravalence mean that the molar ratio of the siRNA molecule to the galactose or N-acetylgalactosamine in the siRNA conjugate is 1:1, 1:2, 1:3 or 1:4, wherein the siRNA conjugate is formed from the siRNA molecule and the conjugating group containing galactose or N-acetylgalactosamine molecule as the targeting group. In some embodiments, the pharmaceutically acceptable targeting group is N-acetylgalactosamine. In some embodiments, where the siRNA of the present disclosure is conjugated to the conjugating group containing N-acetylgalactosamine, the N-acetylgalactosamine molecule is of trivalence or tetravalence. In some embodiments, where the siRNA of the present disclosure is conjugated to the conjugating group containing N-acetylgalactosamine, the N-acetylgalactosamine molecule is of trivalence.

The targeting group may be linked to the siRNA molecule via an appropriate linker.

Those skilled in the art could select appropriate linkers according to the specific kind of the targeting group. These linkers, the kind of the targeting group and the manner of linking to siRNA may be referred to the contents disclosed in WO 2015006740A2, which is incorporated herein by reference in its entirety.

In some embodiments, where the targeting group is N-acetylgalactosamine, the appropriate linker has the structure represented by Formula (301):

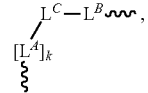

Formula (301)

wherein, k is an integer of 1-3;

$L^A$ is an amide bond-comprising chain moiety having the structure represented by Formula (302), each $L^A$ is respectively linked to a targeting group and the $L^C$ moiety through an ether bond at its two terminals;

Formula (302)

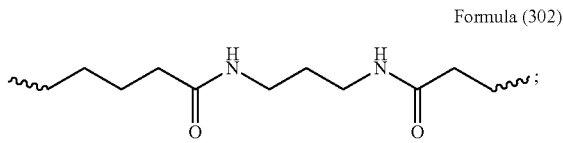

$L^B$ is an N-acylpyrrolidine-comprising chain moiety having the structure represented by Formula (303), wherein the chain moiety has a carbonyl at its one terminal and is linked to the $L^C$ moiety through an amide bond, and has an oxy group at the other terminal and is linked to the siRNA through a phosphoester bond;

Formula (303)

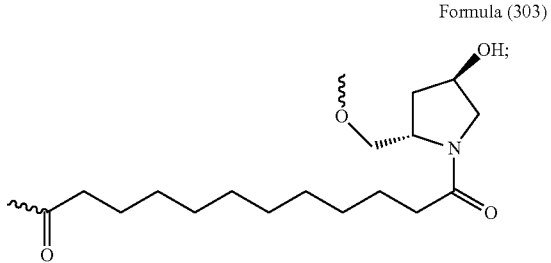

$L^C$ is a bivalent to tetravalent linking group based on hydroxymethyl aminomethane, dihydroxymethyl aminomethane or trihydroxymethyl aminomethane, and is linked to each $L^A$ moiety through ether bond via oxygen atom, and is linked to the $L^B$ moiety through amide bond via nitrogen atom.

Formula (304)

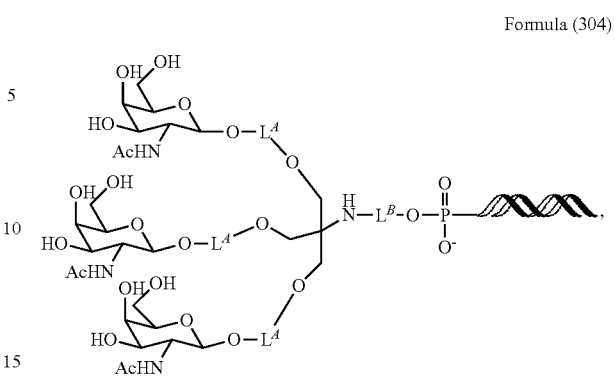

wherein the double helix structure represents a siRNA.

Likewise, the conjugating site between the siRNA and the conjugating group can be at the 3' terminal or 5'-terminal of the sense strand of the siRNA, or at the 5' terminal of the antisense strand, or within the internal sequence of the siRNA.

In some embodiments, the 3' terminal of the sense strand of the siRNA of the present disclosure is covalently conjugated to three N-acetylgalactosamine (GalNAc) molecules via a linker —$(L^A)_3$-trihydroxymethyl aminomethane-$L^B$— to afford a first siRNA conjugate in which the molar ratio of the siRNA molecule to the GalNAc molecule is 1:3 (hereinafter this siRNA conjugate may be referred to as (GalNAc)$_3$-siRNA), and this siRNA conjugate has the structure represented by Formula (305):

Formula (305)

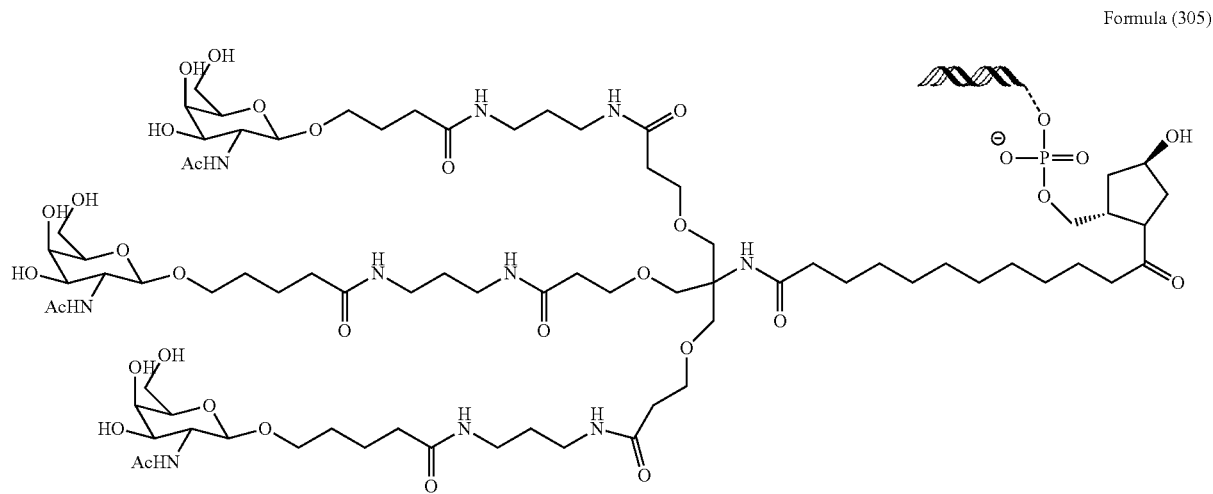

wherein, the double helix structure represents a siRNA, and the linker is linked to the 3' terminal of the sense strand of the siRNA.

In some embodiments, when n=3 and $L^C$ is a tetravalent linking group based on trihydroxymethyl aminomethane, the siRNA conjugate formed by linking N-acetylgalactosamine molecule(s) with a siRNA molecule via —$(L^A)_3$-trihydroxymethyl aminomethane-$L^B$— as a linker has the structure as represented by Formula (304):

In some embodiments, when the targeting group is N-acetylgalactosamine, the appropriate linker has the structure represented by Formula (306):

Formula (306)

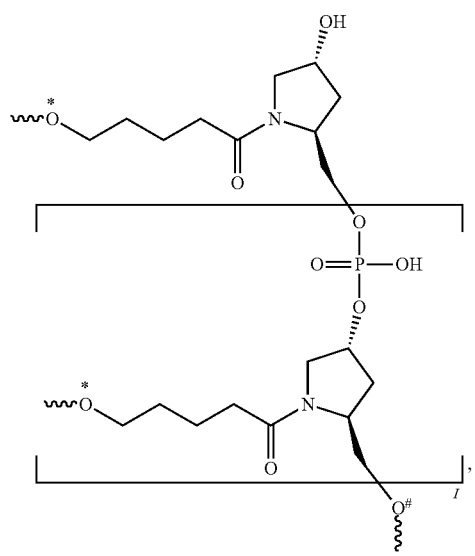

wherein,
l is an integer of 0-3;
* represents the site on the linker where the targeting group is linked through ether bond; and
represents the site on the linker where the siRNA is linked through phosphoester bond.

In some embodiments, when l=2, the first siRNA conjugate has the structure represented by Formula (307):

Formula (307)

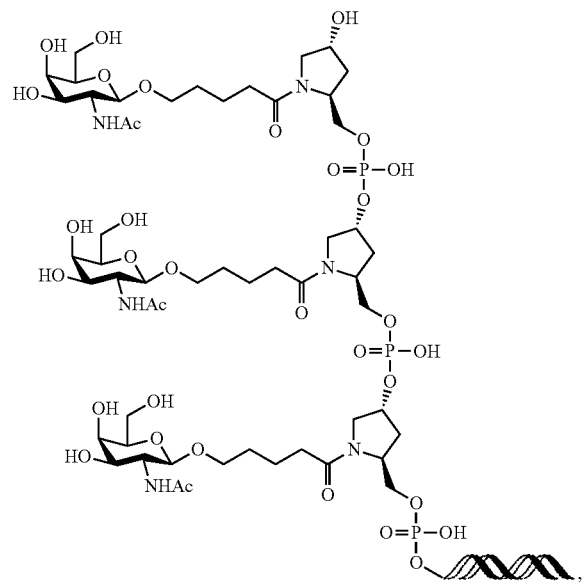

wherein the double helix structure represents a siRNA, and the linker is linked to the 3' terminal of the sense strand of the siRNA.

The above mentioned conjugate may be synthesized by the process that has been described in detail in the prior art. For example, WO2015006740A2 describes in detail the process for preparing various conjugates. The first siRNA conjugate of the present disclosure may be obtained by the process well-known to those skilled in the art. For example, WO 2014025805A1 discloses the process for preparing the structure represented by Formula (305). Rajeev et al. in ChemBioChem 2015, 16, 903-908 describes the process for preparing the structure represented by Formula (307).

Second siRNA Conjugate

In some embodiments, the present disclosure provides a second siRNA conjugate, the second siRNA conjugate has the structure represented by Formula (1):

Formula (1)

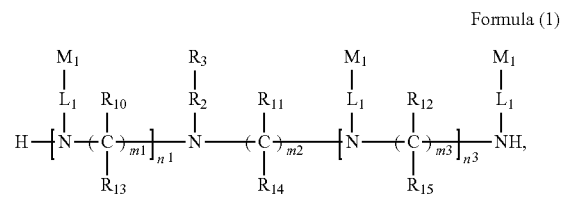

wherein,
n1 is an integer of 1-3, and n3 is an integer of 0-4;
each of m1, m2, and m3 is independently an integer of 2-10;
each of $R_{10}$, $R_{11}$, $R_{12}$, $R_{13}$, $R_{14}$ and $R_{15}$ is independently H, or selected from the group consisting of $C_1$-$C_{10}$ alkyl, $C_1$-$C_{10}$ haloalkyl, and $C_1$-$C_{10}$ alkoxy;
$R_3$ is a group having the structure represented by Formula A59:

(A59)

wherein $E_1$ is OH, SH or $BH_2$, and Nu is a siRNA;
in the siRNA represented by Nu, each nucleotide is independently a modified or unmodified nucleotide; the siRNA represented by Nu comprises a sense strand and an antisense strand; the sense strand comprises a nucleotide sequence 1, and the antisense strand comprises a nucleotide sequence 2; said nucleotide sequence 1 and nucleotide sequence 2 are at least partly reverse complementary to form a double-stranded region, wherein the nucleotide sequence 1 has the same length as the nucleotide sequence represented by SEQ ID NO: 1 with no more than 3 nucleotide differences, and the nucleotide sequence 2 has the same length as the nucleotide sequence represented by SEQ ID NO:2 with no more than 3 nucleotide differences:

(SEQ ID NO: 1)
5'-CAAUAAAGCUGGACAAGAZ-3';

(SEQ ID NO: 2)
5'-Z'UCUUGUCCAGCUUUAUUG-3';

wherein, Z is A and Z' is U, and
the nucleotide sequence 1 comprises a nucleotide $Z_A$ at the corresponding position of Z, the nucleotide sequence 2 comprises a nucleotide $Z'_B$ at the corresponding position of Z', wherein $Z'_B$ is the first nucleotide at 5' terminal of the antisense strand; in the context of the present disclosure, "corresponding position" refers to the same position in the nucleotide sequence by counting from the same terminal of the nucleotide sequence. For example, the first nucleotide at the 3' terminal of nucleotide sequence 1 is a nucleotide at the corresponding position of the first nucleotide at the 3' terminal of SEQ ID NO:1.

$R_2$ is a linear alkylene of 1 to 20 carbon atoms in length, wherein one or more carbon atoms are optionally replaced with one or more groups selected from the group consisting of: C(O), NH, O, S, CH=N, S(O)$_2$, $C_2$-$C_{10}$ alkeylene, $C_2$-$C_{10}$ alkynylene, $C_6$-$C_{10}$ arylene, $C_3$-$C_{18}$ heterocyclylene, and $C_5$-$C_{10}$ heteroarylene, and wherein $R_2$ is optionally substituted by any one or more groups selected from the group consisting of: $C_1$-$C_{10}$ alkyl, $C_6$-$C_{10}$ aryl, $C_5$-$C_{10}$ heteroaryl, $C_1$-$C_{10}$ haloalkyl, —O$C_1$-$C_{10}$ alkyl, alkylphenyl, —$C_1$-$C_{10}$ alkyl-OH, haloalkyl, —S$C_1$-$C_{10}$ alkyl, alkylphenyl, —$C_1$-$C_{10}$ alkyl-SH, haloalkyl, halo, —OH, —SH, —NH$_2$, alkyl-NH$_2$, —N($C_1$-$C_{10}$ alkyl)($C_1$-$C_{10}$ alkyl), —NH($C_1$-$C_{10}$ alkyl), cyano, nitro, —CO$_2$H, —C(O)O($C_1$-$C_{10}$ alkyl), —CON($C_1$-$C_{10}$ alkyl)($C_1$-$C_{10}$ alkyl), —CONH($C_1$-$C_{10}$ alkyl), —CONH$_2$, —NHC(O)($C_1$-$C_{10}$ alkyl), —NHC(O)(phenyl), —N($C_1$-$C_{10}$ alkyl)C(O)($C_1$-$C_{10}$ alkyl), —N($C_1$-$C_{10}$ alkyl)C(O)(phenyl), —C(O)$C_1$-$C_{10}$ alkyl, —C(O)$C_1$-$C_{10}$ alkylphenyl, —C(O)$C_1$-$C_{10}$ haloalkyl, —OC(O)$C_1$-$C_{10}$ alkyl, —SO$_2$($C_1$-$C_{10}$ alkyl), —SO$_2$(phenyl), —SO$_2$($C_1$-$C_{10}$ haloalkyl), —SO$_2$NH$_2$, —SO$_2$NH($C_1$-$C_{10}$ alkyl), —SO$_2$NH(phenyl), —NHSO$_2$($C_1$-$C_{10}$ alkyl), —NHSO$_2$(phenyl), and —NHSO$_2$($C_1$-$C_{10}$ haloalkyl);

each $L_1$ is a linear alkylene having a length of 1 to 70 carbon atoms, wherein one or more carbon atoms are optionally replaced with one or more groups selected from the group consisting of: C(O), NH, O, S, CH=N, S(O)$_2$, $C_2$-$C_{10}$ alkeylene, $C_2$-$C_{10}$ alkynylene, $C_6$-$C_{10}$ arylene, $C_3$-$C_{18}$ heterocyclylene, and $C_5$-$C_{10}$ heteroarylene, and wherein $L_1$ is optionally substituted by any one or more groups selected from the group consisting of: $C_1$-$C_{10}$ alkyl, $C_6$-$C_{10}$ aryl, $C_5$-$C_{10}$ heteroaryl, $C_1$-$C_{10}$ haloalkyl, —O$C_1$-$C_{10}$ alkyl, —O$C_1$-$C_{10}$ alkylphenyl, —$C_1$-$C_{10}$ alkyl-OH, —O$C_1$-$C_{10}$ haloalkyl, —S$C_1$-$C_{10}$ alkyl, —S$C_1$-$C_{10}$ alkylphenyl, alkyl-SH, —S$C_1$-$C_{10}$ haloalkyl, halo, —OH, —SH, —NH$_2$, —$C_1$-$C_{10}$ alkyl-NH$_2$, —N($C_1$-$C_{10}$ alkyl)($C_1$-$C_{10}$ alkyl), —NH($C_1$-$C_{10}$ alkyl), cyano, nitro, —CO$_2$H, —C(O)O($C_1$-$C_{10}$ alkyl), —CON($C_1$-$C_{10}$ alkyl)($C_1$-$C_{10}$ alkyl), —CONH($C_1$-$C_{10}$ alkyl), —CONH$_2$, —NHC(O)($C_1$-$C_{10}$ alkyl), —NHC(O)(phenyl), alkyl)C(O)($C_1$-$C_{10}$ alkyl), —N($C_1$-$C_{10}$ alkyl)C(O)(phenyl), —C(O)$C_1$-$C_{10}$ alkyl, —C(O)$C_1$-$C_{10}$ alkylphenyl, —C(O)$C_1$-$C_{10}$ haloalkyl, —OC(O)$C_1$-$C_{10}$ alkyl, —SO$_2$($C_1$-$C_{10}$ alkyl), —SO$_2$(phenyl), —SO$_2$($C_1$-$C_{10}$ haloalkyl), —SO$_2$NH$_2$, —SO$_2$NH($C_1$-$C_{10}$ alkyl), —SO$_2$NH(phenyl), —NHSO$_2$($C_1$-$C_{10}$ alkyl), —NHSO$_2$(phenyl), and —NHSO$_2$($C_1$-$C_{10}$ haloalkyl).

In some embodiments, $L_1$ may be selected from the group consisting of groups A1-A26 and any combination thereof, wherein the groups A1-A26 have the following structures and definitions:

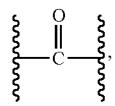
(A1)

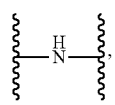
(A2)

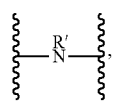
(A3)

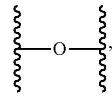
(A4)

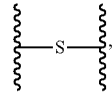
(A5)

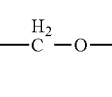
(A6)

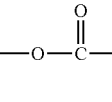
(A7)

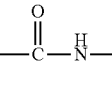
(A8)

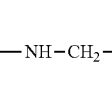
(A9)

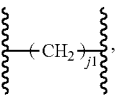
(A10)

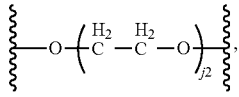
(A11)

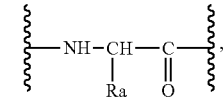
(A12)

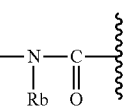
(A13)

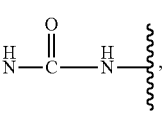
(A14)

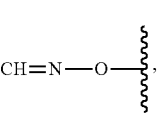
(A15)

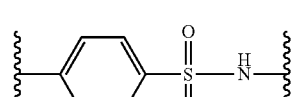
(A16)

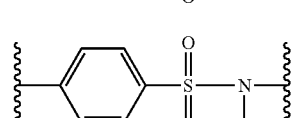
(A17)

wherein, j1 is an integer of 1-20; j2 is an integer of 1-20; R' is a $C_1$-$C_{10}$ alkyl;

Ra is selected from the group consisting of groups of Formulae A27-A45 and any combination thereof:

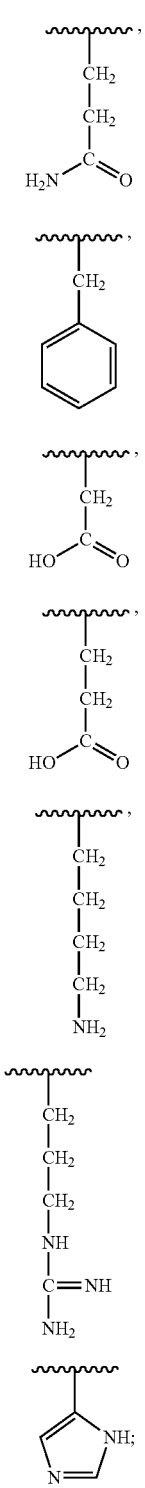

Rb is a $C_1$-$C_{10}$ alkyl; and

⌇⌇⌇ represents a site where a group is attached to the rest of the molecule.

Those skilled in the art would understand that, though $L_1$ is defined as a linear alkyl for convenience, it may not be a linear group or be named differently, such as an amine or alkenyl as a result of the above replacement and/or substitution. For the purpose of the present disclosure, the length of $L_1$ is the atom number in the chain connecting the two attachment points. For this purpose, a ring resulted from replacement of a carbon atom of the linear alkylene, such as a heterocyclylene or heteroarylene, is counted as one atom.

$M_1$ represents a targeting group, of which the definitions and options are the same as the above-mentioned targeting groups. In some embodiments, each $M_1$ is independently selected from one of the ligands that have affinity to the asialoglycoprotein receptor on the surface of mammalian hepatocytes.

When $M_1$ is a ligand having affinity to the asialoglycoprotein receptor on the surface of mammalian hepatocytes, in some embodiments, n1 may be an integer of 1-3, and n3 may be an integer of 0-4 to ensure that there are at least two $M_1$ targeting groups in the conjugate. In some embodiments, n1+n3≥2, so that the number of the $M_1$ targeting groups may be at least 3, thereby allowing the $M_1$ targeting group to more conveniently bind to the asialoglycoprotein receptor on the surface of liver, which may facilitate the endocytosis of the conjugate into cells. Experiments have shown that when the number of the $M_1$ targeting groups is greater than 3, the feasibility of binding the M1 targeting groups to the asialoglycoprotein receptor on the surface of liver is not significantly increased. Therefore, in view of various aspects such as the synthesis convenience, structure/process costs and delivery efficiency, in some embodiments, n1 is an integer of 1-2, n3 is an integer of 0-1, and n1+n3=2-3. In some embodiments, when m1, m2, and m3 are each independently selected from an integer of 2-10, the steric position among a plurality of the $M_1$ targeting groups may be fit for binding the $M_1$ targeting groups to the asialoglycoprotein receptor on the surface of liver. In order to make the conjugate of the present disclosure have simpler structure, easier synthesis and/or reduced cost, in some embodiments, m1, m2 and m3 are each independently an integer of 2-5, in some embodiments, m1=m2=m3. It may be understood by those skilled in the art that when each of $R_{10}$, $R_{11}$, $R_{12}$, $R_{13}$, $R_{14}$, and $R_{15}$ is independently one selected from H, $C_1$-$C_{10}$ alkyl, $C_1$-$C_{10}$ haloalkyl, or $C_1$-$C_{10}$ alkoxy, the purpose of the present disclosure may be achieved without changing the properties of the conjugates of the present disclosure. In some embodiments, $R_{10}$, $R_{11}$, $R_{12}$, $R_{13}$, $R_{14}$, and $R_{15}$ are each independently selected from H, methyl or ethyl. In some embodiments, $R_{10}$, $R_{11}$, $R_{12}$, $R_{13}$, $R_{14}$, and $R_{15}$ are all H. $R_3$ is a group having the structure represented by Formula A59, wherein $E_1$ is OH, SH or $BH_2$. Considering the easy accessibility of the starting materials, in some embodiments, $E_1$ is OH or SH.

$R_2$ is selected to achieve the linkage of N on the nitrogenous backbone to A59. In the context of the present disclosure, a "nitrogenous backbone" refers to a chain structure in which the carbon atom to which $R_{10}$, $R_{11}$, $R_{12}$, $R_{13}$, $R_{14}$, and $R_{15}$ are attached and the N atom are linked to each other. Thus, $R_2$ is a linking group capable of attaching group A59 to the N atom on a nitrogenous backbone in an appropriate manner. In some embodiments, in the case where the second siRNA conjugate is prepared by the solid phase process, it is required that $R_2$ group comprises both a site linking to the N atom on the nitrogenous backbone and a site linking to the P atom in $R_3$. In some embodiments, in $R_2$, the site linking to the N atom on the nitrogenous backbone forms an amide bond with the N atom, and the site linking to the P atom in $R_3$ forms a phosphoester bond with the P atom. In some embodiments, $R_2$ is B5, B6, B5' or B6':

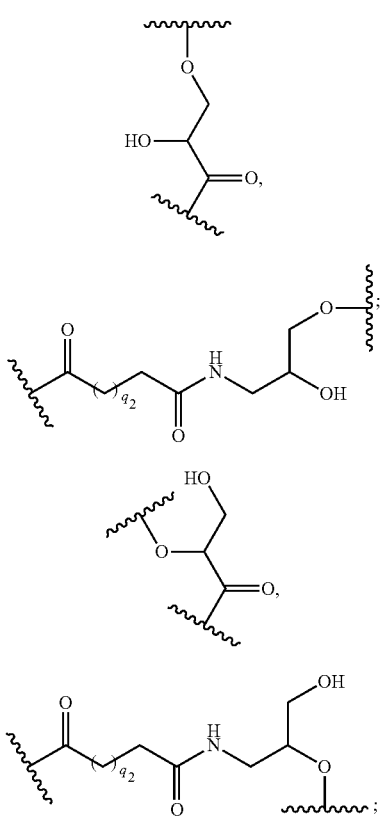

(B5)

(B6)

(B5')

(B6')

wherein, ⌇⌇⌇ represents the site where a group is covalently linked.

$q_2$ may be an integer of 1-10, and in some embodiments, $q_2$ is an integer of 1-5. $L_1$ is used to link the $M_1$ targeting group to the N atom on the nitrogenous backbone, thereby providing liver targeting function for the second siRNA conjugate. In some embodiments, $L_1$ is selected from connection combinations of one or more groups having Formulae A1-A26. In some embodiments, $L_1$ is selected from connection combinations of one or more of A1, A4, A5, A6, A8, A10, A11, and A13. In some embodiments, $L_1$ is selected from connection combinations of at least two of A1, A4, A8, A10, and A11. In some embodiments, $L_1$ is selected from connection combinations of at least two of A1, A8, and A10.

In some embodiments, the length of $L_1$ may be 3 to 25, 3 to 20, 4 to 15, or 5 to 12 atoms. In some embodiments, $L_1$ is 3, 4, 5, 6, 7, 8, 9, 10, 11, 12, 13, 14, 15, 16, 17, 18, 19, 20, 21, 22, 23, 24, 25, 30, 35, 40, 45, 50, 55, 60 atoms in length.

Those skilled in the art would understand that, though $L_1$ is defined as a linear alkyl for convenience, it may not be a linear group or be named differently, such as an amine or alkenyl as a result of the above replacement and/or substitution. For the purpose of the present disclosure, the length of $L_1$ is the atom number in the chain connecting two attachment points. For this purpose, a ring resulted from replacement of a carbon atom of the linear alkylene, such as a heterocyclylene or heteroarylene, is counted as one atom.

In some embodiments, j1 is an integer of 2-10, and in some embodiments is an integer of 3-5. In some embodiments, j2 is an integer of 2-10, and in some embodiments is an integer of 3-5. R' is a $C_1$-$C_4$ alkyl, and in some embodiments is one of methyl, ethyl, and isopropyl. Ra is one of A27, A28, A29, A30, and A31, and in some embodiments is A27 or A28. Rb is a $C_1$-$C_5$ alkyl, and in some embodiments is one of methyl, ethyl, isopropyl, and butyl. In some embodiments, j1, j2, R', Ra, and Rb in Formulae A1-A26 are respectively selected to achieve the linkage between the $M_1$ targeting group and the N atom on the nitrogenous backbone, and to make the steric position among the $M_1$ targeting group more suitable for binding the $M_1$ targeting group to the asialoglycoprotein receptor on the surface of liver.

In some embodiments, the conjugate has the structure represented by Formula (3), (4), (5), (6), (7), (8), (9), (10), (11), (12), (13), (14), (15), (16), (17), (18), (19), (20), (21) or (22):

Formula (3)

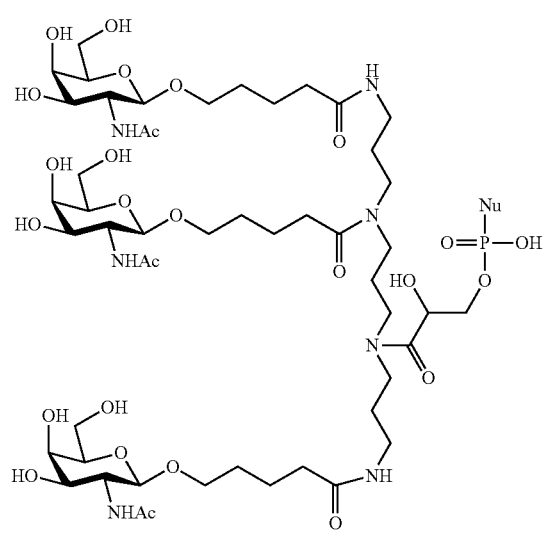

Formula (4)
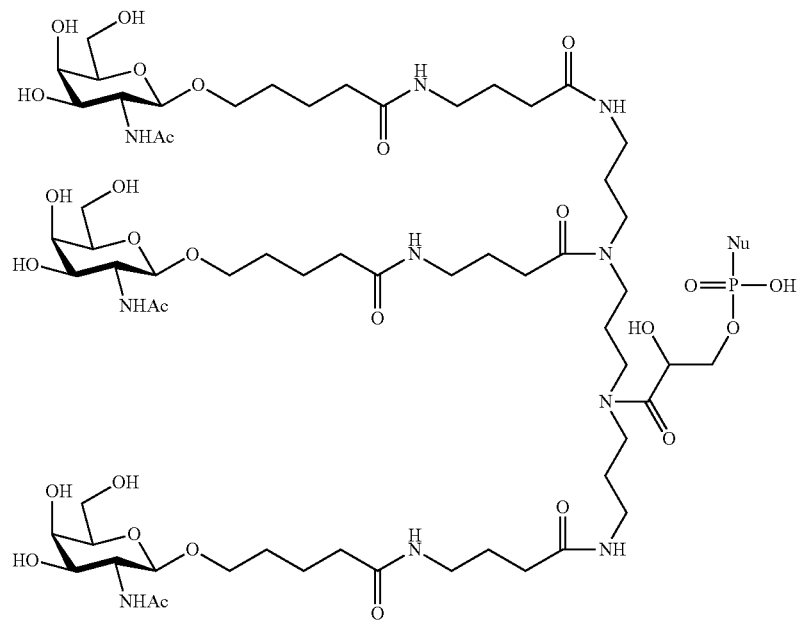
Formula (5)
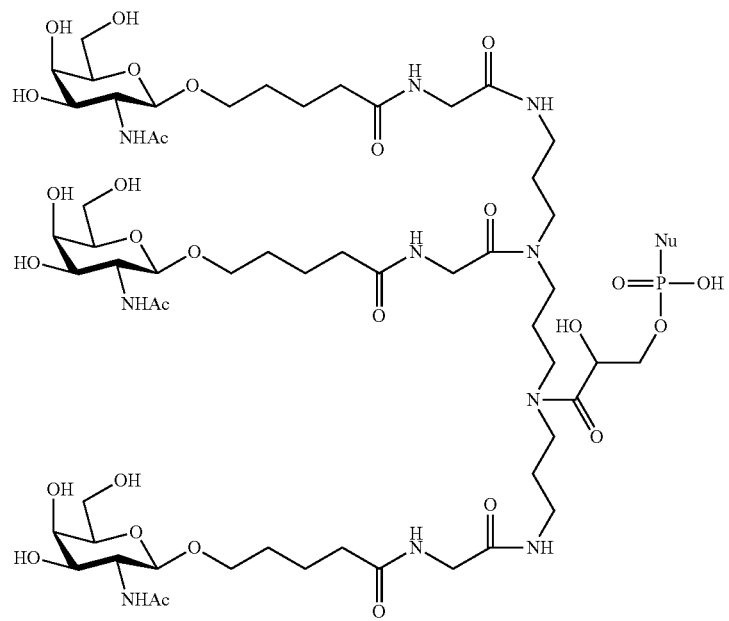

Formula (6)
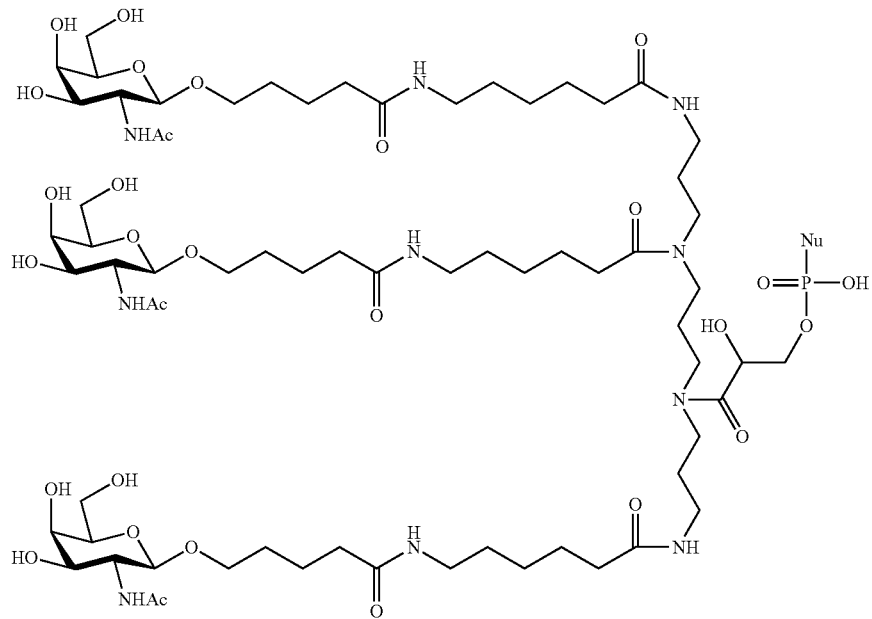
Formula (7)
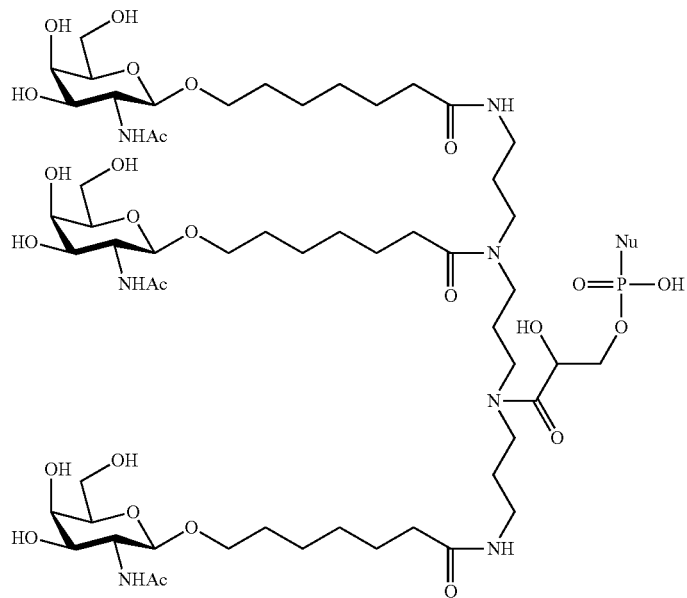

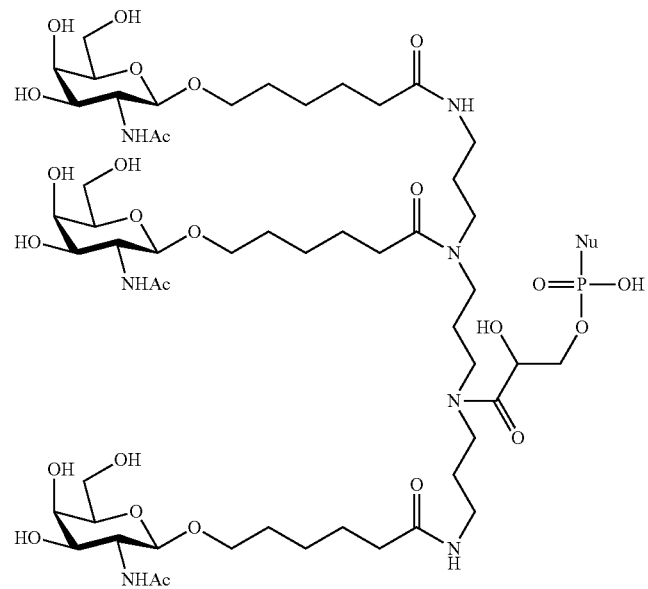
Formula (8)
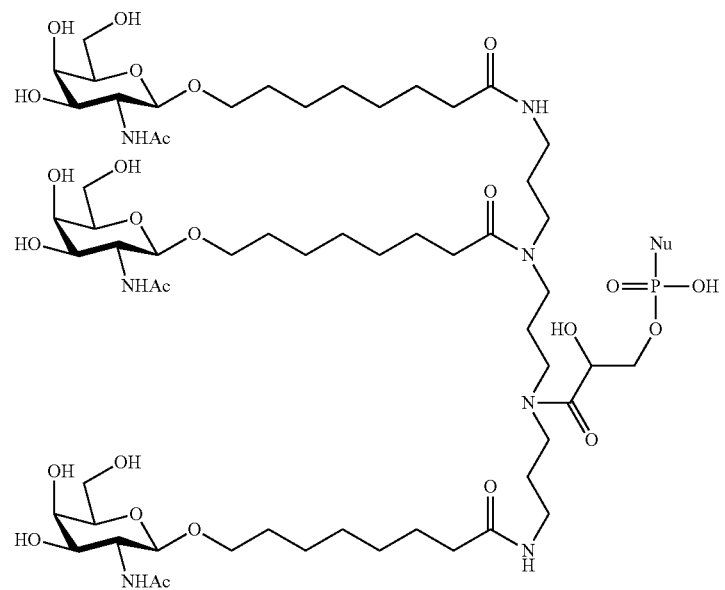
Formula (9)

Formula (10)
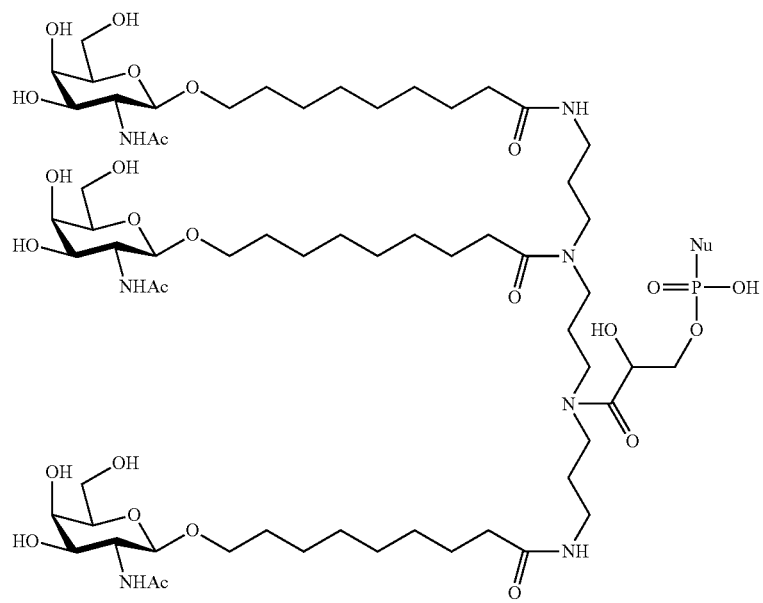
Formula (11)
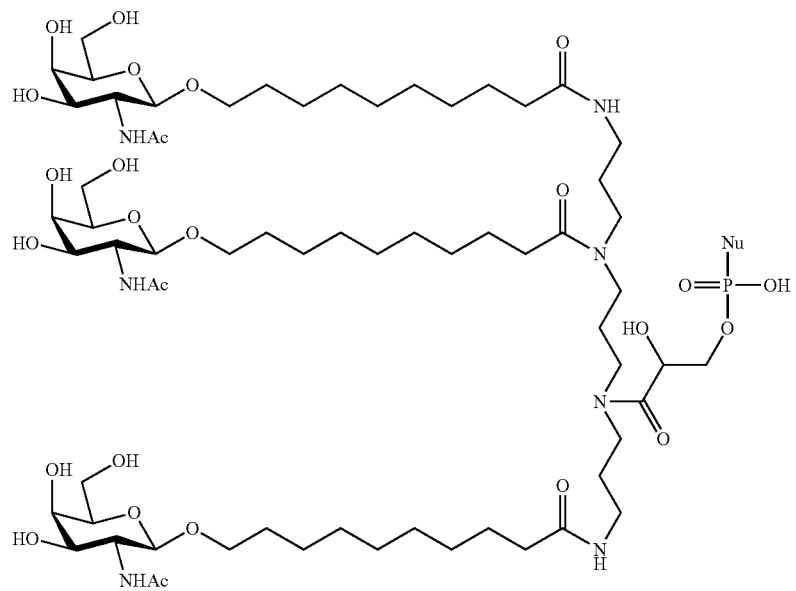

Formula (12)
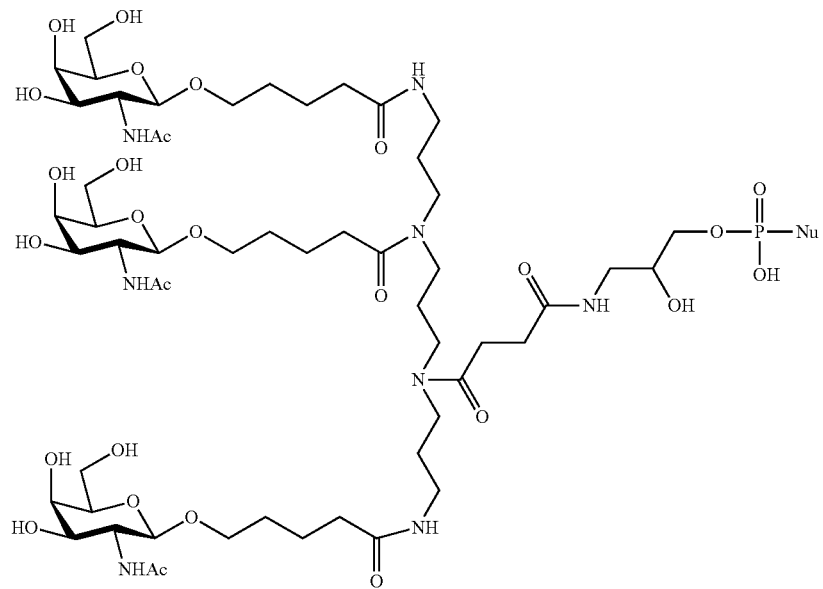
Formula (13)
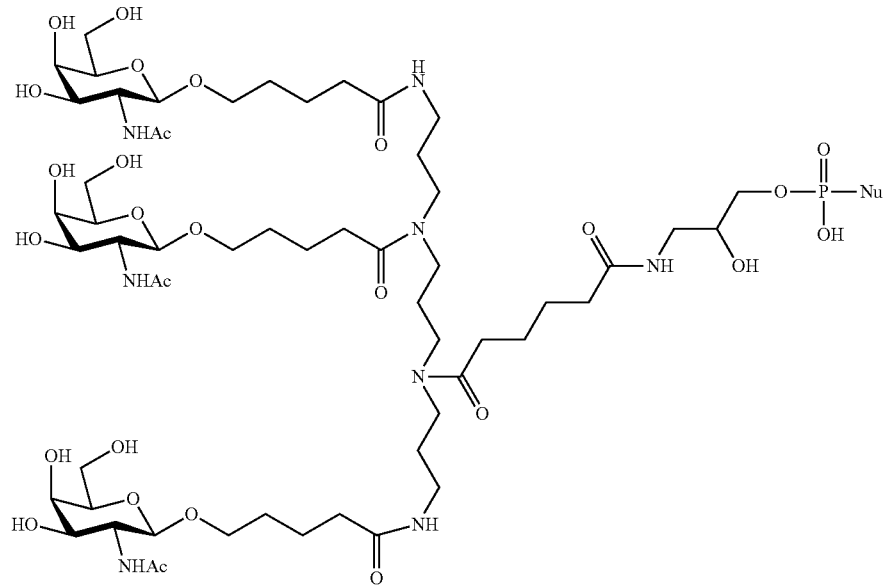

-continued
Formula (14)
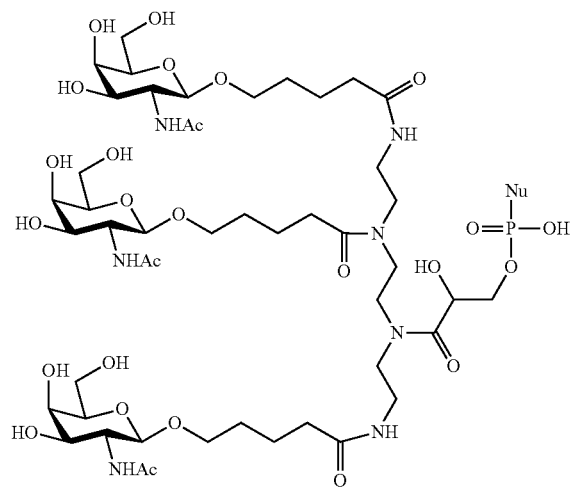
Formula (15)
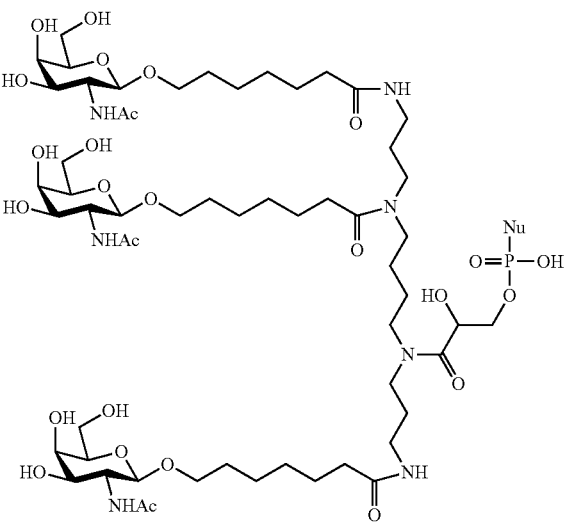
Formula (16)
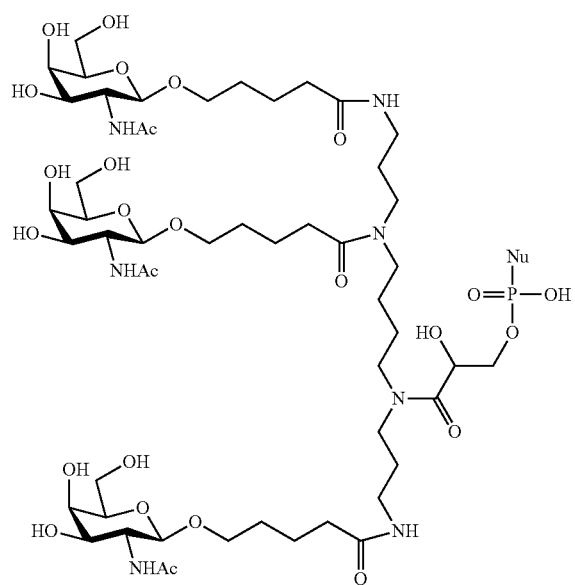
Formula (17)
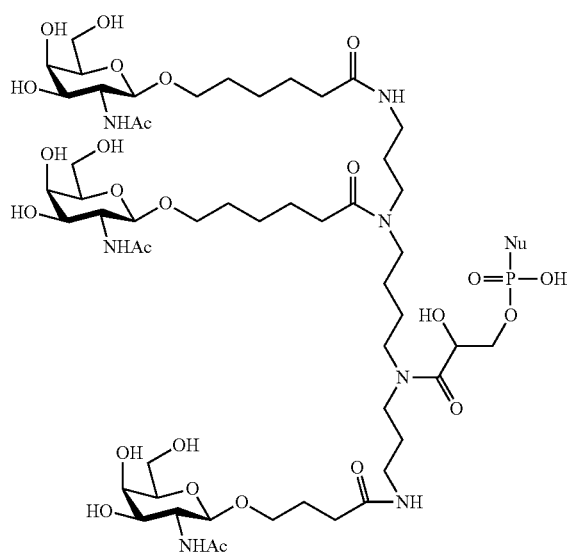
Formula (18)
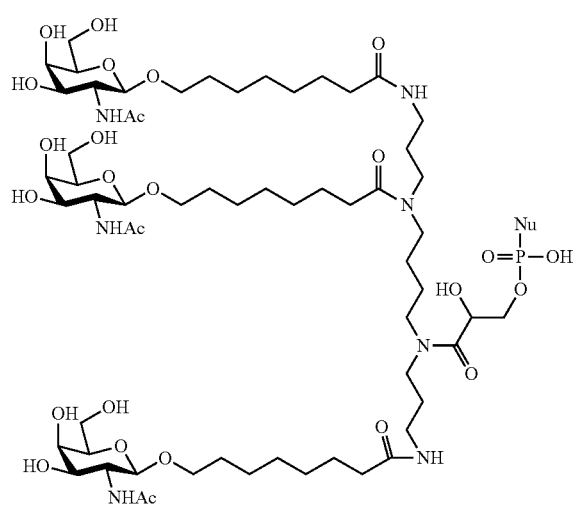
Formula (19)
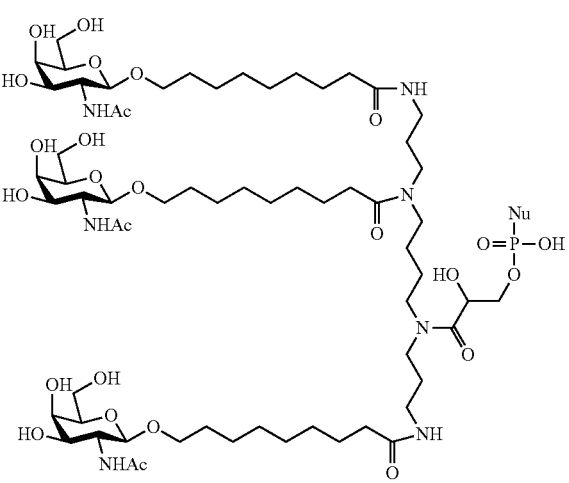

Formula (20)

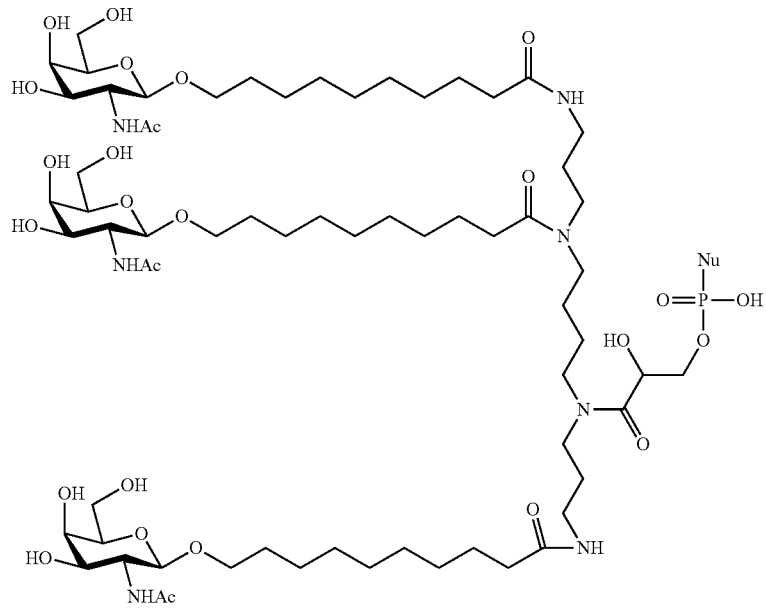

Formula (21)

Formula (22)

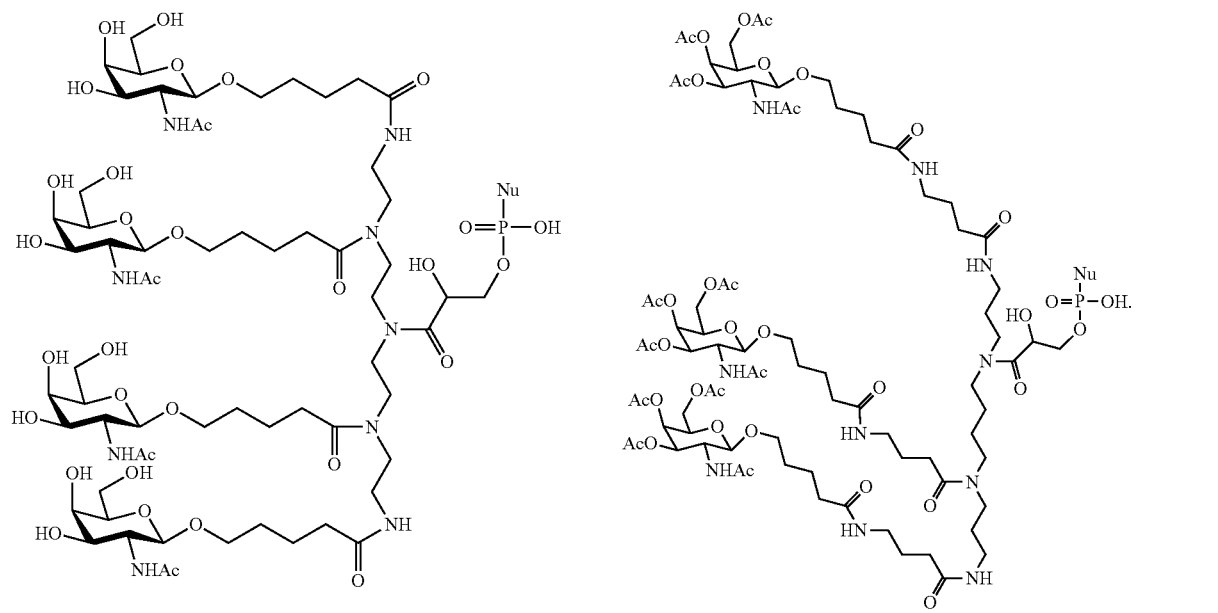

In some embodiments, the P atom in Formula A59 may be linked to any possible position in the siRNA sequence represented by Nu, for example, to any nucleotide in the sense strand or the antisense strand of the siRNA represented by Nu; in some embodiments, the P atom in the Formula A59 may be linked to any nucleotide in the sense strand of siRNA represented by Nu. In some embodiments, the P atom in Formula A59 is linked to a terminal of the sense strand or the antisense strand of the siRNA represented by Nu; in some embodiments, the P atom in the A59 is linked to a terminal of the sense strand of the siRNA represented by Nu. The terminal of the siRNA represented by Nu refers to the first 4 nucleotides counting from a terminal of the sense strand or the antisense strand of the siRNA represented by Nu. In some embodiments, the P atom in Formula A59 is linked to a terminal of the sense strand or the antisense strand of siRNA represented by Nu; in some embodiments, the P atom in Formula A59 is linked to the 3' terminal of the sense strand of the siRNA represented by Nu. In the case where the P atom in Formula A59 is linked to the above position in the sense strand of the siRNA represented by Nu, after entering into cells, the second siRNA conjugate can release a separate antisense strand of the siRNA during unwinding thereby blocking the translation of APOC3 mRNA into a protein and inhibiting the expression of apolipoprotein C3 (ApoC3) gene.

In some embodiments, the P atom in Formula A59 may be linked to any possible position of the nucleotide in the siRNA represented by Nu, for example, to position 5', 2' or 3', or to the base of the nucleotide. In some embodiments, the P atom in Formula A59 may be linked to position 5', 2' or 3' of the nucleotide in the siRNA represented by Nu by forming a phosphodiester bond. In some embodiments, the P atom in Formula A59 is linked to an oxygen atom formed by dehydrogenation of 3'-hydroxy of the nucleotide at 3' terminal of the sense strand of siRNA represented by Nu, or linked to a nucleotide by substituting a hydrogen atom in 2'-hydroxy of a nucleotide of the sense strand of the siRNA represented by Nu, or linked to a nucleotide by substituting a hydrogen atom in 5'-hydroxy of the nucleotide at 5' terminal of the nucleotide in the sense strand of the siRNA represented by Nu.

In some embodiments, there is no more than 1 nucleotide difference between the nucleotide sequence 1 and the nucleotide sequence represented by SEQ ID NO: 1, and/or there is no more than 1 nucleotide difference between the nucleotide sequence 2 and the nucleotide sequence represented by SEQ ID NO:2.

In some embodiments, the nucleotide difference between the nucleotide sequence 2 and the nucleotide sequence represented by SEQ ID NO:2 includes the difference at the position of $Z'_B$, wherein $Z'_B$ is selected from A, C or G; in some embodiments, the nucleotide difference is the difference at the position of $Z'_B$, wherein $Z'_B$ is selected from A, C or G; in some embodiments, $Z_A$ is a nucleotide complementary to $Z'_B$. These nucleotide differences will not significantly reduce the ability of the second siRNA conjugate in inhibiting the target gene(s), and thus these second siRNA conjugates comprising particular nucleotide differences are within the scope of the disclosure.

In some embodiments, the nucleotide sequence 1 is basically reverse complementary, substantially reverse complementary, or completely reverse complementary to the nucleotide sequence 2. "Basically reverse complementary" means that there is no more than 3 base mispairings between two nucleotide sequences; "substantially reverse complementary" means that there is no more than 1 base mispairing between two nucleotide sequences; "completely reverse complementary" means there is no mispairing between two nucleotide sequences.

In some embodiments, the sense strand further comprises a nucleotide sequence 3, the antisense strand further a nucleotide sequence 4, and the nucleotide sequence 3 and the nucleotide sequence 4 each independently have a length of 1 to 4 nucleotides; and the nucleotide sequence 3 and the nucleotide sequence 4 are at corresponding positions; in some embodiments, nucleotide sequence 4 is at least partly complementary to the nucleotide(s) at the corresponding position(s) of target mRNA, and in some embodiments, nucleotide sequence 4 is completely complementary to the nucleotide(s) at the corresponding position(s) of target mRNA.

In some embodiments, the nucleotide sequence 3 is linked to the 5' terminal of the nucleotide sequence 1, the nucleotide sequence 4 is linked to the 3' terminal of the nucleotide sequence 2. In some embodiments, the nucleotide sequence 3 and the nucleotide sequence 4 have the same length and are reverse complementary. Thus, the length of the sense strand and antisense strand may be 19 to 23 nucleotides.

In some embodiments, the nucleotide sequence 3 and the nucleotide sequence 4 both have a length of one nucleotide, and the base of the nucleotide sequence 3 is C; in this case, the length of the double-stranded region may be 20 nucleotides, i.e., the length ratio of the sense strand and antisense strand may be 20/20; or the nucleotide sequence 3 and the nucleotide sequence 4 both have a length of 2 nucleotides, and in the direction from 5' terminal to 3' terminal, the bases of the nucleotide sequence 3 are sequentially C and C; in this case, the length of the double-stranded region may be 21 nucleotides, and the length ratio of the sense strand and the antisense strand may be 21/21; or, the nucleotide sequence 3 and the nucleotide sequence 4 both have a length of 3 nucleotides, and in the direction from 5' terminal to 3' terminal, the bases of nucleotide sequence 3 are sequentially U, C and C; the length of the double-stranded region may be 22 nucleotides, and the length ratio of the sense strand and the antisense strand may be 22/22; or, the nucleotide sequence 3 and the nucleotide sequence 4 both have a length of 4 nucleotides, and in the direction from 5' terminal to 3' terminal, the bases of nucleotide sequence 3 are sequentially C, U, C and C; in this case, the length of the double-stranded region may be 23 nucleotides, and the length ratio of the sense strand and the antisense strand may be 23/23.

In some embodiments, the nucleotide sequence 3 has a length of 2 nucleotides, and in the direction from 5' terminal to 3' terminal, the bases of the nucleotide sequence 3 are sequentially C and C;

It should be understood that the nucleotide sequence 3 and the nucleotide sequence 4 have the same length, and are complementary. Hence, where the base(s) of nucleotide sequence 3 is(are) provided, the base(s) of nucleotide sequence 4 is(are) determined. In some embodiments, the siRNA represented by Nu in Formula (1) further comprises a nucleotide sequence 5, the nucleotide sequence 5 has a length of 1 to 3 nucleotides, and is linked to the 3' terminal of the antisense strand, thereby forming the 3' overhang terminal of the antisense strand. In some embodiments, the length of the nucleotide sequence 5 is 1 or 2 nucleotide(s). In this case, the length ratio of the sense strand and antisense strand of the siRNA represented by Nu is 19/20, 19/21, 20/21, 20/22, 21/22, 21/23, 22/23, 22/24, 23/24 or 23/25.

In some embodiments, the nucleotide sequence 5 has a length of 2 nucleotides, and in the direction from 5' terminal to 3' terminal, the nucleotide sequence 5 is 2 continuous thymine deoxyribonucleotides, 2 continuous uridine ribonucleotides, or 2 nucleotides complementary to target mRNA. Hence, in some embodiments, the length ratio of the sense strand and antisense strand of the siRNA represented by Nu is 19/21 or 21/23. In this case, the conjugate comprising the siRNA has better activity for silencing APOC3 mRNA.

In some embodiments, the sense strand comprises the nucleotide sequence represented by SEQ ID NO:60, and the antisense strand comprises the nucleotide sequence represented by SEQ ID NO:3:

```
                                          (SEQ ID NO: 60)
        5'-CAAUAAAGCUGGACAAGAZ_A-3';

(SEQ ID NO: 3)
        5'-Z'_BUCUUGUCCAGCUUUAUUGGG-3';
``` or, the sense strand comprises the nucleotide sequence represented by SEQ ID NO:4, and the antisense strand comprises the nucleotide sequence represented by SEQ ID NO:5:

```
                                          (SEQ ID NO: 4)
        5'-CCCAAUAAAGCUGGACAAGAZ_A-3';

(SEQ ID NO: 5)
        5'-Z'_BUCUUGUCCAGCUUUAUUGGGAG-3';
``` wherein $Z'_B$ is the first nucleotide at the 5'terminal of the antisense strand, $Z_A$ is selected from A, U, G or C, and $Z'_B$ is a nucleotide complementary to $Z_A$.

In some embodiments, the siRNA represented by Nu is siAP1 or siAP2:

```
siAP1
sense strand:
                                       (SEQ ID NO: 6)
5'-CAAUAAAGCUGGACAAGAA-3';

antisense strand:
                                       (SEQ ID NO: 7)
5'-UUCUUGUCCAGCUUUAUUGGG-3';

siAP2
sense strand:
                                       (SEQ ID NO: 8)
5'-CCCAAUAAAGCUGGACAAGAA-3';

antisense strand:
                                       (SEQ ID NO: 9)
5'-UUCUUGUCCAGCUUUAUUGGGAG-3'.
```

As described above, the nucleotides in the siRNA represented by Nu in Formula (1) are each independently a modified or unmodified nucleotide. In some embodiments, the nucleotides in the siRNA represented by Nu are each independently a unmodified nucleotide; in some embodiments, partial or all the nucleotides in the siRNA represented by Nu are modified nucleotides. These modifications on the nucleotide groups would not lead to significant impair or loss of functions of the second siRNA conjugate of the present disclosure in inhibiting the expression of APOC3 gene.

In some embodiments, the siRNA in the conjugate comprises at least 1 modified nucleotide. In the context of the present disclosure, the used term "modified nucleotide" refers to a nucleotide formed by replacing 2'-hydroxy of the ribose group with other group, or nucleotide analogue, or a nucleotide on which the base is a modified base. The modified nucleotide would not lead to significant impair or loss of functions of siRNA conjugate in inhibiting gene expression. For example, modified nucleotides disclosed in Watts, J. K., G. F. Deleavey and M. J. Damha, Chemically Modified siRNA: tools and applications. Drug Discov Today, 2008.13(19-20): p. 842-55 may be selected.

In some embodiments, at least one nucleotide in the sense strand or the antisense strand is a modified nucleotide, and/or at least one phosphoester group is a phosphoester group with modified group(s). In other words, at least a portion of the phosphoester and/or ribose groups in phosphate-ribose backbone of at least one single strand in the sense strand and the antisense strand are phosphoester and/or ribose group(s) with modified group(s).

In some embodiments, all the nucleotides in the sense strand and/or the antisense strand are modified nucleotides. In some embodiments, each nucleotide in the sense strand and antisense strand is independently a fluoro modified nucleotide or a non-fluoro modified nucleotide.

The inventors of the present disclosure surprisingly found that where the siRNA represented by Nu in the second siRNA conjugate is the siRNA as follows, it achieves highly balanced stability and gene silencing efficiency in plasma.

In some embodiments, the fluoro modified nucleotide is present in the nucleotide sequence 1 and the nucleotide sequence 2; and in the direction from 5' terminal to 3' terminal, the nucleotides at positions 7, 8, 9 of the nucleotide sequence 1 are fluoro modified nucleotides; and in the direction from 5'terminal to 3' terminal, the nucleotides at positions 2, 6, 14 and 16 of the nucleotide sequence 2 are fluoro modified nucleotides.

In some embodiments, there is no more than 5 fluoro modified nucleotides present in the nucleotide sequence 1; in some embodiments, there is no more than 7 fluoro modified nucleotides present in the nucleotide sequence 2.

In some embodiments, in the direction from 5' terminal to 3' terminal, the nucleotides at positions 7, 8 and 9 or at positions 5, 7, 8 and 9 of the nucleotide sequence 1 in the sense strand are fluoro modified nucleotides, and the nucleotides at the other positions in the sense strand are non-fluoro modified nucleotides; in the direction from 5' terminal to 3' terminal, the nucleotides at positions 2, 6, 14 and 16 or at positions 2, 6, 8, 9, 14 and 16 of the nucleotide sequence 2 in the antisense strand are fluoro modified nucleotides, and the nucleotides at the other positions in the antisense strand are non-fluoro modified nucleotides.

The definitions and options of the fluoro modified nucleotides and the non-fluoro modified nucleotides are as described above.

In some embodiments, in the direction from 5' terminal to 3' terminal, the nucleotides at positions 5, 7, 8 and 9 of the nucleotide sequence 1 in the sense strand of the siRNA represented by Nu are fluoro modified nucleotides, and the nucleotides at the other positions in the sense strand of the siRNA are methoxy modified nucleotides; and in the direction from 5' terminal to 3' terminal, the nucleotides at positions 2, 6, 8, 9, 14 and 16 of the nucleotide sequence 2 in the antisense strand of the siRNA represented by Nu are fluoro modified nucleotides, and the nucleotides at the other positions in the antisense strand of the siRNA are methoxy modified nucleotides;

or, in the direction from 5' terminal to 3' terminal, the nucleotides at positions 7, 8 and 9 of the nucleotide sequence 1 in the sense strand of the siRNA represented by Nu are fluoro modified nucleotides, and the nucleotides at the other positions in the sense strand of the siRNA are methoxy modified nucleotides; and in the direction from 5' terminal to 3' terminal, the nucleotides at positions 2, 6, 14 and 16 of the nucleotide sequence 2 in the antisense strand of the siRNA represented by Nu are fluoro modified nucleotides, and the nucleotides at the other positions in the antisense strand of the siRNA are methoxy modified nucleotides.

In some embodiments, the nucleotides have a phosphate group modification. In some embodiments, the phosphate group modification is the phosphorthioate modification represented by the following Formula (101), i.e., replacing the non-bridging oxygen atom in the phosphate diester bond with a sulfur atom, so as to replace the phosphate diester bond with phosphorthioate diester bond. This modification stabilizes the structure of the siRNA and maintains high specificity and high affinity for base pairing.

Formula (101)

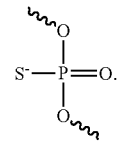

In some embodiments, in the siRNA represented by Nu, a phosphorothioate linkage is present at at least one position selected from the group consisting of the following positions: the position between the first and the second nucleotides at either terminal of the sense or antisense strand, the position between the second and the third nucleotides at either terminal of the sense strand or antisense strand, or any combination thereof. In some embodiments, a phosphorothioate linkage is present at all the above positions except for 5' terminal of the sense strand. In some embodiments, a phosphorothioate linkage is present at all the above positions except for 3' terminal of the sense strand. In some embodiments, a phosphorothioate linkage is present at at least one of the following positions:

the position between the first and second nucleotides at 5' terminal of the sense strand;

the position between the second and third nucleotides at 5' terminal of the sense strand;

the position between the first and second nucleotides at 3' terminal of the sense strand;

the position between the second and third nucleotides at 3' terminal of the sense strand;

the position between the first and second nucleotides at 5' terminal of the antisense strand;

the position between the second and third nucleotides at 5' terminal of the antisense strand;

the position between the first and second nucleotides at 3' terminal of the antisense strand; and the position between the second and third nucleotides at 3' terminal of the antisense strand.

In some embodiments, the nucleotide at 5' terminal of the antisense strand of the siRNA represented by Nu is a 5'-phosphate nucleotide or a 5'-phosphate analogue modified nucleotide.

As well known to those skilled in the art, the 5'-phosphate nucleotide may have the following structure:

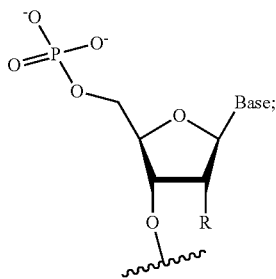

Formula (102)

meanwhile, the common used 5'-phosphate analogue modified nucleotides are well-known to those skilled in the art; as another example, the following 4 nucleotides represented by Formulae (103)-(106) disclosed in Anastasia Khvorova and Jonathan K. Watts, The chemical evolution of oligonucleotide therapies of clinical utility. Nature Biotechnology, 2017, 35(3): 238-48:

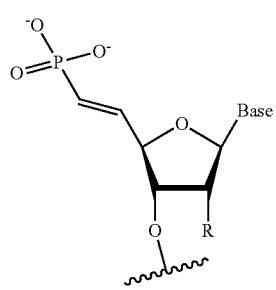

Formula (103)

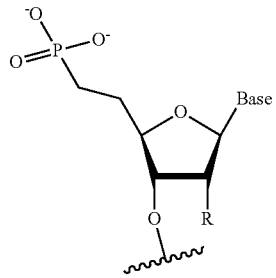

Formula (104)

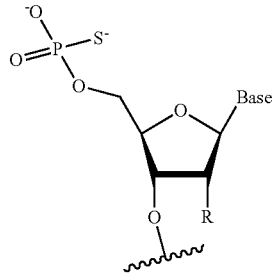

Formula (105)

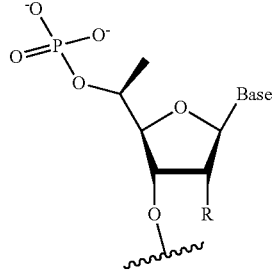

Formula (106)

wherein, R represents a group selected from the group consisting of H, OH, F and methoxy; "Base" represents a base selected from A, U, C, G, or T.

In some embodiments, the 5'-phosphate nucleotide or the 5'-phosphate analogue modified nucleotide is the 5'-phosphate modified nucleotide represented by Formula (102), the nucleotide comprising a vinyl phosphate (E-vinylphosphonate, E-VP) as represented by Formula (103), or the 5'-phosphorothioate modified nucleotide represented by Formula (105).

The inventors of the present disclosure have unexpectedly discovered that the second siRNA conjugate of the present disclosure exhibits a significantly improved stability in plasma, low off-target effect without significantly reduced APOC3 mRNA silencing activity, and relatively high effect in inhibiting blood lipid. Thus, in some embodiments, the siRNA in the second siRNA conjugate represented by Nu may be one of siAP1, siAP2, siAP1-M1, siAP2-M1, siAP1-M2, siAP2-M2, siAP1-M1S, siAP2-M1S, siAP1-M2S, siAP2-M2S, siAP1-M1P1, siAP2-M1P1, siAP1-M2P1, siAP2-M2P1, siAP1-M1 SP1, siAP2-1SP1, siAP1-M2SP1, and siAP2-M2SP1, as shown in Table 1.

Table 1 the sequences of siRNAs in the conjugates of the present disclosure

| siRNA NO: | SEQ ID NO: | Sequence direction 5'-3' |
|---|---|---|
| siAP1 | 6 | CAAUAAAGCUGGACAAGAA |
|  | 7 | UUCUUGUCCAGCUUUAUUGGG |
| siAP2 | 8 | CCCAAUAAAGCUGGACAAGAA |
|  | 9 | UUCUUGUCCAGCUUUAUUGGGAG |
| siAP1-M1 | 10 | CmAmAmUmAfAmAfGfCfUmGmGmAmCmAmAmGmAmAm |
|  | 11 | UmUfCmUmUmGfUmCfCfAmGmCmUmUfUmAfUmUmGmGm |
| siAP2-M1 | 12 | CmCmCmAmAmUmAfAmAfGfCfUmGmGmAmCmAmAmGmAmAm |
|  | 13 | UmUfCmUmUmGfUmCfCfAmGmCmUmUfUmAfUmUmGmGmGmAmGm |
| siAP1-M2 | 14 | CmAmAmUmAmAmAfGfCfUmGmGmAmCmAmAmGmAmAm |
|  | 15 | UmUfCmUmUmGfUmCmCmAmGmCmUmUfUmAfUmUmGmGm |
| siAP2-M2 | 16 | CmCmCmAmAmUmAmAmAfGfCfUmGmGmAmCmAmAmGmAmAm |
|  | 17 | UmUfCmUmUmGfUmCmCmAmGmCmUmUfUmAfUmUmGmGmGmAmGm |
| siAP1-M1S | 18 | CmsAmsAmUmAfAmAfGfCfUmGmGmAmCmAmAmGmAmAm |
|  | 19 | UmsUfsCmUmUmGfUmCfCfAmGmCmUmUfUmAfUmUmGmsGmsGm |
| siAP2-M1S | 20 | CmsCmsCmAmAmUmAfAmAfGfCfUmGmGmAmCmAmAmGmAmAm |
|  | 21 | UmsUfsCmUmUmGfUmCfCfAmGmCmUmUfUmAfUmUmGmGmGmsAmsGm |
| siAP1-M2S | 22 | CmsAmsAmUmAmAmAfGfCfUmGmGmAmCmAmAmGmAmAm |
|  | 23 | UmsUfsCmUmUmGfUmCmCmAmGmCmUmUfUmAfUmUmGmsGmsGm |
| siAP2-M2S | 24 | CmsCmsCmAmAmUmAmAmAfGfCfUmGmGmAmCmAmAmGmAmAm |
|  | 25 | UmsUfsCmUmUmGfUmCmCmAmGmCmUmUfUmAfUmUmGmGmGmsAmsGm |
| siAP1-M1P1 | 10 | CmAmAmUmAfAmAfGfCfUmGmGmAmCmAmAmGmAmAm |
|  | 26 | P1-UmUfCmUmUmGfUmCfCfAmGmCmUmUfUmAfUmUmGmGm |
| siAP2-M1P1 | 12 | CmCmCmAmAmUmAfAmAfGfCfUmGmGmAmCmAmAmGmAmAm |
|  | 27 | P1-UmUfCmUmUmGfUmCfCfAmGmCmUmUfUmAfUmUmGmGmGmAmGm |
| siAP1-M2P1 | 14 | CmAmAmUmAmAmAfGfCfUmGmGmAmCmAmAmGmAmAm |
|  | 28 | P1-UmUfCmUmUmGfUmCmCmAmGmCmUmUfUmAfUmUmGmGm |
| siAP2-M2P1 | 16 | CmCmCmAmAmUmAmAmAfGfCfUmGmGmAmCmAmAmGmAmAm |
|  | 29 | P1-UmUfCmUmUmGfUmCmCmAmGmCmUmUfUmAfUmUmGmGmGmAmGm |
| siAP1-M1SP1 | 18 | CmsAmsAmUmAfAmAfGfCfUmGmGmAmCmAmAmGmAmAm |
|  | 30 | P1-UmsUfsCmUmUmGfUmCfCfAmGmCmUmUfUmAfUmUmGmsGmsGm |
| siAP2-M1SP1 | 20 | CmsCmsCmAmAmUmAfAmAfGfCfUmGmGmAmCmAmAmGmAmAm |
|  | 31 | P1-UmsUfsCmUmUmGfUmCfCfAmGmCmUmUfUmAfUmUmGmGmGmsAmsGm |
| siAP1-M2SP1 | 22 | CmsAmsAmUmAmAmAfGfCfUmGmGmAmCmAmAmGmAmAm |
|  | 32 | P1-UmsUfsCmUmUmGfUmCmCmAmGmCmUmUfUmAfUmUmGmsGmsGm |
| siAP2-M2SP1 | 24 | CmsCmsCmAmAmUmAmAmAfGfCfUmGmGmAmCmAmAmGmAmAm |
|  | 33 | P1-UmsUfsCmUmUmGfUmCmCmAmGmCmUmUfUmAfUmUmGmGmGmsAmsGm |

In the siRNA or the siRNA conjugate of the present disclosure, each pair of adjacent nucleotides are linked by a phosphodiester bond or a phosphorothioate diester bond. The non-bridging oxygen or sulfur atom in the phosphodiester bond or a phosphorothioate diester bond has negative charges, and may be present in the form of hydroxy or sulfhydryl. Moreover, the hydrogen ion in the hydroxy or sulfhydryl may be partially or completely replaced with a cation. The cation may be any cation, such as one of a metal cation, an ammonium cation $NH_4^+$ or an organic ammonium cation. In order to increase solubility, in one embodiment, the cation is selected from one or more of alkali metal cation, an ammonium cation formed by a tertiary amine or a quaternary ammonium cation. The alkali metal ion may be $K^+$ and/or $Na^+$, and the cation formed by a tertiary amine may be ammonium cation formed by triethylamine and/or N,N-diisopropylethylamine. Thus, the siRNA or the first or second siRNA conjugate of the present disclosure may be at least partially present in the form of salt. In one embodiments, the non-bridging oxygen or sulfur atom in the phosphodiester bond or a phosphorothioate diester bond at least partly binds to sodium ion. The siRNA or the first or second siRNA conjugate of the present disclosure is present or partially present in the form of sodium salt.

It is well known to those skilled in the art that a modified nucleotide group may be introduced into the siRNA of the present disclosure by a nucleoside monomer with a corresponding modification. Methods for preparing a nucleoside monomer having a corresponding modification and for introducing a modified nucleotide group into a siRNA are also well known to those skilled in the art. All modified nucleoside monomers may be either commercially available or prepared by known methods.

Preparation of the Second siRNA Conjugate

The second siRNA conjugate may be prepared by any appropriate synthetic routes. In some embodiments, the second siRNA conjugate may be prepared by a method which comprises successively linking nucleoside monomers in 3' to 5' direction according to the nucleotide type and sequence of the sense strand and the antisense strand of the siRNA, under a condition of phosphoramidite solid phase synthesis, wherein the linking of each nucleoside monomer includes a four-step reaction of deprotection, coupling, capping, and oxidation or sulfurization; isolating the sense strand and antisense strand of the siRNA; and annealing; wherein each nucleotide in the siRNA represented by Nu is independently a modified or unmodified nucleotide; the siRNA represented by Nu comprises a sense strand and an antisense strand, the sense strand comprises a nucleotide sequence 1, and the antisense strand comprises a nucleotide sequence 2, the nucleotide sequence 1 and the nucleotide sequence 2 are at least partly reverse complementary to form a double-stranded region, wherein the nucleotide sequence 1 has the same length as the nucleotide sequence represented by SEQ ID NO: 1 with no more than 3 nucleotide differences, and the nucleotide sequence 2 has the same length as the nucleotide sequence represented by SEQ ID NO:2 with no more than 3 nucleotide differences:

5'-CAAUAAAGCUGGACAAGAZ-3'; (SEQ ID NO: 1)

5'-Z'UCUUGUCCAGCUUUAUUG-3'; (SEQ ID NO: 2)

wherein, Z is A and Z' is U, the nucleotide sequence 1 comprises a nucleotide $Z_A$ at the corresponding position of Z, the nucleotide sequence 2 comprises a nucleotide $Z'_B$ at the corresponding position of Z', wherein $Z'_B$ is the first nucleotide at the 5' terminal of the antisense strand; and, wherein the method further comprises contacting the compound represented by Formula (321) with a nucleoside monomer or a nucleotide sequence linked to a solid phase support under a coupling reaction condition in the presence of a coupling reagent, thereby linking the compound represented by Formula (321) to the nucleotide sequence via a coupling reaction. In the following text, the compound represented by Formula (321) is also referred to as a conjugating molecule.

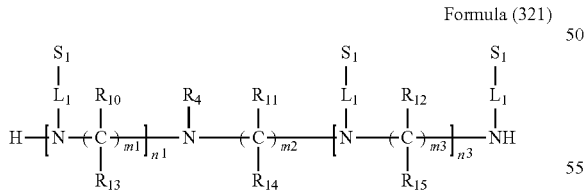

Formula (321)

wherein:

$R_4$ is a moiety capable of binding to the siRNA represented by Nu. In some embodiments, $R_4$ is a moiety capable of binding to the siRNA represented by Nu via a covalent bond. In some embodiments, $R_4$ is a moiety capable of being conjugated to any functional group of siRNA represented by Nu via a phosphodiester bond by a reaction;

each $S_1$ is independently a group formed by replacing all the hydroxyl groups in $M_1$ with YCOO— group, wherein each Y is independently one selected from the group consisting of methyl, trifluoromethyl, difluoromethyl, monofluoromethyl, trichloromethyl, dichloromethyl, monochloromethyl, ethyl, n-propyl, isopropyl, phenyl, halophenyl and alkylphenyl; in some embodiments, Y is methyl;

the definitions and options of n1, n3, m1, m2, m3, $R_{10}$, $R_{11}$, $R_{12}$, $R_{13}$, $R_{14}$, $R_{15}$, $L_1$, and $M_1$ are respectively described as above.

$R_4$ is selected to achieve the linkage to N on the nitrogenous backbone, and to provide a appropriate reaction site for the synthesis of the second siRNA conjugate. In some embodiments, $R_4$ comprises a $R_2$ linking group or a protected $R_2$ linking group, and functional group(s) that can form the structure represented by Formula A59 with siRNA via reaction.

In some embodiments, $R_4$ comprises a first functional group that can react with a group on the siRNA represented by Nu or the nucleoside monomer to form a phosphite ester, and a second functional group that can react with hydroxy or amino to form a covalent bond, or comprises a solid phase support linked by a covalent bond. In some embodiments, the first functional group is a phosphoramidite, a hydroxy or a protected hydroxy. In some embodiments, the second functional group is a phosphoramidite, a carboxylic acid or a carboxylate salt. In some embodiments, the second functional group is a solid phase support linked to the rest of the molecule via a covalent bond, wherein the covalent bond is formed by hydroxy or amino. In some embodiments, the solid phase support is linked via a phosphoester bond, a carboxyl ester bond, or an amide bond. In some embodiments, the solid phase support is a resin.

In some embodiments, the first functional group comprises hydroxy, —$OR_k$ or a group represented by Formula (C3); and/or the second functional group has a structure represented by Formula (C1), (C2), (C3), (C1'), or (C3'):

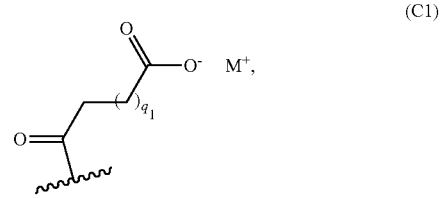

(C1)

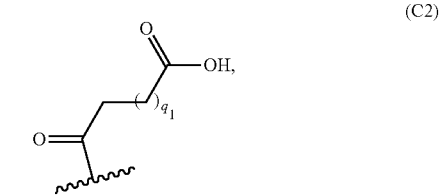

(C2)

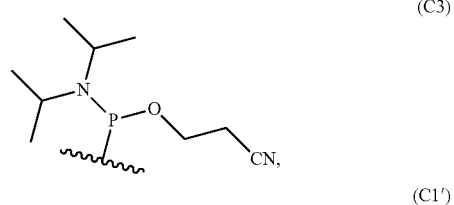

(C3)

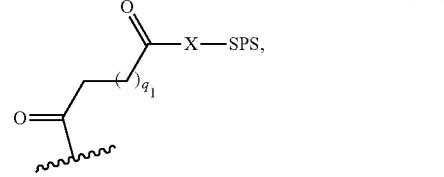

(C1')

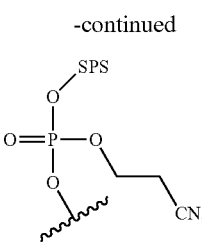

(C3')

wherein $q_1$ is an integer of 1-4, X is O or NH, $M^+$ is a cation, $R_k$ is a hydroxyl protecting group, SPS represents a solid phase support, and ～～～ represents the site where the group is linked to the rest of the molecule.

In some embodiments, the first functional group comprises a phosphoramidite group, such as the group represented by Formula (C3). The phosphoramidite group can form a phosphite ester with a hydroxy at any position (such as a 2'- or 3'-hydroxyl) on a nucleotide by a coupling reaction, and the phosphite ester can form a phosphodiester bond or a phosphorothioate bond represented by Formula A59 via oxydation or sulfuration, so as to conjugate the conjugating molecule to siRNA. Thus, even if the second functional group is not present, the compound represented by Formula (321) will be able to be conjugated with the nucleotide, while not affecting the acquisition of the second siRNA conjugate. Under such circumstances, after obtaining a sense strand or an antisense strand of the siRNA via a method such as phosphoramidite solid phase synthesis, the compound of Formula (321) reacts with the hydroxy on the nucleotide at the terminal of the nucleotide sequence, and a phosphodiester bond linkage or thiophosphoester bond linkage is formed in the following oxydization or sulfurization process, so as to conjugate the compound of Formula (321) to the siRNA.

In some embodiments, the first functional group comprises a protected hydroxy. In some embodiments, the second functional group comprises a group that can react with a solid phase support to provide a conjugating molecule comprising a solid phase support. In some embodiments, the second functional group comprises a carboxyl, a carboxylate salt or a phosphoramidite, such as represented by Formula (C1), (C2) or (C3). When the second functional group comprises a carboxyl or a carboxylate salt, the compound of Formula (321) can react via an esterification or an amidation with a hydroxy or an amino group on a solid phase support, such as a resin, to form a conjugating molecule comprising a solid phase support linked via a carboxylate ester bond. When the second functional group comprises a phosphoramidite functional group, the compound of Formula (321) can couple with a hydroxy group on a universal solid phase support, such as a resin, and form a conjugating molecule comprising a solid phase support linked via a phosphodiester bond by subsequent oxidation. Next, starting from the above product linked to a solid phase support, the nucleoside monomers are successively linked according to the phosphoramidite solid phase synthesis, so as to obtain a sense strand or an antisense strand of the siRNA linked to a conjugating group. In the process of phosphoramidite solid phase synthesis, the first functional group is deprotected, and then coupled with a phosphoramidite group on a nucleoside monomer under a coupling condition.

In some embodiments, the first functional group comprises a hydroxy or a protected hydroxy group; the second functional group comprises a solid phase support linked via a carboxylate ester bond, an amide bond, or a phosphodiester bond, as represented by Formula (C1') or (C3'). Thus, starting from the compound of Formula (321) instead of a solid phase support, the nucleoside monomers are successively linked according to the phosphoramidite solid phase synthesis, so as to obtain a sense strand or an antisense strand of the siRNA linked to a conjugating group.

In some embodiments, the carboxylate may be represented by $-COO^-M^+$, wherein $M^+$ is a cation such as one of a metal cation, an ammonium cation $NH'$ and an organic ammonium cation. In some embodiments, the metal cation may be an alkali metal cation, such as $K^+$ or $Na^+$. In order to increase solubility and facilitate the reaction, in some embodiments, the organic ammonium cation is an ammonium cation formed by a tertiary amine or a quaternary ammonium cation, such as an ammonium cation formed by triethylamine or N,N-diisopropylethylamine. In some embodiments, the carboxylate is a triethylamine carboxylate or an N,N-diisopropylethylamine carboxylate.

In some embodiments, $R_4$ has the structure represented by (B9), (B10), (B9'), (B10'), (B11), (B12), (B11') or B(12'):

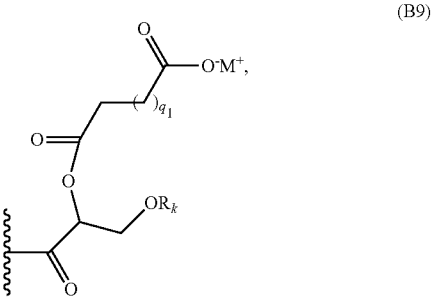

(B9)

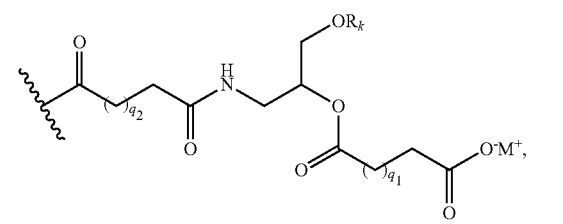

(B10)

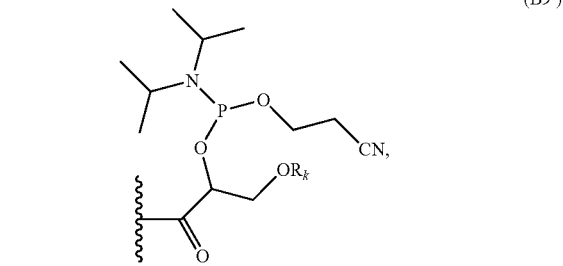

(B9')

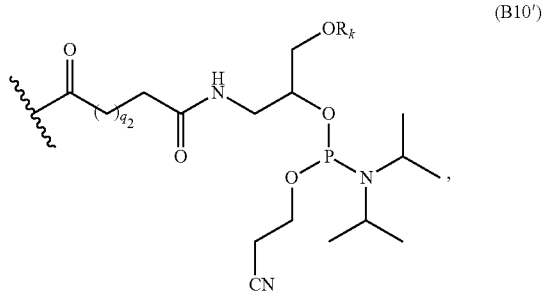

(B10')

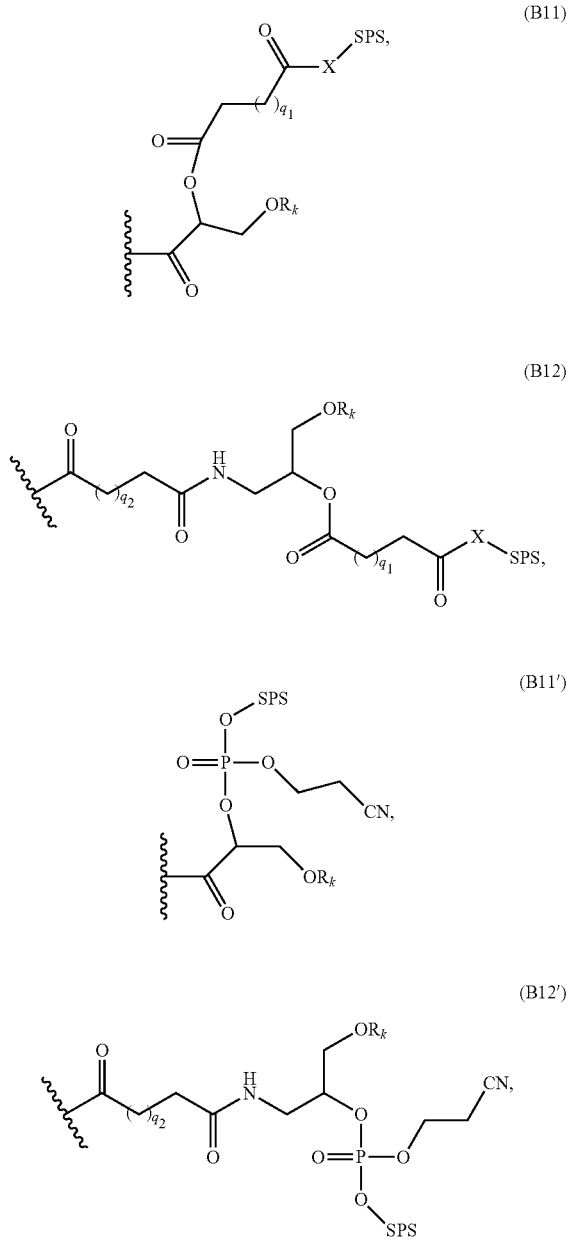

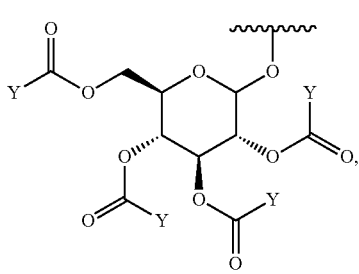

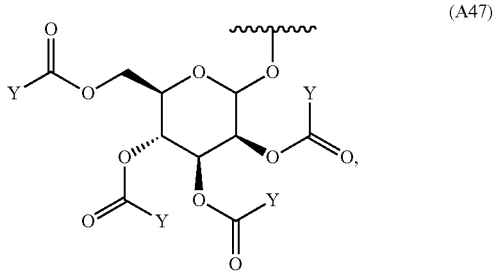

wherein $q_1$ is an integer of 1-4, $q_2$ is an integer of 1-10, X is O or NH, $M^+$ is a cation, $R_k$ is a hydroxy protecting group, SPS represents a solid phase support, and ⁓⁓⁓ represents the site where the group is linked to the rest of the molecule. In some embodiments, $q_1$ is 1 or 2. In some embodiments, $q_2$ is an integer of 1-5. In some embodiments, $R_4$ comprises a structure represented by Formula (B9) or (B10). In some embodiments, $R_4$ comprises a group represented by Formula (B11) or (B12). In some embodiments, $R_k$ is one or more of Tr (trityl), MMTr (4-methoxytrityl), DMTr (4,4'-dimethoxytrityl), and TMTr (4,4',4''-trimethoxytrityl). In some embodiments, $R_k$ may be DMTr, i.e. 4,4'-dimethoxytrityl.

$L_1$ is defined as above.

In some embodiments, $L_1$ is used to link the $M_1$ targeting group to the N atom on the nitrogenous backbone, thereby providing liver targeting function for the second siRNA conjugate. In some embodiments, $L_1$ comprises any one of Formulae A1-A26, and any combination thereof.

It will be readily understood by those skilled in the art that, as compared with the phosphoramidite solid phase synthesis method well-known in the art, the second siRNA conjugate in which the conjugating molecule is linked to any possible position of the nucleotide sequence can be obtained by using the first functional group and optional second functional group. For example, the conjugating molecule is linked to a terminal of the nucleotide sequence, and the conjugating molecule is linked to either terminal of the nucleotide sequence. Correspondingly, unless otherwise indicated, in the following description regarding conjugation preparation, when the reactions such as "deprotection", "coupling", "capping", "oxidation" and "sulfurization" are mentioned, it should be understood that the reaction conditions and agents involved in the phosphoramidite nucleotide solid phase synthesis well-known in the art would also apply to these reactions. Exemplary reaction conditions and agents would be detailed in the following text.

In some embodiments, each $S_1$ is independently a $M_1$. In some embodiments, each $S_1$ is independently a group formed by protecting at least one active hydroxyl group in $M_1$ with a hydroxyl protecting group. In some embodiments, each $S_1$ is independently a group formed by protecting all active hydroxyl groups in $M_1$ with hydroxyl protecting groups. In some embodiments, any hydroxyl protecting group known to a skilled one may be used to protect the active hydroxyl group in $M_1$. In some embodiments, the protected hydroxy is represented by the formula YCOO—, wherein each Y is independently selected from the group consisting of $C_1$-$C_{10}$ alkyl and $C_6$-$C_{10}$ aryl, which is optionally substituted with one or more substituents selected from the group consisting of halo and $C_1$-$C_6$ alkyl. In some embodiments, each Y is independently selected from the group consisting of methyl, trifluoromethyl, difluoromethyl, monofluoromethyl, trichloromethyl, dichloromethyl, monochloromethyl, ethyl, n-propyl, isopropyl, phenyl, halophenyl, and $C_1$-$C_6$ alkylphenyl.

In some embodiments, each $S_1$ is independently selected from the group consisting of Formulae A46-A54:

(A48) 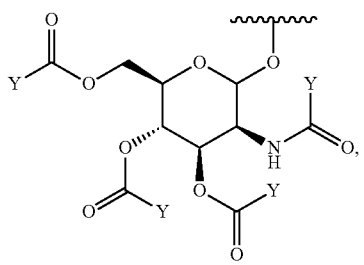

(A49) 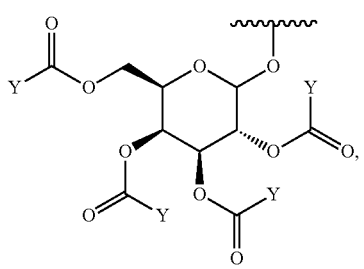

(A50) 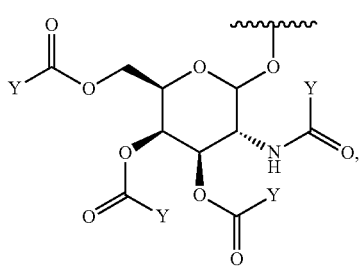

(A51) 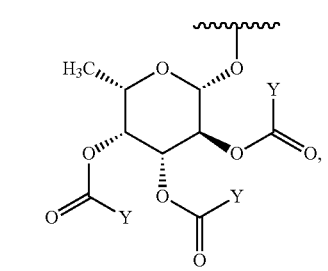

(A52) 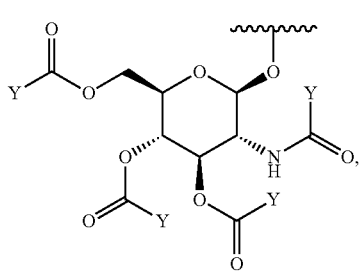

(A53) 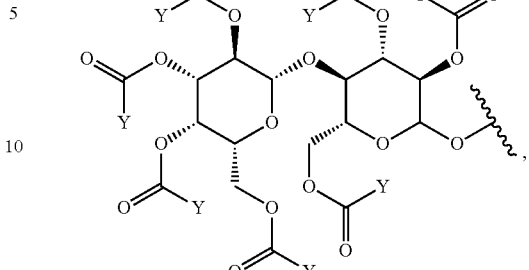

(A54) 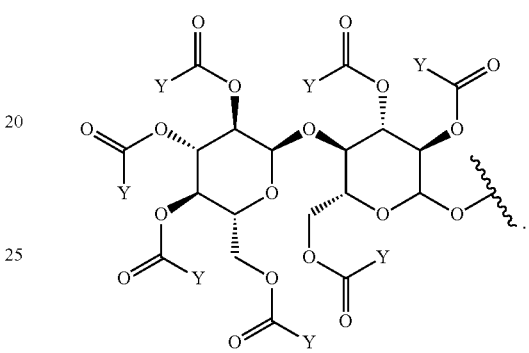

In some embodiments, $S_1$ is A49 or A50.

In some embodiments, each Y is independently selected from one of methyl, trifluoromethyl, difluoromethyl, monofluoromethyl, trichloromethyl, dichloromethyl, monochloromethyl, ethyl, n-propyl, isopropyl, phenyl, halophenyl, and alkylphenyl.

In some embodiments, Y is methyl.

As mentioned above, the method for preparing the second siRNA conjugate further comprises the following steps: synthesizing the other strand of the siRNA (for example, when a sense strand of the siRNA linked to a conjugating group is synthesized in the above step, the method further comprises synthesizing an antisense strand of the siRNA according to the solid phase synthesis method, vice versa), isolating the sense strand and the antisense strand, and annealing. In particular, in the step of isolating, the solid phase support linked to the nucleotide sequence and/or a conjugating molecule is cleaved, and meanwhile the necessary protecting group is removed (in this case, each $S_1$ group in the compound of Formula (321) is converted to the corresponding $M_1$ targeting group), to afford a sense strand (or an antisense strand) of the siRNA linked to a conjugating group and the corresponding antisense strand (or sense strand), wherein the sense strand and the antisense strand are annealed to form a double-strand RNA structure, thereby affording the second siRNA conjugate.

In some embodiments, the method for preparing the second siRNA conjugate comprises the following steps: contacting the compound represented by Formula (321) with the first nucleoside monomer at 3' terminal of the sense strand or the antisense strand under a coupling reaction condition in the presence of a coupling reagent, thereby linking the compound represented by Formula (321) to the first nucleotide in the sequence; successively linking nucleoside monomers in 3' to 5' direction to synthesize a sense or antisense strand of siRNA under the phosphoramidite solid phase synthesis conditions according to the kind and sequence of nucleotides in the desired sense or antisense strand, wherein, the compound of Formula (321) is a compound in which $R_4$ comprises a first functional group that comprises a protected hydroxy and a second functional group having the structure represented by Formula (C1') or (C3'), and the compound of (321) is deprotected before being linked to the first nucleoside monomer, and the linking of each nucleoside monomer comprising a four-step reaction of deprotection, coupling, capping, and oxidation or sulfurization, thus obtaining a sense or antisense strand of nucleotide linked to a conjugating group; successively linking nucleoside monomers in 3' to 5' direction to synthesize the antisense or sense strand of the nucleotide under the phosphoramidite solid phase synthesis conditions according to the kind and sequence of nucleotides in the sense or antisense strand, wherein the linking of each nucleoside monomer includes a four-step reaction of deprotection, coupling, capping, and oxidation or sulfurization; removing the protecting groups and cleaving the solid phase support; obtaining the sense strand and the antisense strand of nucleotide via isolation and purification; and annealing. In some embodiments, the method for preparing the second siRNA conjugate comprises the following steps: successively linking nucleoside monomers in 3' to 5' direction to synthesize the antisense and sense strand according to the kind and sequence of nucleotides in the sense or antisense strand of the double-strand siRNA, wherein the linking of each nucleoside monomer includes a four-step reaction of deprotection, coupling, capping, and oxidation or sulfurization, to obtain the sense strand linked to the solid phase support and the antisense strand linked to the solid phase support; contacting the compound represented by Formula (321) with the sense strand linked to the solid phase support or the antisense strand linked to the solid phase support under a coupling reaction condition in the presence of a coupling reagent, so as to link the compound represented by Formula (321) to the sense strand or antisense strand, wherein the compound represented by Formula (321) is a compound in which $R_4$ comprises a first functional group that is a phosphoramidite group; removing the protecting group and cleaving the solid phase support; obtaining the sense strand or the antisense strand of the siRNA via isolation and purification; and annealing, wherein the sense or antisense strand of the siRNA represented by Nu is linked to a conjugating group.

In some embodiments, the P atom in the Formula A59 is linked to the 3' terminal of the sense strand in the siRNA, and the method for preparing the second siRNA conjugate comprises:

(1) removing the hydroxyl protecting group $P_k$ in the compound of Formula (321) (wherein, the compound of Formula (321) is a compound wherein $R_4$ comprises a first functional group comprising a protected hydroxyl $OR_k$, and a second functional group having the structure represented by Formulas (C1') or (C3')); contacting the deprotected product with a nucleoside monomer to obtain a nucleoside monomer linked to a solid phase support via a conjugating molecule under a coupling reaction condition in the presence of a coupling reagent;

(2) synthesizing a sense strand of the siRNA in 3' to 5' direction by a phosphoramidite solid phase synthesis method, starting from the nucleoside monomer linked to a solid phase support via the conjugating molecule; and (3) synthesizing an antisense strand of the siRNA by a phosphoramidite solid phase synthesis method; and (4) isolating the sense strand and the antisense strand of the siRNA and annealing the same to obtain the second siRNA conjugate.

In particular, in step (1), the method for removing the protecting group $R_k$ in the compound represented by Formula (321) comprises contacting the compound of Formula (321) with a deprotection agent under a deprotection condition. The deprotection condition comprises a temperature of 0-50° C., and in some embodiments of 15-35° C., and a reaction time of 30-300 seconds, and in some embodiments of 50-150 seconds. The deprotection agent may be selected from one or more of trifluoroacetic acid, trichloroacetic acid, dichloroacetic acid, and monochloroacetic acid, and in some embodiments is dichloroacetic acid. The molar ratio of the deprotection agent to the compound represented by Formula (321) is 10:1 to 1000:1, and in some embodiments is 50:1 to 500:1.

The coupling reaction condition and the coupling agent may be any conditions and agents appropriate for the above coupling reaction. In some embodiments, the same condition and agent as the coupling reaction in the solid phase synthesis method employed can be used.

In some embodiments, the coupling reaction condition comprises a reaction temperature of 0-50° C., and in some embodiments, 15-35° C. The molar ratio of the compound of Formula (321) to the nucleoside monomer may be 1:1 to 1:50, and in some embodiments is 1:2 to 1:5. The molar ratio of the compound of Formula (321) to the coupling agent may be 1:1 to 1:50, and in some embodiments is 1:3 to 1:10. The reaction time may be 200-3000 seconds, and in some embodiments is 500-1500 seconds. The coupling agent may be selected from one or more of 1H-tetrazole, 5-ethylthio-1H-tetrazole and 5-benzylthio-1H-tetrazole, and in some embodiments is 5-ethylthio-1H-tetrazole. The coupling reaction may be performed in an organic solvent. The organic solvent may be selected from one or more of anhydrous acetonitrile, anhydrous DMF and anhydrous dichloromethane, and in some embodiments is anhydrous acetonitrile. The amount of the organic solvent may be 3-50 L/mol, and in some embodiments is 5-20 L/mol with respect to the compound represented by Formula (321).

In step (2), a sense strand S of the second siRNA conjugate is synthesized in 3' to 5' direction by the phosphoramidite solid phase synthesis method, starting from the nucleoside monomer linked to a solid phase support via a conjugating molecule prepared in the above steps. In this case, the conjugating group is linked to the 3' terminal of the resulting sense strand.

Other conditions for solid phase synthesis described in steps (2) and (3), including the deprotection condition for the nucleoside monomer, type and amount of the deprotection agent, the coupling reaction condition, type and amount of the coupling agent, the capping reaction condition, type and amount of the capping agent, the oxidation reaction condition, type and amount of the oxidation agent, the sulfuration reaction condition, and type and amount of the sulfuration agent, are various agents, amounts, and conditions conventionally used in the art.

In some embodiments, for example, the solid phase synthesis described in steps (2) and (3) may be performed by using the following conditions:

The deprotection condition for the nucleoside monomer comprises a temperature of 0-50° C., and in some embodiments, 15-35° C., and a reaction time of 30-300 seconds, and in some embodiments, 50-150 seconds. The deprotection agent may be selected from one or more of trifluoroacetic acid, trichloroacetic acid, dichloroacetic acid, and monochloroacetic acid, and in some embodiments is dichloroacetic acid. The molar ratio of the deprotection agent to the protecting group 4,4'-dimethoxytrityl on the solid phase support may be 2:1 to 100:1, and in some embodiments is 3:1 to 50:1. The coupling reaction condition comprises a temperature of 0-50° C., and in some embodiments, 15-35° C. The molar ratio of the nucleic acid sequence linked to the solid phase support to the nucleoside monomer may be 1:1 to 1:50, and in some embodiments is 1:5 to 1:15. The molar ratio of the nucleic acid sequence linked to the solid phase support to the coupling agent may be 1:1 to 1:100, and in some embodiments is 1:50 to 1:80. The reaction time and the coupling agent are selected as above.

The capping reaction condition comprises a temperature of 0-50° C., and in some embodiments, 15-35° C., and a reaction time of 5-500 seconds, and in some embodiments, 10-100 seconds. The capping agent is selected as above. The molar ratio of the total amount of the capping agent to the nucleic acid sequence linked to the solid phase support is 1:100 to 100:1, and in some embodiments is 1:10 to 10:1. In the case where equimolar acetic anhydride and N-methylimidazole are used as a capping agent, the molar ratio of acetic anhydride, N-methylimidazole, and the nucleic acid sequence linked to the solid phase support is 1:1:10-10:10:1, and in some embodiments is 1:1:2-2:2:1.

The oxidation reaction condition comprises a temperature of 0-50° C., and in some embodiments 15-35° C., and a reaction time of 1-100 seconds, and in some embodiments, 5-50 seconds. In some embodiments, the oxidation agent is iodine (and in some embodiments provided as iodine water). The molar ratio of the oxidation agent to the nucleic acid sequence linked to the solid phase support in the coupling step may be 1:1 to 100:1, and in some embodiments is 5:1 to 50:1. In some embodiments, the oxidation reaction is performed in a mixed solvent of tetrahydrofuran:water:pyridine=3:1:1-1:1:3. The sulfuration reaction condition comprises a temperature of 0-50° C., and in some embodiments, 15-35° C., and a reaction time of 50-2000 seconds, and in some embodiments, 100-1000 seconds. In some embodiments, the sulfuration agent is xanthane hydride. The molar ratio of the sulfuration agent to the nucleic acid sequence linked to the solid phase support in the coupling step is 10:1 to 1000:1, and in some embodiments is 10:1 to 500:1. In some embodiments, the sulfuration reaction is performed in a mixed solvent of acetonitrile:pyridine=1:3-3:1.

The method further comprises isolating the sense strand and the antisense strand of the siRNA after linking all nucleoside monomers and before the annealing. Methods for isolation are well known to those skilled in the art and generally comprise cleaving the synthesized nucleotide sequence from the solid phase support, removing the protecting groups on the bases, phosphate groups and ligands, purifying and desalting. The synthesized nucleotide sequence may be cleaved from the solid phase support, and the protecting groups on the bases, phosphate groups and ligands are removed, according to conventional cleavage and deprotection methods in the synthesis of siRNA. For example, the resulting nucleotide sequence linked to the solid phase support is contacted with concentrated aqueous ammonia; during deprotection, the protecting group YCOO— in groups A46-A54 is converted to a hydroxyl group, thus the $S_1$ groups are converted to corresponding $M_1$ groups, providing the conjugate represented by Formula (1). Here, the concentrated aqueous ammonia may be aqueous ammonia of a concentration of 25-30% by weight. The amount of the concentrated aqueous ammonia may be 0.2 ml/µmol-0.8 ml/µmol with respect to the target siRNA sequence.

When there is at least one 2'-TBDMS protection on the synthesized nucleotide sequence, the method further comprises contacting the nucleotide sequence removed from the solid phase support with triethylamine trihydrofluoride to remove the 2'-TBDMS protection. Here, the resulting target siRNA sequence comprises the corresponding nucleoside having a free 2'-hydroxy. The amount of pure triethylamine trihydrofluoride with respect to the target siRNA sequence may be 0.4 ml/µmol-1.0 ml/µmol. As such, the second siRNA conjugate may be obtained.

Methods for purification and desalting are well known to those skilled in the art. For example, nucleic acid purification may be performed by using a preparative ion chromatography purification column with a gradient elution of NaBr or NaCl; after collection and combination of the product, a reversed phase chromatography purification column may be used for desalting.

In the second siRNA conjugate, the non-bridging oxygen atom or sulfur atom in the phosphodiester bond or thiophosphate diester bond between the nucleotides substantially binds to a sodium ion, and the second siRNA conjugate is substantially present in the form of a sodium salt. Other forms of the second siRNA conjugate may be obtained by using a well-known ion exchange method in which said sodium ion is replaced with a hydrogen ion and/or another cation. The cation ion is described as above.

During synthesis, the purity and molecular weight of the nucleic acid sequence may be determined at any time, in order to control the synthesis quality more conveniently.

Such determination methods are well known to those skilled in the art. For example, the purity of the nucleic acid may be determined by ion exchange chromatography, and the molecular weight may be determined by liquid chromatography-mass spectrometry (LC-MS).

Methods for annealing are also well known to those skilled in the art. For example, the synthesized sense strand (S strand) and antisense strand (AS strand) may be simply mixed in water for injection in an equimolar ratio, heated to 70-95° C., and then cooled at room temperature to form a double stranded structure via hydrogen bond. As such, the second siRNA conjugate is thus obtained.

After obtaining the conjugate of the present disclosure, in some embodiments, the second siRNA conjugate thus synthesized may also be characterized by using a method such as LC-MS by the means such as molecular weight detection, to confirm that the synthesized siRNA conjugate is the second siRNA conjugate as a designed target and the synthesized siRNA sequence is the desired siRNA sequence, for example, is one of the sequences listed in Table 1.

The compound represented by Formula (321) is prepared by the following method comprising: contacting a compound represented by Formula (313) with a cyclic anhydride under esterification reaction condition in the presence of a base and an esterification catalyst in an organic solvent; ion exchanging and isolating the compound represented by Formula (321):

Formula (313)

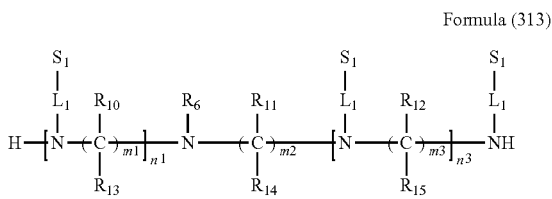

wherein the definitions and options of n1, n3, m1, m2, m3, $R_{10}$, $R_{11}$, $R_{12}$, $R_{13}$, $R_{14}$, $R_{15}$, $L_1$, $S_1$ are respectively described as above;

$R_6$ is a group for providing $R_4$ of Formula (321). In some embodiments, for example, $R_6$ has a structure represented by Formula (A61):

(A61)

wherein, $R_i$ is any group capable of linking to the N atom on the nitrogenous backbone, linking to $R_kO$ and linking to a free hydroxy group; $R_k$ is a hydroxy protecting group. In this case, a compound represented by Formula (321) is obtained, where $R_4$ comprises a first functional group as a hydroxy protecting group and a second functional group having the structure represented by Formula (C1) or (C2). The esterification reaction condition includes a reaction temperature of 0-100° C. and a reaction time of 8-48 hours. In some embodiments, the esterification reaction condition comprises a reaction temperature of 10-40° C. and a reaction time of 20-30 hours.

In some embodiments, the organic solvent comprises one or more of an epoxy solvent, an ether solvent, an haloalkane solvent, dimethyl sulfoxide, N,N-dimethylformamide, and N,N-diisopropylethylamine. In some embodiments, the epoxy solvent is dioxane and/or tetrahydrofuran, the ether solvent is diethyl ether and/or methyl tert-butyl ether, and the haloalkane solvent is one or more of dichloromethane, trichloromethane and 1,2-dichloroethane. In some embodiments, the organic solvent is dichloromethane. The amount of the organic solvent is 3-50 L/mol, and in some embodiments, 5-20 L/mol with respect to the compound represented by Formula (313).

In some embodiments, the cyclic anhydride is one of succinic anhydride, glutaric anhydride, adipic anhydride or pimelic anhydride, and in some embodiments is succinic anhydride. The molar ratio of the cyclic anhydride to the compound represented by Formula (313) is 1:1 to 10:1, and in some embodiments is 2:1 to 5:1. The esterification catalyst may be any catalyst capable of catalyzing the esterification, such as 4-dimethylaminopyridine. The molar ratio of the catalyst to the compound represented by Formula (313) is 1:1 to 10:1, and in some embodiments is 2:1 to 5:1. In some embodiments, the base may be any inorganic base, organic base or combination thereof. Considering the solubility as well as the product stability, the base may be, for example, an organic base of tertiary amine. In some embodiments, the organic base of tertiary amine is triethylamine or N,N-diisopropylethylamine. The molar ratio of the tertiary amine to the compound represented by Formula (313) is 1:1 to 20:1, and in some embodiments is 3:1 to 10:1.

The ion exchange serves to convert the compound represented by Formula (321) to a desired form of carboxylic acid or salt thereof. The method of ion exchange is well known to those skilled in the art, and the above conjugating molecule in which the cation is $M^+$ may be obtained by using suitable ion exchange solution and ion exchange condition, which is not described here in detail. In some embodiments, a triethylamine phosphate solution is employed in the ion exchange reaction. The concentration of the triethylamine phosphate solution is 0.2-0.8 M, and in some embodiments is 0.4-0.6 M. In some embodiments, the amount of the triethylamine phosphate solution is 3-6 L/mol, and in further embodiment is 4-5 L/mol with respect to the compound represented by Formula (313).

The compound represented by Formula (321) may be isolated from the reaction mixture using any suitable isolation method. In some embodiments, the compound represented by Formula (321) may be isolated by removal of solvent via evaporation followed by chromatography, for example, using the following two chromatographic conditions for the isolation: (1) normal phase purification of silica gel: 200-300 mesh silica gel filler, with gradient elution of 1 wt ‰ triethylamine-containing dichloromethane:methanol=100:18-100:20; or (2) reverse phase purification: C18 and C8 reverse phase filler, with gradient elution of methanol:acetonitrile=0.1:1-1:0.1. In some embodiments, the solvent may be removed directly to obtain a crude product of the compound represented by Formula (321), which may be used directly in subsequent reactions.

In some embodiments, the method for preparing the compound represented by Formula (321) further comprises: further contacting the product obtained from the above ion exchange with a solid phase support with an amino or hydroxy group under a condensation reaction condition in the presence of a condensing agent and an organic base of tertiary amine in an organic solvent. In this case, a compound represented by Formula (321) is obtained, wherein $R_4$ comprises a first functional group containing a hydroxy protecting group and a second functional group having a structure represented by Formula (C1').

The solid phase support is one of the supports used in solid phase synthesis of siRNA, some of which are well known to those skilled in the art. For example, the solid phase support may be selected from solid phase supports having an active hydroxy or amino functional group. In some embodiments, the solid phase support is an amino or hydroxy resin. In some embodiments, the amino or hydroxy resin has a particle size of 100-400 mesh, and surface amino or hydroxy loading of 0.2-0.5 mmol/g. The ratio of the compound represented by Formula (321) to the solid phase support is 10 μmol compound per gram of the solid phase support (μmol/g) to 400 μmol/g. In some embodiments, the ratio of compound of Formula (321) to the solid phase support is 50 μmol/g to 200 μmol/g.

The organic solvent may be any suitable solvent or mixture of solvents known to those skilled in the art. In some embodiments, the organic solvent is one or more of acetonitrile, an epoxy solvent, an ether solvent, an haloalkane solvent, dimethyl sulfoxide, N,N-dimethylformamide, and N,N-diisopropylethylamine. In some embodiments, the epoxy solvent is dioxane and/or tetrahydrofuran, the ether solvent is diethyl ether and/or methyl tert-butyl ether, the haloalkane solvent is one or more of dichloromethane, trichloromethane and 1,2-dichloroethane. In some embodiments, the organic solvent is acetonitrile. The amount of the organic solvent is 20-200 L/mol, in some embodiments is 50-100 L/mol with respect to the compound represented by Formula (321).

In some embodiments, the condensing agent may be benzotriazol-1-yl-oxytripyrrolidinophosphonium hexafluorophosphate, 3-diethoxyphosphoryl-1,2,3-benzotriazol-4 (3H)-one and/or O-benzotriazol-tetramethyluronium hexafluorophosphate. In some embodiments, the condensing agent is O-benzotriazol-tetramethyluronium hexafluorophosphate. The molar ratio of the condensing agent to the compound represented by Formula (321) is 1:1 to 20:1, and in further embodiments, 1:1 to 5:1.

In some embodiments, the organic base of tertiary amine is triethylamine and/or N,N-diisopropylethylamine, and in some embodiments is N,N-diisopropylethylamine. The molar ratio of the organic base of tertiary amine to the compound represented by Formula (321) is 1:1 to 20:1, and in some embodiments is 1:1 to 5:1.

In some embodiments, the method for preparing the compound represented by Formula (321) further comprises: contacting the obtained product of condensation reaction with a capping reagent and an acylation catalyst under a capping reaction condition in an organic solvent, and isolating the compound represented by Formula (321). The capping reaction serves to remove any active functional groups that are not completely reacted, so as to avoid unnecessary by-products in subsequent reactions. The capping reaction condition comprises a reaction temperature of 0-50° C., and in some embodiments, 15-35° C., and a reaction time of 1-10 hours, and in some embodiments, 3-6 hours. The capping reagent may be a capping reagent used in solid phase synthesis of siRNA, which are well known to those skilled in the art.

In some embodiments, the capping reagent is composed of capping reagent 1 (cap1) and capping reagent 2 (cap2). The capping reagent 1 is N-methylimidazole, and in some embodiments provided as a mixed solution of N-methylimidazole in pyridine/acetonitrile, wherein the volume ratio of pyridine to acetonitrile is 1:10 to 1:1, and in some embodiments is 1:3 to 1:1. The ratio of the total volume of pyridine and acetonitrile to the volume of N-methylimidazole is 1:1 to 10:1, and in some embodiments is 3:1 to 7:1. The capping reagent 2 is acetic anhydride. In some embodiments, the capping reagent 2 is provided as a solution of acetic anhydride in acetonitrile, wherein the volume ratio of acetic anhydride to acetonitrile is 1:1 to 1:10, and in further embodiments is 1:2 to 1:6.

In some embodiments, the ratio of the volume of the mixed solution of N-methylimidazole in pyridine/acetonitrile to the mass of the compound of Formula (321) is 5 ml/g-50 ml/g, and in some embodiments is 15 ml/g-30 ml/g. The ratio of the volume of the solution of acetic anhydride in acetonitrile to the mass of the compound of Formula (321) is 0.5 ml/g-10 ml/g, and in some embodiments is 1 ml/g-5 ml/g. In some embodiments, the capping reagent is equimolar acetic anhydride and N-methylimidazole. In some embodiments, the organic solvent is one or more of acetonitrile, an epoxy solvent, an ether solvent, an haloalkane solvent, dimethyl sulfoxide, N,N-dimethylformamide, and N,N-diisopropylethylamine. In some embodiments, the organic solvent is acetonitrile. In some embodiments, the amount of the organic solvent is 10-50 L/mol, and in some embodiments 5-30 L/mol with respect to the compound represented by Formula (321).

In some embodiments, the acylation catalyst may be selected from any catalyst that can be used for esterification condensation or amidation condensation, such as alkaline heterocyclic compounds. In some embodiments, the acylation catalyst is 4-dimethylaminopyridine. The ratio of the mass of the catalyst to the mass of the compound represented by Formula (321) may be 0.001:1 to 1:1, and in some embodiments is 0.01:1 to 0.1:1.

In some embodiments, the compound represented by Formula (321) may be isolated from the reaction mixture by any suitable isolation methods. In some embodiments, the compound of Formula (321) may be obtained by thoroughly washing with an organic solvent and filtering to remove unreacted reactants, excess capping reagent and other impurities, wherein the organic solvent is selected from acetonitrile, dichloromethane, or methanol, and in some embodiments is acetonitrile.

In some embodiments, the method for preparing the conjugating molecule represented by Formula (321) comprises contacting a compound represented by Formula (313) with a phosphorodiamidite under a coupling reaction condition in the presence of a coupling agent in an organic solvent, and isolating the compound represented by Formula (321). In this case, a compound represented by Formula (321) is obtained, wherein $R_4$ comprises a first functional group containing a hydroxy protecting group and a second functional group comprising the structure represented by Formula (C3). In some embodiments, the coupling reaction condition comprises a reaction temperature of 0-50° C., such as 15-35° C. The molar ratio of the compound of Formula (313) to the phosphorodiamidite may be 1:1 to 1:50, such as 1:5 to 1:15. The molar ratio of the compound of Formula (313) to the coupling agent may be 1:1 to 1:100, such as 1:50 to 1:80. The reaction time may be 200-3000 seconds, for example, 500-1500 seconds. The phosphorodiamidite may be, such as bis(biisopropylamino)(2-cyanoethoxy)phosphine, which may be commercially available or prepared according to methods well-known in the art. The coupling agent is selected from one or more of 1H-tetrazole, 5-ethylthio-1H-tetrazole and 5-benzylthio-1H-tetrazole, such as 5-ethylthio-1H-tetrazole. The coupling reaction may be performed in an organic solvent. The organic solvent is selected from one or more of anhydrous acetonitrile, anhydrous DMF and anhydrous dichloromethane, for example, anhydrous acetonitrile. In some embodiments, the amount of the organic solvent may be 3-50 L/mol, such as 5-20 L/mol with respect to the compound represented by Formula (313). By the coupling reaction, the hydroxy group in the compound (313) reacts with the phosphorodiamidite to form a phosphoramidite group. In some embodiments, the solvent may be removed directly to obtain a crude product of the compound represented by Formula (321), which may be used directly in subsequent reactions.

In some embodiments, the method for preparing the compound represented by Formula (321) further comprises the following steps: further contacting the isolated product with a solid phase support with hydroxy group(s) under a coupling reaction condition in the presence of a coupling agent in an organic solvent, followed by capping, oxidation, and isolation, to obtain the compound represented by Formula (321), wherein $R_4$ comprises a first functional group containing a hydroxy protecting group and a second functional group having the structure represented by Formula (C3').

In some embodiments, the solid phase support is a solid phase support used in solid phase synthesis of nucleic acid, such as a deprotected universal solid phase support, which is commercially available (such as NittoPhase®HL UnyLinker™ 300 Oligonucleotide Synthesis Support, Kinovate Life Sciences, represented by Formula B80):

(B80)

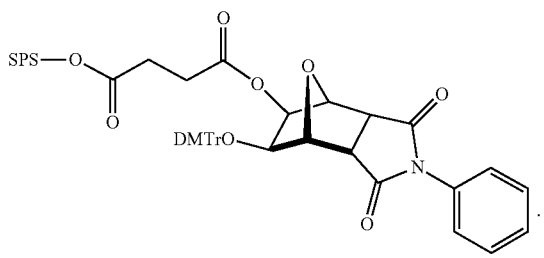

A deprotection reaction is well known in the art. In some embodiments, the deprotection condition comprises a temperature of 0-50° C., such as 15-35° C., and a reaction time of 30-300 seconds, such as 50-150 seconds. The deprotection agent may be selected from one or more of trifluoroacetic acid, trichloroacetic acid, dichloroacetic acid, and monochloroacetic acid, and in some embodiments is dichloroacetic acid. The molar ratio of the deprotection agent to the protecting group -DMTr (4,4'-dimethoxytrityl) on the solid phase support may be 2:1 to 100:1, such as 3:1 to 50:1. By such deprotection, reactive free hydroxy groups are obtained on the surface of the solid phase support, for facilitating the subsequent coupling reaction.

The coupling reaction condition and the coupling agent may be selected as above. By such coupling, the free hydroxy group formed in the deprotection reacts with the phosphoramidite group, so as to form a phosphite ester linkage.

In some embodiments, the capping reaction condition comprises a temperature of 0-50° C., such as 15-35° C., and a reaction time of 5-500 seconds, such as 10-100 seconds. The capping reaction is performed in the presence of capping agent. The selection and the amount of the capping agent may be described above.

The oxidation reaction condition may comprise a temperature of 0-50° C., such as 15-35° C., and a reaction time of 1-100 seconds, such as 5-50 seconds. The oxidation agent may be, for example, iodine (in some embodiments, provided as iodine water). In some embodiments, the molar ratio of the oxidation agent to the phosphite group is 1:1 to 100:1, for example, 5:1 to 50:1. In some embodiments, the oxidation reaction is performed in a mixed solvent of tetrahydrofuran:water:pyridine=3:1:1-1:1:3.

In some embodiments, $R_6$ is B7 or B8:

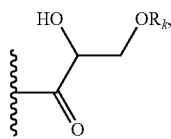
(B7)

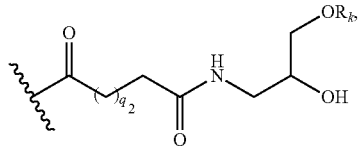
(B8)

wherein $q_2$ is defined as above.

In this case, the compound of Formula (313) may be obtained by the following preparation method comprising: contacting the compound represented by Formula (314) with a compound represented by Formula (A-1) or (A-2) under an amidation reaction condition in the presence of an condensing agent for amidation reaction and an organic base of tertiary amine, in an organic solvent, and followed by isolation:

Formula (314)

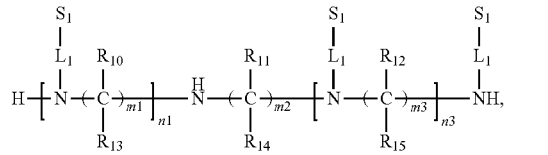

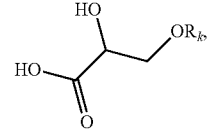
(A-1)

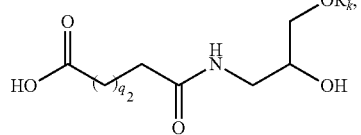
(A-2)

wherein, the definitions and options of n1, n3, m1, m2, m3, $R_{10}$, $R_{11}$, $R_{12}$, $R_{13}$, $R_{14}$, $R_{15}$, $L_1$, $S_1$, $q_2$ and $R_k$ are respectively described above.

The amidation reaction condition may comprise a reaction temperature of 0-100° C. and a reaction time of 1-48 hours. In some embodiments, the amidation reaction condition is a reaction temperature of 10-40° C. and a reaction time of 2-16 hours. In some embodiments, the organic solvent is one or more of an alcohol solvent, an epoxy solvent, an ether solvent, an haloalkane solvent, dimethyl sulfoxide, N,N-dimethylformamide, and N,N-diisopropylethylamine. In some embodiments, the alcohol solvent is one or more of methanol, ethanol and propanol, and in some embodiments is ethanol. In some embodiments, the epoxy solvent is dioxane and/or tetrahydrofuran. In some embodiments, the ether solvent is diethyl ether and/or methyl tert-butyl ether. In some embodiments, the haloalkane solvent is one or more of dichloromethane, trichloromethane and 1,2-dichloroethane. In some embodiments, the organic solvent is dichloromethane. The amount of the organic solvent is 3-50 L/mol, and in further embodiments is 3-20 L/mol with respect to the compound represented by Formula (314).

In some embodiments, the condensing agent for amidation reaction is benzotriazol-1-yl-oxytripyrrolidinophosphonium hexafluorophosphate, 3-(diethoxyphosphoryloxy)-1,2,3-benzotrizin-4(3H)-one, 4-(4,6-dimethoxytriazin-2-yl)-4-methylmorpholine hydrochloride, 2-ethoxy-1-ethoxycarbonyl-1,2-dihydroquinoline (EEDQ) or O-benzotriazol-tetramethyluronium hexafluorophosphate, and in further embodiments is 3-(diethoxyphosphoryloxy)-1,2,3-benzotrizin-4(3H)-one. The molar ratio of the condensing agent for amidation reaction to the compound represented by Formula (314) may be 1:1 to 10:1, and in some embodiments is 2.5:1 to 5:1.

In some embodiments, the organic base of tertiary amine is triethylamine or N,N-diisopropylethylamine, and in further embodiments is N,N-diisopropylethylamine. The molar ratio of the organic base of tertiary amine to the compound represented by Formula (314) may be 3:1 to 20:1, and in some embodiments is 5:1 to 10:1.

In some embodiments, the compounds of Formulae (A-1) and (A-2) may be prepared by any suitable means. For example, when $R_k$ is a DMTr group, the compound of Formula (A-1) may be prepared by reacting calcium glycerate with DMTrCl. Similarly, the compound of Formula (A-2) may be prepared by firstly contacting 3-amino-1,2-propanediol with a cyclic anhydride which may have 4-13 carbon atoms, and in some embodiments 4-8 carbon atoms, followed by reacting with DMTrCl. It will be readily understood by those skilled in the art that the selection of different cyclic anhydride corresponds to different values for $q_2$ in the compound of Formula (A-2). For example, when the cyclic anhydride is succinic anhydride, $q_2=1$; when the cyclic anhydride is glutaric anhydride, $q_2=2$, and so on.

In some variations, the compound of Formula (313) can also be prepared by successively reacting the compound represented by Formula (314) with the cyclic anhydride, 3-amino-1,2-propanediol, and DMTrCl. It will be readily understood by those skilled in the art that these variations would not affect the structure and function(s) of the compound of Formula (313), and these variations are readily achieved by those skilled in the art on the basis of the above methods.

Similarly, the compound represented by Formula (313) may be isolated from the reaction mixture by any suitable isolation methods. In some embodiments, the compound represented by Formula (313) may be isolated by removal of solvent via evaporation followed by chromatography. For example, the following two sets of chromatographic conditions may be employed for isolation, (1) normal phase purification of silica gel: 200-300 mesh silica gel filler, with gradient elution of petroleum ether:ethylacetate:dichloromethane:N,N-dimethylformamide=1:1:1:0.5-1:1:1:0.6; and (2) reverse phase purification: C18 and C8 reverse phase fillers, with gradient elution of methanol:acetonitrile=0.1:1-1:0.1. In some embodiments, the solvent may be removed directly to obtain a crude product of the compound represented by Formula (313), which may be directly used in subsequent reactions.

In some embodiments, the compound represented by Formula (314) may be obtained by the following preparation method comprising: contacting the compound represented by Formula (315) with haloacetic acid under a deprotection reaction condition in an organic solvent, and followed by isolation:

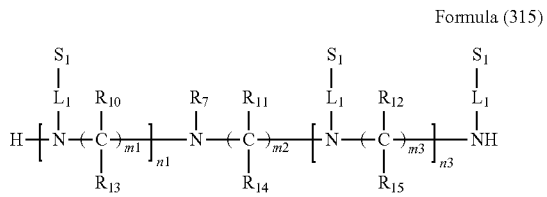

Formula (315)

wherein, $R_7$ is selected from the group represented by Formula (330), (331), (332) or (333), and in some embodiments, $R_7$ has the structure represented by Formula (330):

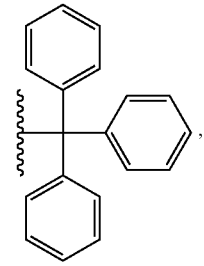

Formula (330)

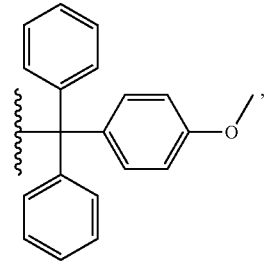

Formula (331)

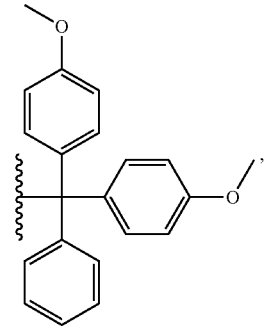

Formula (332)

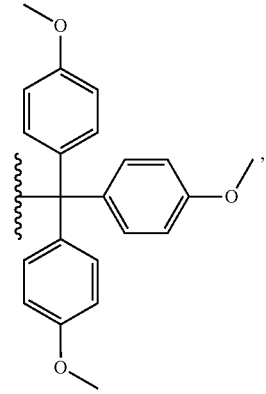

Formula (333)

wherein the definitions and options of n1, n3, m1, m2, m3, $R_{10}$, $R_{11}$, $R_{12}$, $R_{13}$, $R_{14}$, $R_{15}$, $L_1$ and $S_1$ are respectively described as above.

The haloacetic acid may be selected from one or more of dichloroacetic acid, trichloroacetic acid, monochloroacetic acid and trifluoroacetic acid, and in some embodiments is dichloroacetic acid.

The deprotection reaction condition may comprise a reaction temperature of 0-100° C. and a reaction time of 0.1-24 hours, and in some embodiments comprises a reaction temperature of 10-40° C. and a reaction time of 0.5-16 hours.

In some embodiments, the organic solvent is one or more of an epoxy solvent, an ether solvent, an haloalkane solvent, dimethyl sulfoxide, N,N-dimethylformamide, and N,N-diisopropylethylamine. In some embodiments, the epoxy solvent is dioxane and/or tetrahydrofuran. In some embodiments, the ether solvent is diethyl ether and/or methyl tert-butyl ether. In some embodiments, the haloalkane solvent is one or more of dichloromethane, trichloromethane and 1,2-dichloroethane. In some embodiments, the organic solvent is dichloromethane. The amount of the organic solvent is 3-50 L/mol, and in further embodiments 5-20 L/mol with respect to the compound represented by Formula (315).

The molar ratio of the haloacetic acid to the compound represented by Formula (315) may be 5:1 to 100:1, and in some embodiments is 10:1 to 50:1.

Similarly, the compound represented by Formula (314) may be isolated from the reaction mixture by any suitable isolation method. In some embodiments, the compound represented by Formula (314) may be isolated by removal of solvent via evaporation followed by chromatography, for example, using the following two sets of chromatographic conditions for isolation: (1) normal phase purification of silica gel: 200-300 mesh silica gel filler, with gradient elution of dichloromethane:methanol=100:30-100:40; and (2) reverse phase purification: C18 and C8 reverse phase fillers, with gradient elution of methanol:acetonitrile=0.1:1-1:0.1. In some embodiments, the solvent may be removed directly to obtain a crude product of the compound represented by Formula (314), which may be directly used in subsequent reactions. The compound represented by Formula (315) may be obtained by the following preparation method comprising: contacting the compound represented by Formula (317) with the compound represented by Formula (316) under a condensation reaction condition in the presence of a condensing agent for amidation reaction and an organic base of tertiary amine, in an organic solvent, and followed by isolation:

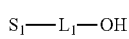
Formula (316)

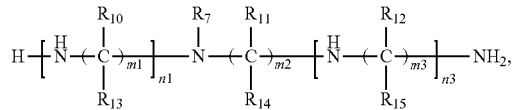
Formula (317)

wherein the definitions and options of n1, n3, m1, m2, m3, $R_7$, $R_{10}$, $R_{11}$, $R_{12}$, $R_{13}$, $R_{14}$, $R_{15}$, $L_1$ and $S_1$ are respectively described as above.

The compound of Formula (316) may be compounds disclosed in J. Am. Chem. Soc. 2014, 136, 16958-16961. Alternatively, the compound of Formula (316) may be prepared by those skilled in the art by various methods. For example, some compounds of Formula (316) may be prepared according to the disclosed method in Example 1 of U.S. Pat. No. 8,106,022 B2, which is incorporated herein by reference in its entirety.

In some embodiments, the condensation reaction condition comprises a reaction temperature of 0-100° C. and a reaction time of 0.1-24 hours. In some embodiments, the reaction temperature is 10-40° C. and the reaction time is 0.5-16 hours. The molar ratio of the compound represented by Formula (316) to the compound represented by Formula (317) may be 2:1 to 10:1, and in some embodiments is 2.5:1 to 5:1.

In some embodiments, the organic solvent is one or more of acetonitrile, an epoxy solvent, an ether solvent, an haloalkane solvent, dimethyl sulfoxide, N,N-dimethylformamide and N,N-diisopropylethylamine. In some embodiments, the epoxy solvent is dioxane and/or tetrahydrofuran. In some embodiments, the ether solvent is diethyl ether and/or methyl tert-butyl ether. In some embodiments, the haloalkane solvent is one or more of dichloromethane, trichloromethane and 1,2-dichloroethane. In some embodiments, the organic solvent is acetonitrile. The amount of the organic solvent may be 3-50 L/mol, and in some embodiments is 5-20 L/mol with respect to the compound represented by Formula (317).

In some embodiments, the condensing agent for amidation reaction is benzotriazol-1-yl-oxytripyrrolidinophosphonium hexafluorophosphate, 3-(diethoxyphosphoryloxy)-1,2,3-benzotrizin-4(3H)-one (DEPBT), O-benzotriazoltetramethyluronium hexafluorophosphate or 4-(4,6-dimethoxytriazin-2-yl)-4-methylmorpholine hydrochloride, and in further embodiments is 4-(4,6-dimethoxytriazin-2-yl)-4-methylmorpholine hydrochloride. The molar ratio of the condensing agent for amidation reaction to the compound represented by Formula (317) may be 2:1 to 10:1, and in some embodiments is 2.5:1 to 5:1.

The organic base of tertiary amine may be N-methylmorpholine, triethylamine or N,N-diisopropylethylamine, and in some embodiments is N-methylmorpholine. The molar ratio of the organic base of tertiary amine to the compound represented by Formula (317) may be 3:1 to 20:1, and in some embodiments is 5:1 to 10:1. Similarly, the compound represented by Formula (315) may be isolated from the reaction mixture by any suitable isolation method. In some embodiments, the compound represented by Formula (315) is isolated by removal of solvent via evaporation followed by chromatography, for example, using the following two sets of chromatographic conditions for isolation: (1) normal phase purification of silica gel: 200-300 mesh silica gel filler, with gradient elution of dichloromethane:methanol=100:5-100:7; (2) reverse phase purification: C18 and C8 reverse phase fillers, with gradient elution of methanol:acetonitrile=0.1:1-1:0.1. In some embodiments, the solvent may be removed directly to obtain a crude product of the compound represented by Formula (315), which may be used directly in subsequent reactions. In some embodiments, the compound of Formula (317) is reacted with a sufficient amount of one compound of Formula (316) in one batch to obtain the desired compound of Formula (315), wherein all $S_1$-$L_1$ moieties are identical. In some embodiments, the compound of Formula (317) is reacted in batches with different compounds of Formula (316), i.e., the compounds of Formula (316) having different $L_1$ and/or $S_1$, as desired, so as to obtain the compound of Formula (315) having two or more types of $S_1$ and/or $L_1$ therein. For example, 1 eq of the compound of Formula (317) may be firstly contacted with 2 eq of a first compound of Formula (316) so that a first $S_1$-$L_1$ moiety is linked to the two terminal primary amine groups in the compound of Formula (317), and then contacted with the (n3+n1-1) eq of a second compound of Formula (316) so that a second $S_1$-$L_1$ moiety is linked to the (n3+n1-1) secondary amine groups (wherein the definition and scope of n3 and n1 are defined above) in the compound of Formula (317).

In some embodiments, the compound represented by Formula (317) may be obtained by the following preparation method comprising: contacting the compound represented by Formula (318) with methylamine aqueous solution under a deprotection reaction condition in the presence of an organic solvent, and follow by isolation:

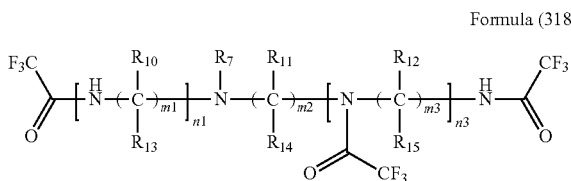

Formula (318)

wherein the definitions and options of n1, n3, m1, m2, m3, $R_7$, $R_{10}$, $R_{11}$, $R_{12}$, $R_{13}$, $R_{14}$ and $R_{15}$ are respectively defined above.

The deprotection reaction condition may comprise a reaction temperature of 0-150° C. and a reaction time of 5-72 hours, and in some embodiments comprises a reaction temperature of 20-80° C. and a reaction time of 10-30 hours.

The organic solvent may be selected from alcohols, and in some embodiments is one of methanol, ethanol and isopropanol, and in further embodiments is methanol. The amount of the organic solvent may be 1-20 L/mol, and in some embodiments is 1.5-10 L/mol with respect to the compound represented by Formula (318).

The concentration of the methylamine aqueous solution may be 30%-40% by mass, and the molar ratio of methylamine to the compound represented by Formula (318) may be 10:1 to 500:1, and in some embodiments is 50:1 to 200:1.

Similarly, the compound represented by Formula (317) may be isolated from the reaction mixture using any suitable isolation method. In some embodiments, the compound represented by Formula (317) may be isolated by removal of solvent via evaporation followed by chromatography, for example, using the following two sets of chromatographic conditions for isolation: (1) normal phase purification of silica gel: 200-300 mesh silica gel filler, with gradient elution of dichloromethane:methanol:aqueous ammonia (25 wt %)=1:1:0.05-1:1:0.25; and (2) reverse phase purification: C18 and C8 reverse phase fillers, with gradient elution of methanol:acetonitrile=0.1:1-1:0.1. In some embodiments, the solvent may be removed directly to obtain a crude product of the compound represented by Formula (317), which may be used directly in subsequent reactions.

The compound represented by Formula (318) may be obtained by the following preparation method comprising: contacting the compound represented by Formula (319) with triphenylchloromethane (TrCl), diphenylethylphenylchloromethane, phenyldiethylphenylchloromethane or triethylphenylchloromethane, and in some embodiments with triphenylchloromethane (TrCl), under a substitution reaction condition in the presence of an organic solvent, and followed by isolation:

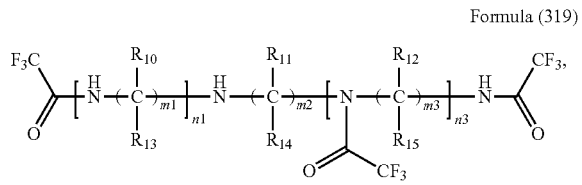

Formula (319)

wherein the definitions and options of n1, n3, m1, m2, m3, $R_{10}$, $R_{11}$, $R_{12}$, $R_{13}$, $R_{14}$ and $R_{15}$ are respectively defined as above.

The substitution reaction condition may comprise a reaction temperature of 0-100° C. and a reaction time of 5-72 hours, and in some embodiments comprises a reaction temperature of 10-40° C. and a reaction time of 10-30 hours.

Triphenylchloromethane (TrCl), diphenylethylphenylchloromethane, phenyldiethylphenylchloromethane or triethylphenylchloromethane are commercially available. The molar ratio of triphenylchloromethane (TrCl), diphenylethylphenylchloromethane, phenyldiethylphenylchloromethane or triethylphenylchloromethane to the compound represented by Formula (319) may be 1:1 to 10:1, and in some embodiments is 1:1 to 3:1.

The organic solvent may be one or more of an epoxy solvent, an ether solvent, an haloalkane solvent, dimethyl sulfoxide, N,N-dimethylformamide, and N,N-diisopropylethylamine. In some embodiments, the epoxy solvent is dioxane and/or tetrahydrofuran. In some embodiments, the ether solvent is diethyl ether and/or methyl tert-butyl ether. In some embodiments, the haloalkane solvent is one or more of dichloromethane, trichloromethane and 1,2-dichloroethane. In some embodiments, the organic solvent is dichloromethane. The amount of the organic solvent may be 3-50 L/mol, and in some embodiments is 5-20 L/mol with respect to the compound represented by Formula (319).

Similarly, the compound represented by Formula (318) may be isolated from the reaction mixture by any suitable isolation method. In some embodiments, the compound represented by Formula (318) may be isolated by removal of solvent via evaporation followed by chromatography, for example, using the following two sets of chromatographic conditions for isolation: (1) normal phase purification of silica gel: 200-300 mesh silica gel filler, with gradient elution of methanol:dichloromethane=0.01:1-0.5:1 or gradient elution of methanol:dichloromethane:ethyl acetate:petroleum ether=0.1:1:1:1-1:1:1:1; and (2) reverse phase purification: C18 and C8 reverse phase fillers, with gradient elution of methanol:acetonitrile=0.1:1-1:0.1. In some embodiments, the solvent may be removed directly to obtain a crude product of the compound represented by Formula (318), which may be used directly in subsequent reactions.

In some embodiments, the compound represented by Formula (319) may be obtained by the following preparation method comprising: contacting the compound represented by Formula (320) with ethyl trifluoroacetate under a substitution reaction condition in an organic solvent, and followed by isolation:

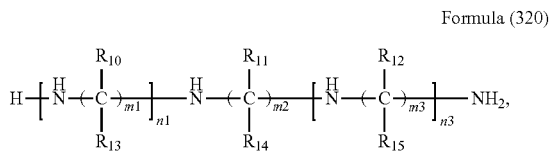

Formula (320)

wherein the definitions and options of n1, n3, m1, m2, m3, $R_{10}$, $R_{11}$, $R_{12}$, $R_{13}$, $R_{14}$ and $R_{15}$ are respectively defined as above.

In some embodiments, the organic solvent is one or more of acetonitrile, an epoxy solvent, an ether solvent, an haloalkane solvent, dimethyl sulfoxide, N,N-dimethylformamide, and N,N-diisopropylethylamine. In some embodiments, the epoxy solvent is dioxane and/or tetrahydrofuran. In some embodiments, the ether solvent is diethyl ether and/or methyl tert-butyl ether. In some embodiments, the haloalkane solvent is one or more of dichloromethane, trichloromethane and 1,2-dichloroethane. In some embodiments, the organic solvent is acetonitrile. The amount of the organic solvent may be 1-50 L/mol, and in some embodiments is 1-20 L/mol with respect to the compound represented by Formula (320).

The substitution reaction condition may comprise a reaction temperature of 0-100° C. and a reaction time of 5-72 hours, and in some embodiments comprises a reaction temperature of 10-40° C. and a reaction time of 10-30 hours.

The compound represented by Formula (320) may be commercially purchased, or obtained by methods known to the skilled in the art. For example, in the case that m1=m2=m3=3, n1=1, n3=2, and each of $R_{10}$, $R_{11}$, $R_{12}$, $R_{13}$, $R_{14}$ and $R_{15}$ is H, the compound represented by Formula (320) is commercially available from Alfa Aesar Inc.

The molar ratio of ethyl trifluoroacetate to the compound represented by Formula (320) may be 2:1 to 10:1, and in some embodiments is 3:1 to 5:1.

Similarly, the compound represented by Formula (319) may be isolated from the reaction mixture using any suitable isolation method. In some embodiments, the compound represented by Formula (319) may be isolated by removal of solvent via evaporation followed by chromatography, for example, using the following two sets of chromatographic conditions for isolation: (1) normal phase purification of silica gel: 200-300 mesh silica gel filler, with gradient elution of methanol:dichloromethane=0.01:1-0.5:1 or gradient elution of methanol:dichloromethane:ethyl acetate:petroleum ether=0.1:1:1:1-1:1:1:1; and (2) reverse phase purification: C18 and C8 reverse phase fillers, with gradient elution of methanol:acetonitrile=0.1:1-1:0.1. In some embodiments, the solvent may be removed directly to obtain a crude product of the compound represented by Formula (319), which may be used directly in subsequent reactions.

For the first or second siRNA conjugate of the present disclosure, it may also be used in combination with other pharmaceutically acceptable excipients, which may be one or more of various formulations or compounds conventionally employed in the art. Please see the above description of the pharmaceutical composition of the present disclosure for details.

Use of the Modified siRNA, the Pharmaceutical Composition Comprising siRNA, the First siRNA Conjugate and the Second siRNA Conjugate of the Present Disclosure In some embodiments, the present disclosure provides the use of the modified siRNA, the pharmaceutical composition, the first siRNA conjugate and/or the second siRNA conjugate in the preparation of a medicament for treating and/or preventing dyslipidemia caused by overexpression of apolipoprotein C3 (ApoC3).

In some embodiments, the present disclosure provides a method for treating dyslipidemia caused by overexpression of apolipoprotein C3 (ApoC3), wherein the method comprises administering an effective amount of the modified siRNA, the pharmaceutical composition, the first siRNA conjugate and/or the second siRNA conjugate of the present disclosure to a subject.

The purpose of treating dyslipidemia may be achieved through the mechanism of RNA interference by administering the siRNA active ingredient to a subject in need thereof. Therefore, the modified siRNA, the pharmaceutical composition, the first siRNA conjugate and/or the second siRNA conjugate of the present disclosure may be used for preventing and/or treating dyslipidemia, or for preparing a medicament for preventing and/or treating dyslipidemia.

The dyslipidemia refers to abnormal blood lipid caused by over-expression of APOC3 gene in hepatocytes, and generally manifests itself as increased level(s) of any one or more of lipids such as triglyceride and cholesterol and/or lipoprotein in blood. A high level of blood lipid is highly associated with hypertension, cardiovascular disease, diabetes and other pathological conditions. Hypertriglyceridemia is related to atherosclerosis, and would lead to pancreatitis. The dyslipidemia of the present disclosure includes, but not limited to, hypercholesteremia, hypertriglyceridemia or atherosclerosis.

As used herein, the term "administration/administrate" refers to placing the modified siRNA, the pharmaceutical composition, the first siRNA conjugate and/or the second siRNA conjugate into a subject by a method or route that at least partly locates the modified siRNA, the pharmaceutical composition, the first siRNA conjugate and/or the second siRNA conjugate of the present disclosure at a desired site to achieve a desired effect. The administration routes suitable for the method of the present disclosure include topical administration and systemic administration. In general, topical administration results in the delivery of more the modified siRNA, the pharmaceutical composition, the first siRNA conjugate and/or the second siRNA conjugate of the present disclosure to a particular site as compared to the whole body of the subject; while systemic administration results in the delivery of the modified siRNA, the pharmaceutical composition, the first siRNA conjugate and/or the second siRNA conjugate of the present disclosure to basically the whole body of the subject. Considering that the present disclosure is intended to provide means for the prevention and/or treatment of dyslipidemia, in some embodiments, an administration mode that can deliver drugs to the liver is employed.

The administration to a subject may be achieved by any suitable route known in the art, including, but is not limited to, oral or parenteral route, including intravenous administration, intramuscular administration, subcutaneous administration, transdermal administration, endrotracheal administration (aerosol), pulmonary administration, nasal administration, rectal administration and topical administration (including buccal administration and sublingual administration). The administration frequency may be once or more times daily, weekly, biweekly, monthly, or yearly. The used dosage of the siRNA, the pharmaceutical composition, the first siRNA conjugate and/or the second siRNA conjugate of the present disclosure may be a conventional dose in the art, which may be determined according to various parameters, especially the age, weight and gender of the subject. Toxicity and therapeutic efficacy can be determined by standard pharmaceutical procedures in cell cultures or experimental animals, e.g., by determining LD50 (the dose that is lethal to 50% of the population) and ED50 (the dose that can cause 50% of the maximum response intensity in the quantitative response, or the dose that can cause a positive response in 50% of the experimental subjects in the qualitative response). The dose range for human may be derived based on the data obtained from cell culture assays and animal studies.

When administrating the siRNA, the pharmaceutical composition, the first siRNA conjugate and/or the second siRNA conjugate of the present disclosure is administered, for example, to C57BL/6J mice having a weight of 18 to 25 g or to ob/ob mice having a weight of 30 to 45 g, either male or female, with an age of 6 to 12 weeks, on the basis of the amount of the siRNA: (i) for the first siRNA conjugate and/or the second siRNA conjugate, the dose of siRNA thereof may be from 0.001 to 100 mg/kg body weight, in further embodiments 0.01 to 50 mg/kg body weight, in more further embodiments from 0.05 to 20 mg/kg body weight, and in still more further embodiments from 0.1 to 10 mg/kg body weight; (ii) for a pharmaceutical composition formed from a siRNA and a pharmaceutically acceptable support, the dosage of siRNA thereof may be from 0.001 to 50 mg/kg body weight, in further embodiments from 0.01 to 10 mg/kg body weight, in more further embodiments from 0.05 to 5 mg/kg body weight, and in still more further embodiments from 0.1 to 3 mg/kg body weight.

In some embodiments, the present disclosure provides a method of inhibiting the expression of apolipoprotein C3 (ApoC3) gene in hepatocytes, which comprises contacting an effective amount of the modified siRNA, the pharmaceutical composition, the first siRNA conjugate and/or the second siRNA conjugate of the present disclosure with the hepatocytes, and introducing the modified siRNA, the pharmaceutical composition, the first siRNA conjugate and/or the second siRNA conjugate of the present disclosure into the hepatocytes, so as to achieve the object of inhibiting the expression of APOC3 gene in hepatocytes through the mechanism of RNA interference. The hepatocytes may be selected from hepatoma cell lines such as Hep3B, HepG2 or Huh7, and isolated liver primary cells. In some embodiments, the hepatocytes are Huh7 hepatoma cells.

In the case where the expression of APOC3 gene in a cell is inhibited by using the method of the present disclosure, the amount of siRNA in the modified siRNA, the pharmaceutical composition, the first siRNA conjugate and/or the second siRNA conjugate of the present disclosure is generally an amount sufficient to reduce the expression of the target gene and result in an extracellular concentration of 1 pM to 1 μM, or 0.01 nM to 100 nM, or 0.05 nM to 50 nM, or 0.05 nM to about 5 nM on the surface of the target cells. The amount required to achieve this local concentration will vary with various factors, including the delivery method, the delivery site, the number of cell layers between the delivery site and the target cells or tissue, the delivery route (topical or systemic), etc. The concentration at the delivery site may be significantly higher than that on the surface of the target cells or tissue.

Kit

The present disclosure provides a kit, which comprises an effective amount of at least one of the modified siRNA, the pharmaceutical composition, the first siRNA conjugate and the second siRNA conjugate of the present disclosure.

In some embodiments, the kit of the present disclosure may provide a modified siRNA in a container. In some embodiments, the kit of the present disclosure may comprise a container comprising a pharmaceutically acceptable excipient. In some embodiments, the kit of the present disclosure further comprises other ingredients, such as stabilizers or preservatives. In some embodiments, the kit of the present disclosure may comprise at least one additional therapeutic agent in a container different than the container comprising the modified siRNA of the present disclosure. In some embodiments, the kit may comprise an instruction for mixing the modified siRNA with a pharmaceutically acceptable carrier and/or excipient or other ingredients (if present).

In the kit of the present disclosure, the modified siRNA and the pharmaceutically acceptable carrier and/or excipient as well as the modified siRNA, the pharmaceutical composition, the first siRNA conjugate and/or the second siRNA conjugate and/or the conjugate, and/or the pharmaceutically acceptable excipient may be provided in any form, such as in a liquid form, a dried form or a lyophilized form. In some embodiments, the modified siRNA and the pharmaceutically acceptable carrier and/or excipient and the pharmaceutical composition and/or conjugate and optional pharmaceutically acceptable excipient(s) are substantially pure and/or sterilized. In some embodiments, sterilized water may be provided in the kit of the present disclosure.

The present disclosure will be further illustrated by way of the following preparation examples and examples, but will not be limited to them.

EXAMPLES

Hereinafter, the present disclosure will be described in detail by way of examples. Unless otherwise specified, the reagents and culture media used in following examples are all commercially available, and operations used such as nucleic acid electrophoresis and real-time PCR are all performed according to methods described in Molecular Cloning (Cold Spring Harbor Laboratory Press (1989)).

HEK293A cells were provided by Nucleic acid technology laboratory, Institute of Molecular Medicine, Peking University and cultured in DMEM complete media (Hyclone company) containing 20% fetal bovine serum (FBS, Hyclone company) and 0.2% by volume of Penicillin-Streptomycin (Gibco, Invitrogen company) at 37° C. in an incubator containing 5% $CO_2$/95% air.

Huh7 cells were purchased from the Stem Cell Bank of Chinese Academy of Science and cultured in DMEM complete media (Hyclone company) containing 10% fetal bovine serum (FBS, Hyclone company) and 1% nonessential amino acid (NEAA, Corning company) at 37° C. in an incubator containing 5% $CO_2$/95% air.

When the siRNA or the siRNA conjugate against APOC3 gene synthesized in the present disclosure or the siRNA or the siRNA conjugate as negative control was used to transfect cells, Lipofectamine™2000 (Invitrogen) was used as a transfection reagent. The specific procedures thereof may refer to the instruction provided by the manufacturer.

Unless otherwise specified, ratios of reagents provided below are all calculated by volume ratio (v/v).

The animal models used are as follows:
Human APOC3 transgenic mice: B6; CBA-Tg(APOC3) 3707Bres/J, purchased from Jackson Lab in the United States of America;
cynomolgus monkeys: provided by Suzhou CTI Biotechnology Co., Ltd.

All the experimental data are expressed as $\overline{X}\pm SEM$, and the data are analyzed by using Graphpad prism 5.0 statistical analysis software. The data are initially tested for normal distribution and homogeneity of variance. If the data meet normal distribution (p>0.20) and homogeneity of variance (p>0.10), comparison among groups would be performed by LSD method using one-way analysis of variance for multiple comparisons. $P<0.05$ is considered statistically significant. If the data fail to meet normal distribution or homogeneity of variance, differences among groups would be performed by using Krushkal-Wallis H Method for Non-parametric Test. If the results obtained by Krushkal-Wallis H test are significant (p<0.05), pairwise comparisons among groups would be conducted after rank transformation of the data. $P<0.05$ is considered to be statistically significant.

Preparation Example 1. The Preparations of Conjugates 1-3

In this preparation example, conjugates 1-3 (hereinafter also referred to as L10-siAP1M2SVP, L10-siAP1M2 SP and L10-siAP1M2SPs conjugate respectively) were synthesized. The above-mentioned conjugates were those formed by conjugating L-9 conjugating molecule with the siRNA No. siAP1M2SVP, siAP1M2SP, or siAP1M2SPs. The sequences of the conjugated siRNAs in said conjugates were shown in Table 3.
(1-1) Synthesis of Compound L-10:
Compound L-10 was synthesized according to the following method.
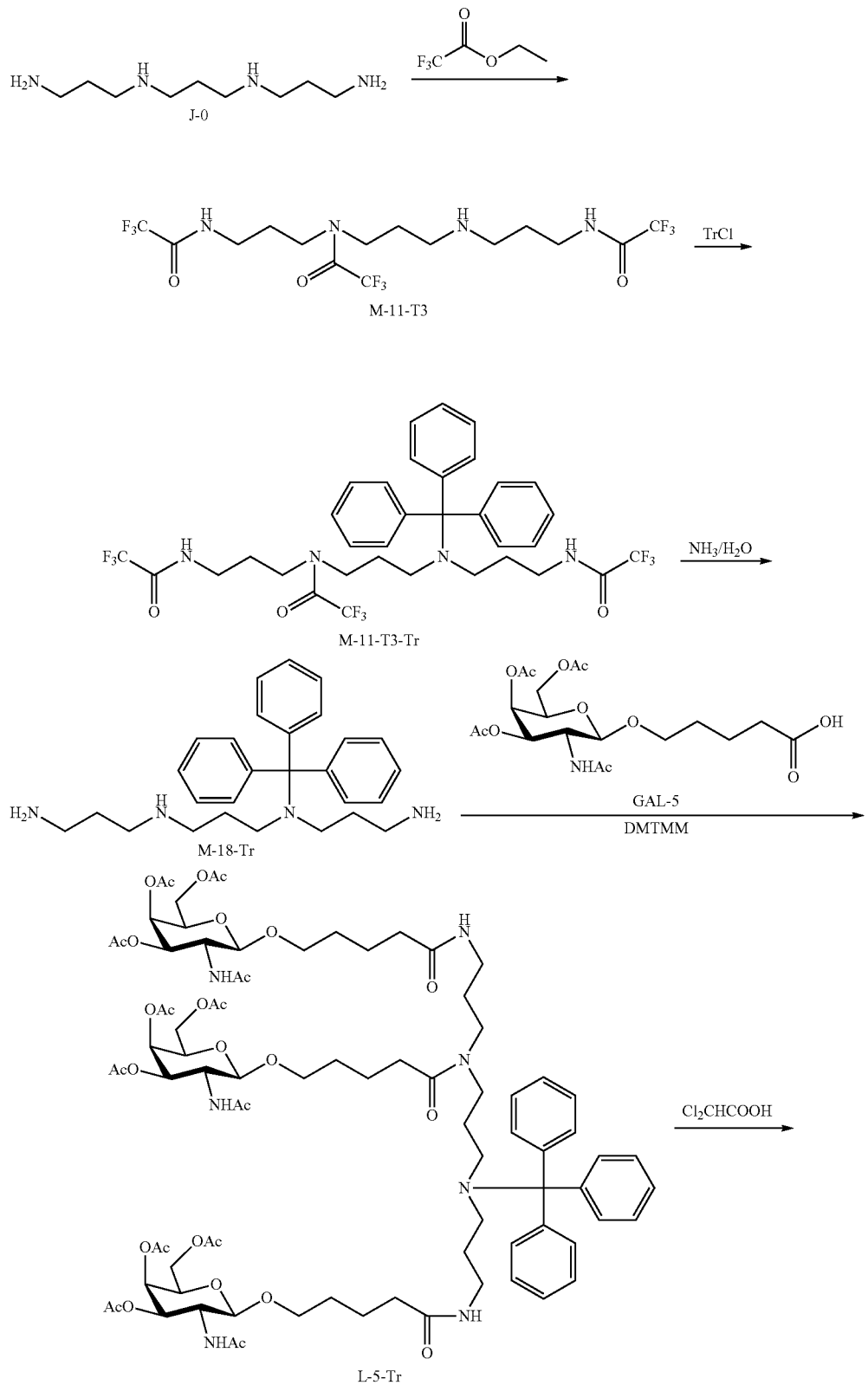

-continued
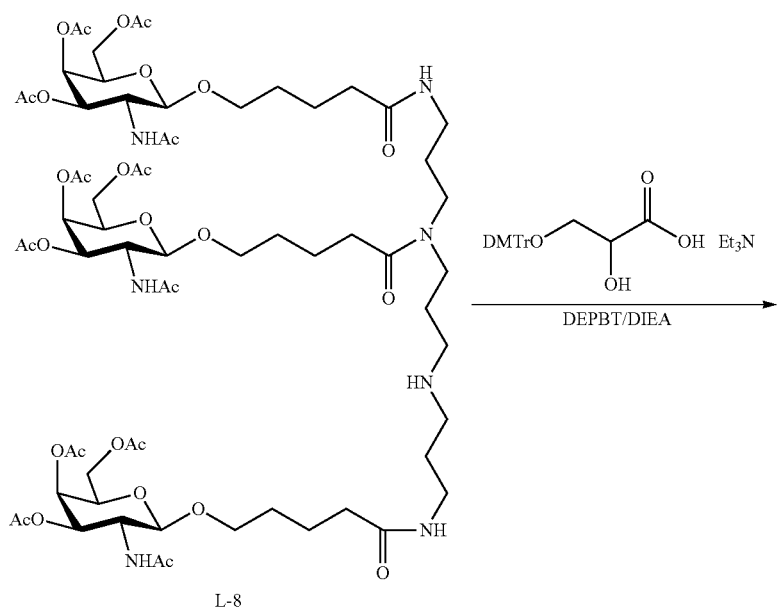
L-8
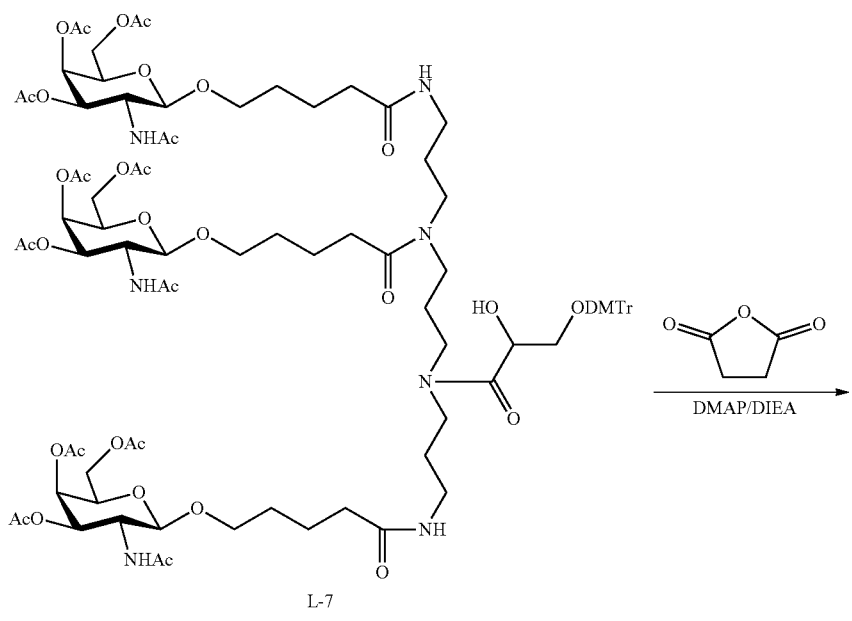
L-7

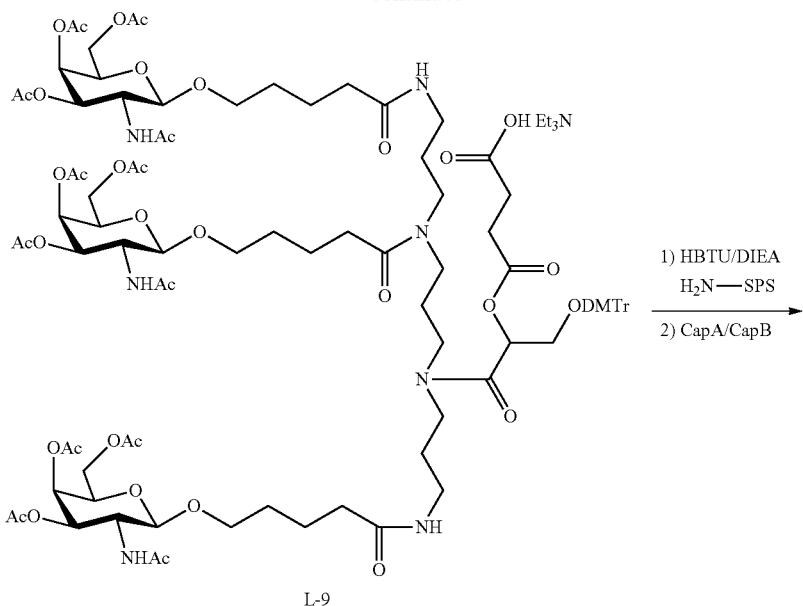
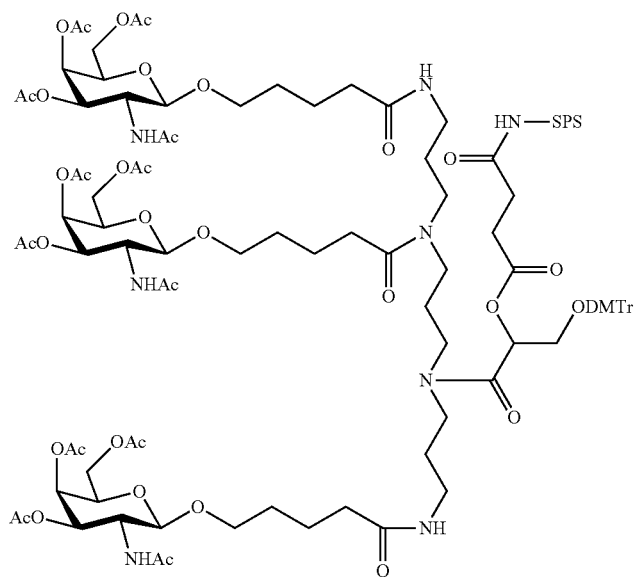

(1-1-1) Synthesis of the Conjugating Terminal Segment GAL-5:

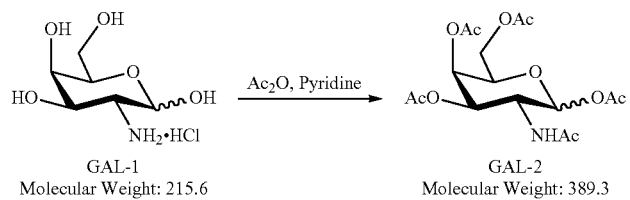

GAL-1
Molecular Weight: 215.6

GAL-2
Molecular Weight: 389.3

GAL-3
Molecular Weight: 329.3

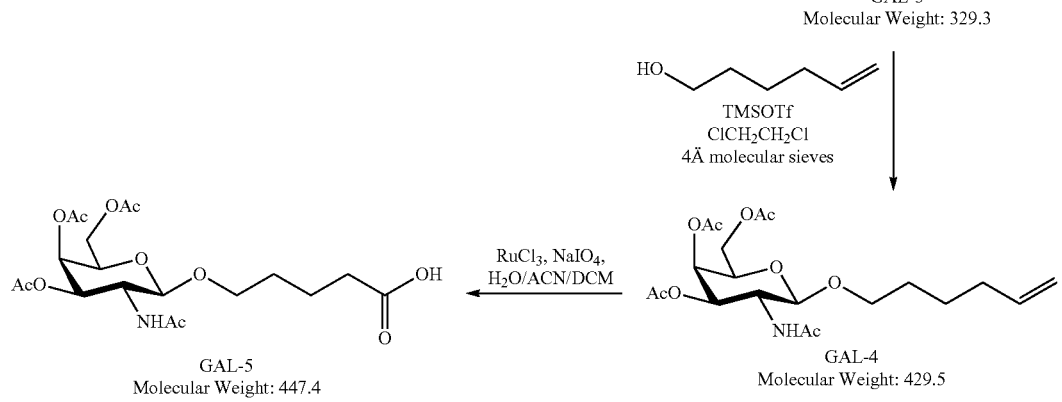

GAL-5
Molecular Weight: 447.4

GAL-4
Molecular Weight: 429.5

(1-1-1a) Synthesis of GAL-2:

100.0 g of GAL-1 (N-acetyl-D-galactosamine hydrochloride, CAS No.: 1772-03-8, purchased from Ning Bo hongxiang bio-chem Co., Ltd., 463.8 mmol) was dissolved in 1000 ml of anhydrous pyridine, to which 540 ml of acetic anhydride (purchased from Enox Inc., 5565.6 mmol) was added in an ice water bath to react for 1.5 hours under stirring at room temperature. The resulting reaction solution was poured into 10 L of ice water and was subjected to suction filtration under reduced pressure. The residue was washed with 2 L of ice water, and then added with a mixed acetonitrile/toluene solvent (v/v ratio of acetonitrile:toluene=1:1) until complete dissolution. The solvent was evaporated to give 130.0 g of product GAL-2 as a white solid.

(1-1-1b) Synthesis of GAL-3:

GAL-2 (35.1 g, 90.0 mmol) obtained in step (1-1-1a) was dissolved in 213 ml of anhydrous 1,2-dichloroethane, to which 24.0 g of TMSOTf (CAS No.: 27607-77-8, purchased from Macklin Inc., 108.0 mmol) was added in an ice water bath and under nitrogen atmosphere to react overnight at room temperature.

400 ml dichloromethane was added to the reaction solution for dilution, filtered with diatomite, and then 1 L saturated aqueous sodium bicarbonate solution was added to the resulting reaction solution and stirred evenly. The organic phase was isolated. The aqueous phase was extracted twice, each with 300 ml of dichloroethane, and the organic phases were combined and washed with 300 ml of saturated aqueous sodium bicarbonate solution and 300 ml of saturated brine, respectively. The organic phase was isolated and dried with anhydrous sodium sulfate. The solvent was evaporated under reduced pressure to give 26.9 g of product GAL-3 as a light yellow viscous syrup.

(1-1-1c) Synthesis of GAL-4:

GAL-3 (26.9 g, 81.7 mmol) obtained in step (1-1-1b) was dissolved in 136 ml of anhydrous 1,2-dichloroethane, added with 30 g of 4 Å molecular sieve as a dry powder followed by 9.0 g of 5-hexen-1-ol (CAS No.: 821-41-0, purchased from Adamas-beta Inc., 89.9 mmol), and stirred for 30 minutes at room temperature. 9.08 g of TMSOTf (40.9 mmol) was added in an ice bath and nitrogen atmosphere to react overnight under stirring at room temperature. The 4 Å molecular sieve powder was removed by filtration. 300 ml dichloroethane was added to the filtrate for dilution, filtered with diatomite, and then 500 ml of saturated aqueous sodium bicarbonate solution was added to the resulting reaction solution and stirred for 10 minutes for washing. The organic phase was isolated. The aqueous phase was extracted once with 300 ml of dichloroethane. The organic phases were combined and washed with 300 ml of saturated aqueous sodium bicarbonate solution and 300 ml of saturated brine respectively. The organic phase was isolated and dried with anhydrous sodium sulfate. The solvent was evaporated under reduced pressure to give 41.3 g of product GAL-4 as a yellow syrup, which was directly used in the next oxidation reaction without purification.

(1-1-1d) Synthesis of GAL-5:

GAL-4 (14.9 g, 34.7 mmol) obtained according to the method described in step (1-1-1c) was dissolved in a mixed solvent of 77 ml of dichloromethane and 77 ml of acetonitrile, added with 103 ml of deionized water and 29.7 g of sodium periodate (CAS No.: 7790-28-5, purchased from Aladdin Inc., 138.8 mmol) respectively, and stirred in an ice bath for 10 minutes. Ruthenium trichloride (CAS No.: 14898-67-0, available from Energy Chemical, 238 mg, 1.145 mmol) was added to react overnight at room temperature. The resulting reaction solution was diluted by adding 300 ml of water, stirred, and adjusted to a pH of about 7.5 by adding saturated sodium bicarbonate. The organic phase was isolated and discarded. The aqueous phase was extracted three times, each with 200 ml of dichloromethane, and the organic phase resulted from the extraction was discarded. The aqueous phase resulted from the extraction was adjusted to a pH of about 3 with citric acid solid and extracted three times, each with 200 ml of dichloromethane, and the organic phases were combined and dried with (1-1-2) Synthesis of M-11-T3:

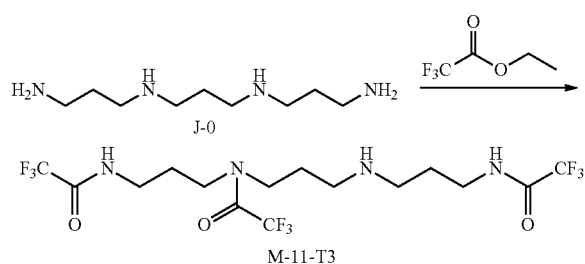

J-0 (1.883 g, 10 mmol, purchased from Alfa Aesar) was dissolved in 25 ml of acetonitrile, added with triethylamine (4.048 g, 40 mmol), and cooled to 0° C. in an ice water bath. Ethyl trifluoroacetate (5.683 g, 40 mmol) was added to react for 22 hours at room temperature. The solvent was evaporated under reduced pressure, and the residue was foam-dried with a vacuum oil pump for 18 hours to give 5.342 g of crude solid product M-11-T3, which was directly used in subsequent reaction without further purification. MS m/z: $C_{15}H_{22}F_9N_4O_3$, $[M+H]^+$, calcd: 477.35, measured: 477.65.

(1-1-3) Synthesis of M-11-T3-Tr:

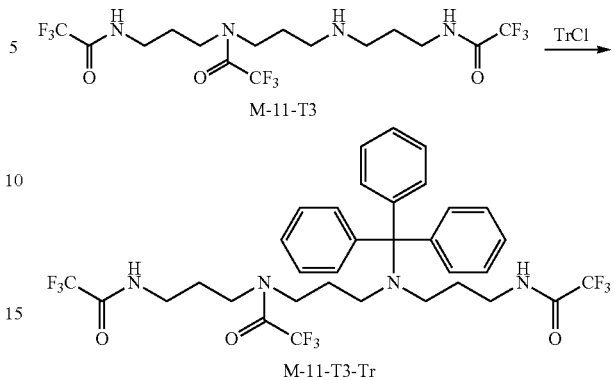

The crude product M-11-T3 (5.342 g, 10 mmol) was dissolved in 50 ml of dichloromethane. The resulting reaction solution was added with TrCl (3.345 g, 12 mmol) and triethylamine (1.518 g, 15 mmol) to react for 20 hours under stirring at room temperature. The reaction solution was washed twice, each with 20 ml of saturated sodium bicarbonate and once with 20 ml of saturated brine. The organic phase was dried with anhydrous sodium sulfate and filtered. The solvent was evaporated under reduced pressure, and the residue was foam-dried with a vacuum oil pump overnight to give 7.763 g of crude solid product M-11-T3-Tr. MS m/z: $C_{34}H_{36}F_9N_4O_3$, $[M+Na]^+$, calcd: 741.25, measured: 741.53. The crude solid product M-11-T3-Tr was then used in the next step for synthesis of M-18-Tr without purification.

(1-1-4) Synthesis of M-18-Tr:

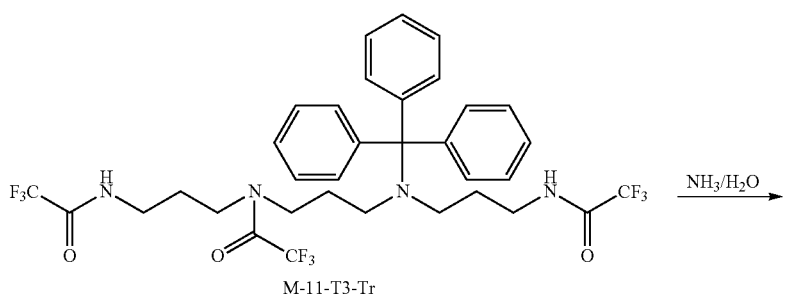

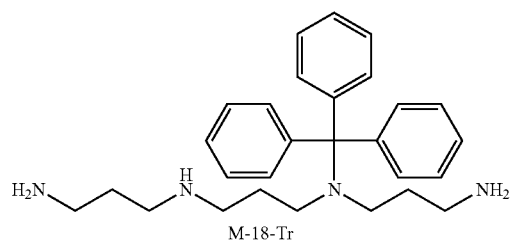

The crude product M-11-T3-Tr (7.763 g, 10 mmol) obtained in step (1-1-3) was dissolved in 100 ml of methanol, and added with 100 ml of aqueous methylamine solution (40 mass %) to react for 23 hours under stirring at 50° C. Insoluble particles were removed by filtration. The solvent was evaporated under reduced pressure, and the residue was added with 200 ml of mixed solvent of DCM:methanol in a volume ratio of 1:1, washed with 50 ml of saturated sodium bicarbonate. The aqueous phase was extracted three times, each with 50 ml of dichloromethane. The organic phases were combined, dried with anhydrous sodium sulfate and filtered. The solvent was evaporated under reduced pressure, and the residue was foam-dried with a vacuum oil pump overnight, and purified by using a normal phase silica gel column having 200-300 mesh. The column was packed with petroleum ether, added with 1 wt % triethylamine for neutralizing the acidity of silica gel, and eluted with a gradient elution of dichloromethane:methanol:aqueous ammonia (25 wt %)=1:1:0.05-1:1:0.25. The eluate of product was collected, the solvent was evaporated to dryness under reduced pressure, and the residue was foam-dried with a vacuum oil pump to give 2.887 g of pure product M-18-Tr. $^1$H NMR (400 MHz, DMSO) δ7.47-7.39 (m, 6H), 7.32-7.24 (m, 6H), 7.19-7.12 (m, 3H), 2.60-2.47 (m, 4H), 2.46-2.19 (m, 13H), 1.70-1.55 (m, 4H), 1.40 (p, J=6.8 Hz, 2H). MS m/z: $C_{28}H_{39}N_4$, $[M+H]^+$, calcd: 431.65, measured: 432.61.

(1-1-5) Synthesis of L-5-Tr:

M-18-Tr (2.02 g, 4.69 mmol) obtained in step (1-1-4) and GAL-5 (6.93 g, 15.48 mmol) obtained in step (1-1-1) were mixed and dissolved in 47 ml of acetonitrile, and added with N-methylmorpholine (3.13 g, 30.96 mmol) and 4-(4,6-dimethoxytriazin-2-yl)-4-methylmorpholine hydrochloride (DMTMM, 4.28 g, 15.48 mmol) to react for 2 hours under stirring at room temperature. The resulting reaction solution was diluted with 200 ml of dichloromethane. The organic phase was washed with 100 ml of a saturated sodium bicarbonate solution and 100 ml of saturated brine, dried with anhydrous sodium sulfate, and filtered. Then the solvent was evaporated under reduced pressure to give a crude product. The crude product was purified by using a normal phase silica gel column having 200-300 mesh. The column was packed with petroleum ether, added with 1 wt % triethylamine for neutralizing the acidity of silica gel, and eluted with a gradient elution of dichloromethane:methanol=100:5-100:7. The eluate of product was collected, and the solvent was evaporated under reduced pressure to give 7.49 g of pure product L-5-Tr. $^1$H NMR (400 MHz, DMSO) δ7.83-7.10 (m, 4H), 7.67-7.60 (m, 1H), 7.44-7.34 (m, 6H), 7.33-7.24 (m, 6H), 7.20-7.15 (m, 3H), 5.22 (s, 3H), 4.97 (d, J=11.3 Hz, 3H), 4.49 (d, J=8.4 Hz, 3H), 4.06-3.07 (m, 9H), 3.95-3.83 (m, 3H), 3.77-3.64 (m, 3H), 3.45-3.35 (m, 3H), 3.12-2.87 (m, 8H), 2.30-2.15 (m, 3H), 2.11-1.98 (m, 22H), 1.95-1.84 (m, 11H), 1.81-1.61 (m, 14H), 1.54-1.36 (m, 14H). MS m/z: $C_{85}H_{119}N_7O_{30}$, $[M+H]^+$, calcd: 1718.81, measured: 1718.03.

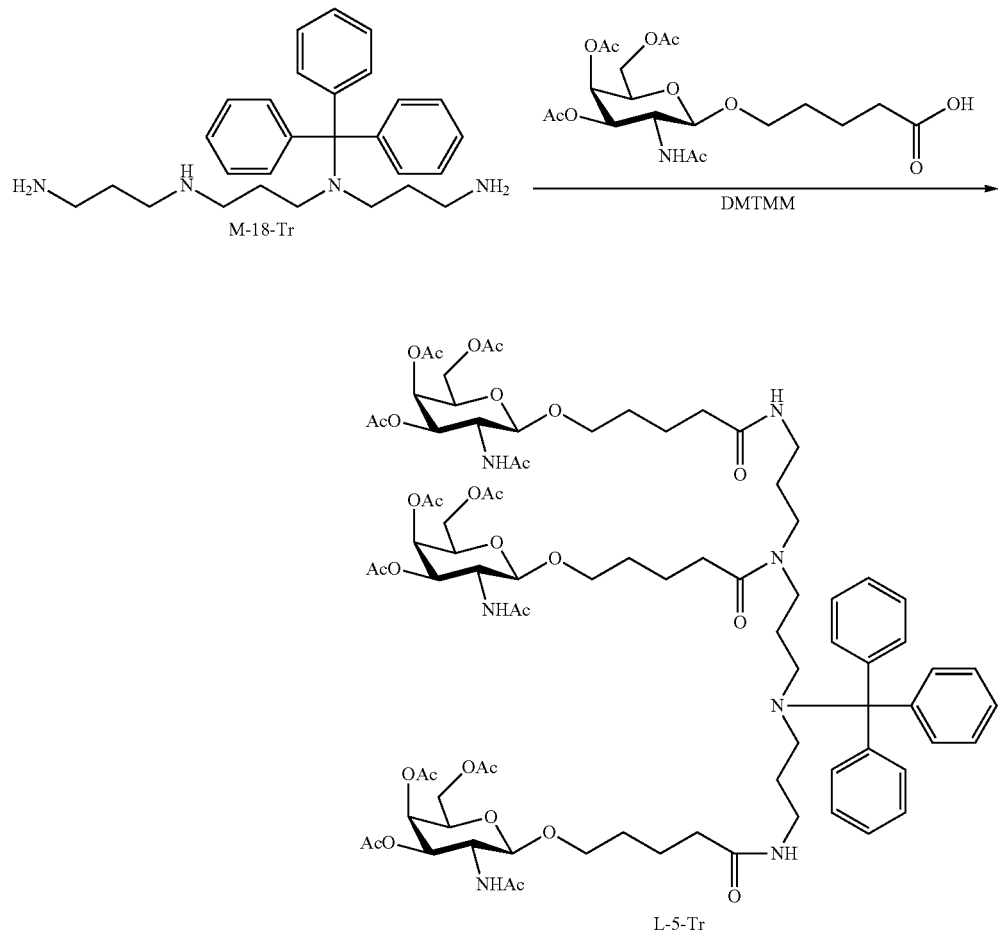

(1-1-6) Synthesis of L-8:

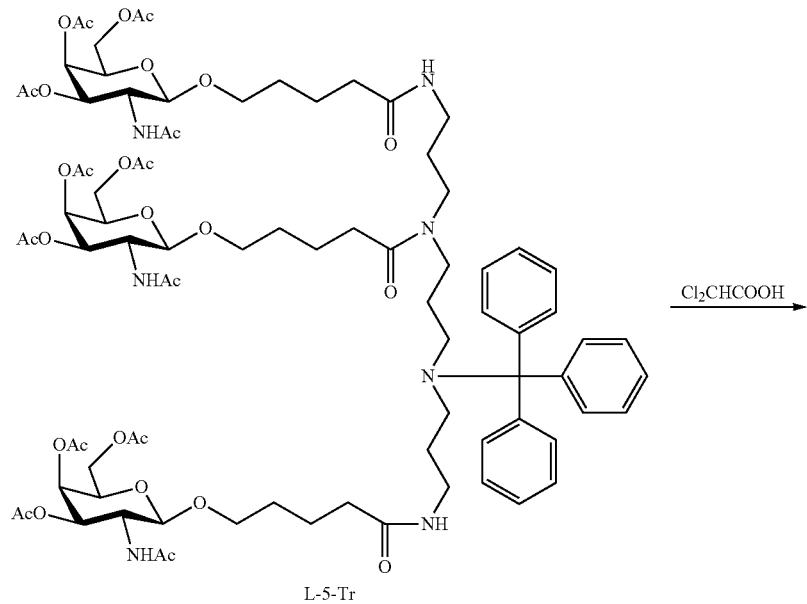

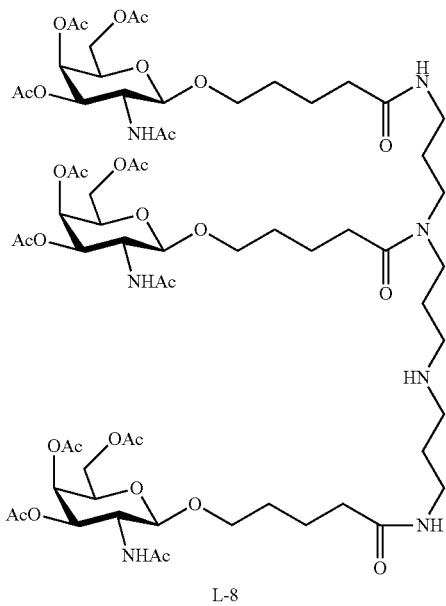

L-5-Tr (5.94 g, 3.456 mmol) obtained in step (1-1-5) was dissolved in 69 ml of dichloromethane, and added with dichloroacetic acid (13.367 g, 103.67 mmol) to react for 2 hours at room temperature. The resulting reaction solution was diluted by adding 100 ml of dichloromethane, washed and adjusted to pH 7-8 with saturated sodium bicarbonate solution. The aqueous phase was extracted six times, each with 30 ml of dichloromethane. The organic phases were combined, dried with anhydrous sodium sulfate, and filtered. Then the solvent was evaporated to dryness under reduced pressure to give a crude product. The crude product was purified by using a normal phase silica gel column having 200-300 mesh. The column was added with 10 wt % triethylamine for neutralizing the acidity of silica gel, equilibrated with 1 wt ‰ triethylamine, and eluted with a gradient elution of dichloromethane:methanol=100:30-100:40. The eluate of product was collected, and the solvent was evaporated under reduced pressure to give 4.26 g of pure product L-8. $^1$H NMR (400 MHz, DMSO) δ 7.84 (d, J=9.0 Hz, 3H), 7.27-7.23 (m, 1H), 7.13-7.18 (m, 1H), 5.22 (d, J=3.1 Hz, 3H), 4.97 (dd, J=11.3, 3.1 Hz, 3H), 4.48 (d, J=8.4 Hz, 3H), 4.09-3.98 (m, 9H), 3.88 (dd, J=19.3, 9.3 Hz, 3H), 3.75-3.66 (m, 3H), 3.44-3.38 (m, 3H), 3.17-3.30 (m, 4H), 3.10-2.97 (m, 4H), 2.35-2.20 (m, 6H), 2.15-2.08 (m, 9H), 2.07-1.98 (m, 13H), 1.94-1.87 (m, 9H), 1.81-1.74 (m, 9H), 1.65-1.42 (m, 18H). MS m/z: $C_{85}H_{119}N_7O_{30}$, $[M+H]^+$, calcd: 1477.59, measured: 1477.23.

(1-1-7a) Synthesis of A-1:

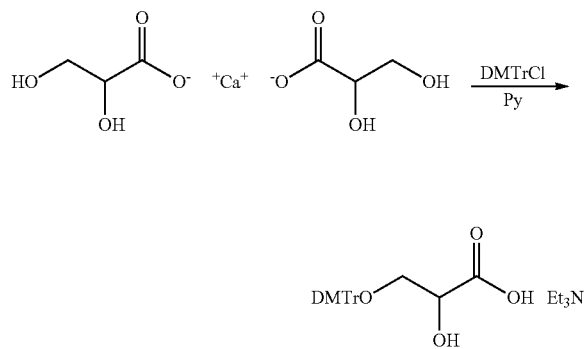

DMTrCl (4,4'-dimethoxytrityl chloride, 38.12 g, 112.5 mmol) was dissolved in 450 ml of anhydrous pyridine, and added with calcium DL-glycerate hydrate (12.88 g, 45.0 mmol) to react for 22 hours at 45° C. The resulting reaction solution was filtered. The filter cake was rinsed with 200 ml of DCM, and the filtrate was concentrated under reduced pressure. The residue was redissolved in 500 ml of dichloromethane and washed twice, each with 200 ml of 0.5 M triethylamine phosphate (pH=7-8). The aqueous phase was extracted twice, each with 200 ml of dichloromethane. The organic phases were combined, dried with anhydrous sodium sulfate, and filtered. The solvent was evaporated under reduced pressure, and the residue was purified by using a normal phase silica gel column having 200-300 mesh, eluted with a gradient elution of petroleum ether:ethyl acetate:dichloromethane:methanol=1:1:1:0.35-1:1:1:0.55.

The eluate of product was collected, and the solvent was evaporated to dryness under reduced pressure. The residue was redissolved in 500 ml of dichloromethane, and washed once with 200 ml of 0.5 M triethylamine phosphate. The aqueous phase was extracted twice, each with 200 ml of dichloromethane. The organic phases were combined, dried with anhydrous sodium sulfate, and filtered. The solvent was evaporated under reduced pressure, and the residue was subject to a reduced pressure with a vacuum oil pump overnight to give 20.7 g of product A-1 as a white solid. $^1$H NMR (400 MHz, DMSO-d6) δ 7.46 (ddd, J=6.5, 2.3, 1.1 Hz, 1H), 7.40-7.28 (m, 7H), 6.89-6.81 (m, 4H), 4.84 (d, J=5.0 Hz, 1H), 4.36-4.24 (m, 1H), 4.29 (s, 6H), 3.92 (dd, J=12.4, 7.0 Hz, 1H), 3.67 (dd, J=12.3, 7.0 Hz, 1H), 2.52 (q, J=6.3 Hz, 6H), 1.03 (t, J=6.3 Hz, 9H). MS m/z: $C_{24}H_{23}O_6$, $[M-H]^-$, calcd: 407.15, measured: 406.92.

(1-1-7b) Synthesis of L-7:

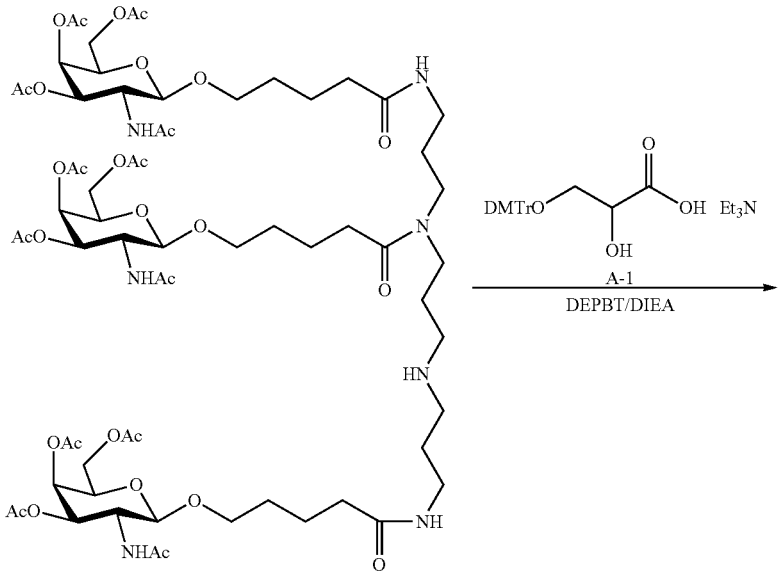

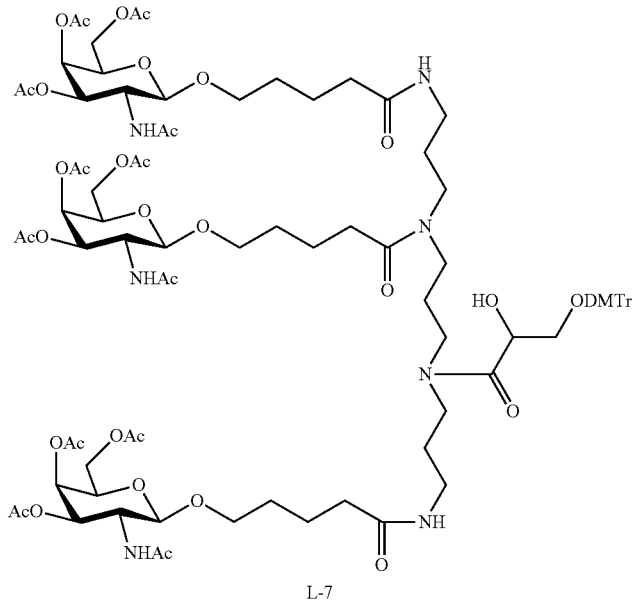

L-7

L-8 (2.262 g, 1.532 mmol) obtained in step (1-1-6) and A-1 (2.342 g, 4.596 mmol) obtained in step (1-1-7a) were mixed and dissolved in 16 ml of dichloromethane, added with 3-(diethoxyphosphoryloxy)-1,2,3-benzotrizin-4(3H)-one (DEPBT, 1.375 g, 4.596 mmol), and further added with diisopropylethylamine (1.188 g, 9.191 mmol) to react for 2 hours under stirring at 25° C.'. The organic phase was washed with 10 ml of saturated sodium bicarbonate. The aqueous phase was extracted three times, each with 10 ml of dichloromethane. The organic phases was washed with 10 ml of saturated brine, and the aqueous phase isolated was extracted twice, each with 10 ml of dichloromethane, and the obtained organic phases were combined, dried with anhydrous sodium sulfate and filtered. The solvent was evaporated under reduced pressure, and the residue was foam-dried overnight with a vacuum oil pump to give 4.900 g of crude product. The crude product was subjected to a column purification. The column was filled with 120 g of normal phase silica gel having 200-300 mesh, and added with 20 ml triethylamine for neutralizing the acidity of silica gel. The column was equilibrated with petroleum ether containing 1 wt % triethylamine and eluted with a gradient elution of petroleum ether:ethyl acetate:dichloromethane:N, N-dimethylformamide=1:1:1:0.5-1:1:1:0.6. The eluate of product was collected, and the solvent was evaporated under reduced pressure to give 2.336 g of pure product L-7. $^1$H NMR (400 MHz, DMSO) δ7.90-7.78 (m, 4H), 7.75-7.64 (m, 1H), 7.38-7.18 (m, 9H), 6.91-6.83 (m, 4H), 5.25-5.10 (m, 4H), 4.97 (dd, J=11.2, 3.2 Hz, 3H), 4.48-4.30 (m, 4H), 4.02 (s, 9H), 3.93-3.84 (m, 3H), 3.76-3.66 (m, 9H), 3.45-3.35 (m, 3H), 3.24-2.98 (m, 10H), 2.30-2.20 (m, 2H), 2.11-1.88 (m, 31H), 1.80-1.40 (m, 28H). MS m/z: $C_{90}H_{128}N_7O_{35}$, [M-DMTr]$^+$, calcd: 1564.65, measured: 1564.88.

(1-1-8) Synthesis of L-9:

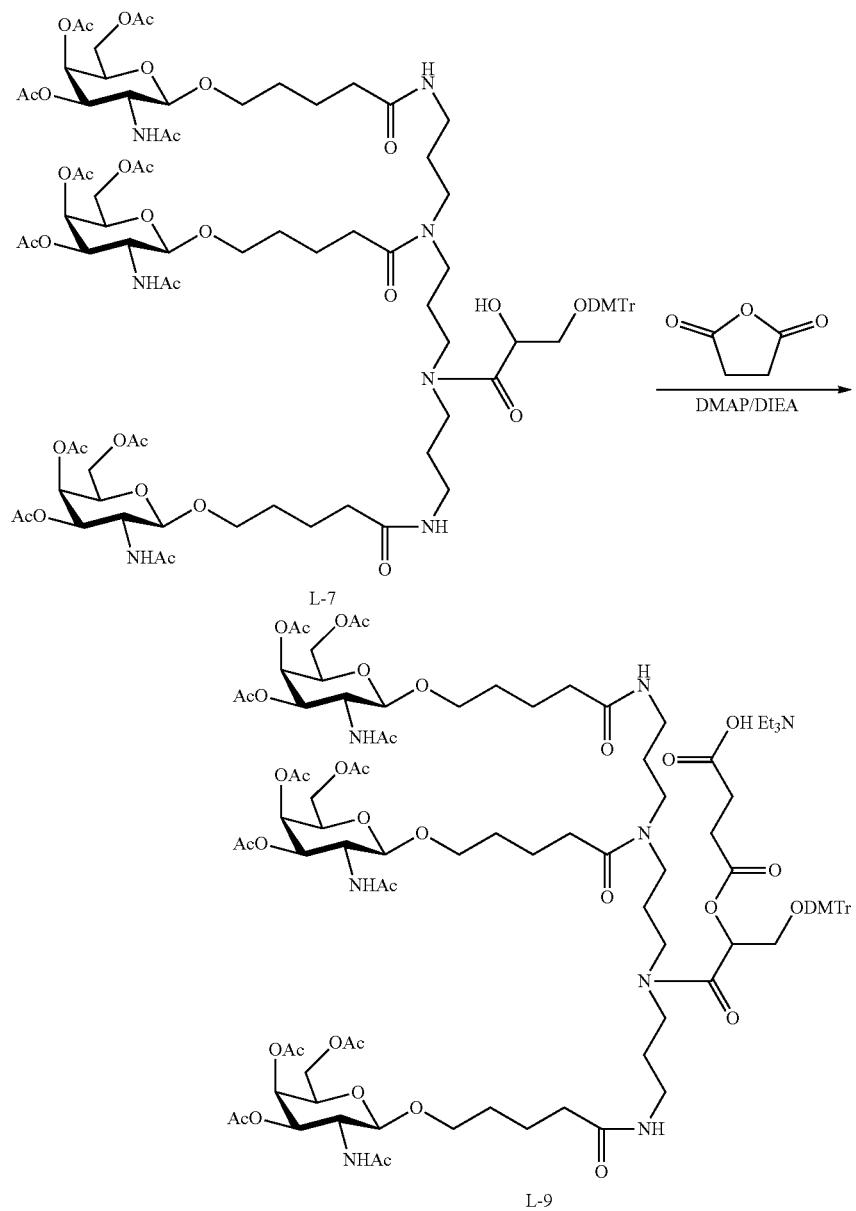

L-7 (2.300 g, 1.26 mmol) obtained in step (1-1-7b), succinic anhydride (0.378 g, 3.78 mmol) and 4-dimethylaminopyridine (DMAP, 0.462 g, 3.78 mmol) were mixed and dissolved in 13 ml of dichloromethane, then added with diisopropylethylamine (DIPEA, 0.814 g, 6.30 mmol), and stirred for 24 hours at 25° C. The resulting reaction solution was washed with 5 ml of 0.5 M triethylamine phosphate. The aqueous phase was extracted three times, each with 5 ml of dichloromethane. The organic phases were combined, and evaporated under reduced pressure to give 2.774 g of crude product. The crude product was subjected to a column purification. The column was filled with 60 g of normal phase silica gel having 200-300 mesh, and added with 1 wt % triethylamine for neutralizing the acidity of silica gel. The column was equilibrated with dichloromethane and eluted with a gradient elution of 1 wt ‰ triethylamine-containing dichloromethane:methanol=100:18-100:20. The eluate of product was collected, and the solvent was evaporated under reduced pressure to give 1.874 g of pure L-9 conjugating molecule. $^1$H NMR (400 MHz, DMSO) δ 8.58 (d, J=4.2 Hz, 1H), 7.94-7.82 (m, 3H), 7.41-7.29 (m, 5H), 7.22 (d, J=8.1 Hz, 5H), 6.89 (d, J=8.3 Hz, 4H), 5.49-5.37 (m, 1H), 5.21 (d, J=3.0 Hz, 3H), 4.97 (d, J=11.1 Hz, 3H), 4.49 (d, J=8.2 Hz, 3H), 4.02 (s, 9H), 3.88 (dd, J=19.4, 9.4 Hz, 3H), 3.77-3.65 (m, 9H), 3.50-3.39 (m, 6H), 3.11-2.90 (m, 5H), 2.61-2.54 (m, 4H), 2.47-2.41 (m, 2H), 2.26-2.17 (m, 2H), 2.15-1.95 (m, 22H), 1.92-1.84 (m, 9H), 1.80-1.70 (m, 10H), 1.65-1.35 (m, 17H), 1.31-1.19 (m, 4H), 0.96 (t, J=7.1 Hz, 9H). MS m/z: $C_{94}H_{132}N_7O_{38}$, [M-DMTr]$^+$, calcd: 1664.72, measured: 1665.03.

(1-1-9) Synthesis of Compound L-10:

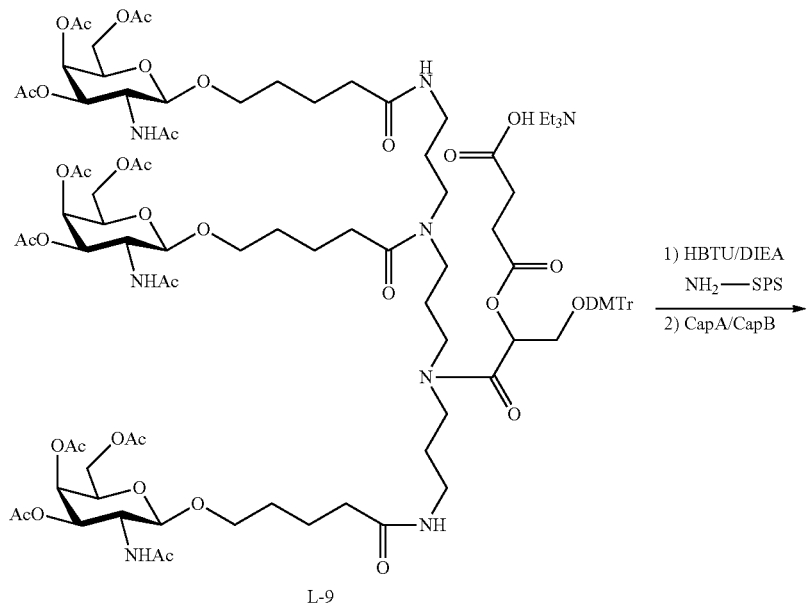

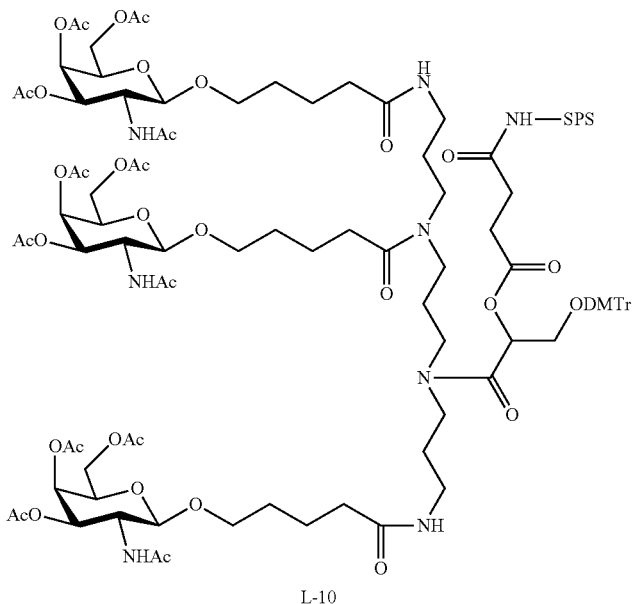

In this step, compound L-10 was prepared by linking the L-9 conjugating molecule to a solid phase support.

The L-9 conjugating molecule (0.233 g, 0.1126 mmol) obtained in step (1-1-8), O-benzotriazol-tetramethyluronium hexafluorophosphate (HBTU, 0.064 g, 0.1689 mmol) and diisopropylethylamine (DIPEA, 0.029 g, 0.2252 mmol) were mixed and dissolved in 19 ml of acetonitrile, and stirred at room temperature for 5 minutes.

Aminomethyl resin (0.901 g, 100-200 mesh, amino loading: 400 μmol/g, purchased from Tianjin Nankai HECH-ENG S&T Co., Ltd.) was added into the reaction solution. The reaction was performed on a shaker at 25° C. and 220 rpm/min for 15 hours, followed by filtration. The filter cake was rinsed twice, each with 30 ml of DCM; three times, each with 30 ml of acetonitrile; and once with 30 ml of ethyl ether; and then dried for 2 hours with a vacuum oil pump. Then a capping reaction was performed by adding starting-materials (CapA, CapB, 4-dimethylaminopyridine (DMAP) and acetonitrile) according to the feeding ratio shown in Table 2. The reaction was placed on a shaker at 25° C. and 200 rpm/min for 5 hours. The reaction solution was filtered. The filter cake was rinsed three times, each with 30 ml of acetonitrile, and was subjected to suction filtration to dryness, and then was dried overnight under a reduced pressure with a vacuum oil pump to give 1.100 g of compound L-10 (i.e., L-9 conjugating molecule linked to a solid phase support), with a loading of 90.8 μmol/g.

TABLE 2

The feeding ratio of capping reaction

| Starting materials | Amount | grade | Lot No. | Manufacturer |
|---|---|---|---|---|
| CapA | 20 ml | — | — | — |
| CapB | 2.3 ml | — | — | — |
| DMAP | 0.01 g | analytical pure | I1422139 | Aladdin |
| acetonitrile | 2.3 ml | spectroscopic pure | O15161001 | CINC (Shanghai) Co., Ltd |

In the above table, Cap A and Cap B are solutions of capping reagents. Cap A is a solution of 20% by volume of N-methylimidazole in a mixture of pyridine/acetonitrile, wherein the volume ratio of pyridine to acetonitrile is 3:5. Cap B is a solution of 20% by volume of acetic anhydride in acetonitrile.

(1-2) Synthesis of Sense Strands of Conjugates 1-3

Since the sense strands of conjugates 1-3 have the same sequence, they were prepared by the same method.

Nucleoside monomers were linked one by one in 3' to 5' direction according to the sequence of nucleotides in the sense strand by the phosphoramidite solid phase synthesis method, starting the cycles from the compound L-10 prepared in the above step. The linking of each nucleoside monomer included a four-step reaction of deprotection, coupling, capping, and oxidation or sulfuration. In particular, when a phosphoester linkage was present between two nucleotides, a four-step reaction of deprotection, coupling, capping, and oxidation was included during linking of the later nucleoside monomer; and when a phosphorothioate linkage was present between two nucleotides, a four-step reaction of deprotection, coupling, capping, and sulfurization was included during linking of the later nucleoside monomer. The synthesis condition was given as follows:

The nucleoside monomers were provided in a 0.1 M solution in acetonitrile. The conditions were the same for each deprotection reaction, i.e., a temperature of 25° C., a reaction time of 70 seconds, a solution of dichloroacetic acid in dichloromethane (3% v/v) as a deprotection reagent, and a molar ratio of dichloroacetic acid to the protecting group 4,4'-dimethoxytrityl on the solid phase support of 5:1.

The conditions were the same for each coupling reaction, including a temperature of 25° C., a molar ratio of the nucleic acid sequence linked to the solid phase support to nucleoside monomers of 1:10, a molar ratio of the nucleic acid sequence linked to the solid phase support to a coupling reagent of 1:65, a reaction time of 600 seconds, and a coupling reagent of 0.5 M solution of 5-ethylthio-1H-tetrazole in acetonitrile.

The conditions were the same for each capping reaction, including a temperature of 25° C. and a reaction time of 15 seconds. The capping reagent was a mixed solution of Cap A and Cap B in a molar ratio of 1:1; and a molar ratio of the capping reagent to the nucleic acid sequence linked to the solid phase support was acetic anhydride:N-methylimidazole: the nucleic acid sequence linked to the solid phase support=1:1:1.

The conditions were the same for each oxidation reaction, including a temperature of 25° C., a reaction time of 15 seconds, and 0.05 M iodine water as an oxidation reagent; and a molar ratio of iodine to the nucleic acid sequence linked to the solid phase support in the coupling step was 30:1. The reaction was carried out in a mixed solvent of tetrahydrofuran:water:pyridine=3:1:1.

The conditions were the same for each sulfuration reaction, including a temperature of 25° C., a reaction time of 300 seconds, and xanthane hydride as a sulfurization reagent. The molar ratio of the sulfurization reagent to the nucleic acid sequence linked to the solid phase support in the coupling step was 120:1. The reaction was carried out in a mixed solvent of acetonitrile:pyridine=1:1.

The conditions for cleavage and deprotection were as follows: The synthesized nucleotide sequence linked to the support was added to 25 wt % aqueous ammonia to react for 16 hours at 55° C., and the aqueous ammonia was used in an amount of 0.5. The liquid was removed, and the residue was concentrated in vacuum to dryness.

Purification and desalination: purification of the nucleic acid was achieved by using a preparative ion chromatography column (Source 15Q) with a gradient elution of NaCl. Specifically, eluent A: 20 mM sodium phosphate (pH 8.1), solvent: water/acetonitrile=9:1 (v/v); eluent B: 1.5 M sodium chloride, 20 mM sodium phosphate (pH 8.1), solvent: water/acetonitrile=9:1 (v/v); elution gradient: the ratio of eluent A:eluent B=100:0-50:50. The eluate of product was collected, combined and desalted by using a reversed phase chromatography column. The specific condition included that a Sephadex column was used for desalination, with Sephadex-G25 as the filler and deionized water for eluting.

Detection: The purity was determined by ion exchange chromatography (IEX-HPLC), and the molecular weight was analyzed by Liquid Chromatography-Mass Spectrometry (LC-MS). The sense strand has a calculated molecular weight of 7649.55. For the batches of the sense strand of conjugate 1, the measured value was 7649.1; and for the batches of the sense strands of conjugates 2 and 3, the measured value was 7648.8. The measured value was in conformity with the calculated value, indicating that a sense strand S conjugated with L-9 conjugating molecule at 3' terminal was synthesized.

(1-3) Synthesis of an Antisense Strand (1-3A) Preparation of Antisense Strand of Conjugate 1

The antisense strand AS of the conjugate 1 is synthesized by using a universal solid phase support (UnyLinker™ loaded NittoPhase®HL Solid Supports, Kinovate Life Sciences Inc.) according to a solid phase phosphoramidite method. Deprotection, coupling, capping, and oxidization or sulfuration reaction in the solid phase synthesis method, cleavage and deprotection, and purification and desalting are conducted under the same conditions as those in the synthesis of sense strand.

Detection: The purity was determined by ion exchange chromatography (IEX-HPLC), and the molecular weight was analyzed by Liquid Chromatography-Mass Spectrometry (LC-MS), with a calculated value of 6991.46 and a measured value of 6991.0. The measured value was in conformity with the calculated value, indicating that antisense strand AS having target sequence was synthesized.

In particular, vinyl phosphate modified 2'-methoxy modified uracil nucleoside monomer (VP-Um) was synthesized according to the following method:

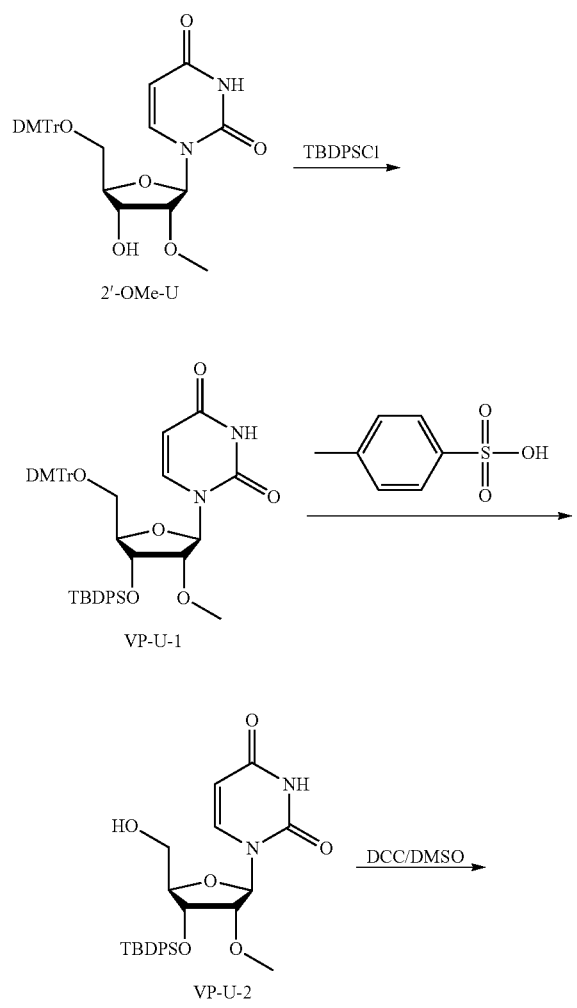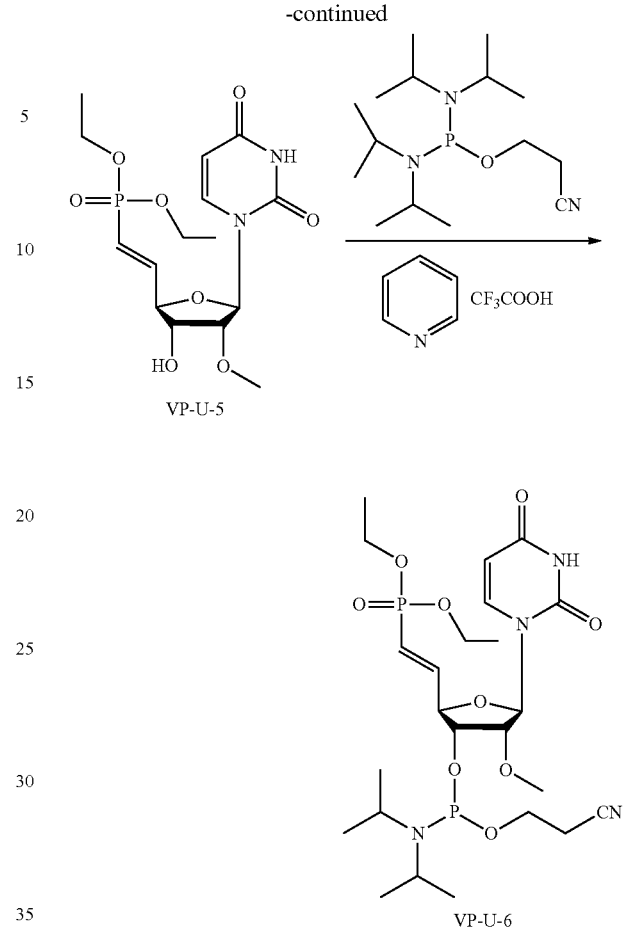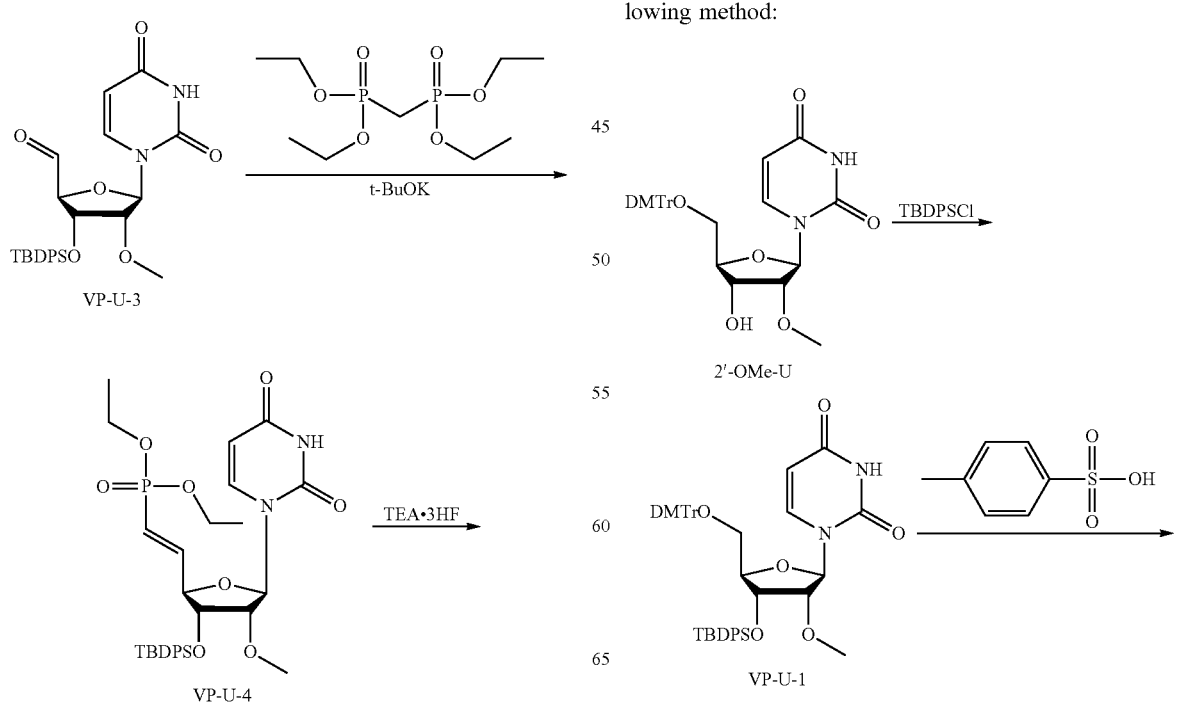
(1-3-1) Synthesis of VP-U-2
VP-U-2 molecule was synthesized according to the following method:

-continued

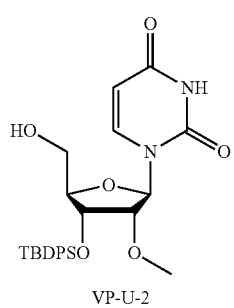

VP-U-2

A 2'-methoxy modified uracil nucleoside (2'-OMe-U, 51.30 g, 91.6 mmol), tert-butyl diphenylchlorosilane (TBDPSCl, 50.35 g, 183.2 mmol), and imidazole (12.47 g, 183.2 mmol) were mixed and dissolved in 450 ml of N,N-dimethylformamide (DMF) to react for 20 hours under stirring at room temperature. DMF was removed by evaporation, and the residue was dissolved with 600 ml of dichloromethane and washed with 300 ml of saturated sodium bicarbonate. The aqueous phase was extracted three times, each with 300 ml of dichloromethane. The organic phases were combined, washed with 5% oxalic acid until an aqueous phase of pH<5 was obtained. The solvent was evaporated to give a crude product VP-U-1, which was directly used in the subsequent synthesis of VP-U-2.

The crude product VP-U-1 was dissolved in 100 ml of dichloromethane, and then stirred for 10 minutes in an ice bath. 450 ml of 2% p-toluenesulfonic acid solution (with a mixed solvent of methanol and dichloromethane in a volume ratio of 3:7) pre-cooled in a refrigerator at 4° C. was added to react for 10 minutes. The reaction was quenched by addition of 200 ml of saturated sodium bicarbonate. The organic phase was washed by addition of saturated sodium bicarbonate solution to pH=8. Aqueous phases were combined and extracted twice, each with 200 ml of dichloromethane. The organic phases were combined and washed once with 200 ml of saturated brine. The solvent was evaporated to dryness, and the residue was purified by using a normal phase silica gel column having 200-300 mesh. The column was packed with petroleum ether and eluted with a gradient elution of petroleum ether:ethyl acetate:dichloromethane:methanol=1:1:1:0.05-1:1:1:0.25. The eluate was collected, the solvent was evaporated to dryness under reduced pressure, and the residue was foam-dried with a vacuum oil pump to give a total of 40.00 g of pure product VP-U-2. $^1$H NMR (400 MHz, DMSO-d6) δ 7.96 (d, J=7.8 Hz, 1H), 7.64 (dtd, J=5.1, 4.0, 2.2 Hz, 4H), 7.41-7.30 (m, 6H), 6.79 (d, J=4.7 Hz, 1H), 5.73 (d, J=7.6 Hz, 1H), 4.94 (t, J=7.0 Hz, 1H), 4.12 (td, J=4.6, 3.9 Hz, 1H), 4.05 (dd, J=4.8, 4.0 Hz, 1H), 3.96 (t, J=4.7 Hz, 1H), 3.68 (ddd, J=11.8, 7.0, 4.6 Hz, 1H), 3.57-3.46 (m, 1H), 3.39 (s, 3H), 1.05 (s, 8H). MS m/z: $C_{26}H_{33}N_2O_6S_1$, $[M+H]^+$, calcd: 497.21, measured: 497.45.

(1-3-2) Synthesis of Synthesis of VP-U-4:

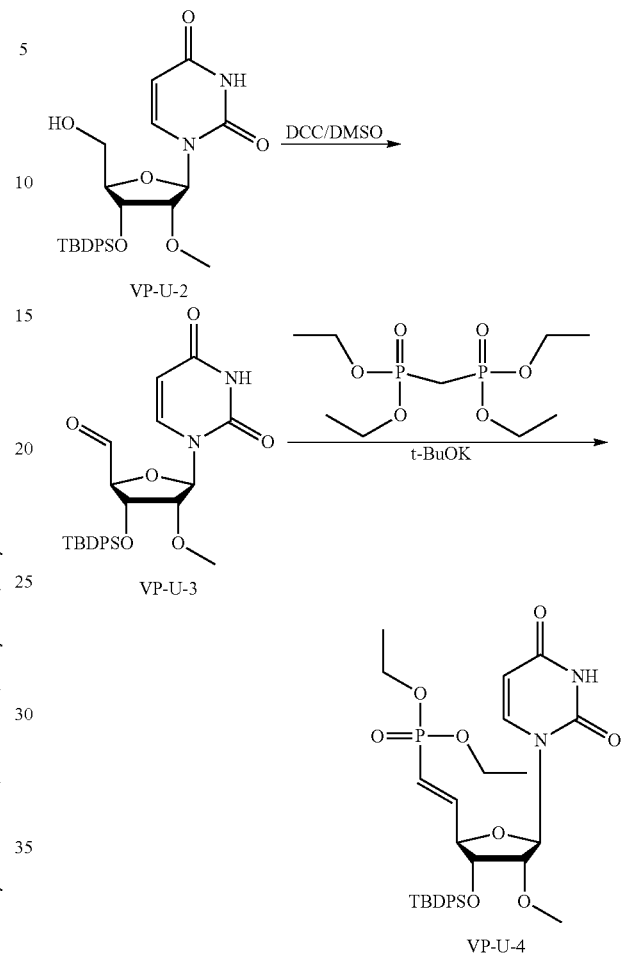

VP-U-2 (19.84 g, 40.0 mmol), dicyclohexylcarbodiimide (DCC, 16.48 g, 80.0 mmol), pyridine (4.20 g, 53.2 mmol), and trifluoroacetic acid (6.61 g, 53.2 mmol) were mixed and dissolved in 200 ml of dimethyl sulfoxide (DMSO) to react for 20 hours under stirring at room temperature. In addition, tetraethyl methylenediphosphate (21.44 g, 74.4 mmol) was dissolved in 120 ml of THF, cooled in an ice bath, added with t-BuOK (11.36 g, 101.2 mmol) at a temperature of the ice bath to react for 10 min, warmed to room temperature to react for 0.5 h and added into the above reaction liquid over about 1 h. The reaction was carried out for 1 h at a temperature of the ice bath and then warmed to room temperature to react for 18 h. The reaction was quenched by addition of water. The aqueous phase was extracted three times, each with 200 ml of dichloromethane. The organic phases were combined and washed once with 200 ml of saturated brine. The solvent was evaporated to dryness, and the residue was purified by using a normal phase silica gel column having 200-300 mesh. The column was packed with petroleum ether and eluted with a gradient elution of petroleum ether:ethyl acetate=1:1-1:4. The eluate was collected, the solvent was evaporated under reduced pressure, and the residue was foam-dried with a vacuum oil pump to give a total of 14.00 g of pure product VP-U-4. $^1$H NMR (400 MHz, DMSO-d6) δ 7.96 (d, J=7.8 Hz, 1H), 7.64 (dtd, J=5.1, 4.0, 2.2 Hz, 4H), 7.41-7.30 (m, 6H), 6.82-6.71 (m, 2H), 5.90 (ddd, J=25.9, 15.0, 1.0 Hz, 1H), 5.73 (d, J=7.6 Hz, 1H), 4.36-4.21 (m, 3H), 4.18 (t, J=4.9 Hz, 1H), 4.05 (ddq, J=9.7, 8.5, 6.9 Hz, 2H), 3.87 (t, J=4.8 Hz, 1H), 3.39 (s, 3H), 1.32 (td, J=6.9, 0.7 Hz, 6H), 1.05 (s, 8H). MS m/z: $C_{31}H_{42}N_2O_8Psi$, $[M+H]^+$, calcd: 629.24, measured: 629.51.

(1-3-3) Synthesis of VP-U-5

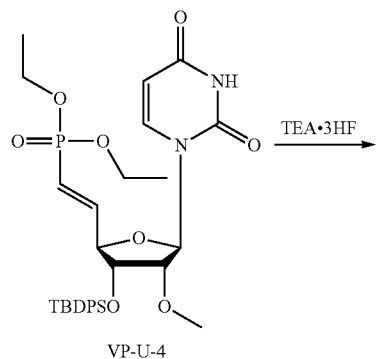

(1-3-4) Synthesis of VP-U-6:

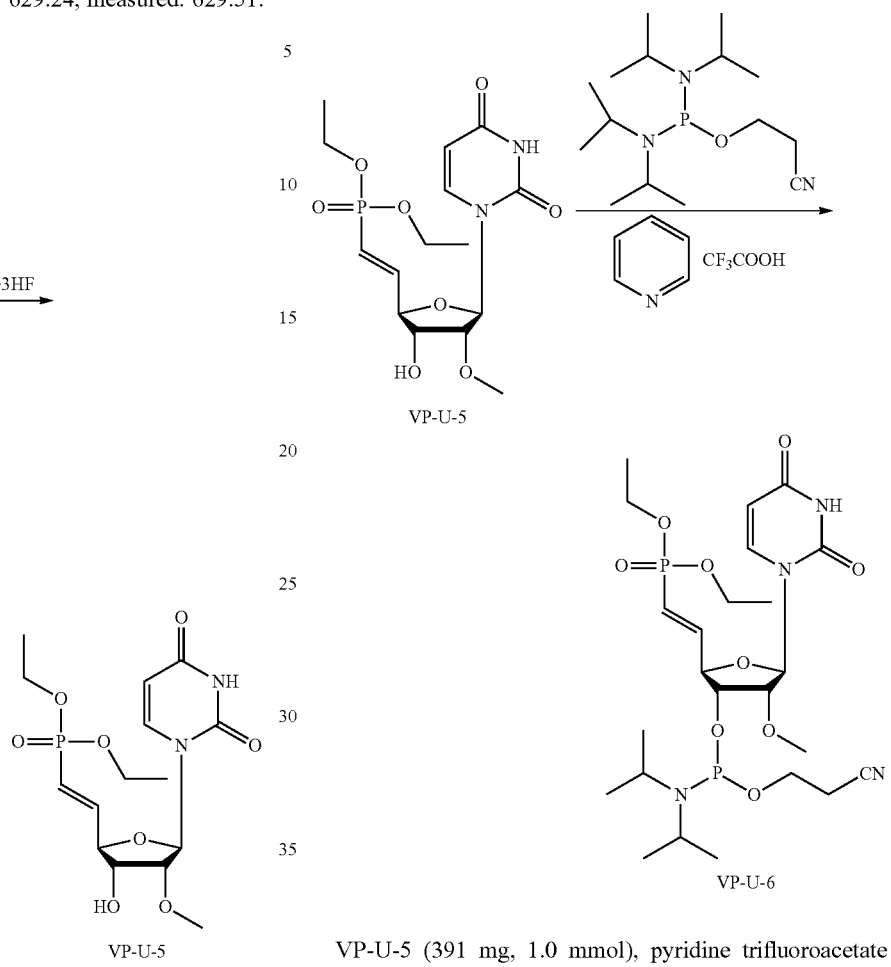

VP-U-4 (14.00 g, 22.29 mmol) was dissolved in 100 ml of tetrahydrofuran, added with triethylamine trihydrofluoride (17.96 g, 111.45 mmol), and stirred at room temperature for 20 hours to react completely. The solvent was directly evaporated to dryness and the residue was dissolved in dichloromethane; the above evaporation and dissolution steps were additionally repeated twice, each with 50 ml of dichloromethane, to give a crude product. The crude product was purified by using a normal phase silica gel column having 200-300 mesh. The column was packed with petroleum ether and eluted with a gradient elution of petroleum ether:ethyl acetate:dichloromethane:methanol=1:1:1:0.05-1:1:1:0.25. The eluate of product was collected, the solvent was evaporated to dryness under reduced pressure, and the residue was foam-dried with a vacuum oil pump to give a total of 6.70 g of pure product VP-U-5. $^1H$ NMR (400 MHz, DMSO-d6) δ 7.96 (d, J=7.8 Hz, 1H), 6.77 (dd, J=15.0, 6.2 Hz, 1H), 5.99-5.82 (m, 2H), 5.73 (d, J=7.6 Hz, 1H), 5.27 (d, J=5.1 Hz, 1H), 5.10 (dd, J=5.3, 4.7 Hz, 1H), 4.29 (ddq, J=9.8, 8.6, 7.0 Hz, 2H), 4.17 (ddd, J=6.2, 5.2, 1.0 Hz, 1H), 4.12-3.98 (m, 3H), 3.39 (s, 2H), 1.32 (td, J=6.9, 0.6 Hz, 6H). MS m/z: $C_{15}H_{24}N_2O_8P$, $[M+H]^+$, calcd: 391.13, measured: 391.38.

VP-U-5 (391 mg, 1.0 mmol), pyridine trifluoroacetate (0.232 g, 1.2 mmol), N-methylimidazole (0.099 g, 1.2 mmol), and bis(diisopropylamino)(2-cyanoethoxy)phosphine (0.452 g, 1.5 mmol) were added to 10 ml of anhydrous dichloromethane in argon atmosphere to react for 5 hours under stirring at room temperature. The solvent was evaporated to dryness, and then the residue was purified by column chromatography (200-300 mesh normal phase silica gel, with a gradient elution of dichloromethane:acetonitrile (containing 0.5 wt % triethylamine)=3:1-1:3). The eluate of product was collected and concentrated to remove the solvent to give a total of 508 mg of target product VP-U-6. $^{31}P$ NMR (161 MHz, DMSO-d6) δ 150.34, 150.29, 17.07, 15.50. MS m/z: $C_{24}H_{41}N_4O_9P_2$, $[M+H]^+$, calcd: 591.23, measured: 591.55. This showed that VP-U-6 is target product VP-Um, which was involved in the synthesis of RNA strand as a nucleoside monomer.

(1-3B) Preparation of an Antisense Strand of Conjugate 2:

The antisense strand of conjugate 2 differs from the antisense strand of conjugate 1 only in the first nucleotide modification at the 5' terminal. In the preparation of an antisense strand according to solid-phase phosphoramidite method, the finally linked nucleoside monomer is 2'-methoxy modified uracil nucleoside monomer (Um), and the CPR-I monomer (purchased from Suzhou GenePharma Inc. as Cat#13-2601-XX) was linked to the 5' terminal of the antisense strand through a four-step reaction of deprotection, coupling, capping and oxydization to form 5'-phosphate modification.

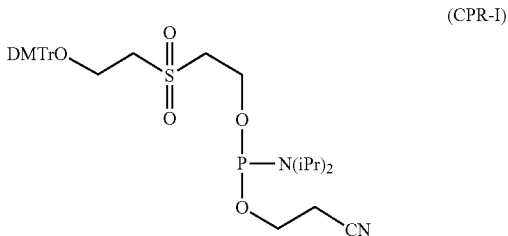

(CPR-I)

In the synthesis, the universal solid phase support and the conditions of deprotection, coupling, capping, and oxidization or sulfuration, the cleavage and deprotection, and purification and desalting are the same as those in the synthesis of sense strand.

The purity was determined by ion exchange chromatography (IEX-HPLC), and the molecular weight was analyzed by Liquid Chromatography-Mass Spectrometry (LC-MS), with a calculated value of 6995.47 and a measured value of 6994.8. The measured value was in conformity with the calculated value, indicating that antisense strand AS having target sequence was synthesized.

(1-3C) Synthesis of the Antisense Strand of Conjugate 3

The antisense strand of conjugate 3 with a 5'-phosphorothioate modification was prepared by employing the same process as that in the synthesis of the antisense strand of conjugate 2, except that: when CPR-I is linked, the above oxidization reaction condition was replaced with a sulfuration reaction condition.

The purity was determined by ion exchange chromatography (IEX-HPLC), and the molecular weight was analyzed by Liquid Chromatography-Mass Spectrometry (LC-MS), with a calculated value of 7011.53 and a measured value of 7010.9. The measured value was in conformity with the calculated value, indicating that antisense strand AS having target sequence was synthesized.

(1-4) Synthesis of Conjugates 1-3

For conjugate 1, the S strand and the AS strand were dissolved in water for injection to give a solution of 40 mg/mL, respectively. They are mixed in an equimolar ratio, heated for 15 min at 50° C., and then cooled to room temperature to form a double stranded structure via hydrogen bonds. The conjugate was diluted to a concentration of 0.2 mg/mL by using ultra-pure water (homemade by Milli-Q ultra-pure water instrument, with resistivity of 18.2MΩ*cm (25° C.)). The molecular weight was measured by LC-MS (Liquid Chromatography-Mass Spectrometry) (purchased from Waters Corp., model: LCT Premier). The measured value was in conformity with the calculated value, indicating that the synthesized conjugate 1 was the designed target double stranded nucleic acid sequence with the L9 conjugating molecule.

For conjugates 2-3, they were prepared by the same method and their molecular weight was measured by the same method. The measured values were in conformity with the calculated values, indicating that the synthesized conjugates were the designed target double stranded nucleic acid sequences with the L9 conjugating molecules. Conjugates 1-4 have the structure as shown by Formula (3).

Preparation Example 2. Preparation of Conjugates 4-21 and Comparative Conjugates 1-2

Comparative conjugates 1-2 were synthesized, and conjugates 4-21 were expected to be prepared by using the same method as that in Preparation Example 1, except that: 1) the siRNAs respectively have the sequences as shown in Table 3 corresponding to comparative conjugates 1-2 and conjugates 4-21; 2) when the target sequence comprises unmodified nucleotides, in the cleavage and deprotection conditions, after treatment with aqueous ammonia, the product was dissolved in N-methylpyrrolidone in an amount of 0.4 ml/μmol, followed by addition of 0.3 ml/μmol of triethylamine and 0.6 ml/μmol of triethylamine trihydrofluoride, with respect to the amount of the single strand nucleic acid, thereby removing the 2'-TBDMS protection on ribose.

TABLE 3

| siRNA Conjugates | | | | | |
|---|---|---|---|---|---|
| siRNA Conjugate | No. | | Sequence Direction 5'-3' | | SEQ ID NO |
| conjugate1 | L10-siAP1M2SVP | S | CmsAmsAmUmAmAmAfGfCfUmGmGmAmCmAm AmGmAmAm | | 22 |
| | | AS | VP-UmsUfsCmUmUmGfUmCmCmAmGmCmUmUf UmAfUmUmGmsGmsGm | | 40 |
| conjugate2 | L10-siAP1M2SP | S | CmsAmsAmUmAmAmAfGfCfUmGmGmAmCmAm AmGmAmAm | | 22 |
| | | AS | P-UmsUfsCmUmUmGfUmCmCmAmGmCmUmUfU mAfUmUmGmsGmsGm | | 42 |
| conjugate3 | L10-siAP1M2SPs | S | CmsAmsAmUmAmAmAfGfCfUmGmGmAmCmAm AmGmAmAm | | 22 |
| | | AS | Ps-UmsUfsCmUmUmGfUmCmCmAmGmCmUmUfU mAfUmUmGmsGmGm | | 43 |
| conjugate4 | L10-siAP1 | S | CAAUAAAGCUGGACAAGAA | | 6 |
| | | AS | UUCUUGUCCAGCUUUAUUGGG | | 7 |
| conjugate5 | L10-siAP2 | S | CCCAAUAAAGCUGGACAAGAA | | 8 |
| | | AS | UUCUUGUCCAGCUUUAUUGGGAG | | 9 |
| conjugate6 | L10-siAP1M1 | S | CmAmAmUmAfAmAfGfCfUmGmGmAmCmAmAm GmAmAm | | 10 |
| | | AS | UmUfCmUmUmGfUmCfCfAmGmCmUmUfUmAfU mUmGmGmGm | | 11 |

TABLE 3-continued

| siRNA Conjugate | No. | | Sequence Direction 5'-3' | SEQ ID NO |
|---|---|---|---|---|
| conjugate7 | L10-siAP2M1 | S | CmCmCmAmAmUmAfAmAfGfCfUmGmGmAmCm AmAmGmAmAm | 12 |
| | | AS | UmUfCmUmUmGfUmCfCfAmGmCmUmUfUmAfU mUmGmGmAmGm | 13 |
| conjugate8 | L10-siAP1M2 | S | CmAmAmUmAmAmAfGfCfUmGmGmAmCmAmA mGmAmAm | 14 |
| | | AS | UmUfCmUmUmGfUmCmCmAmGmCmUmUfUmAf UmUmGmGmGm | 15 |
| conjugate9 | L10-siAP2M2 | S | CmCmCmAmAmUmAmAmAfGfCfUmGmGmAmCm AmAmGmAmAm | 16 |
| | | AS | UmUfCmUmUmGfUmCmCmAmGmCmUmUfUmAf UmUmGmGmAmGm | 17 |
| conjugate10 | L10-siAP1M1VP | S | CmAmAmUmAfAmAfGfCfUmGmGmAmCmAmAm GmAmAm | 10 |
| | | AS | VP-UmUfCmUmUmGfUmCfCfAmGmCmUmUfUmA fUmUmGmGmGm | 34 |
| conjugate11 | L10-siAP2M1VP | S | CmCmCmAmAmUmAfAmAfGfCfUmGmGmAmCm AmAmGmAmAm | 12 |
| | | AS | VP-UmUfCmUmUmGfUmCfCfAmGmCmUmUfUmA fUmUmGmGmGmAmGm | 35 |
| conjugate12 | L10-siAP1M2VP | S | CmAmAmUmAmAmAfGfCfUmGmGmAmCmAmA mGmAmAm | 14 |
| | | AS | VP-UmUfCmUmUmGfUmCmCmAmGmCmUmUfU mAfUmUmGmGmGm | 36 |
| conjugate13 | L10-siAP2M2VP | S | CmCmCmAmAmUmAmAmAfGfCfUmGmGmAmCm AmAmGmAmAm | 16 |
| | | AS | VP-UmUfCmUmUmGfUmCmCmAmGmCmUmUfU mAfUmUmGmGmGmAmGm | 37 |
| conjugate14 | L10-siAP1M1S | S | CmsAmsAmUmAfAmAfGfCfUmGmGmAmCmAmA mGmAmAm | 18 |
| | | AS | UmsUfsCmUmUmGfUmCfCfAmGmCmUmUfUmAf UmUmGmsGmsGm | 19 |
| conjugate15 | L10-siAP2M1S | S | CmsCmsCmAmAmUmAfAmAfGfCfUmGmGmAmC mAmAmGmAmAm | 20 |
| | | AS | UmsUfsCmUmUmGfUmCfCfAmGmCmUmUfUmAf UmUmGmGmGmsAmsGm | 21 |
| conjugate16 | L10-siAP1M2S | S | CmsAmsAmUmAmAmAfGfCfUmGmGmAmCmAm AmGmAmAm | 22 |
| | | AS | UmsUfsCmUmUmGfUmCmCmAmGmCmUmUfUm AfUmUmGmsGmsGm | 23 |
| conjugate17 | L10-siAP2M2S | S | CmsCmsCmAmAmUmAmAmAfGfCfUmGmGmAmC mAmAmGmAmAm | 24 |
| | | AS | UmsUfsCmUmUmGfUmCmCmAmGmCmUmUfUm AfUmUmGmGmGmsAmsGm | 25 |
| conjugate18 | L10-siAP1M1SVP | S | CmsAmsAmUmAfAmAfGfCfUmGmGmAmCmAmA mGmAmAm | 18 |
| | | AS | VP-UmsUfsCmUmUmGfUmCfCfAmGmCmUmUfU mAfUmUmGmsGmsGm | 38 |
| conjugate19 | L10-siAP2M1SVP | S | CmsCmsCmAmAmUmAfAmAfGfCfUmGmGmAmC mAmAmGmAmAm | 20 |
| | | AS | VP-UmsUfsCmUmUmGfUmCfCfAmGmCmUmUfU mAfUmUmGmGmGmsAmsGm | 39 |
| conjugate20 | L10-siAP1M2SVP | S | CmsAmsAmUmAmAmAfGfCfUmGmGmAmCmAm AmGmAmAm | 22 |
| | | AS | VP-UmsUfsCmUmUmGfUmCmCmAmGmCmUmUf UmAfUmUmGmsGmsGm | 40 |
| conjugate21 | L10-siAP2M2SVP | S | CmsCmsCmAmAmUmAmAmAfGfCfUmGmGmAmC mAmAmGmAmAm | 24 |
| | | AS | VP-UmsUfsCmUmUmGfUmCmCmAmGmCmUmUf UmAfUmUmGmGmGmsAmsGm | 41 |

TABLE 3-continued siRNA Conjugates

| siRNA Conjugate | No. | | Sequence Direction 5'-3' | SEQ ID NO |
|---|---|---|---|---|
| conjugate22 | P10-siAP1M2SVP | S | CmsAmsAmUmAmAmAfGfCfUmGmGmAmCmAm AmGmAmAm | 22 |
| | | AS | VP-UmsUfsCmUmUmGfUmCmCmAmGmCmUmUf UmAfUmUmGmsGmsGm | 40 |
| conjugate23 | R5-siAP1M2SVP | S | CmsAmsAmUmAmAmAfGfCfUmGmGmAmCmAm AmGmAmAm | 22 |
| | | AS | VP-UmsUfsCmUmUmGfUmCmCmAmGmCmUmUf UmAfUmUmGmsGmsGm | 40 |
| conjugate24 | LA5-siAP1M2SVP | S | CmsAmsAmUmAmAmAfGfCfUmGmGmAmCmAm AmGmAmAm | 22 |
| | | AS | VP-UmsUfsCmUmUmGfUmCmCmAmGmCmUmUf UmAfUmUmGmsGmsGm | 40 |
| conjugate25 | LB5-siAP1M2SVP | S | CmsAmsAmUmAmAmAfGfCfUmGmGmAmCmAm AmGmAmAm | 22 |
| | | AS | VP-UmsUfsCmUmUmGfUmCmCmAmGmCmUmUf UmAfUmUmGmsGmsGm | 40 |
| conjugate26 | V8-siAP1M2SVP | S | CmsAmsAmUmAmAmAfGfCfUmGmGmAmCmAm AmGmAmAm | 22 |
| | | AS | VP-UmsUfsCmUmUmGfUmCmCmAmGmCmUmUf UmAfUmUmGmsGmsGm | 40 |
| conjugate27 | W8-siAP1M2SVP | S | CmsAmsAmUmAmAmAfGfCfUmGmGmAmCmAm AmGmAmAm | 22 |
| | | AS | VP-UmsUfsCmUmUmGfUmCmCmAmGmCmUmUf UmAfUmUmGmsGmsGm | 40 |
| conjugate28 | X8-siAP1M2SVP | S | CmsAmsAmUmAmAmAfGfCfUmGmGmAmCmAm AmGmAmAm | 22 |
| | | AS | VP-UmsUfsCmUmUmGfUmCmCmAmGmCmUmUf UmAfUmUmGmsGmsGm | 40 |
| conjugate29 | Z5-siAP1M2SVP | S | CmsAmsAmUmAmAmAfGfCfUmGmGmAmCmAm AmGmAmAm | 22 |
| | | AS | VP-UmsUfsCmUmUmGfUmCmCmAmGmCmUmUf UmAfUmUmGmsGmsGm | 40 |
| conjugateF1 | FIN-siAP1M1SVP | S | CmsAmsAmUmAfAmAfGfCfUmGmGmAmCmAmA mGmAmAm | 18 |
| | | AS | VP-UmsUfsCmUmUmGfUmCfCfAmGmCmUmUfU mAfUmUmGmsGmsGm | 38 |
| conjugateF2 | FIN-siAP1M1S | S | CmsAmsAmUmAfAmAfGfCfUmGmGmAmCmAmA mGmAmAm | 18 |
| | | AS | UmsUfsCmUmUmGfUmCfCfAmGmCmUmUfUmAf UmUmGmsGmsGm | 19 |
| conjugateF3 | FIN-siAP2M1SVP | S | CmsCmsCmAmAmUmAfAmAfGfCfUmGmGmAmC mAmAmGmAmAm | 20 |
| | | AS | VP-UmsUfsCmUmUmGfUmCfCfAmGmCmUmUfU mAfUmUmGmGmsAmsGm | 39 |
| conjugateF4 | FIN-siAP2M1S | S | CmsCmsCmAmAmUmAfAmAfGfCfUmGmGmAmC mAmAmGmAmAm | 20 |
| | | AS | UmsUfsCmUmUmGfUmCfCfAmGmCmUmUfUmAf UmUmGmGmsAmsGm | 21 |
| conjugateF5 | FIN-siAP2M2S | S | CmsCmsCmAmAmUmAmAmAfGfCfUmGmGmAmC mAmAmGmAmAm | 24 |
| | | AS | UmsUfsCmUmUmGfUmCmCmAmGmCmUmUfUm AfUmUmGmGmsAmsGm | 25 |
| comparative conjugate1 | L10-siHBX1M1SVP | S | CmsCmsUmUmGfAmGfGfCfAmUmAmCmUmUmC mAmAmAm | 44 |
| | | AS | VPUmsUfsUmGmAmAfGmUfAfUmGmCmCmUfCm AfAmGmGmsUmsUm | 45 |
| comparative conjugate2 | L10-siNCM2S | S | UmsUmsCmUmCmCmGfAfAfCmGmUmGmUmCmA mCmGmUm | 46 |
| | | AS | AmsCfsGmUmGmAfCmAmCmGmUmUmCmGfGm AfGmAmAmsCmsUm | 47 |

TABLE 3-continued

| siRNA Conjugate | No. | | Sequence Direction 5'-3' | SEQ ID NO |
|---|---|---|---|---|
| comparative conjugate3 | (GalNAc)3-69535 | S | GmsCmsUmUmAmAmAmAmGfGmGfAmCmAmGm UmAmUmUmCmAm | 48 |
| | | AS | UmsGfsAmAmUmAmCmUmGmUmCmCfCmUfUm UmUmAmAmGmCmsAmsAm | 49 |

Preparation Example 3. Preparation of P10-siAP1M2SP Conjugate (Conjugate 22) (3-1) Synthesis of Compound P-10

Compound P-10 was synthesized according to the following method:

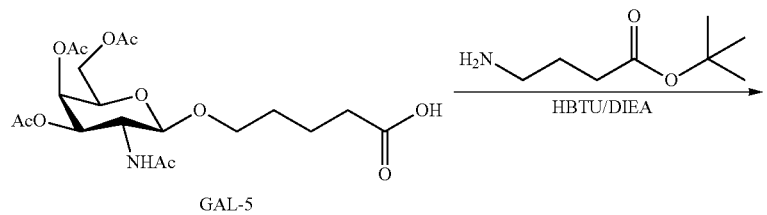

GAL-5

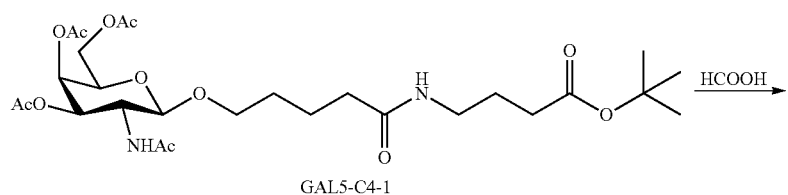

GAL5-C4-1

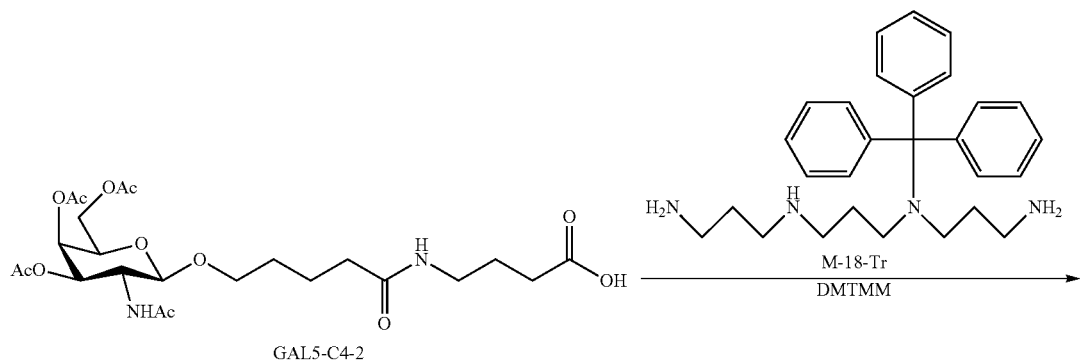

GAL5-C4-2

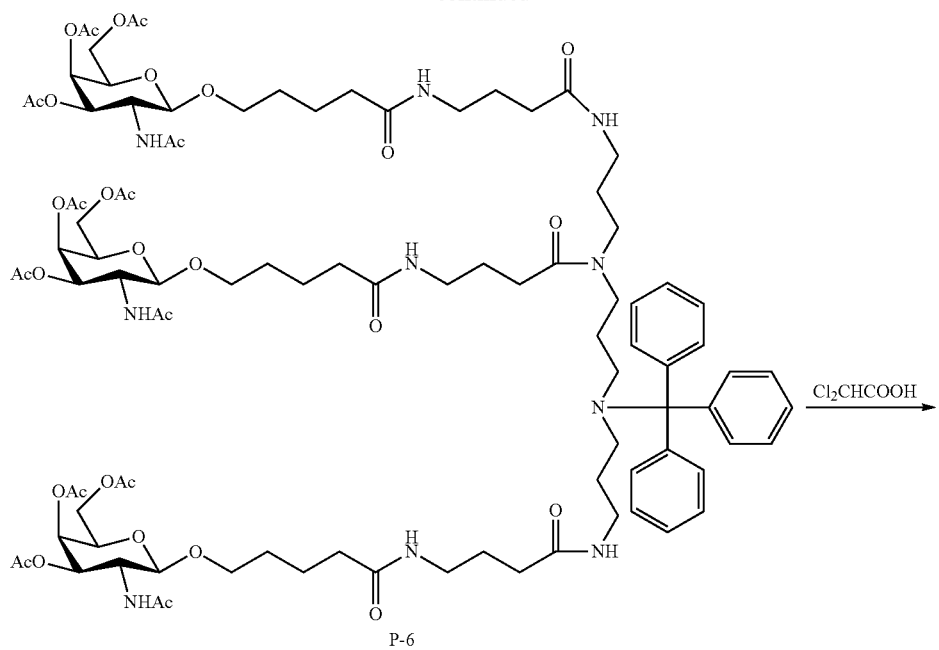
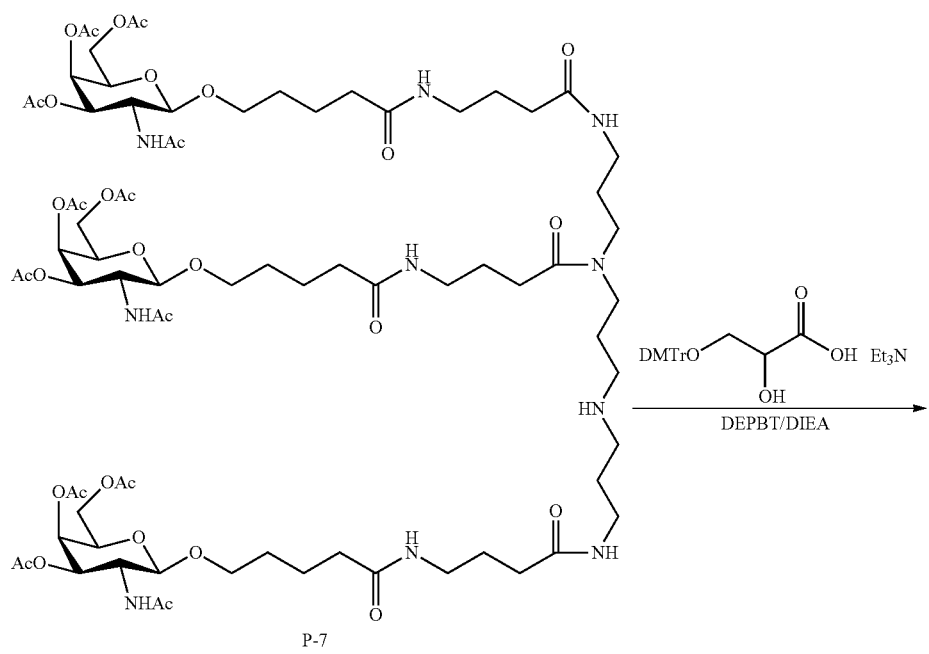

-continued
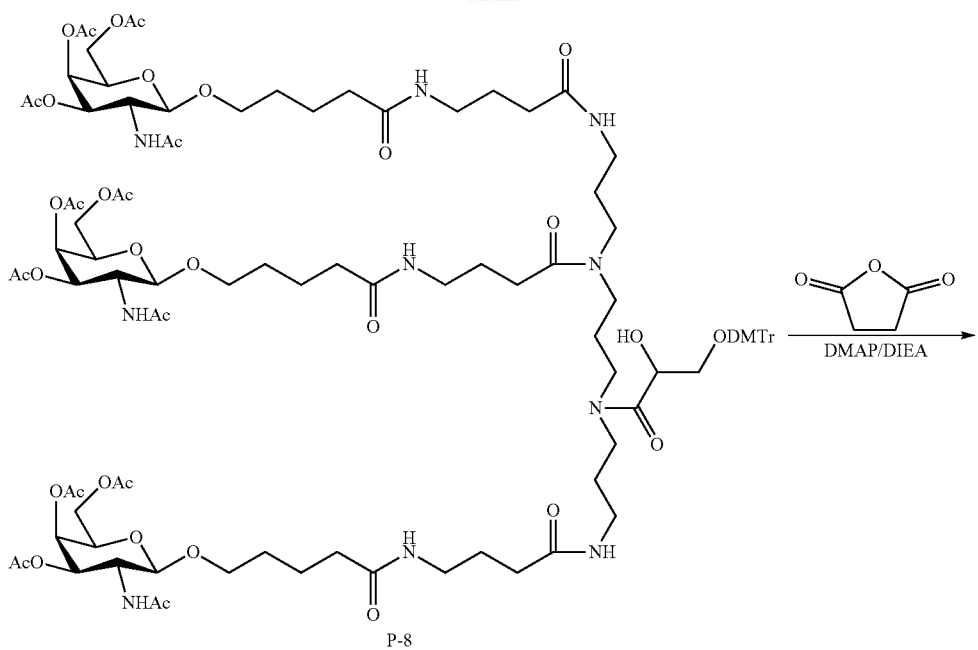
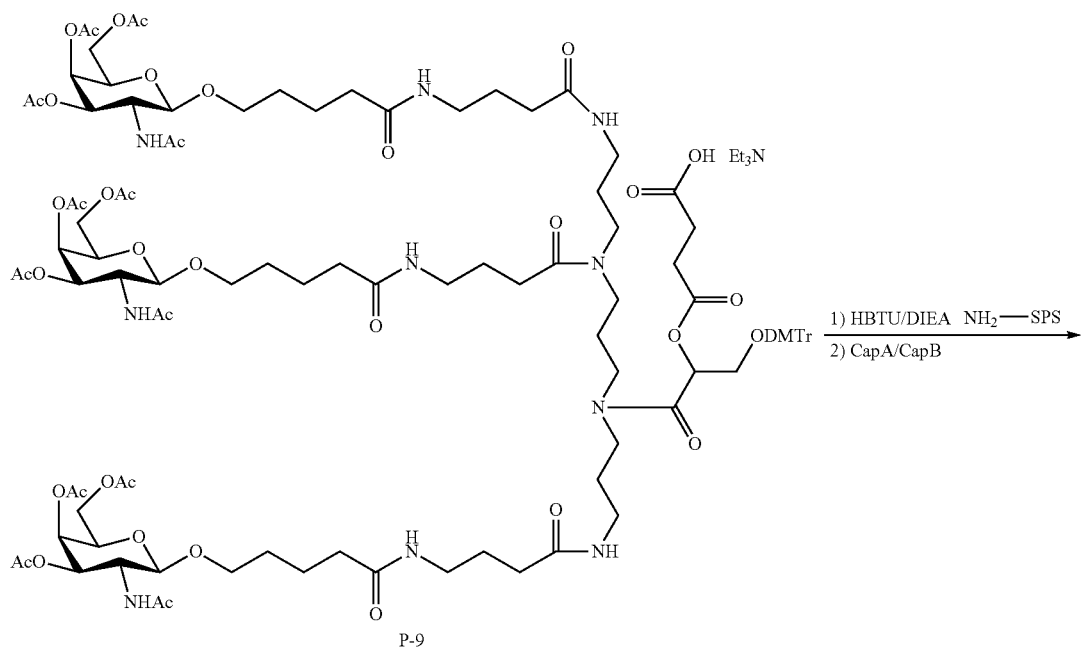

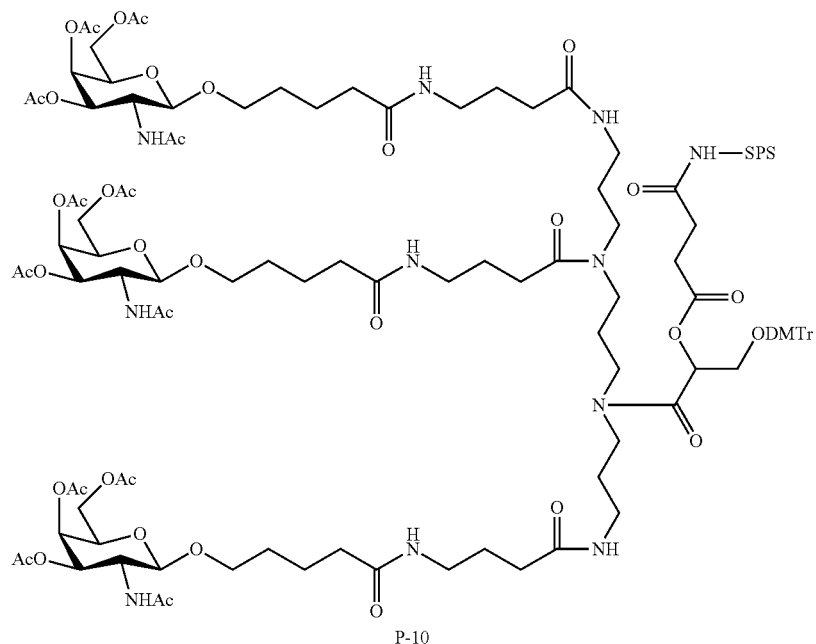

P-10

(3-1-1) Synthesis of GAL5-C4-1

GAL-5 (13.43 g, 30.0 mmol) obtained according to the method described in (1-1-1) above, t-butyl 4-aminobutyrate hydrochloride (5.87 g, 30.0 mmol), O-benzotriazol-tetramethyluronium hexafluorophosphate (13.65 g, 36.0 mmol) and diisopropylethylamine (11.63 g, 90.0 mmol) were added to 40 ml of N,N-dimethylformamide, dissolved uniformly and then stirred at room temperature to react for 5 hours. 300 ml of saturated aqueous sodium bicarbonate solution was added to the reaction solution, and then extracted three times, each with 200 ml of ethyl acetate. The organic phases were combined and washed once with 200 ml of saturated brine. The organic phase was isolated and dried with anhydrous sodium sulfate. The solvent was evaporated to dryness under reduced pressure to give 30.3 g of crude product GAL5-C4-1 as oil, which was directly used in the next reaction.

(3-1-2) Synthesis of GAL5-C4-2

The crude product GAL5-C4-1 (30.3 g, 30 mmol) obtained in step (3-1-1) was dissolved in 180 ml of formic acid and stirred at room temperature to react for 16 hours. The solvent was evaporated to dryness. The residue was purified by column chromatography (200-300 mesh normal phase silica gel, with a gradient elution of dichloromethane:methanol=100:18-100:20). The eluate was collected and concentrated to remove the solvents to give a total of 14.84 g of target product GAL5-C4-2.

(3-1-3) Synthesis of P-6:

M-18-Tr (2.02 g, 4.69 mmol) obtained according to the method described in step (1-1-4) and GAL5-C4-2 (8.24 g, 15.48 mmol, combination of 2 batches) obtained in step (3-1-2) were mixed and dissolved in 47 ml of acetonitrile, added with N-methylmorpholine (3.13 g, 30.96 mmol) followed by 4-(4,6-dimethoxytriazin-2-yl)-4-methylmorpholine hydrochloride (DMTMM, 4.28 g, 15.48 mmol) to react for 2 hours under stirring at room temperature. The resulting reaction solution was diluted with 20 ml of dichloromethane. The organic phase was washed with 10 ml of saturated sodium bicarbonate solution and 10 ml of saturated brine, respectively. All organic phases were combined, dried with anhydrous sodium sulfate, and filtered. The solvent was evaporated to dryness under reduced pressure to give a crude product, which was purified by using a normal phase silica gel column having 200-300 mesh. The column was packed with petroleum ether, added with 1 wt % triethylamine for neutralizing the acidity of silica gel, and eluted with a gradient elution of dichloromethane:methanol=100:5-100:7. The eluate of product was collected, and the solvent was evaporated to dryness under reduced pressure to give a total of 8.27 g of pure product P-6.

(3-1-4) Synthesis of P-7:

P-6 (6.82 g, 3.456 mmol) obtained in (3-1-3) above was dissolved in 69 ml of dichloromethane, and added with dichloroacetic acid (13.367 g, 103.67 mmol) to react for 2 hours at room temperature. The resulting reaction solution was diluted by adding 100 ml of dichloromethane, washed and adjusted to pH 7-8 with saturated sodium bicarbonate solution. The aqueous phase was extracted six times, each with 30 ml of dichloromethane. The organic phases were combined, dried with anhydrous sodium sulfate, and filtered. Then the solvent was evaporated to dryness under reduced pressure to give a crude product. The crude product was purified by using a normal phase silica gel column having 200-300 mesh. The column was added with 10 wt % triethylamine for neutralizing the acidity of silica gel. The column was equilibrated with 1 wt ‰ triethylamine and eluted with a gradient elution of dichloromethane:methanol=100:30-100:40. The eluate of product was collected, and the solvent was evaporated under reduced pressure to give a total of 4.82 g of P-7. MS m/z: $C_{78}H_{127}N_{10}O_{33}$, $[M+H]^+$, calcd: 1732.91, measured: 1735.73.

(3-1-5) Synthesis of P-8:

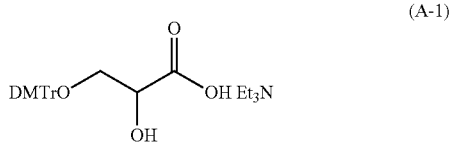

(A-1)

P-7 (2.653 g, 1.532 mmol) and A-1 (2.342 g, 4.596 mmol) were mixed and dissolved in 16 ml of dichloromethane, and added with 3-diethoxyphosphoryl-1,2,3-benzotriazol 4(3H)-one (DEPBT) (1.375 g, 4.596 mmol) followed by diisopropylethylamine (1.188 g, 9.191 mmol) to react for 2 hours under stirring at 25° C. The organic phase was washed with 10 ml of saturated sodium bicarbonate. The aqueous phase was extracted three times, each with 10 ml of dichloromethane. The organic phase was washed with 10 ml of saturated brine. The aqueous phase was extracted twice, each with 10 ml of dichloromethane. All the organic phases were combined, dried with anhydrous sodium sulfate and filtered. The solvent was evaporated to dryness under reduced pressure, and the residue was foam-dried overnight with a vacuum oil pump to give a crude product. The crude product was subjected to a column purification. The column was filled with 120 g of normal phase silica gel having 200-300 mesh, and added with 20 ml triethylamine for neutralizing the acidity of silica gel. The column was equilibrated with petroleum ether containing 1 wt % triethylamine and eluted with a gradient elution of petroleum ether:ethylacetate:dichloromethane:N,N-dimethylformamide=1:1:1:0.5-1:1:1:0.6. The eluate of product was collected, and the solvent was evaporated to dryness under reduced pressure to give a total of 2.793 g of pure product P-8.

(3-1-6) Synthesis of P-9:

P-8 (490 mg, 0.231 mmol), succinic anhydride (69 mg, 0.693 mmol) and 4-dimethylaminopyridine (DMAP, 68 mg, 0.554 mmol) were mixed and dissolved in 2.3 ml of dichloromethane, and added with diisopropylethylamine (DIPEA, 149 mg, 1.155 mmol) to react for 21 hours under stirring at 25° C. 50 ml dichloromethane was added to the resulting reaction solution for dilution, and then washed with 100 ml of 0.5 M triethylamine phosphate. The aqueous phase was extracted three times, each with 10 ml of dichloromethane. The organic phases were combined, and the solvent was evaporated to dryness under reduced pressure to give a crude product. The crude product was subjected to a column purification. The column was filled with 80 g of normal phase silica gel having 200-300 mesh, and added with 1 wt % triethylamine for neutralizing the acidity of silica gel. The column was equilibrated with dichloromethane and eluted with a gradient elution of dichloromethane containing 1 wt ‰ triethylamine:methanol=100:18-100:20. The eluate of product was collected, and the solvent was evaporated to dryness under reduced pressure to give a total of 200 mg of pure product, P-9 conjugating molecule. MS m/z: $C_{106}H_{153}N_{10}O_{41}$, $[M-DMTr]^+$, calcd: 1921.05, measured: 1920.97.

(3-1-7) Synthesis of P-10:

P-10 was prepared by the same method as that in step (1-1-9) of Preparation Example 1, except that L-9 conjugating molecule was replaced with P-9 conjugating molecule to produce P-9 conjugating molecule linked to the solid phase support.

(3-2) Synthesis of P10-siAP1M2SVP Conjugate

Conjugate 22 was prepared by the same method as that in steps (1-2), (1-3A) and (1-4) of Preparation Example 1, except that compound L-10 was replaced with compound P-10 to start the synthesis of a sense strand. It was expected that P10-siAP1M2SVP conjugate having the structure represented by Formula (4) can be obtained.

Preparation Example 4. Preparation of R5-siAP1M2SVP Conjugate (Conjugate 23)

(4-1) Synthesis of Compound R-5

Compound R-5 was synthesized according to the following method:

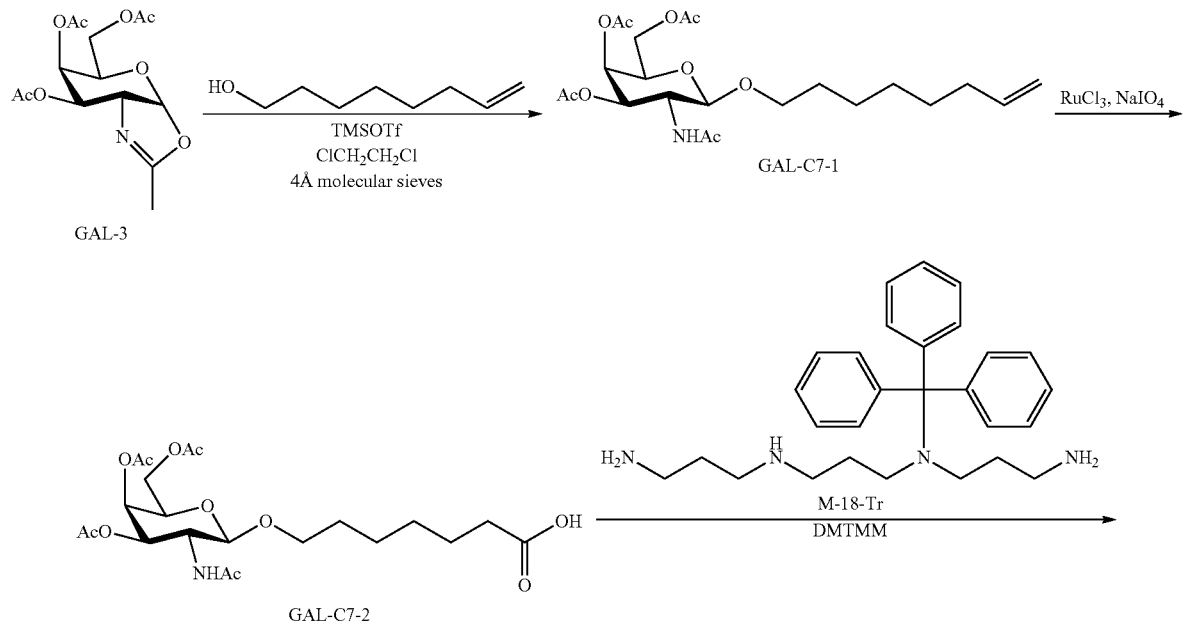

-continued
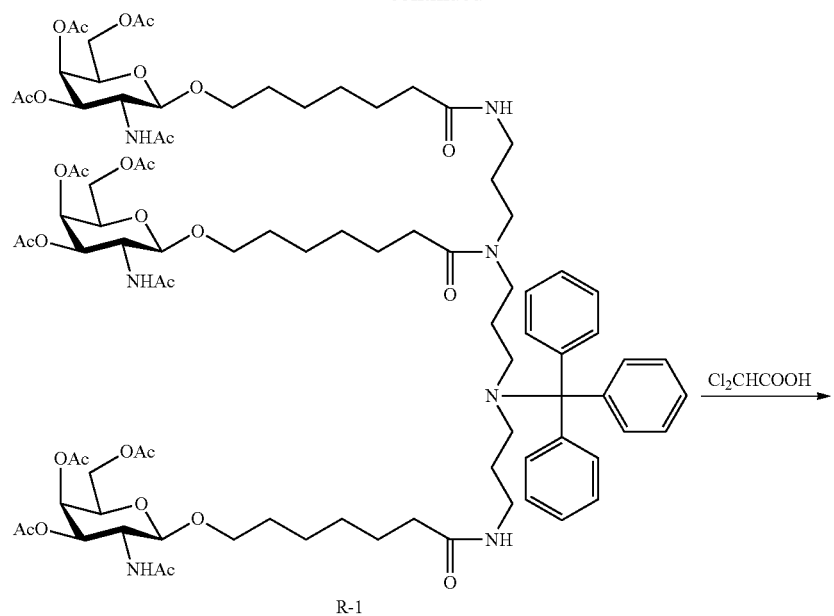
R-1
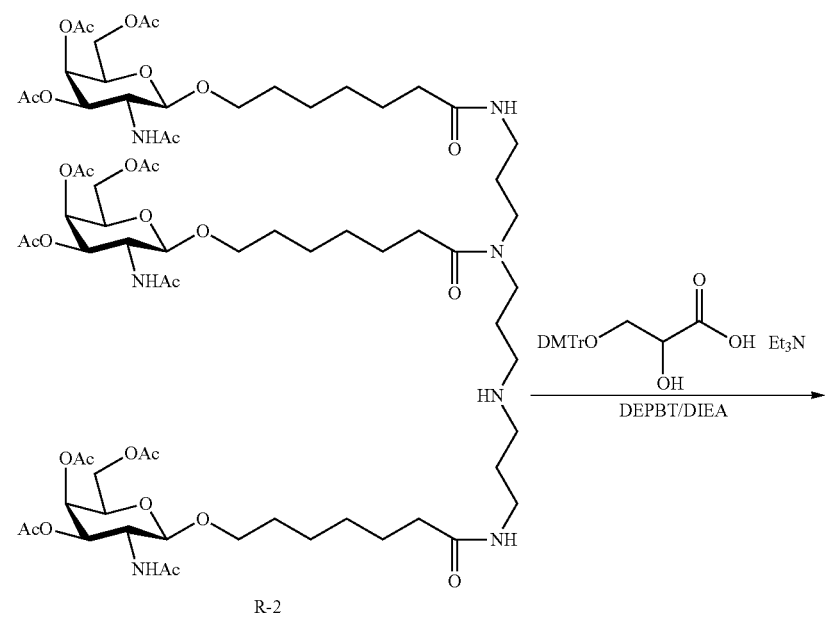
R-2

-continued
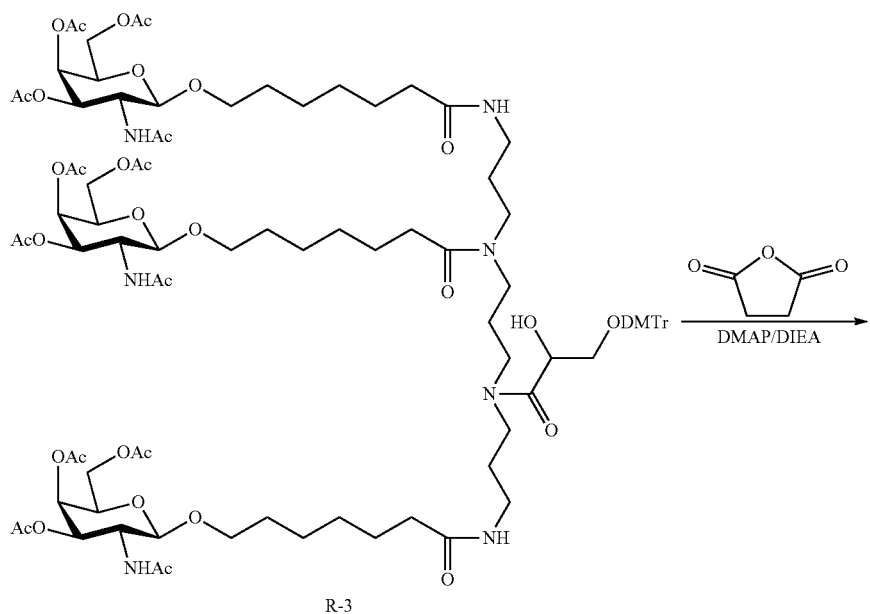
R-3
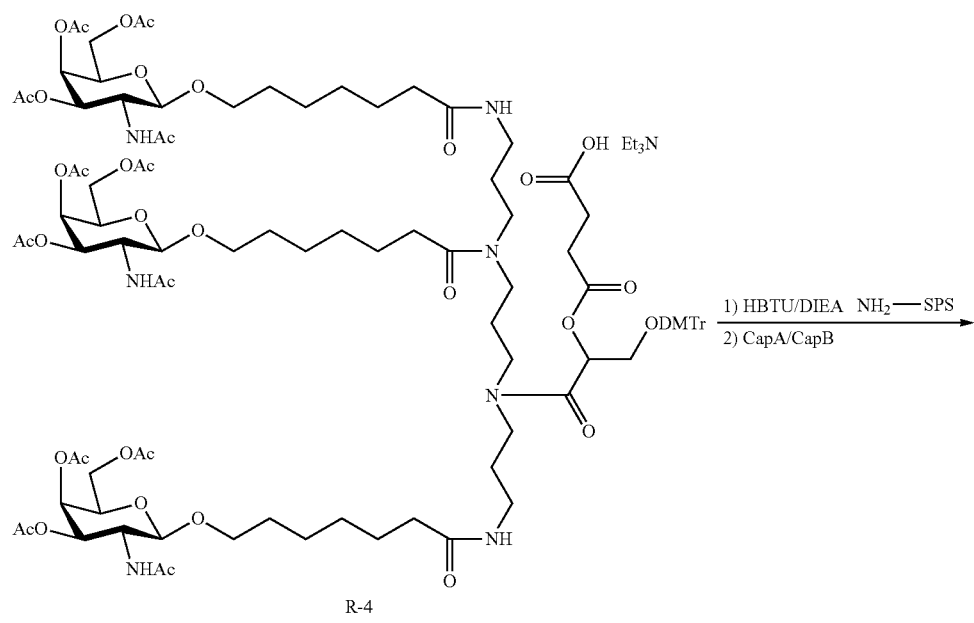
R-4

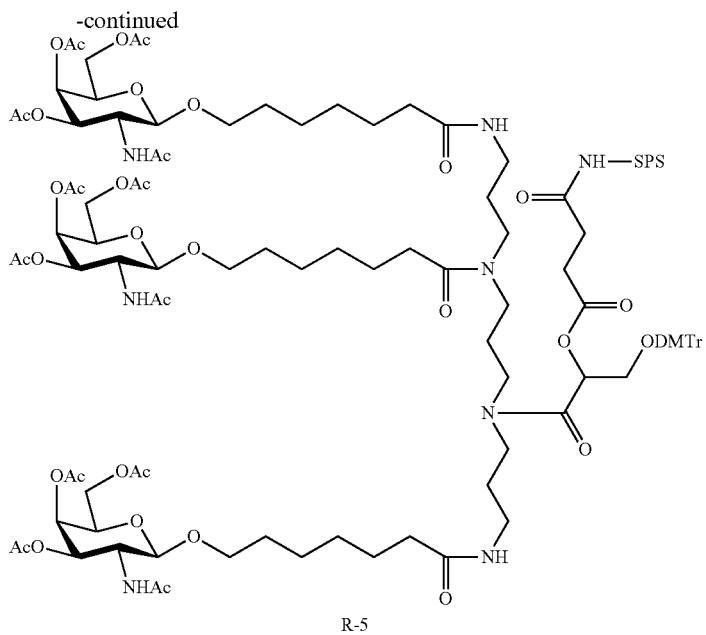

R-5

(4-1-1) Synthesis of GAL-C7-1

GAL-3 (26.4 g, 80.2 mmol) obtained according to the method described in step (1-1-1b) was dissolved in 134 ml of anhydrous 1,2-dichloroethane, and added with 60 g of 4 Å molecular sieve as a powder followed by 7-octen-1-ol (11.3 g, 88.2 mmol) to react for 10 minutes under stirring at room temperature. Trimethylsilyl trifluoromethanesulphonate (TMSOTf, 8.9 g, 40.1 mmol) was added in an ice bath and nitrogen atmosphere to react for 24 hours under stirring at room temperature. The 4 Å molecular sieve powder was removed by filtration. 500 ml of saturated aqueous sodium bicarbonate solution was added to the filtrate for washing. The organic phase was isolated. The aqueous phase was extracted once with 100 ml of dichloromethane. The organic phases were combined and washed once with 250 ml of saturated brine. The organic phase was isolated and dried with anhydrous sodium sulfate. The solvent was evaporated to dryness under reduced pressure to give 33.3 g of product GAL-C7-1 as yellow syrup, which was directly used in the next oxidation reaction without purification.

(4-1-2) Synthesis of GAL-C7-2

GAL-C7-1 (33.3 g, 72.8 mmol) obtained in step (4-1-1) was dissolved in a mixed solvent of 160 ml of dichloromethane and 160 ml of acetonitrile, added with 216 ml of water and sodium periodate solid (62.3 g, 291.2 mmol) respectively, stirred in an ice water bath for 10 minutes, and added with a catalyst ruthenium trichloride (498 mg, 2.4 mmol). The reaction was naturally warmed to room temperature and stirred for 23 hours. The resulting reaction solution was diluted by adding 200 ml of water, stirred, and adjusted to pH 7.5 by adding saturated sodium bicarbonate. The organic phase was isolated and discarded. The aqueous phase was extracted three times, each with dichloromethane. The organic phase was discarded. The aqueous phase was adjusted to a pH of about 3 with citric acid solid, extracted three times, each with 200 ml of dichloromethane. All the organic phases were combined, dried with anhydrous sodium sulfate. The solvent was evaporated under reduced pressure, and then the residue was purified by column chromatography (200-300 mesh normal phase silica gel, with a gradient elution of dichloromethane:methanol=100:18-100:20) to give 22.4 g of product GAL-C7-2 as a white foamy solid. MS m/z: $C_{21}H_{32}NO_{11}$, $[M+H]^+$, calcd: 476.50, measured: 475.94.

(4-1-3) Synthesis of R-1:

M-18-Tr (2.02 g, 4.69 mmol) obtained according to the method described in step (1-1-4) and GAL-C7-2 (7.36 g, 15.48 mmol) were mixed and dissolved in 47 ml of acetonitrile, added with N-methylmorpholine (3.13 g, 30.96 mmol) followed by 4-(4,6-dimethoxytriazin-2-yl)-4-methylmorpholine hydrochloride (DMTMM, 4.28 g, 15.48 mmol) to react for 2 hours under stirring at room temperature. The resulting reaction solution was diluted with 200 ml of dichloromethane. The organic phase was washed with 100 ml of saturated sodium bicarbonate solution and 100 ml of saturated brine, respectively. The organic phases were combined, dried with anhydrous sodium sulfate, and filtered. The solvent was evaporated to dryness under reduced pressure to give a crude product, which was purified by using a normal phase silica gel column having 200-300 mesh. The column was packed with petroleum ether, added with 1 wt % triethylamine for neutralizing the acidity of silica gel, and eluted with a gradient elution of dichloromethane:methanol=100:5-100:7. The eluate of product was collected and evaporated to dryness under reduced pressure to give 7.82 g of pure product R-1.

(4-1-4) Synthesis of R-2:

R-1 (6.23 g, 3.456 mmol) was dissolved in 69 ml of dichloromethane, and added with dichloroacetic acid (13.367 g, 103.67 mmol) to react for 2 hours at room temperature. The resulting reaction solution was diluted by adding 100 ml of dichloromethane, washed and adjusted to pH 7-8 with saturated sodium bicarbonate solution. The aqueous phase was extracted six times, each with 30 ml of dichloromethane. The organic phases were combined, dried with anhydrous sodium sulfate, and filtered. Then the solvent was evaporated to dryness under reduced pressure to give a crude product. The crude product was purified by using a normal phase silica gel column having 200-300 mesh. The column was added with 10 wt % triethylamine for neutralizing the acidity of silica gel. The column was equilibrated with 1 wt ‰ triethylamine and eluted with a gradient elution of dichloromethane:methanol=100:30-100:40. The solvent was evaporated to dryness under reduced pressure to give 4.49 g of pure product R-2.

(4-1-5) Synthesis of R-3:

R-2 (2.391 g, 1.532 mmol) and A-1 (2.342 g, 4.596 mmol) were mixed and dissolved in 16 ml of dichloromethane, and added with 3-(diethoxyphosphoryloxy)-1,2,3-benzotrizin-4 (3H)-one (DEPBT, 1.375 g, 4.596 mmol) followed by diisopropylethylamine (1.188 g, 9.191 mmol) to react for 2 hours under stirring at 25° C. The organic phase was washed with 10 ml of saturated sodium bicarbonate. The aqueous phase was extracted three times, each with 10 ml of dichloromethane. The organic phase was washed with 10 ml of saturated brine. The aqueous phase was extracted twice, each with 10 ml of dichloromethane. All the organic phases were combined, dried with anhydrous sodium sulfate, and filtered. The solvent was evaporated to dryness under reduced pressure, and the residue was foam-dried overnight with a vacuum oil pump to give a crude product. The crude product was subjected to a column purification. The column was filled with 120 g of normal phase silica gel having 200-300 mesh, and added with 20 ml triethylamine for neutralizing the acidity of silica gel. The column was equilibrated with petroleum ether containing 1 wt % triethylamine and eluted with a gradient elution of petroleum ether:ethylacetate:dichloromethane:N,N-dimethylformamide=1:1:1:0.5-1:1:1:0.6. The solvent was evaporated to dryness under reduced pressure to give 2.642 g of pure product R-3.

(4-1-6) Synthesis of R-4:

R-3 (795 mg, 0.4074 mmol), succinic anhydride (82 mg, 0.8148 mmol) and 4-dimethylaminopyridine (DMAP, 100 mg, 0.8148 mmol) were mixed and dissolved in 4 ml of dichloromethane, and added with diisopropylethylamine (DIPEA, 100 mg, 0.8148 mmol) to react for 18 hours under stirring at 25° C. The resulting reaction solution was washed with 5 ml of 0.5 M triethylamine phosphate. The aqueous phase was extracted three times, each with 5 ml of dichloromethane. The organic phases were combined, and evaporated to dryness under reduced pressure to give a crude product. The crude product was subjected to a column purification. The column was filled with 30 g of normal phase silica gel having 200-300 mesh, and added with 1 wt % triethylamine for neutralizing the acidity of silica gel. The column was equilibrated with dichloromethane and eluted with a gradient elution of dichloromethane containing 1 wt ‰ triethylamine:methanol=100:18-100:20. The eluate of product was collected, and the solvent was evaporated to dryness under reduced pressure to give 505 mg of pure product of R-4 conjugating molecule.

(4-1-7) Synthesis of R-5 Conjugating Molecule

R-5 was prepared by a method the same as that in step (1-1-9) of Preparation Example 1, except that L-9 conjugating molecule was replaced with R-4 conjugating molecule to produce R-4 conjugating molecule linked to the solid phase support.

(4-2) Synthesis of R5-siAP1M2SVP Conjugate

Conjugate 23 was prepared by the same method as those in steps (1-2), (1-3A) and (1-4) in Preparation Example 1, except that R-10 compound was replaced with R-5 compound to start the synthesis of sense strand. It was expected that R5-siAP1M2SVP conjugate having the structure represented by Formula (7) can be produced.

Preparation Example 5. Preparation of LA5-siAP1M2SVP Conjugate (Conjugate 24)

It was expected that LA-5 compound can be synthesized according to following process route.

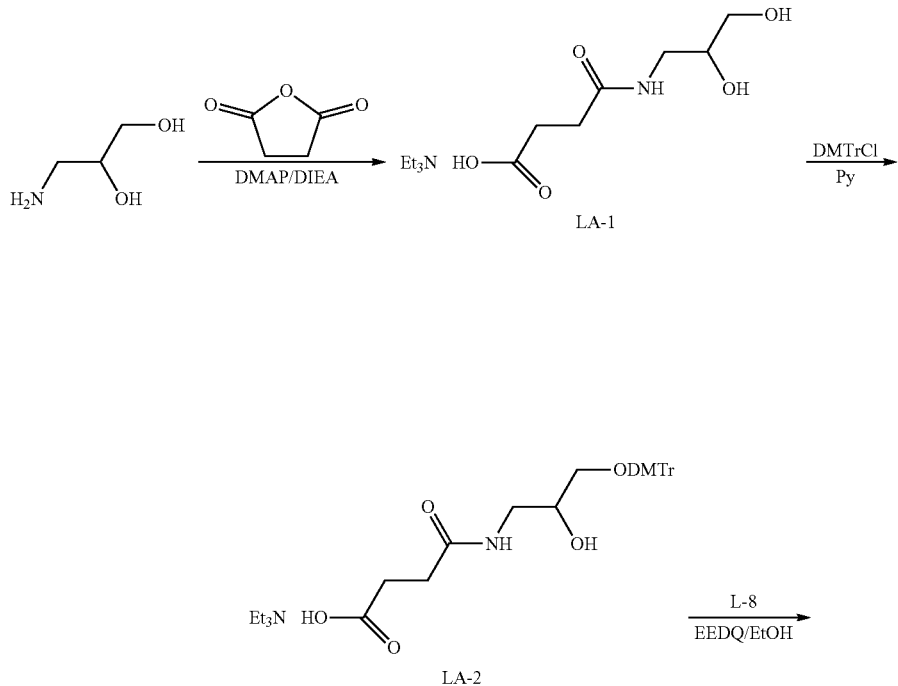

-continued
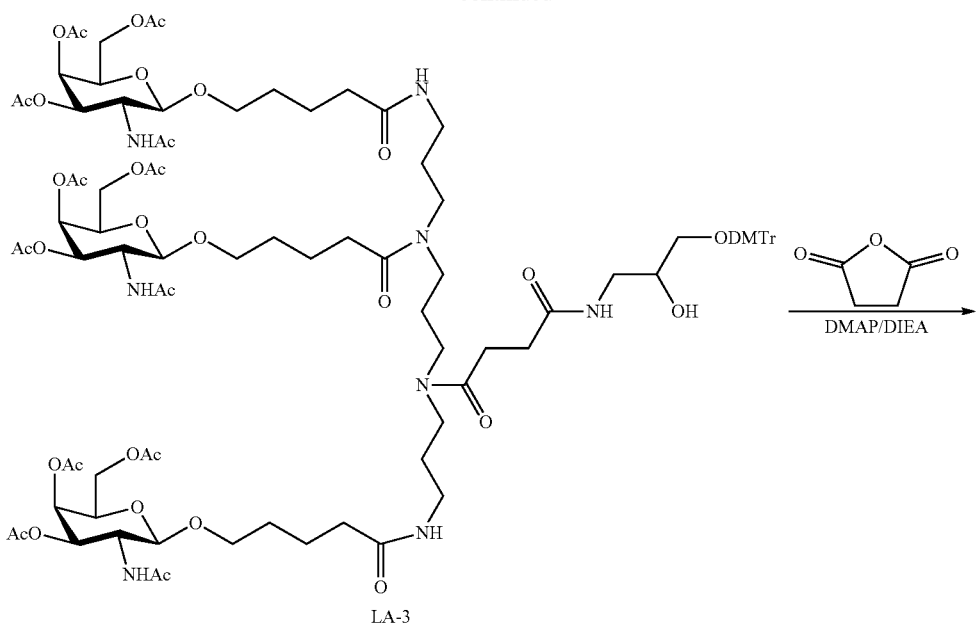
LA-3
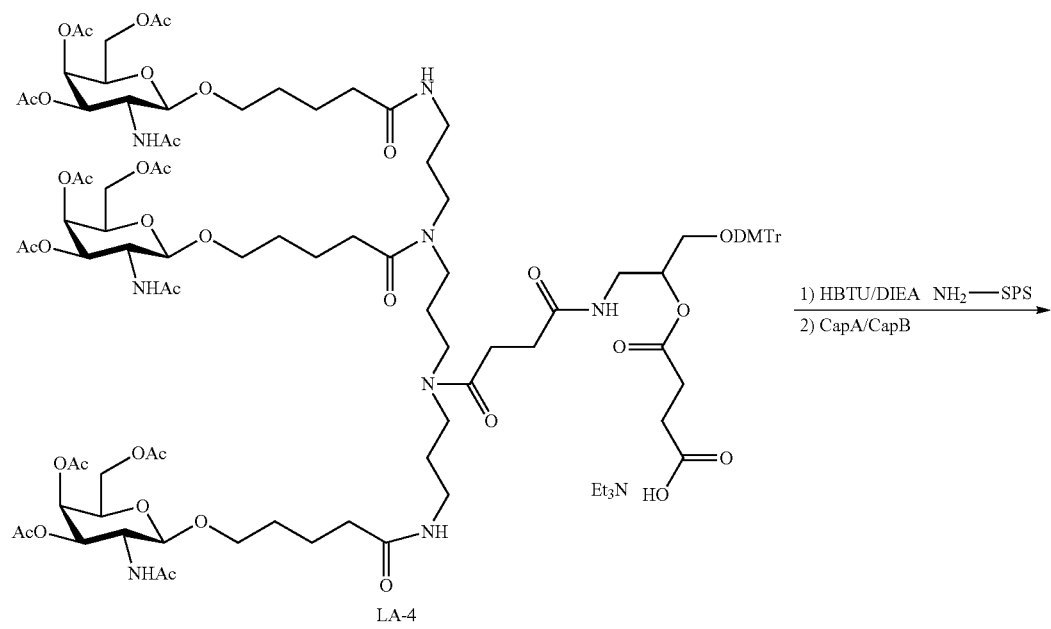
LA-4

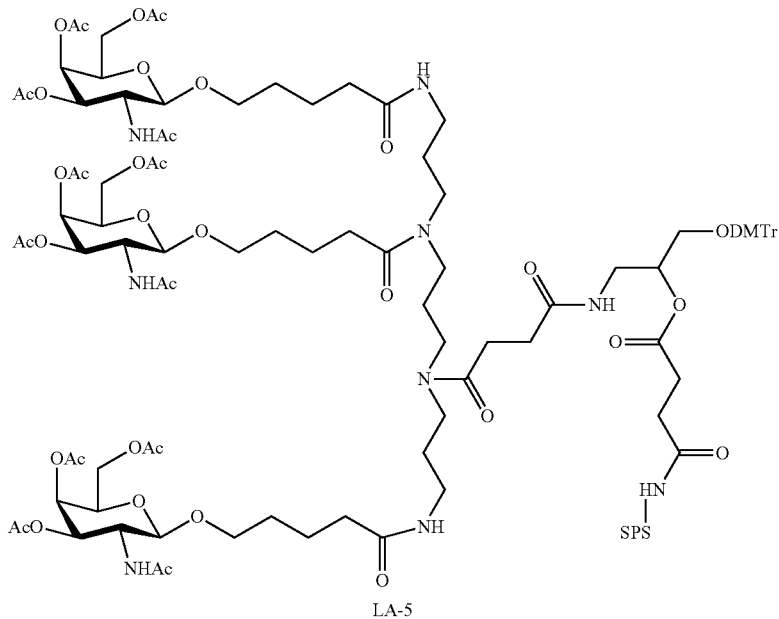

LA-5

Conjugate 24 was prepared by the same method as those in steps (1-2), (1-3A) and (1-4) of Preparation Example 1, except that L-10 compound was replaced with LA-5 compound to start the synthesis of the sense strand. It was expected that LA5-siAP1M2SVP conjugate having the structure represented by Formula (12) can be produced.

Preparation Example 6. Preparation of LB5-siAP1M2SVP Conjugate (Conjugate 25)

(6-1) Synthesis of LB-5 Compound

LB-5 compound was synthesized according to the following method:

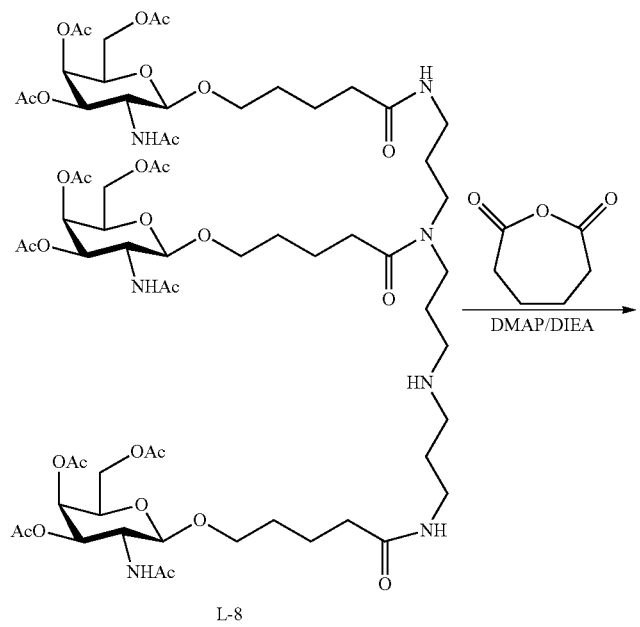

L-8

-continued
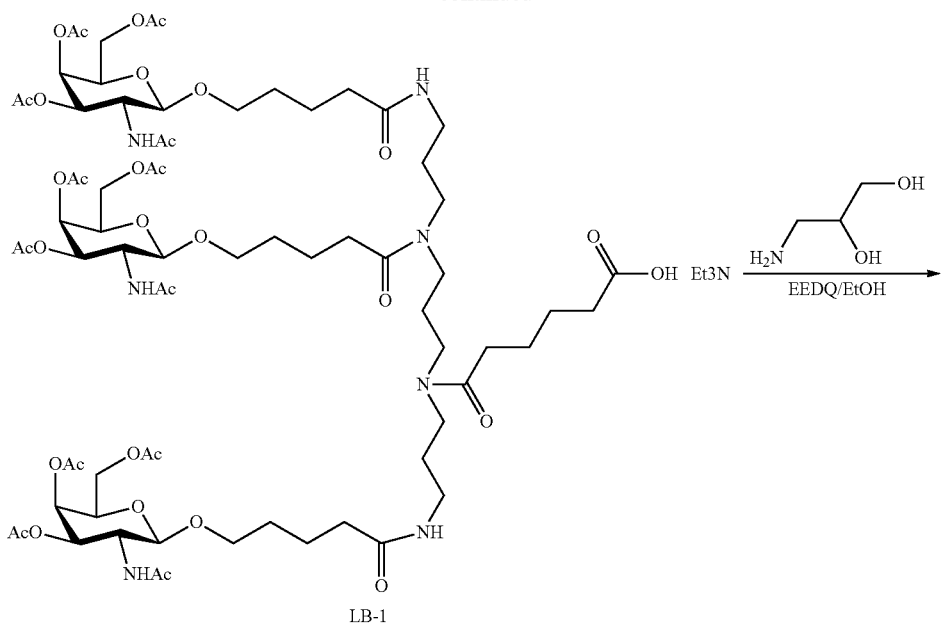
LB-1
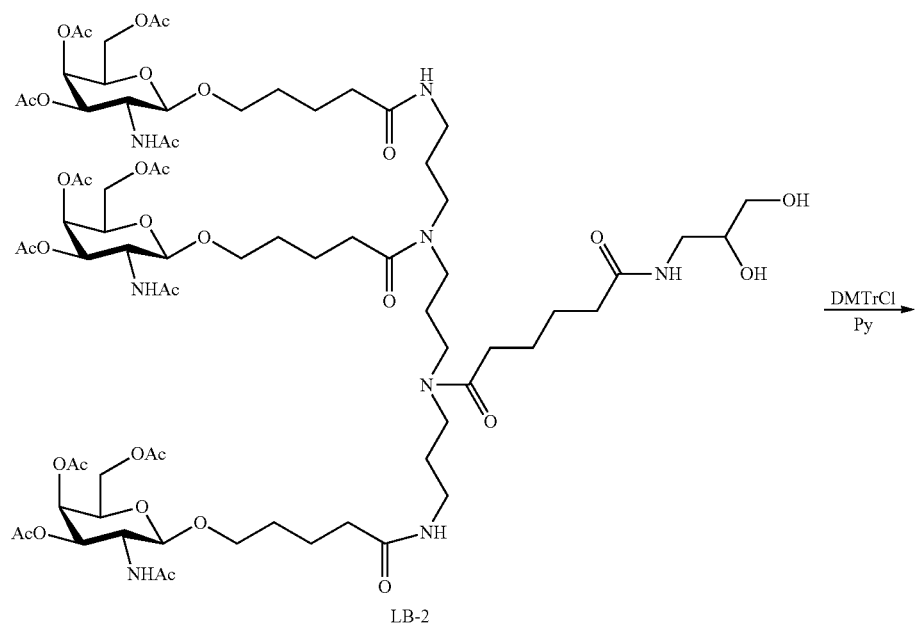
LB-2

-continued
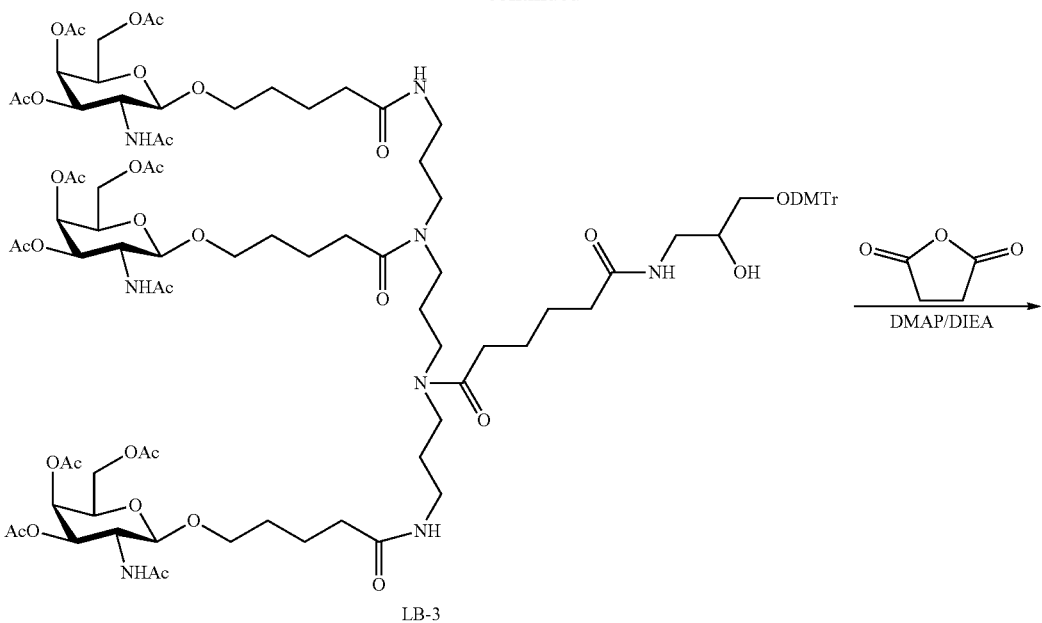
LB-3
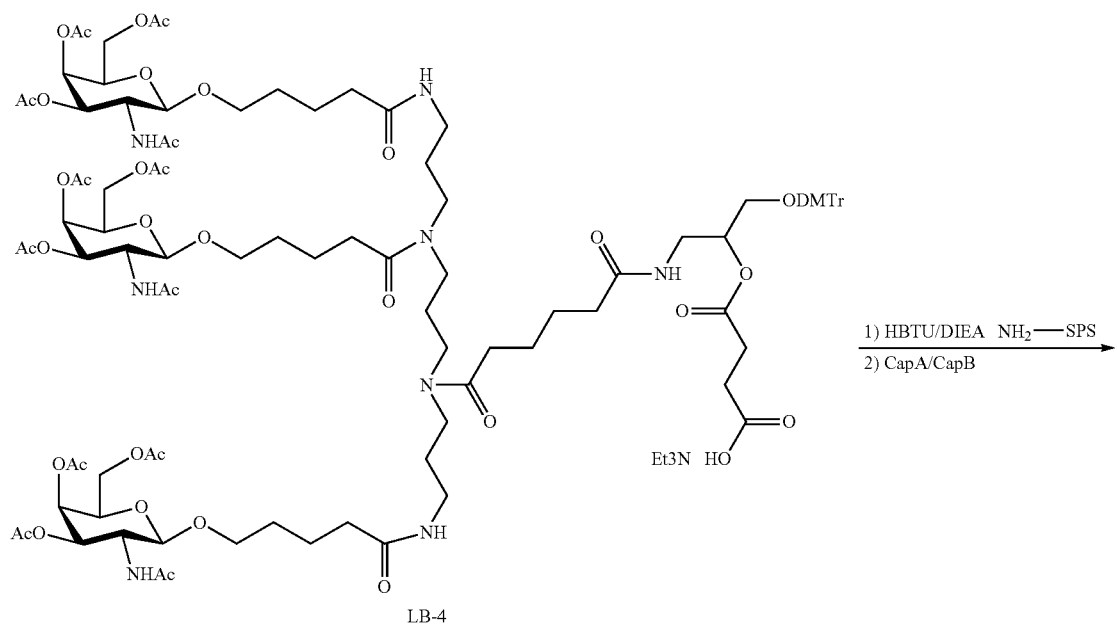
LB-4

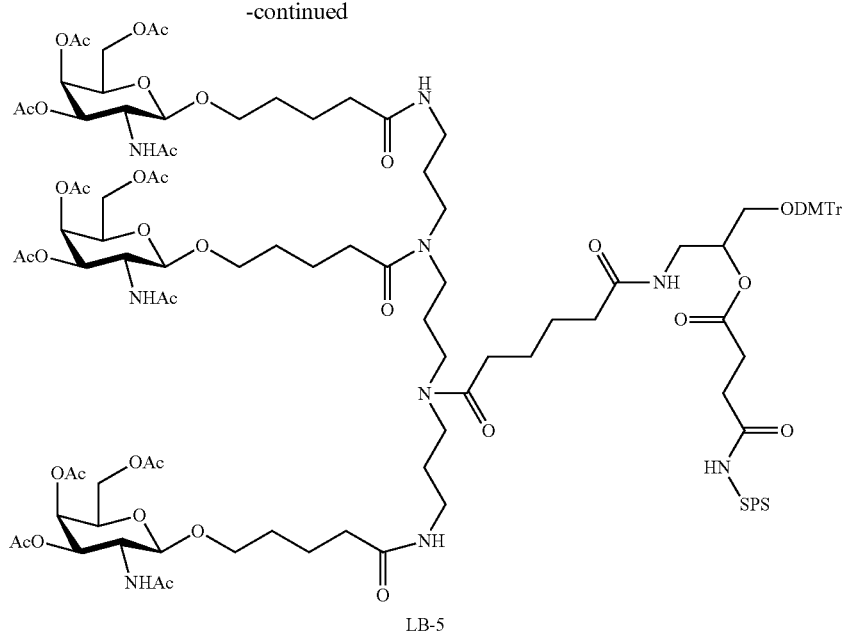

LB-5

(6-1-1) Synthesis of LB-1:

L-8 (5.0 g, 3.386 mmol) obtained according to the method described in step (1-1-6), adipic anhydride (870 mg, 6.772 mmol) and 4-dimethylaminopyridine (DMAP, 827 mg, 6.772 mmol) were mixed and dissolved in 130 ml of dichloromethane, and added with diisopropylethylamine (DIPEA, 2.2 g, 16.931 mmol) to react for 4 hours under stirring at 25° C. The resulting reaction solution was diluted by adding 70 ml dichloromethane, and then washed with 0.5 M triethylamine phosphate. The aqueous phase was extracted four times, each with 10 ml of dichloromethane. The organic phases were combined, and evaporated to dryness under reduced pressure to give a crude product. The crude product was subjected to a column purification. The column was filled with 120 g of normal phase silica gel having 200-300 mesh, and added with 1 wt % triethylamine for neutralizing the acidity of silica gel. The column was equilibrated with dichloromethane and eluted with a gradient elution of petroleum ether:ethyl acetate:dichloromethane:methanol=1:1:1:0.2-1:1:1:1. The solvent was evaporated to dryness under reduced pressure to give 4.267 g of pure product LB-1.

(6-1-2) Synthesis of LB-2:

LB-1 (4.697 g, 2.753 mmol, combination of 2 batches) obtained according to the method described in step (6-1-1), 3-amino-1,2-propanediol (313 mg, 3.442 mmol), 4-(4,6-dimethoxytriazin-2-yl)-4-methylmorpholine hydrochloride (DMTMM, 953 mg, 3.442 mmol) and N-methylmorpholine (700 mg, 6.884 mmol) were sequentially added to the mixture of 30 ml of acetonitrile and 3 ml of methanol to react overnight under stirring at room temperature. The solvent was evaporated to dryness, and the residue was purified by column chromatography (200-300 mesh normal phase silica gel, with a gradient elution of dichloromethane:methanol=1:0.07-1:0.5). The eluate of product was collected and concentrated to remove the solvent to give 3.27 g of target product LB-2.

(6-1-3) Synthesis of LB-3:

LB-2 (2.27 g, 1.353 mmol) was dissolved in 14 ml of anhydrous pyridine, and added with 4,4'-dimethoxytrityl chloride (688 mg, 2.03 mmol) to react overnight under stirring at room temperature. The reaction was quenched by addition of 150 ml of methanol. The solvent was evaporated to dryness, and the residue was purified by column chromatography (200-300 mesh normal phase silica gel, with a gradient elution of dichloromethane:methanol=1:0.05-1:0.2). The eluate of product was collected and concentrated to remove the solvent to give 1.647 g of target product LB-3.

(6-1-4) Synthesis of LB-4:

LB-3 (822 mg, 0.415 mmol), succinic anhydride (83 g, 0.83 mmol) and 4-dimethylaminopyridine (DMAP, 102 mg, 0.83 mmol) were mixed and dissolved in 4 ml of dichloromethane, added with DIPEA (270 mg, 2.075 mmol), and stirred at 25° C. to react overnight. The resulting reaction liquid was washed with 0.5 M triethylamine phosphate for three times. The aqueous phase was extracted three times, each with 2 ml of dichloromethane. The organic phases were combined, and the solvent was evaporated to dryness under reduced pressure to give a crude product. The crude product was subjected to a column purification. The column was filled with normal phase silica gel having 200-300 mesh, and added with 5 wt % triethylamine for neutralizing the acidity of silica gel. The column was equilibrated with petroleum ether and eluted with a gradient elution of 1 wt ‰ triethylamine-containing dichloromethane:methanol=100:5-100:20. The solvent was evaporated to dryness under reduced pressure to give 787 mg of pure product, LB-4 conjugating molecule.

(6-1-5) Synthesis of LB-5:

LB-5 was prepared by the same method as that in step (1-1-9) of Preparation Example 1, except that L-9 conjugating molecule was replaced with LB-4 conjugating molecule to produce the LB-4 conjugating molecule linked to the solid support.

(6-2) Synthesis of LB5-siAP1M2SVP Conjugate

Conjugate 25 was prepared by the same methods as those in steps (1-2), (1-3A) and (1-4) of Preparation Example 1, except that L-10 compound was replaced with LB-5 compound to start the synthesis of the sense strand. It was expected that LB5-siAP1M2SVP having the structure represented by Formula (13) can be produced.
Preparation Example 7. Synthesis of V8-siAP1M2SVP Conjugate (Conjugate 26)
It was expected that V-8 compound can be synthesized according to the following process route:
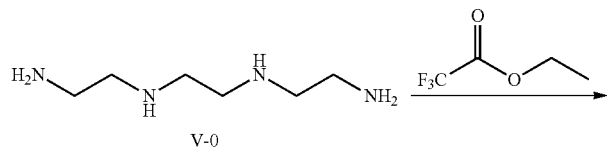
V-0
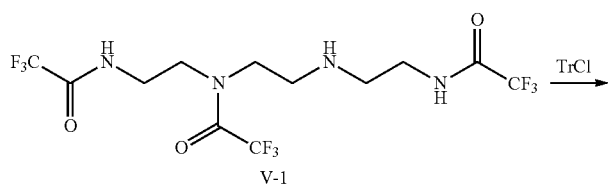
V-1
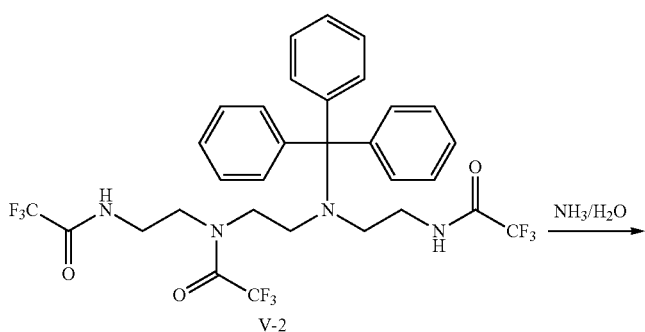
V-2
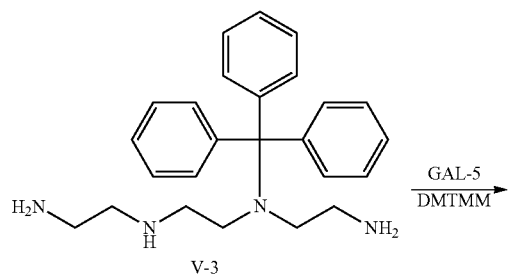
V-3

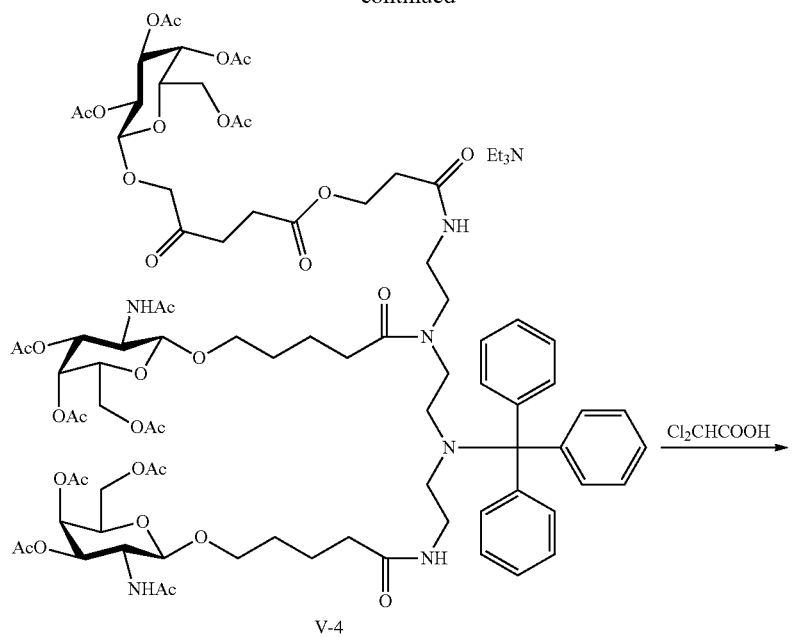
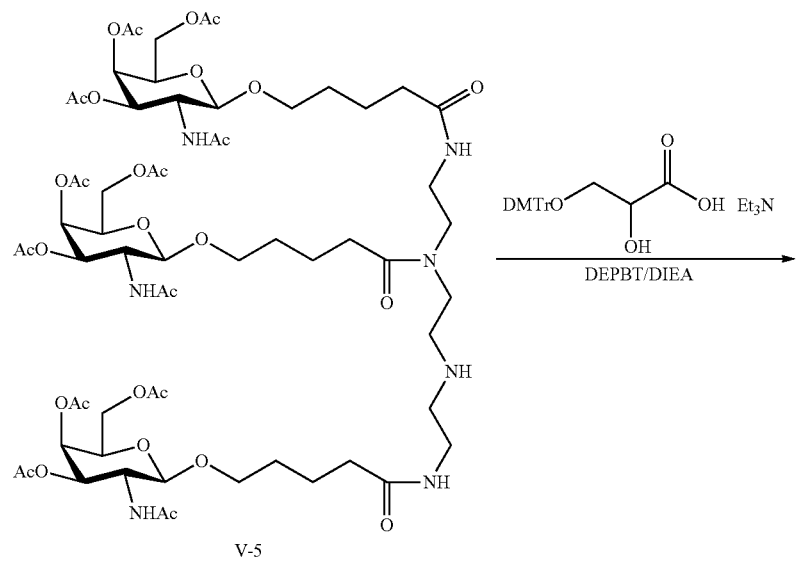

-continued
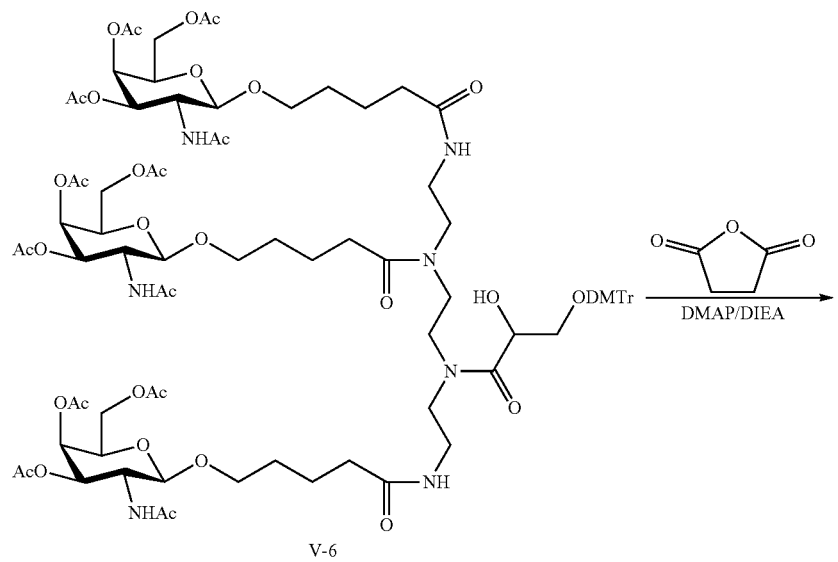
V-6
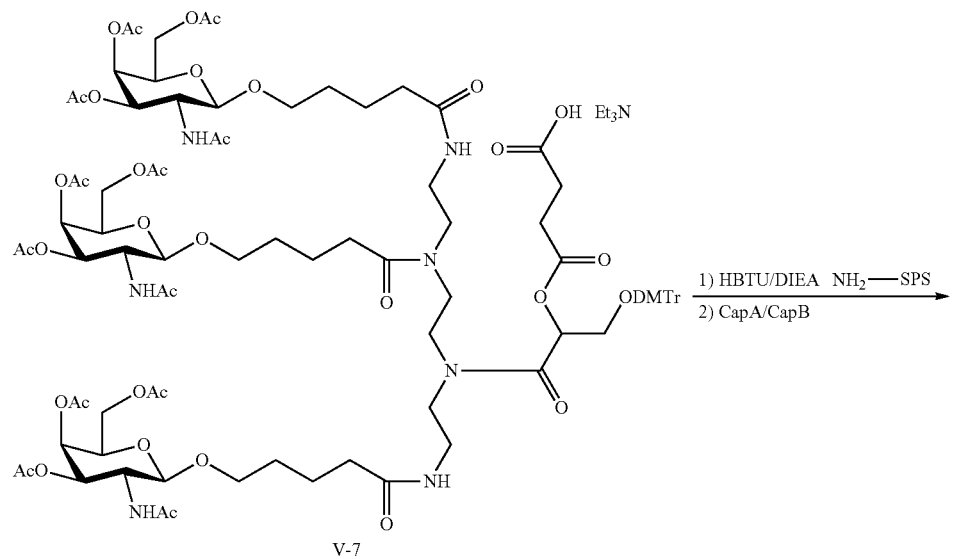
V-7
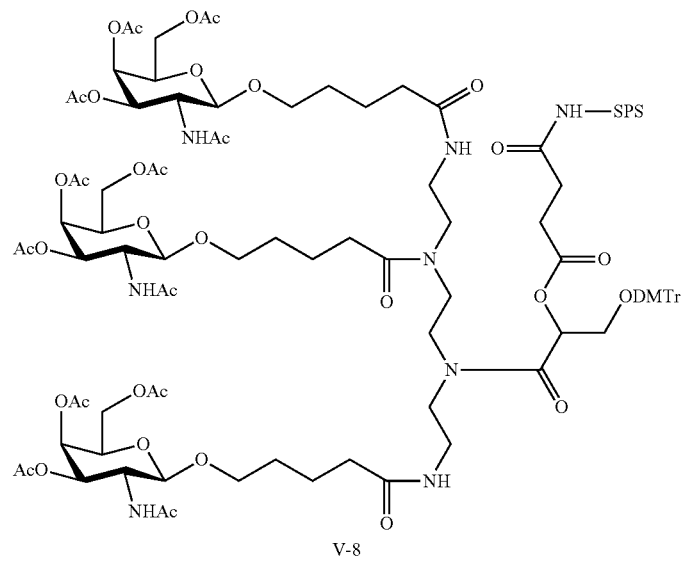
V-8

Conjugate 26 was prepared according to the same methods as those in steps (1-2), (1-3A) and (1-4) of Preparation Example 1, except that L-10 compound was replaced with V-8 compound to start the synthesis of the sense strand. It was expected that V8-siAP1M2SVP having the structure represented by Formula (14) can be obtained.

Preparation Example 8. Synthesis of W8-siAP1M2SVP Conjugate (Conjugate 27)

(8-1) Synthesis of W-8 Compound

W-8 compound was synthesized according to the following method:

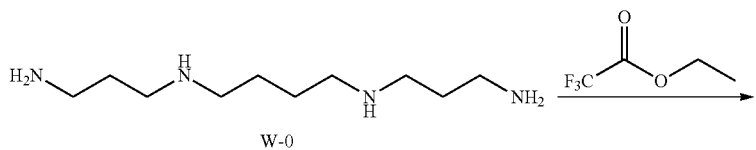

W-0

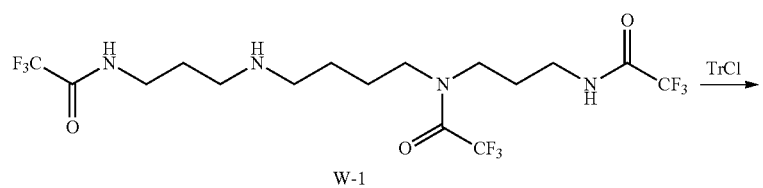

W-1

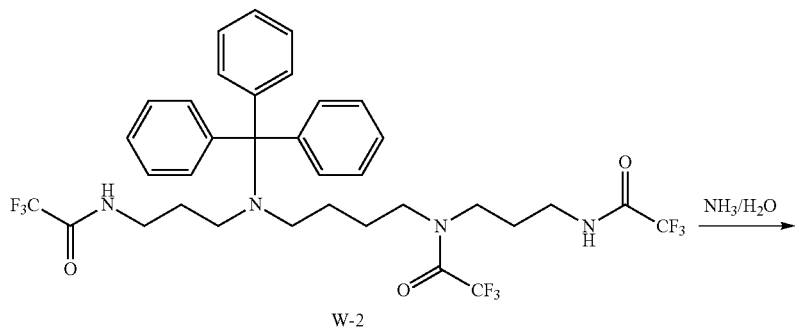

W-2

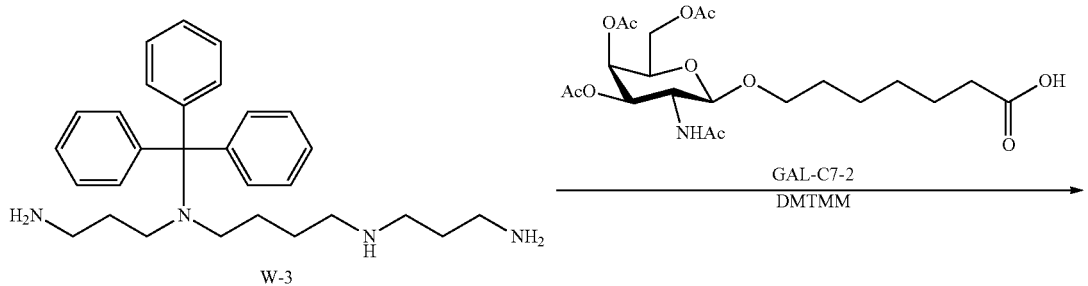

W-3

-continued
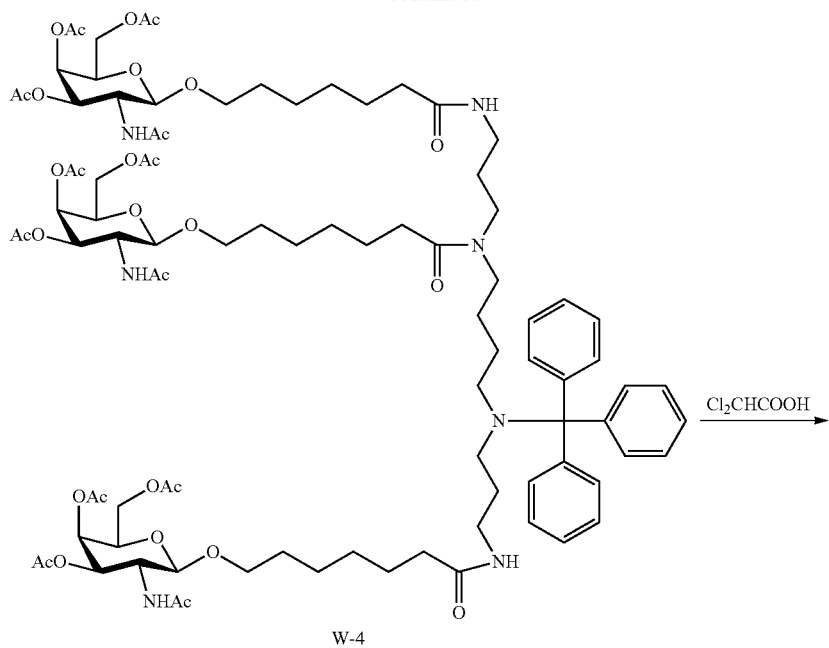
W-4
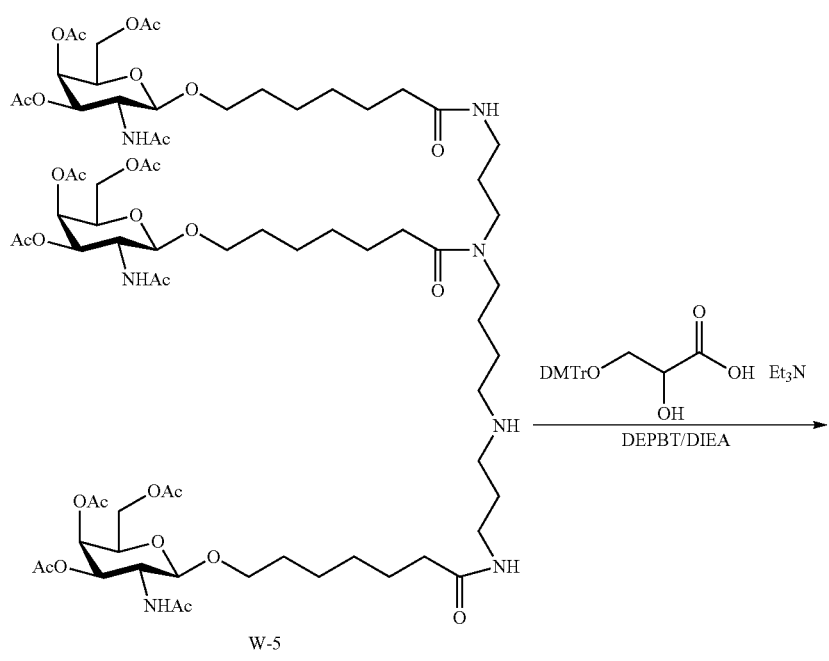
W-5

-continued
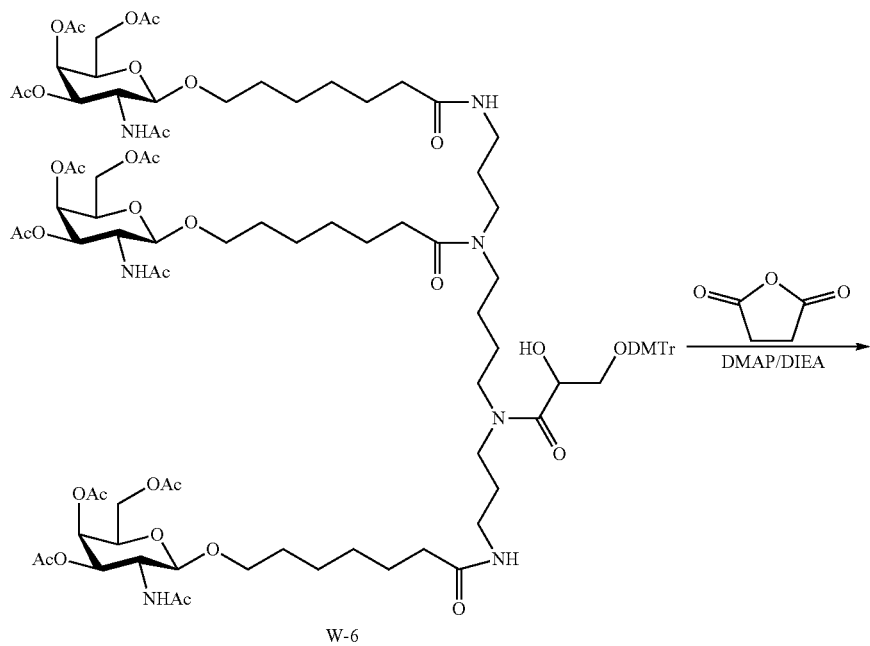
W-6
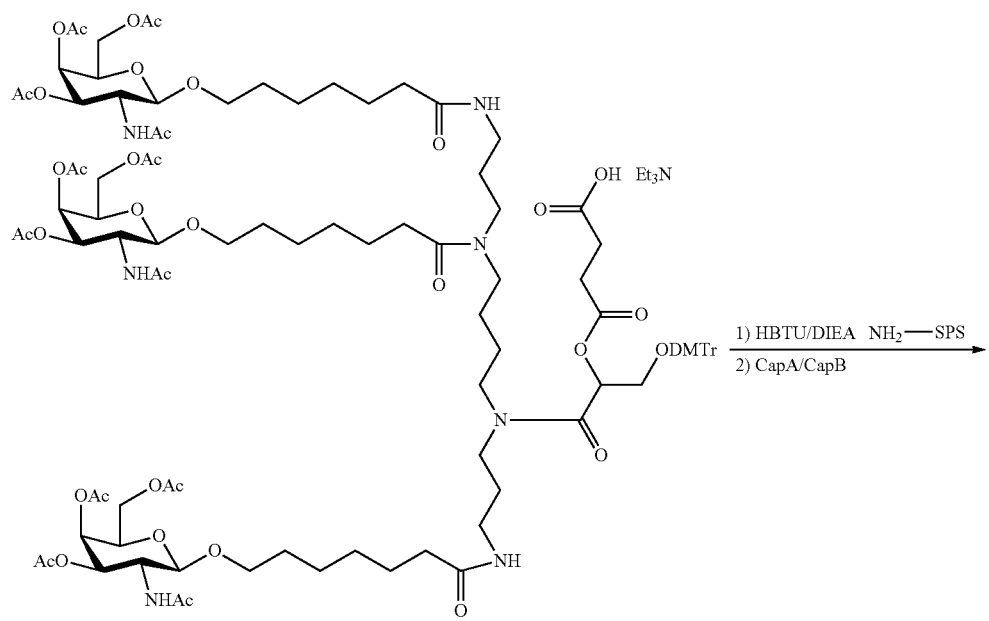
W-7

-continued

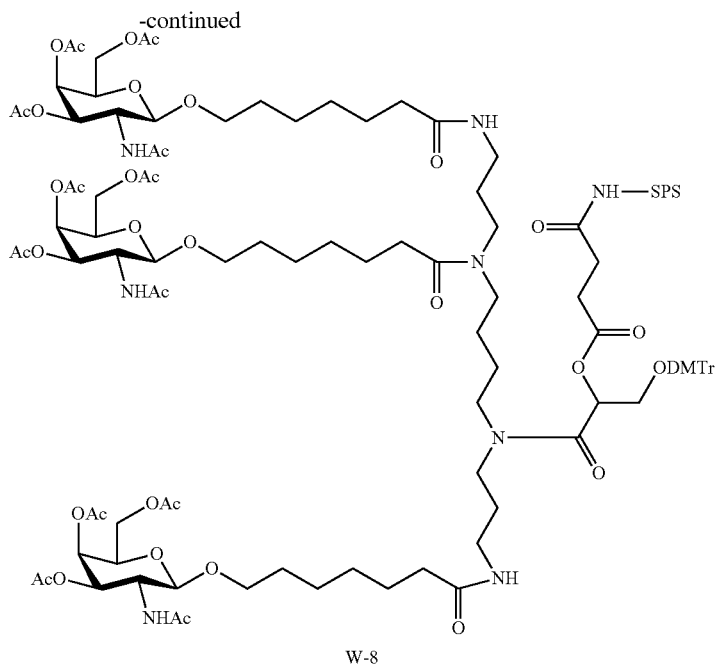

W-8

(8-1-1) Synthesis of W-1:

W-0 (2.024 g, 10 mmol) was dissolved in 25 ml of acetonitrile, added with triethylamine (4.048 g, 40 mmol), and cooled to about 0° C. in an ice water bath. Ethyl trifluoroacetate (5.683 g, 40 mmol) was added to react for 22 hours at room temperature. The solvent was evaporated to dryness under reduced pressure, and the residue was foam-dried with a vacuum oil pump for 18 hours to give 5.835 g of crude solid product W-1.

(8-1-2) Synthesis of W-2:

The crude product W-1 (5.835 g, 10 mmol) was dissolved in 50 ml of dichloromethane. TrCl (3.345 g, 12 mmol) and triethylamine (1.518 g, 15 mmol) were added to react for 20 hours under stirring at room temperature. The resulting reaction solution was washed twice with 20 ml of saturated sodium bicarbonate and once with 20 ml of saturated brine. The organic phases were combined, dried with anhydrous sodium sulfate, and filtered. The organic solvent was evaporated to dryness under reduced pressure, and the residue was foam-dried with a vacuum oil pump overnight to give 8.012 g of crude solid product W-2. The crude solid product W-2 was used in the next deprotection reaction without treatment.

(8-1-3) Synthesis of W-3:

The crude product W-2 (8.012 g, 10 mmol) was dissolved in 100 ml of methanol, and added with 100 ml of aqueous methylamine solution (40 wt %) to react for 23 hours under stirring at 50° C. Insoluble particles were removed by filtration. The solvent was evaporated to dryness under reduced pressure. The residue was added with 200 ml of mixed solvent of DCM:methanol in a volume ratio of 1:1. The organic phase was washed with 50 ml of saturated sodium bicarbonate. The aqueous phase was extracted three times, each with 50 ml of dichloromethane. The organic phases were combined, dried with anhydrous sodium sulfate, and filtered. The solvent was evaporated to dryness under reduced pressure. The residue was foam-dried with a vacuum oil pump overnight, and purified by using a normal phase silica gel column having 200-300 mesh. The column was packed with petroleum ether, added with 1 wt % triethylamine for neutralizing the acidity of silica gel, and eluted with a gradient elution of dichloromethane:methanol: aqueous ammonia (25 wt %)=1:1:0.05-1:1:0.25. The eluate of product was collected. The solvent was evaporated to dryness under reduced pressure, and the residue was foam-dried with a vacuum oil pump to give 3.062 g of pure product W-3.

(8-1-4) Synthesis of W-4:

W-3 (0.675 g, 1.517 mmol) and GAL-C7-2 (2.60 g, 5.46 mmol) were mixed and dissolved in 47 ml of acetonitrile, added with diisopropylethylamine (1.57 g, 12.14 mmol) followed by 3-(diethoxyphosphoryloxy)-1,2,3-benzotrizin-4 (3H)-one (DEPBT, 1.816 g, 6.04 mmol) to react for 2.5 hours under stirring at room temperature. The resulting reaction solution was diluted with 100 ml of dichloromethane. The organic phase was washed with 80 ml of saturated sodium bicarbonate solution and 80 ml of saturated brine, respectively. The organic phases were combined, dried with anhydrous sodium sulfate, and filtered. The solvent was evaporated to dryness under reduced pressure to give a crude product, which was purified by using a normal phase silica gel column having 200-300 mesh. The column was packed with petroleum ether, added with 1 wt % triethylamine for neutralizing the acidity of silica gel, and eluted with a gradient elution of dichloromethane:methanol=100:5-100:7. The eluate of product was collected, and evaporated to dryness under reduced pressure to give 1.610 g of pure product W-4.

(8-1-5) Synthesis of W-5:

W-4 (1.61 g, 0.886 mmol) was dissolved in 125 ml of dichloromethane, and added with dichloroacetic acid (3.5 ml, 42.43 mmol) to react for 1 hour at room temperature. The resulting reaction solution was neutralized by adding 150 ml of pyridine. The solvent was evaporated to dryness under reduced pressure to give a crude product. The crude product was purified by using a normal phase silica gel column having 200-300 mesh. The column was added with 10 wt % triethylamine for neutralizing the acidity of silica gel. The column was equilibrated with 1 wt ‰ triethylamine and eluted with a gradient elution of dichloromethane:methanol=100:30-100:40. The eluate of product was collected, and the solvent was evaporated to dryness under reduced pressure to give 1.26 g of pure product W-5.

(8-1-6) Synthesis of W-6:

W-5 (1.25 g, 0.793 mmol) and A-1 (1.21 g, 2.38 mmol) obtained according to the method described in step (1-1-7a) were mixed and dissolved in 12 ml of dichloromethane, and added with 3-(diethoxyphosphoryloxy)-1,2,3-benzotrizin-4(3H)-one (DEPBT, 0.712 g, 2.38 mmol) followed by diisopropylethylamine (0.615 g, 4.76 mmol) to react for 3 hours under stirring at 25° C. The organic phase was washed with 80 ml of saturated sodium bicarbonate. The aqueous phase was extracted three times, each with 10 ml of dichloromethane. The organic phases were combined and washed with 10 ml of saturated brine. The organic phases were combined, dried with anhydrous sodium sulfate, and filtered. The solvent was evaporated to dryness under reduced pressure, and the residue was foam-dried overnight with a vacuum oil pump to give a crude product. The crude product was subjected to a column purification. The column was filled with 185 g of normal phase silica gel having 200-300 mesh, and added with 20 ml triethylamine for neutralizing the acidity of silica gel. The column was equilibrated with petroleum ether containing 1 wt % triethylamine and eluted with a gradient elution of petroleum ether:ethylacetate:dichloromethane:N,N-dimethylformamide=1:1:1:0.1-1:1:1:0.7. The eluate of product was collected, and the solvent was evaporated to dryness under reduced pressure to give 1.57 g of pure product W-6.

(8-1-7) Synthesis of W-7:

W-6 (1.238 g, 0.63 mmol), succinic anhydride (0.189 g, 1.89 mmol) and 4-dimethylaminopyridine (DMAP, 0.231 g, 1.89 mmol) were mixed and dissolved in 7 ml of dichloromethane, and added with DIEA (0.407 g, 3.15 mmol) to react for 24 hours under stirring at 25° C. The resulting reaction solution was washed with 5 ml of 0.5 M triethylamine phosphate. The aqueous phase was extracted three times, each with 5 ml of dichloromethane. The organic phases were combined, and evaporated to dryness under reduced pressure to give a crude product. The crude product was subjected to a column purification. The column was filled with 30 g of normal phase silica gel having 200-300 mesh, and added with 1 wt % triethylamine for neutralizing the acidity of silica gel. The column was equilibrated with dichloromethane and eluted with a gradient elution of 1 wt ‰ triethylamine-containing dichloromethane:methanol=100:18-100:20. The eluate of product was collected, and the solvent was evaporated to dryness under reduced pressure to give 1.033 g of pure product, W-7 conjugating molecule. MS m/z: $C_{101}H_{146}N_7O_{38}$, $[M-DMTr]^+$, calcd: 1763.92, measured: 1763.21.

(8-1-8) Synthesis of W-8:

W-8 was prepared by the same method as that in step (1-1-9) of Preparation Example 1, except that L-9 conjugating molecule was replaced with W-7 conjugating molecule to produce the W-7 conjugating molecule linked to the solid support.

(8-2) Synthesis of W8-siAP1M2SVP Conjugate

Conjugate 27 was prepared by the same methods as those in steps (1-2), (1-3A) and (1-4) of Preparation Example 1, except that L-10 compound was replaced with W-8 compound to start the synthesis of the sense strand. It was expected that W8-siAP1M2SVP having the structure represented by Formula (15) can be obtained.

Preparation Example 9. Preparation of X8-siAP1M2SVP Conjugate (Conjugate 28)

It was expected that X-8 compound can be synthesized according to the following process route:

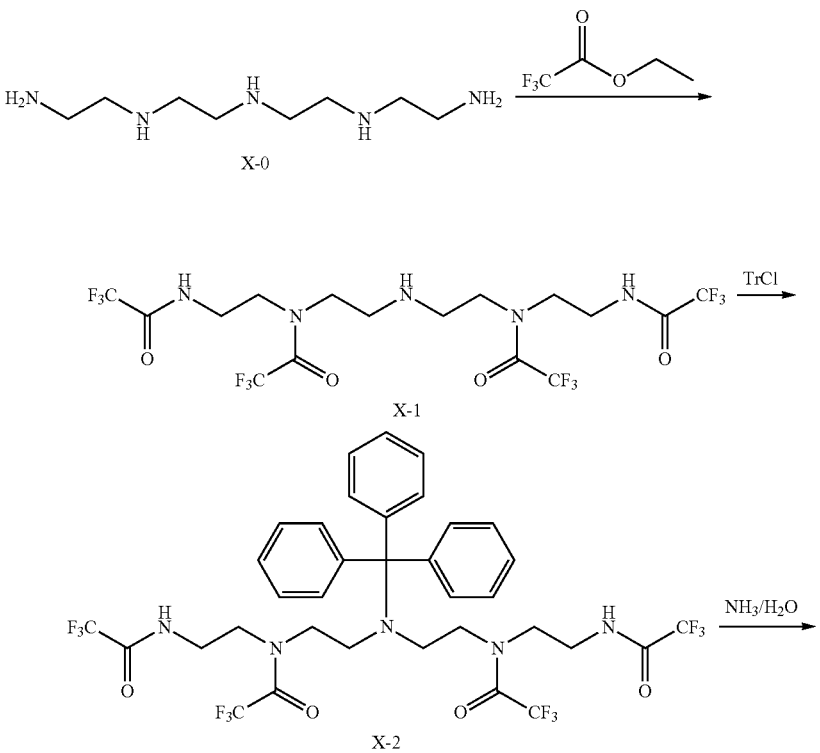

-continued
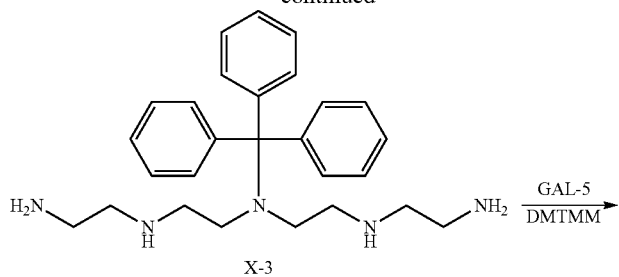
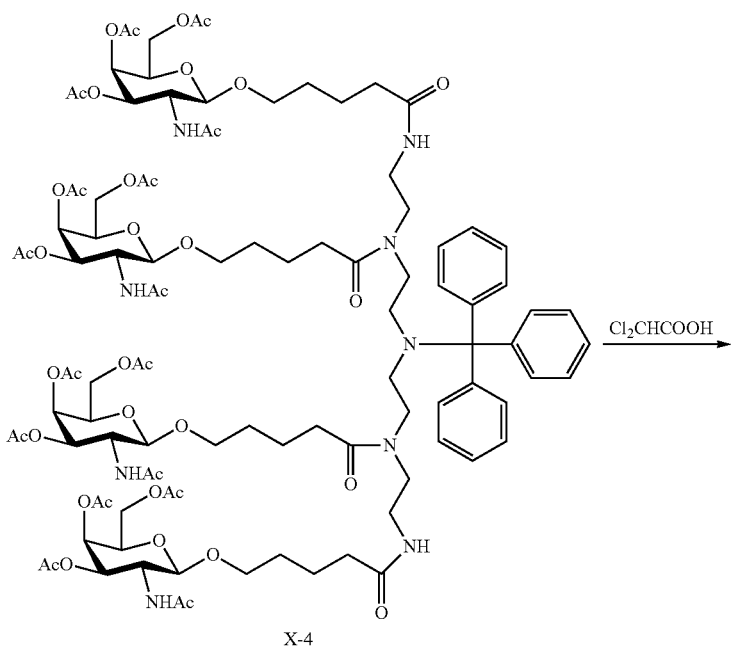
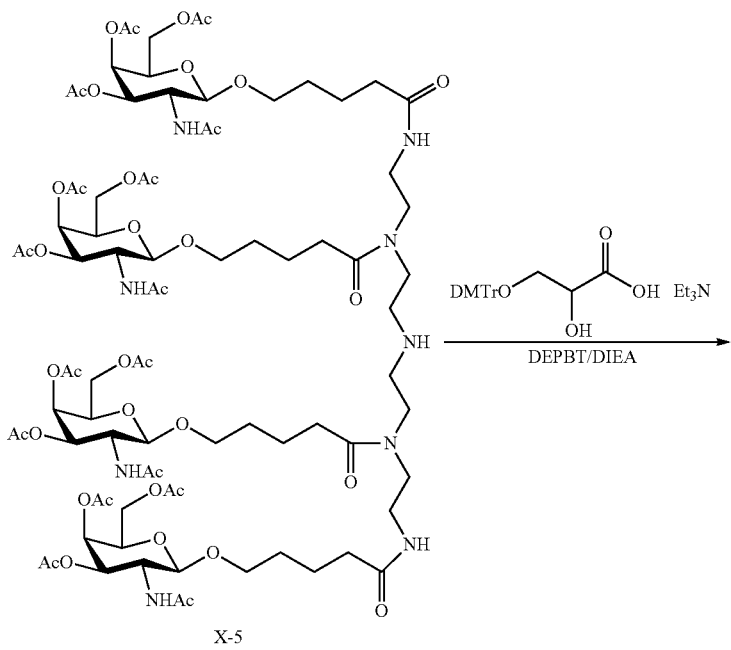

-continued
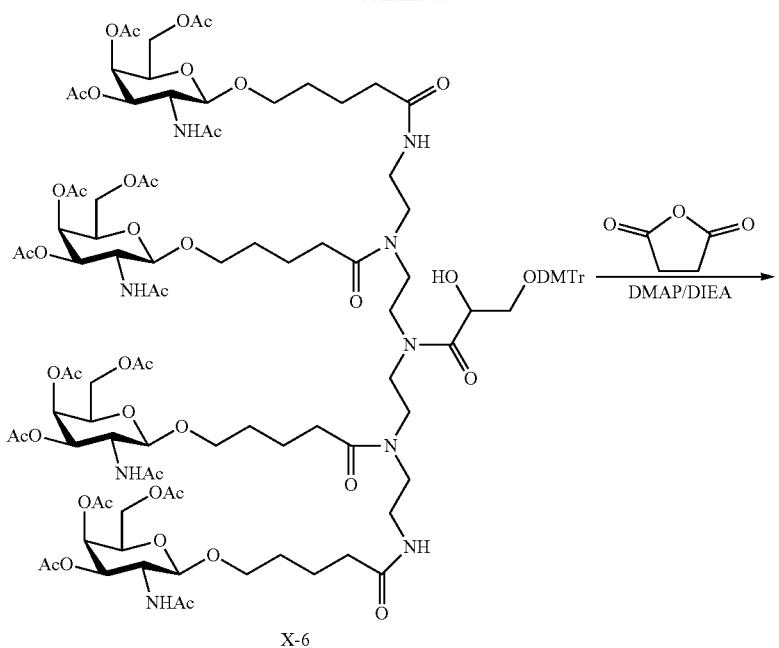
X-6
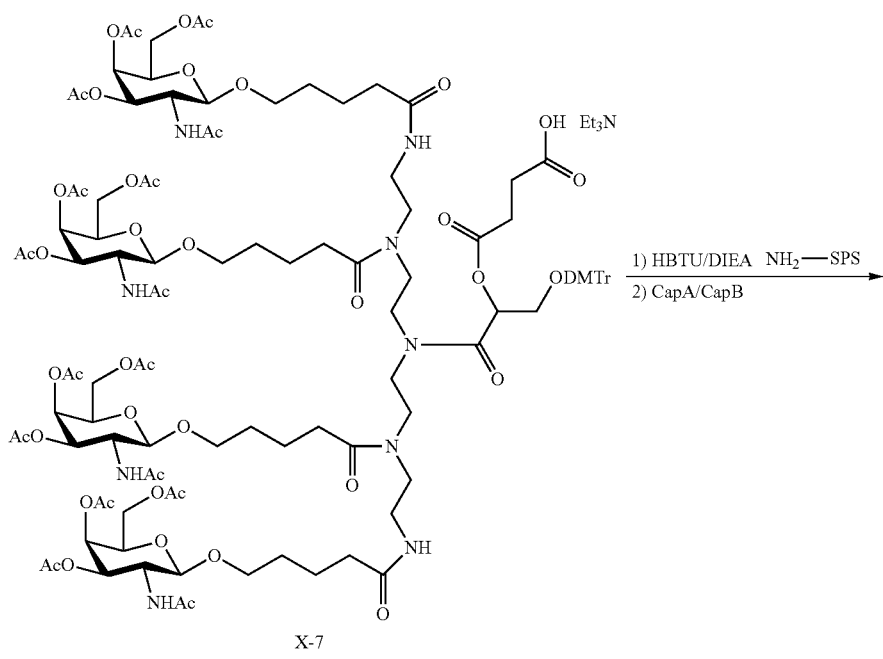
X-7

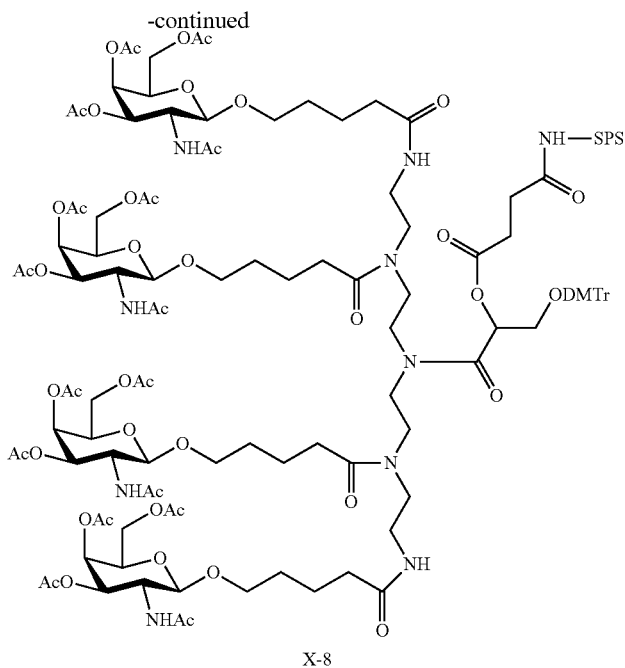

X-8

Conjugate 28 was prepared by the same methods as those in steps (1-2), (1-3A) and (1-4) of Preparation Example 1, except that L-10 compound was replaced with X-8 compound to start the synthesis of the sense strand. It was expected that X8-siAP1M2SVP having the structure represented by Formula (21) can be produced.

Preparation Example 10. Preparation of Z5-siAP1M2SVP Conjugate (Conjugate 29)

(10-1) Synthesis of Z-5 Compound

Z-5 compound was synthesized according to the following method:

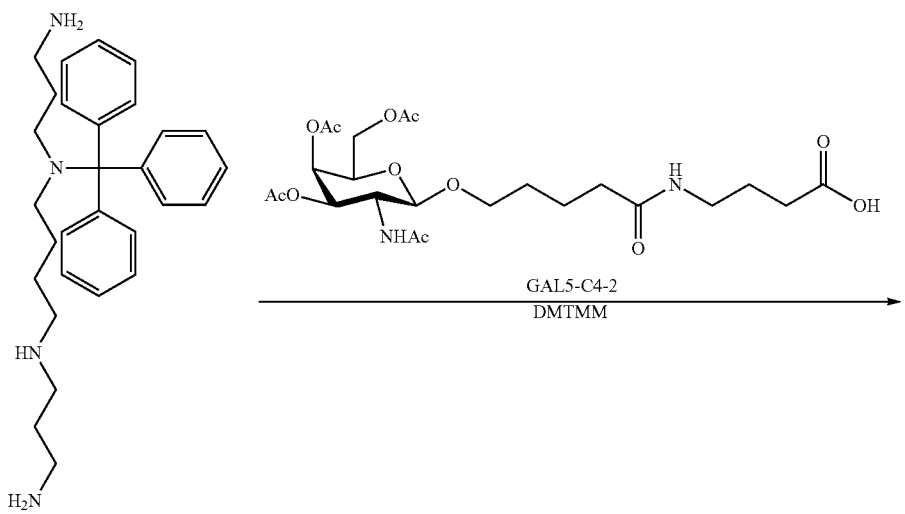

W-3

-continued
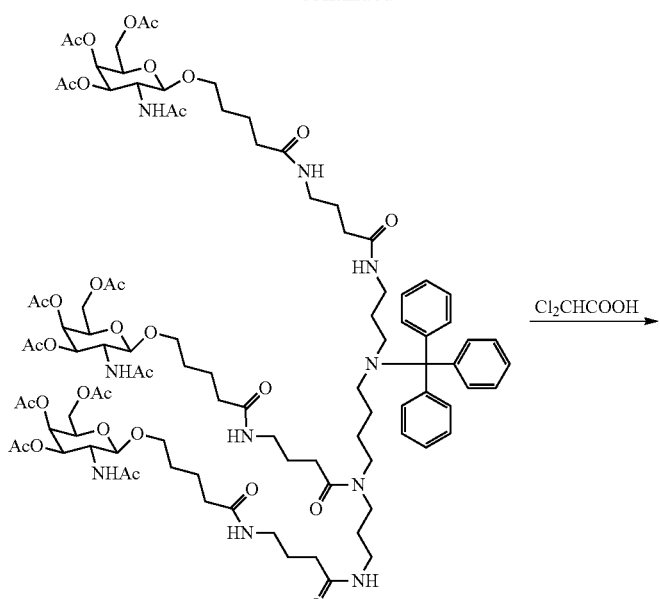
Z-1
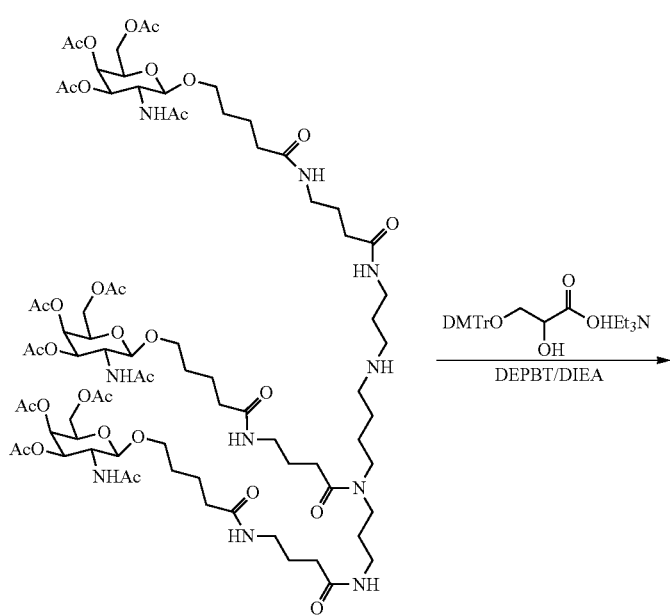
Z-2

-continued
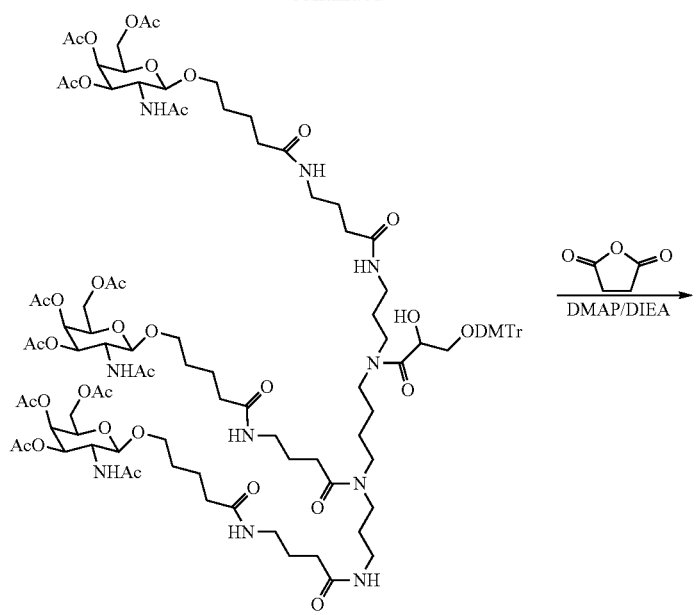
Z-3
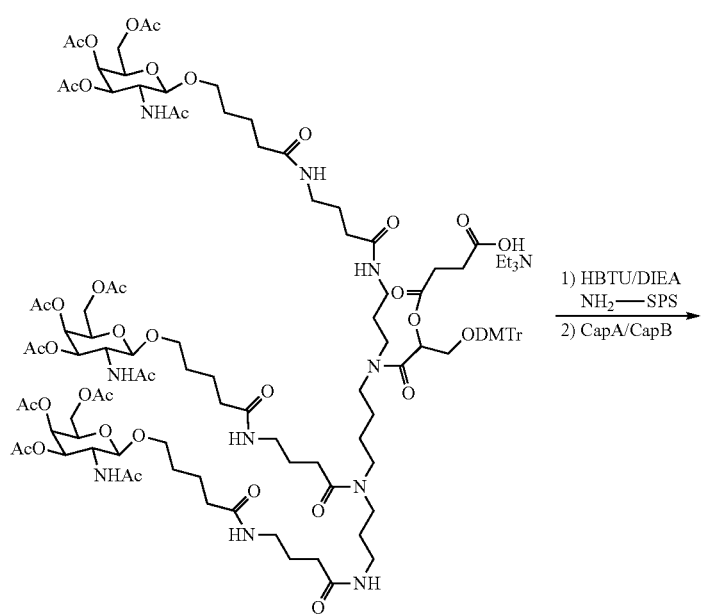
Z-4

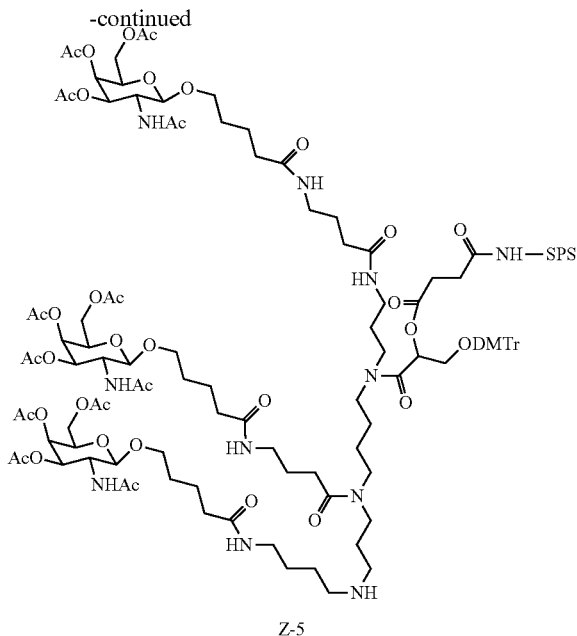

Z-5

(10-1-1) Synthesis of Z-1:

W-3 (1.50 g, 3.37 mmol) obtained according to the method described in step (8-1-3) and GAL5-C4-2 (7.18 g, 13.48 mmol) obtained according to the method described in step (3-1-2) were mixed and dissolved in 34 ml of dichloromethane, added with diisopropylethylamine (3.48 g, 26.96 mmol) followed by 3-(diethoxyphosphoryloxy)-1,2,3-benzotrizin-4(3H)-one (DEPBT, 4.04 g, 13.48 mmol) to react for 4.5 hours under stirring at room temperature. The resulting liquid solution was diluted with 100 ml of dichloromethane. The organic phase was washed with 80 ml of saturated sodium bicarbonate solution and 80 ml of saturated brine, respectively. The organic phases were combined, dried with anhydrous sodium sulfate, and filtered. The solvent was evaporated to dryness under reduced pressure to give a crude product, which was purified by using a normal phase silica gel column having 200-300 mesh. The column was packed with petroleum ether, added with 1 wt % triethylamine for neutralizing the acidity of silica gel, and eluted with a gradient elution of dichloromethane:methanol=30:1-15:1. The eluate of product was collected and evaporated to dryness under reduced pressure to give 3.97 g of pure product Z-1. MS m/z: $C_{98}H_{143}N_{10}O_{33}$, $[M+H]^+$, calcd: 1987.98, measured: 1987.90.

(10-1-2) Synthesis of Z-2:

Z-1 (3.97 g, 2.00 mmol) was dissolved in 250 ml of dichloromethane, and added with dichloroacetic acid (10.941 g, 84.85 mmol) to react for 1 hour at room temperature. The resulting reaction solution was neutralized to neutral by adding pyridine. The solvent was evaporated to dryness under reduced pressure to give a crude product. The column was filled with 220 g 200-300 mesh normal phase silica gel, and added with 10 wt % pyridine for neutralizing the acidity of silica gel. The column was equilibrated with 1 wt ‰ pyridine and eluted with a gradient elution of dichloromethane:methanol=10:1-2:1. The eluate of product was collected, and the solvent was evaporated to dryness under reduced pressure to give 3.49 g of pure product Z-2. MS m/z: $C_{79}H_{129}N_{10}O_{33}$, $[M+H]^+$, calcd: 1746.94, measured: 1746.90.

(10-1-3) Synthesis of Z-3:

Z-2 (3.49 g, 2.0 mmol) and A-1 (3.06 g, 6.0 mmol) obtained according to the method described in step (1-1-7a) were mixed and dissolved in 30 ml of dichloromethane, and added with 3-(diethoxyphosphoryloxy)-1,2,3-benzotrizin-4(3H)-one (DEPBT, 1.80 g, 6.0 mmol) followed by diisopropylethylamine (1.55 g, 12.0 mmol) to react for 3 hours under stirring at 25° C. 100 ml dichloromethane was added to the resulting reaction solution for dilution. The organic phase was washed twice, each with 30 ml of saturated sodium bicarbonate. The aqueous phase was extracted with 10 ml of dichloromethane. The organic phases were combined and washed with 50 ml of saturated brine. All the organic phases were combined and dried with anhydrous sodium sulfate, and filtered. The solvent was evaporated to dryness under reduced pressure, and the residue was foam-dried overnight with a vacuum oil pump to give a crude product. The crude product was subjected to a column purification. The column was filled with 200 g of normal phase silica gel having 200-300 mesh, and added with 20 ml triethylamine for neutralizing the acidity of silica gel. The column was equilibrated with petroleum ether containing 1 wt % triethylamine and eluted with a gradient elution of dichloromethane:methanol=25:1-15:1. The eluate of product was collected, and the solvent was evaporated to dryness under reduced pressure to give 2.2 g of pure product Z-3. MS m/z: $C_{103}H_{151}N_{10}O_{38}$, $[M+H]^+$, calcd: 2136.02, measured: 2136.20.

(10-1-4) Synthesis of Z-4:

Z-3 (2.10 g, 0.983 mmol) was dissolved in 14.8 ml of dichloromethane containing DIEA (0.635 g, 4.915 mmol). The resulting solution was added with 4-dimethylaminopyridine (DMAP, 240 mg, 1.966 mmol) and stirred to clarity. Succinic anhydride (197 mg, 1.966 mmol) was added to react for 18 hours under stirring at 25° C. The resulting reaction solution was diluted by adding 50 ml dichloromethane, and then washed with 80 ml of 0.5 M triethylamine phosphate. The aqueous phase was extracted twice, each with 50 ml of dichloromethane. The organic phases were combined, and evaporated to dryness under reduced pressure to give a crude product. The crude product was subjected to a column purification. The column was filled with 188 g of normal phase silica gel having 200-300 mesh, and added with 1 wt % triethylamine for neutralizing the acidity of silica gel. The column was equilibrated with dichloromethane and eluted with a gradient elution of dichloromethane containing 1 wt ‰ triethylamine:methanol=10:1-3:1. The eluate of product was collected, and the solvent was evaporated to dryness under reduced pressure to give 1.95 g of pure product, Z-4 conjugating molecule. MS m/z: $C_{107}H_{155}N_{10}O_{41}$, $[M+H]^+$, calcd: 1935.07, measured: 1935.29.

(10-1-5) Synthesis of Z-5

Z-5 was prepared by the same method as that in step (1-1-9) of Preparation Example 1, except that L-9 conjugating molecule was replaced with Z-4 conjugating molecule to produce Z-4 Conjugating Molecule linked to the solid support.

(10-2) Synthesis of Z5-siAP1M2SVP Conjugate

Conjugate 29 was prepared by the same method as those in steps (1-2), (1-3A) and (1-4) of Preparation Example 1, except that L-10 compound was replaced with Z-5 compound to start the synthesis of the sense strand. It was expected that Z5-siAP1M2SVP conjugate having the structure represented by Formula (22) can be produced.

Preparation Example 11. Preparation of Conjugates F1-F5

In the present Preparation Example, conjugates F1-F5 (hereinafter also referred to as FIN-siAP1M1SVP, FIN-siAP1M1S, FIN-siAP2M1SVP, FIN-siAP2M1S and FIN-siAP2M2S conjugate respectively) were synthesized. The sequences of the conjugated siRNAs in the conjugates are shown in Table 3.

(11-1) Synthesis of FIN-2 Conjugating Molecule

FIN-2 conjugating molecule was synthesized with reference to the preparation method described in Rajeev et al., ChemBioChem 2015, 16, 903-908 according to the following process route.

(11-1-1) Synthesis of Compound PRO-10

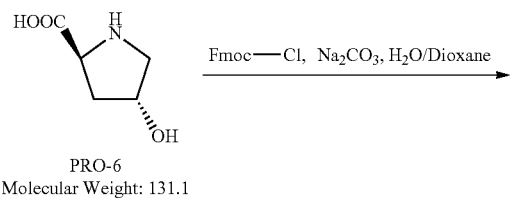

PRO-6
Molecular Weight: 131.1

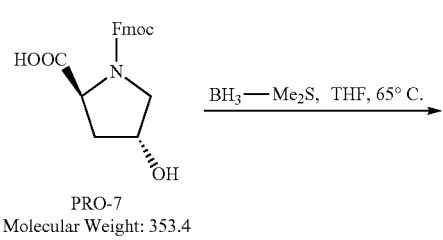

PRO-7
Molecular Weight: 353.4

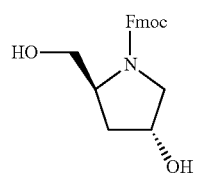

PRO-8
Molecular Weight: 339.4

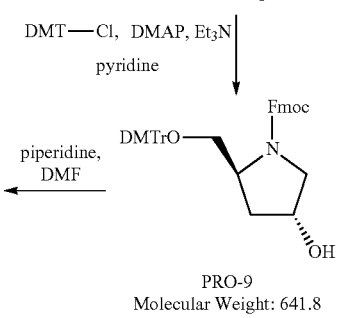

PRO-10
Molecular Weight: 419.5

PRO-9
Molecular Weight: 641.8

(11-1-1-a) Synthesis of PRO-7

2.93 g of PRO-6 (L-hydroxyproline, CAS No.: 51-35-4, purchased from Energy Chemical, 22.4 mmol) was dissolved in 22.5 ml of 1,4-dioxane (CAS No.: 123-91-1) and added with 34 ml of 10% (w/w) aqueous $Na_2CO_3$ solution, to form a suspension. 6.95 g of Fmoc-Cl (9-fluorenylmethyl chloroformate, CAS No.: 28920-43-6, purchased from Energy Chemical, 26.8 mmol) was dissolved in 34 ml of 1,4-dioxane, added into the above suspension in an ice bath, and naturally warmed to room temperature for reacting overnight. The reaction liquid was poured into 150 ml of ice water, and extracted three times, each with 100 ml of methyl t-butyl ether. The organic phase was discarded. The aqueous phase was adjusted to pH≤5 with concentrated hydrochloric acid, extracted twice with 100 ml of ethyl acetate. All the organic phases were combined and dried with anhydrous sodium sulfate. The solvent was evaporated to dryness under reduced pressure to give 7.83 g of product PRO-7 as a white foamy solid. $^1$H NMR (400 MHz, DMSO-$d_6$) δ 7.91 (t, J=7.2 Hz, 2H), 7.67 (d, J=7.5 Hz, 2H), 7.48-7.39 (m, 2H), 7.38-7.27 (m, 2H), 5.17 (s, 1H), 4.27 (s, 2H), 4.23-4.11 (m, 2H), 3.55-3.41 (m, 3H), 2.31-2.10 (m, 1H), 2.08-1.88 (m, 1H). HRMS (ESI) m/z calcd for $C_{20}H_{19}NO_5$ $[M-H]^-$ 352.1190, measured: 352.1033.

(11-1-1b) Synthesis of PRO-8

7.83 g of PRO-7 (22.2 mmol) was dissolved in 80 ml of THF (CAS No.: 109-99-9), heated to 65° C. in an oil bath, added with 36.6 ml of 2 mol/L solution of $BH_3$-$Me_2S$ in THF (CAS No. 13292-87-0, purchased from J&K Scientific Ltd., 73.2 mmol) under reflux, and refluxed continually to react for 3 hours. The reaction liquid was poured out, and the remaining solid was dissolved in methanol. To the resulting reaction liquid, methanol was added under stirring until no gas emitted, and stirred continually for 30 minutes. The solvent was evaporated under reduced pressure, and then the residue was purified three times with petroleum ether to give 7.1 g of product PRO-8 as a white solid. $^1$H NMR (400 MHz, DMSO-d6) δ 7.91 (t, J=6.7 Hz, 2H), 7.67 (d, J=7.2 Hz, 2H), 7.49-7.39 (m, 2H), 7.38-7.26 (m, 2H), 5.18 (dd, J=6.1, 3.8 Hz, 1H), 4.28 (s, 2H), 4.23-4.13 (m, 2H), 3.55-3.38 (m, 2H), 2.32-2.11 (m, 1H), 2.08-1.89 (m, 1H). HRMS (ESI) m/z calcd for $C_{20}H_{21}NO_4$ $[M+Na]^+$ 362.1368, measured: 362.1012.

(11-1-1c) Synthesis of PRO-9

7.1 g of PRO-8 (21 mmol) was dissolved in 100 ml of pyridine, and added with 14.2 g of DMTr-Cl (4,4'-dimethoxytrityl chloride, 42 mmol) to react for 5 hours under stirring at room temperature. The solvent was removed by evaporation under reduced pressure. The resulting crude product was dissolved in ethyl acetate and filtered to remove salt impurities. The solvent was evaporated under reduced pressure, and then the residue was purified by using a silica gel column. For purification, the crude product dissolved in DCM was loaded onto the silica gel column that was alkalified with pyridine beforehand. DMTr-Cl was eluted with DCM containing 1% (v/v) pyridine, and then the product was eluted with ethyl acetate. The eluate of product was collected, and the solvent was evaporated to dryness under reduced pressure to give 8.2 g of product PRO-9 as a white solid. HRMS (ESI) m/z calcd for $C_{41}H_{39}NO_6$ [M+Na]$^+$ 664.2675, measured: 664.2348; C18 RP-HPLC (Lot Number: JJS160324-1); purity: 94.20%.

(11-1-1d) Synthesis of PRO-10

8.2 g of PRO-9 (12.8 mmol) was dissolved in 64 ml of DMF (N,N-dimethylformamide) and added with 40 ml of piperidine (384 mmol) to react for 30 minutes under stirring at room temperature. The reaction liquid was poured into 300 ml of ice water and extracted three times, each with 150 ml of ethyl acetate. The organic phases were combined, washed with 200 ml of saturated brine, and then dried with anhydrous sodium sulfate. The solvent was evaporated to dryness under reduced pressure, and then the residue was purified by using a silica gel column. For purification, the crude product dissolved in DCM was loaded onto the silica gel column that was alkalified with pyridine beforehand. Fmoc was eluted with DCM containing 1% (v/v) pyridine, and then the product was eluted with ethyl acetate. The eluate of product was collected, and the solvent was evaporated to dryness under reduced pressure to give 4.65 g of product PRO-10 as a white solid. $^1$H NMR (400 MHz, DMSO-d$_6$) δ 7.40 (d, J=7.2 Hz, 2H), 7.35-7.18 (m, 7H), 6.93-6.84 (m, 4H), 4.56 (d, J=3.9 Hz, 1H), 4.12 (s, 1H), 3.74 (s, 6H), 3.46-3.37 (m, 1H), 2.88 (ddd, J=18.5, 10.0, 5.5 Hz, 2H), 2.75 (dd, J=8.7, 5.8 Hz, 1H), 2.62 (dd, J=11.0, 2.7 Hz, 1H), 1.74-1.65 (m, 1H), 1.40 (ddd, J=12.9, 8.5, 5.9 Hz, 1H); HRMS (ESI) m/z calcd for $C_{26}H_{29}NO_4$ [M+Na]$^+$ 442.1994, measured: 442.1999; C18 RP-HPLC (Lot Number: JJS160329-1), purity: 97.07%.

(11-1-2) Synthesis of FIN-1

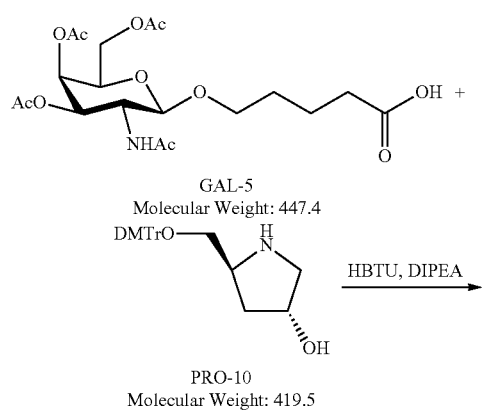

GAL-5
Molecular Weight: 447.4

PRO-10
Molecular Weight: 419.5

HBTU, DIPEA →

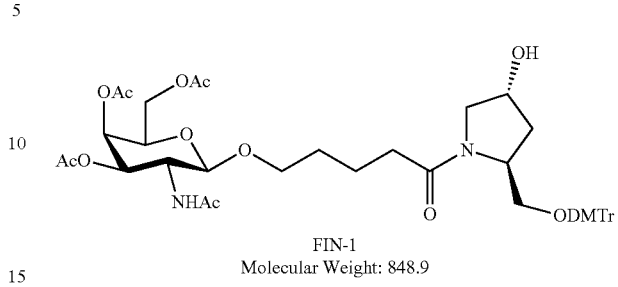

FIN-1
Molecular Weight: 848.9

GAL-5 (4.5 g, 10 mmol) obtained according to the method described in (1-1-1) was dissolved in 40 ml of DMF, sequentially added with 3.9 g of DIPEA (N,N-diisopropylethylamine, CAS No.: 7087-68-5, purchased from Aladdin Inc., 30 mmol) and 3.8 g of HBTU (benzotriazol-N,N,N',N'-tetramethyluronium hexafluorophosphate, CAS No.: 94790-37-2, purchased from Aladdin Inc., 11 mmol), and stirred at room temperature for 10 minutes. PRO-10 (4.2 g, 10 mmol) obtained in step (11-1-1d) was dissolved in 40 ml of DMF, and then added into the above reaction liquid. The resulting reaction liquid was dried by addition of anhydrous sodium sulfate and stirred at room temperature for 2 hours. The reaction liquid was poured into 120 ml of ice water and extracted three times, each with 60 ml of ethyl acetate. The organic phases were combined, washed with 20 ml of water and 20 ml of saturated brine, respectively. The organic phase was isolated, dried with anhydrous sodium sulfate. The solvent was evaporated under reduced pressure, and then the residue was purified by using a silica gel column. For purification, a sample was loaded onto the silica gel column that was alkalified with pyridine beforehand, and was eluted with dichloromethane (DCM) solution containing 1% (v/v) triethylamine and 1% (v/v) methanol. The eluate of product was collected, and the solvent was evaporated to dryness under reduced pressure to give 6.5 g of product FIN-1 as a light yellow foamy solid. $^1$H NMR (400 MHz, DMSO-d$_6$) δ 7.83 (d, J=9.2 Hz, 1H), 7.32 (t, J=6.6 Hz, 4H), 7.20 (td, J=8.9, 3.5 Hz, 5H), 6.93-6.84 (m, 4H), 5.21 (d, J=3.2 Hz, 1H), 5.04-4.90 (m, 2H), 4.49 (s, 1H), 4.40 (d, J=4.4 Hz, 0.8H), 4.31 (d, J=5.0 Hz, 0.2H), 4.15 (s, 1H), 4.03 (s, 3H), 3.93 (s, 1H), 3.74 (s, 7H), 3.59 (dt, J=12.0, 6.0 Hz, 1H), 3.50-3.40 (m, 1H), 3.39-3.25 (m, 3H), 3.13 (dd, J=8.9, 5.2 Hz, 1H), 3.00 (dq, J=9.3, 5.3, 4.3 Hz, 1H), 2.22 (s, 2H), 2.07 (s, 3H), 1.99 (s, 3H), 1.90 (s, 4H), 1.74 (s, 3H), 1.50 (s, 3H), 1.36 (s, 1H). C18 RP-HPLC (Lot Number: LJ160422), purity: 95.45%.

(11-1-3) Synthesis of FIN-2

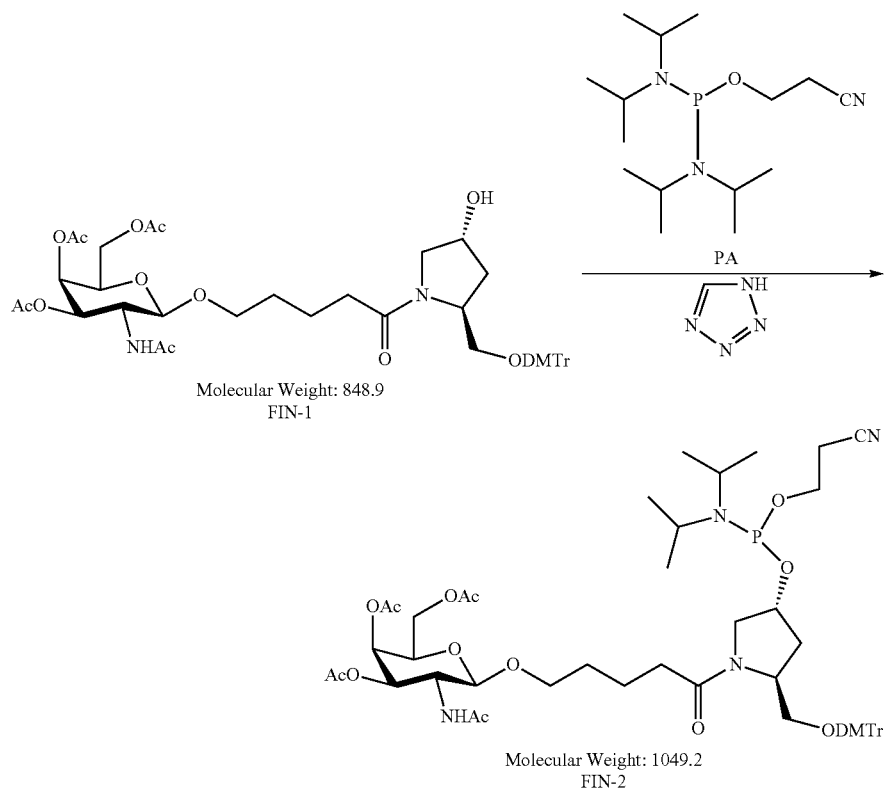

FIN-1 (3.0 g, 3.53 mmol) obtained in step (11-1-2) was azeotropically dehydrated with acetonitrile, and subjected to suction to dryness under reduced pressure. The resulting residue was dissolved in 10 ml of DMF, added with 2.13 g of PA (bis(diisopropylamino)(2-cyanoethoxy)phosphine, purchased from Adamas Inc., product No. 11356B, 7.06 mmol) and 346 mg tetrazole (CAS No.: 288-94-8, purchased from Aladdin Inc., 4.94 mmol) in nitrogen atmosphere, and stirred to react at room temperature. The reaction was added with a further 10 ml of DMF and continually stirred to react for 1 hour. The solvent was removed by evaporation under reduced pressure, and then the residue was purified by silica gel column chromatography. For purification, the crude product dissolved in DCM was loaded onto the silica gel column that alkalified with pyridine beforehand, and eluted with ethyl acetate. The eluate of product was collected, and the solvent was evaporated under reduced pressure to give 4.5 g of crude product as a colorless syrup. The crude product was completely dissolved in 50% (v/v) aqueous acetonitrile solution and purified by using a medium pressure purification column (C-18, 330 g, 300 Å) that was alkalified with a solution of 1% (v/v) pyridine in acetonitrile beforehand. The product peak was collected by gradient elution and the solvent was evaporated under reduced pressure to give 2.2 g of product as a white powder, FIN-2 conjugating molecule. $^{31}$P NMR (162 MHz, CDCl3) δ 148.04, 147.94, 147.62, 147.19, purity of $^{31}$P NMR: 92%; purity of C18 RP-HPLC: 90.54%.

(11-2) Linking FIN-2 Conjugating Molecule to a Solid Phase Support

The conjugating group (FIN_FIN_FIN) was linked to the 3' terminal of the sense strand of RNA by linking the FIN-2 conjugating molecule obtained in step (11-1-3) to a universal solid phase support (UnyLinker™ loaded NittoPhase®L Solid Supports) according to the nucleic acid solid phase synthesis method through three reaction cycles.

The above linking was proceeded according to the preparation method described in Rajeev et al., Chem Bio Chem 2015, 16, 903-908. Specifically, started from the above-mentioned universal solid phase support, the hydroxy protecting group was firstly removed from the above-mentioned universal solid phase support, and the solid phase support was subsequently brought into contact and coupled with the FIN-2 conjugating molecule under the coupling condition in the presence of a coupling agent, and a FIN conjugating molecule connected to the solid phase support was obtained after the capping and oxidation reaction. Moreover, the hydroxy protecting group DMTr was removed from the FIN conjugating molecule connected to the solid phase support, and the solid phase support was further brought into contact and coupled with another FIN-2 conjugating molecule, followed by capping and oxidation reaction. By repeating the above steps of Deprotection-Coupling-Capping-Oxidation, a third FIN-2 conjugating molecule was connected, and a conjugating group (FIN_FIN_FIN) connected to the solid phase support was thus obtained.

In the above reactions, the reaction conditions for deprotection, coupling, capping and oxidization, as well as the amounts of solvents and reagents are the same as those in the solid phase synthesis of nucleic acid described in the above step (1-2).

(11-3) Synthesis of Conjugates F1-F5

Conjugates F1-F5 were prepared by the same methods as those in steps (1-2), (1-3) and (1-4) of Preparation Example 1, except that 1) the sense strand was synthesized starting from the compound produced in step (11-2); and 2) the conjugated siRNA had the sequences corresponding to conjugates F1-F5 shown in Table 3.

The molecular weight was measured by LC-MS (Liquid Chromatography-Mass Spectrometry, purchased from Waters Corp., model: LCT Premier). The result showed that the measured values were in conformity with the calculated values, and thus it was confirmed that the synthesized conjugates were the designed target compounds having the structure represented by Formula (307).

Preparation Example 12. Preparation of Comparative Conjugate 3

In the present preparation example, comparative conjugate 3 was synthesized. The conjugated siRNAs in this conjugate has the sequence shown in Table 3. This conjugate has the same structure as compound AD-69535 in U.S. application Ser. No. 15/597,225.

(12-1) Synthesis of (GalNAc)₃ Conjugating Molecule

Compound 30, i.e., the conjugating molecule containing the above mentioned linker —(L$^A$)₃-trihydroxymethylaminomethane-L$^B$— and N-acetylgalactosamine molecule as a targeting group (wherein each L$^A$ can be linked to one N-acetylgalactosamine molecule so that one linker can be linked to three N-acetylgalactosamine molecules), was synthesized according to the preparation method described in WO2014025805A1. This conjugating molecule can also be referred to herein as (GalNAc)₃ conjugating molecule, and the structure of compound 30 was as follows:

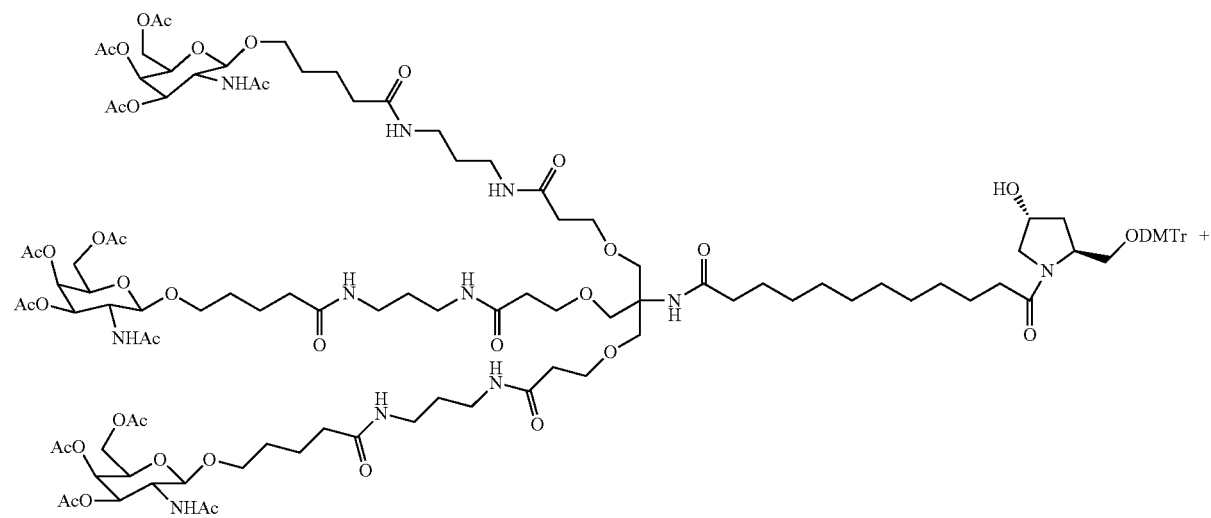

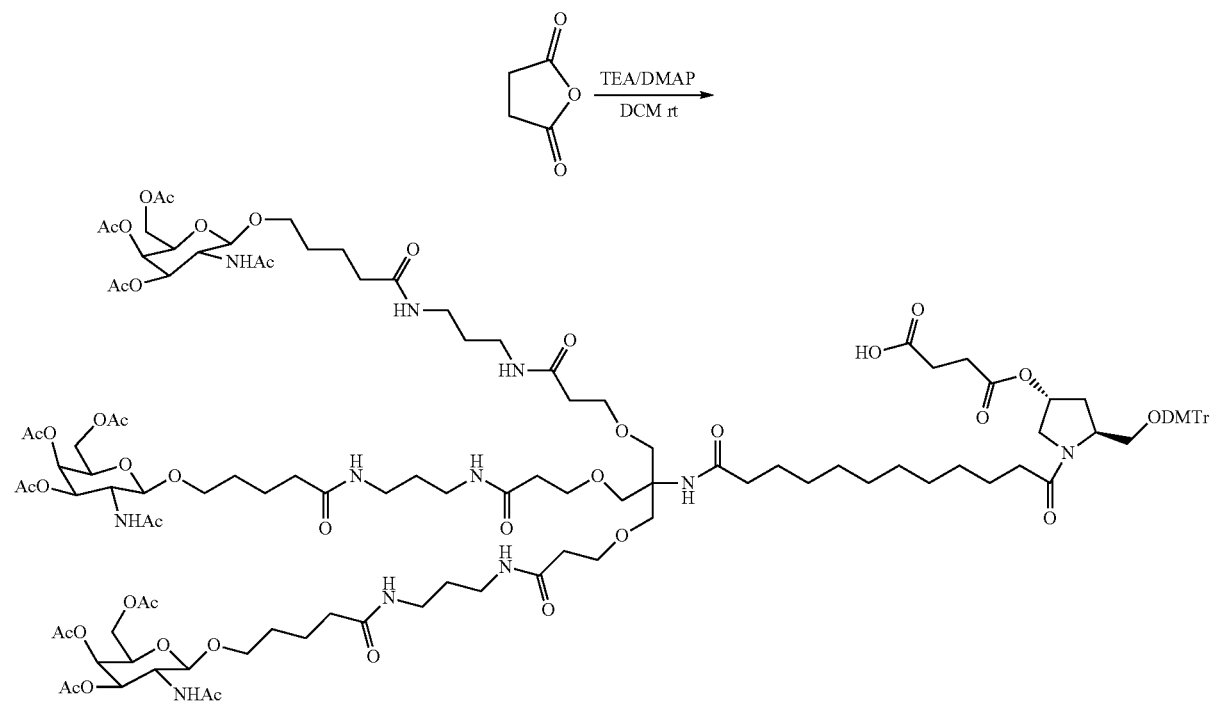

(12-2) Linking (GalNAc)$_3$ Conjugating Molecule to a Solid Phase Support

The (GalNAc)$_3$ conjugating molecule was linked to the solid phase support by the same method as that in step (1-1-9) of Preparation Example 1, thereby obtaining (GalNAc)$_3$ conjugating molecule linked to a solid phase support.

(12-3) Synthesis of Comparative Conjugate 1

Comparative conjugate 1 was prepared by the same methods as those in steps (1-2), (1-3) and (1-4) of Preparation Example 1, except that 1) the sense strand was synthesized starting from the compound produced in step (12-2); and 2) the conjugated siRNA had sequences represented by No. (GalNAc)$_3$-69535 as shown in Table 3.

The molecular weight was measured by LC-MS (Liquid Chromatography-Mass Spectrometry, purchased from Waters Corp., model: LCT Premier). The result showed that the measured values were in conformity with the theoretical values, and thus it was confirmed that the synthesized conjugate was the designed target compound having structure represented by Formula (305).

After the preparation of the conjugates of the present disclosure, they were lyophilized to solid powder via standard process and stored until used. When used, they can be resolved with such as water for injection to a solution at a desired concentration.

Experimental Example 1

This experiment investigated the inhibitory activity in vitro of the siRNA conjugates of the present disclosure.

Experimental Example 1-1: On-Target Activity In Vitro in psiCHECK System

In this experimental example, conjugates F1-F5 were investigated in psiCHECK system in vitro for the on-target activity, i.e., conjugates F1-F5 were tested for the activity of targeting completely matching target sequence (in which the nucleotide sequence is complete complementary to the full-length nucleotide sequence of the antisense strand of the conjugate).

According to the method described by Kumico Ui-Tei et. al., Functional dissection of siRNA sequence by systematic DNA substitution: modified siRNA with a DNA seed arm is a powerful tool for mammalian gene silencing with significantly reduced off-target effect. Nucleic Acids Research, 2008.36(7), 2136-2151, a plasmid for detection was constructed and co-transfected with the siRNA conjugates to be detected into HEK293A cells. The on-target activity of the siRNA conjugates were reflected by the expression level of a dual-luciferase reporter gene.

Specific steps are as follows:

[1] Construction of a Plasmid for Detection

The on-target plasmid was constructed using psiCHECK™-2 (Promega™) plasmid. This plasmid contains a target sequence, which is completely complementary to all 21-nucleotide sequence of the antisense strand in the conjugates to be detected. The target sequence was cloned into the Xho I/Not I site of the psiCHECK™-2 plasmid.

[2] Transfection

In a 96-well plate, the siRNA conjugates and the above plasmid were respectively co-transfected according to the instructions of Lipofectamine™ 2000 (Invitrogen). Specifically, 10 ng of plasmid was transfected per well, using 0.2 μL of Lipofectamine™ 2000; and the final concentrations (based on the concentration of siRNA) of the conjugates were 0.5 nM, 0.1 nM, and 0.02 nM in succession. For each group, those untreated with the conjugates were used as control (con). 3 replicate wells were used per group.

NC is a universal negative control B01001 with no homology to the target gene sequence (GenePharma Co., Ltd).

[3] Detection 24 hours post co-transfection, the HEK293A cells were lysed by using a dual luciferase reporter gene assay kit (Promega, cat. E2940) according to the instruction manual to detect the expression level of the dual luciferase reporter gene. The Renilla luciferase protein level (Ren) was normalized to the firefly luciferase protein level (Fir). The results are shown in FIG. 1.

The results indicate that conjugates F1-F5 all have good inhibitory activity in vitro, and show high inhibitory rate of 87%-97% at high concentrations.

Experimental Example 1-2. Detection of IC$_{50}$ in psiCHECK System In Vitro

This experimental example investigated the IC$_{50}$ of conjugate 1 in psiCHECK system in vitro.

The on-target plasmid of conjugate 1 was constructed using the same method as that in Experimental Example 1-1. The final concentration of conjugate 1 was double diluted from 1 nM to finally 0.001 nM, with a total of 11 concentrations. The dose-response curve was fitted according to the activity results measured at different siRNA concentrations, by using Function log(inhibitor) vs. response—Variable slope of Graphpad 5.0 software. The IC$_{50}$ value of the conjugate 1 was calculated according to the does-response curve.

$$Y = Bot + \frac{Top - Bot}{1 + 10^{(\log IC_{50} - X) \times HillSlope}}$$

wherein

Y is the expression level of remaining mRNA,

X is the logarithm of the concentration of transfected siRNA,

Bot is the Y value at the bottom of the steady-state phase,

Top is the Y value at the top of the steady-state phase,

LogIC$_{50}$ is the X value when Y is the median value between the bottom and the top, and HillSlope is the slope of the curve.

According to the test, the IC$_{50}$ of conjugate 1 in psi-CHECK system in vitro was 0.0174 nM, showing that siRNA conjugate of the present disclosure has high activity in vitro.

Experimental Example 1-3. Detection of IC$_{50}$ in Cell Line In Vitro

This experimental example investigated the inhibitory efficiency of conjugate 2 against the expression amount of APOC3 mRNA in Huh7 cells in vitro.

Conjugate 2 was transfected to Huh7 human cells by using Lipofectamine™ 2000. The final concentrations (based on the amount of siRNA) of siRNA conjugates were 3-fold diluted from 3 nM to 0.004 nM, with a total of 7 concentrations. 2 replicate wells were used for each concentration.

The expression amount of APOC3 mRNA in Huh7 cells transfected with various concentrations of conjugate 2 were detected by Quantitative Real-Time PCR. Specific steps are as follows: 24 hours post cultivation of the transfected cells, the total RNA was extracted and obtained by using Trizol (Thermo Fisher) according to the standard procedure for total RNA extraction; 1 μg of total RNA were individually reverse transcribed into cDNA by using reverse transcription kit (Promega, Cat.A3500) according to the operation method in the instructions thereof. The expression amount of APOC3 mRNA was detected by using the template cDNA according to the steps in the instructions by using 2×Ultra SYBR Mixture (with ROX) (Beijing Cowin Biosicences Co., Ltd, Cat. CW0956). In this case, the PCR primers used for amplifying APOC3 and β-actin as an internal control gene are shown in Table 4.

TABLE 4

The sequences of the primers for detection

| Genes | Upstream Primers | Downstream Primers |
|---|---|---|
| Human APOC3 | 5'-GTGACCGATGGCTTCAGTTC-3' (SEQ ID NO: 50) | 5'-ATGGATAGGCAGGTGGACTT-3' (SEQ ID NO: 51) |
| Human β-actin | 5'-CCAACCGCGAGAAGATGA-3' (SEQ ID NO: 52) | 5'-CCAGAGGCGTACAGGGATAG-3' (SEQ ID NO: 53) |

The expression amount of APOC3 mRNA was calculated by the following equation: the expression amount of APOC3 mRNA=(the expression amount of APOC3 mRNA in the test group/the expression amount of (3-actin mRNA in the test group)/(the expression amount of APOC3 mRNA in the control group/the expression amount of β-actin mRNA in the control group)×100%.

The inhibition rate of the conjugate against APOC3 mRNA is (1−the expression amount of APOC3 mRNA)×100%. In particular, the test groups are Huh7 cells treated with conjugate 2 at various concentrations, and the control group is Huh7 cells untreated with conjugate 2.

The $IC_{50}$ of 0.0085 nM for conjugates 2 in Huh7 cells in vitro was obtained by using the same method as that in Experimental Example 1-2, on the basis of the measured inhibition rate of conjugates 2 at different concentration against the expression amount of APOC3 mRNA. This indicates that the siRNA conjugate of the present disclosure has higher activity in vitro.

Experimental Example 2. This Experiment Investigated the Inhibition Rate of siRNA Conjugate Against APOC3 mRNA In Vivo Experimental Example 2-1

This experimental example investigated the inhibition efficiency of conjugate 1 against the expression amount of APOC3 in liver tissues in human APOC3 transgenic mice.

Human APOC3 transgenic mice (B6;CBA-Tg(APOC3) 3707Bres/J) were randomly divided into groups according to TG content >2 mmol/L (5 mice in each group), and conjugate 1, comparative conjugate 1 and Normal Saline (NS) were administrated to the mice in each group respectively. The drug dosages for all animals were calculated according to the body weight. A single dose was injected subcutaneously, with two dosages for the siRNA conjugates (based on the amount of siRNA) of 1 mg/kg and 0.1 mg/kg respectively. The conjugates were provided respectively as 0.2 mg/ml and 0.02 mg/ml in 0.9% sodium chloride aqueous solutions, and were administered in a volume of 5 mL/kg. Mice were sacrificed at day 14 after administration. The liver was collected and kept with RNA later (Sigma Aldrich), and the liver tissue was homogenized with a tissue homogenizer. Then the total RNA was extracted and obtained by using Trizol (Thermo Fisher) according to the standard procedure for total RNA extraction.

The expression amount of APOC3 mRNA in liver tissue was measured by the real-time fluorescent qPCR same as that in Experimental Example 1-3. In the fluorescent qPCR, β-actin is used as internal control gene and the expression amounts of APOC3 and β-actin were respectively detected using the primer designed for APOC3 and the primer designed for β-actin.

The sequences of the primers for detection are shown in Table 5.

TABLE 5

The sequences of the primers for detection

| Genes | Upstream Primers | Downstream Primers |
|---|---|---|
| Human APOC3 | 5'-GTGACCGATGGCTTCAGTTC-3' (SEQ ID NO: 50) | 5'-ATGGATAGGCAGGTGGACTT-3' (SEQ ID NO: 51) |
| Mouse β-actin | 5'-AGCTTCTTTGCAGCTCCTTCGTTG-3' (SEQ ID NO: 54) | 5'-TTCTGACCCATTCCCACCATCACA-3' (SEQ ID NO: 55) |

Figure 2:
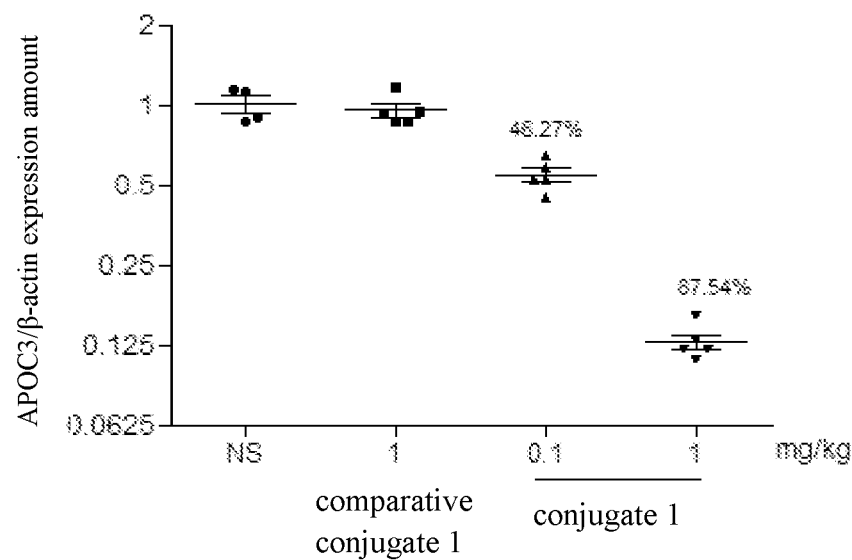
FIG. 2 shows the inhibition rate of conjugate 1 against the expression amount of APOC3 mRNA in liver tissues of human APOC3 transgenic mice at day 14.

The expression amount of APOC3 mRNA in liver and the inhibition rate of the conjugates against APOC3 mRNA were calculated by the same method as that in Experimental Example 1-3. In particular, the control group was a group of control mice administrated with NS in this experiment and each test group was a group of mice administrated with different siRNA conjugates, respectively. The results are shown in FIG. 2.

The results show that conjugate 1 exhibits significant inhibitory effect on the human APOC3 gene in transgenic mice.

Experimental Example 2-2

This experimental example investigated the inhibition rate of Conjugate 1 against the expression amount of APOC3 mRNA in liver tissue of cynomolgus monkey in vivo, and the effect thereof on blood lipid level.

CTI Biotechnology (Suzhou) Co., Ltd. was authorized to perform this experimental example. Cynomolgus monkeys (body weight: 2-4 kg, age: 3-5 years old) were randomly divided into two groups, one male and one female per group. Conjugate 1 and comparative conjugate 2 were administered individually. The drug dosages for all animals were calculated according to the body weight. A single dose was injected subcutaneously, with the dosage for the siRNA conjugate (based on the amount of siRNA) of 3 mg/kg. The conjugates were provided respectively in the form of 3 mg/ml NaCl injection solutions (Shandong Kelun Pharmaceutical Co., Ltd.) and the administration volume was 1 mL/kg. The day on which the first dose is administrated was defined as Test Day 1 (D1), and one day before administration was defined as Day 0 (D0).

The blood samples were taken from the vein of the animals before administration and at day 7, 14, 21 and 28 after administration. The contents of the substances to be detected in serum were measured at each time point. The substances to be detected include blood lipids (total cholesterol (CHO) and triglyceride (TG)), and transaminases (glutamic pyruvic transaminase (ALT) and glutamic oxaloacetic transaminase (AST)). The substances to be detected were normalized. The inhibition rate of each substance to be detected was calculated by the equation: the inhibition rate=(1−the content of the substance to be detected in the test group after administration)/the content of the substance to be detected in the test group before administration)×100%. The inhibition rate against triglyceride (TG) is shown in Table 6.

As measured by real-time fluorescent qPCR, relative to the comparative conjugate 2, conjugate 1 had an inhibition rate of 55.3% against APOC3 mRNA in the female animals and an inhibition rate of 78.5% against APOC3 mRNA in the male animals. This experiment indicates that conjugate 1 also shows significant inhibitory effect on APOC3 gene in non-human primate and significant inhibitory effect on TG in serum. At the same time, no abnormalities were found in terms of liver function.

Experimental Example 3

This experiment investigated the effects of the siRNA conjugate of the present disclosure on blood lipid content in vivo.

Experimental Example 3-1

This experiment example investigated the effects of conjugate 1 on the contents of total cholesterol (CHO) and triglyceride (TG) in serum of human APOC3 transgenic mice in vivo.

Human APOC3 transgenic mice (B6; CBA-Tg(APOC3) 3707Bres/J) were randomly divided into groups according to TG content >2 mmol/L (7 mice for each group): (1) NS control group; (2) conjugate 1 (3 mg/kg) group; (3) conjugate 1 (1 mg/kg) group. The drug dosages for all animals were calculated according to the body weight. A single dose was injected subcutaneously. The siRNA conjugate was provided respectively in the form of 0.6 mg/ml and 0.2 mg/ml of 0.9% NaCl aqueous solutions. The administration volume was 5 mL/kg.

TABLE 6

| The content of TG and the inhibition rate against TG | | | | | | | | | |
|---|---|---|---|---|---|---|---|---|---|
| | | Content of TG (mmol/L) | | | | Inhibition rate against TG (%) | | | |
| Conjugate | Time point | D0 | D7 | D14 | D21 | D28 | D7 | D14 | D21 | D28 |
| Conjugate 1 | Male M | 0.88 | 0.32 | 0.35 | 0.42 | 0.3 | 63.6 | 60.2 | 52.3 | 65.9 |
| | Female F | 0.75 | 0.31 | 0.4 | 0.52 | 0.23 | 58.7 | 46.7 | 30.7 | 69.3 |

The content of transaminase was measured at each detection point after administration, and no abnormalities was found in terms of liver function.

The animals were sacrificed at day 28 after administration, and the liver was collected. According to general observations, no abnormalities were found. RNA was extracted from liver tissue by the same method as that in Experimental Example 2-1, and the expression amount of APOC3 mRNA in liver was measured. The sequences of the primers for detection are shown in Table 7.

The blood was taken from mouse orbital venous plexus before administration (marked as day 0) and at days 7, 14, 21, 28, 35, 42, 49, 63, 77, 91, 112, 133, 147, 154, 161, 175 and 189 after administration respectively. The contents of total cholesterol (CHO) and triglyceride (TG) in serum were measured at each time point.

The blood taken from the orbit was about 100 µl each time, and the serum was no less than 20 µl after centrifugation. The contents of total cholesterol (CHO) and triglyc-

TABLE 7

| The sequences of the primers for detection | | |
|---|---|---|
| Genes | Upstream Primers | Downstream Primers |
| Monkey APOC3 | 5'-TTGAACCCTGAGGCCAAACC-3' (SEQ ID NO: 56) | 5'-CGGTAGGAGGGCACTGAGAA-3' (SEQ ID NO: 57) |
| Monkey GAPDH | 5'-GGGAGCCAAAAGGGTCATCA-3' (SEQ ID NO: 58) | 5'-CGTGGACTGTGGTCATGAGT-3' (SEQ ID NO: 59) | eride (TG) in serum were further measured by using a PM1P000/3 full-automatic serum biochemical analyzer (SABA, Italy).

> The normalized blood lipid level=(the blood lipid content in the test group after administration/the blood lipid content in the test group before administration)×100%.

> The inhibition rate against blood lipid level=(1−the blood lipid content in the test group after administration/the blood lipid content in the test group before administration)×100%. Blood lipid refers to total cholesterol (CHO) or triglyceride (TG).

Figure 3A:
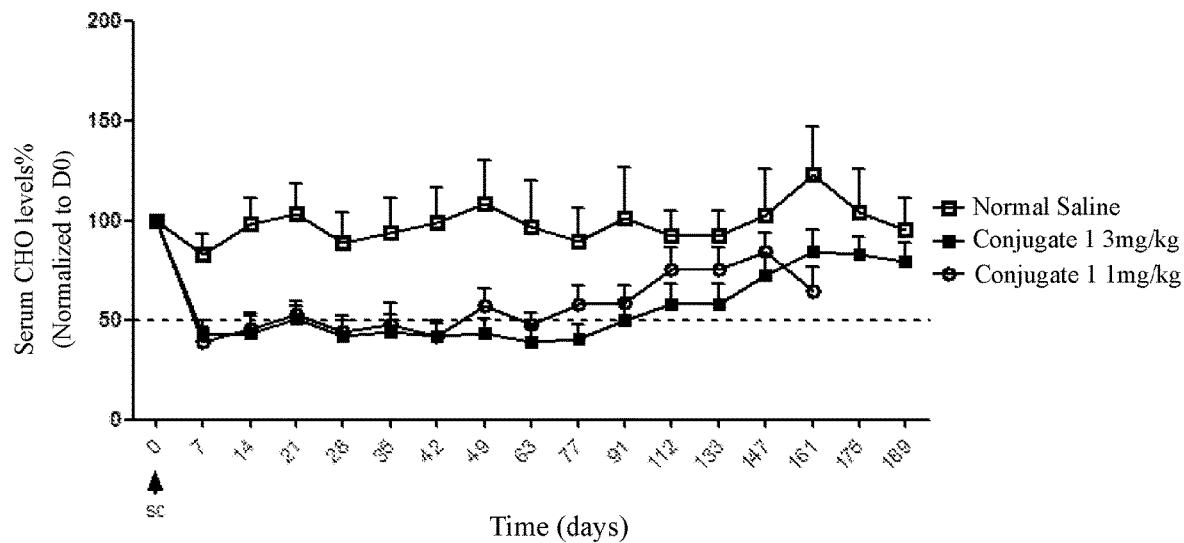
FIGS. 3A and 3B show the inhibition rate of conjugate 1 at different doses on blood lipid, indicated by total cholesterol (CHO) and triglyceride (TG) in serum.
Figure 3B:
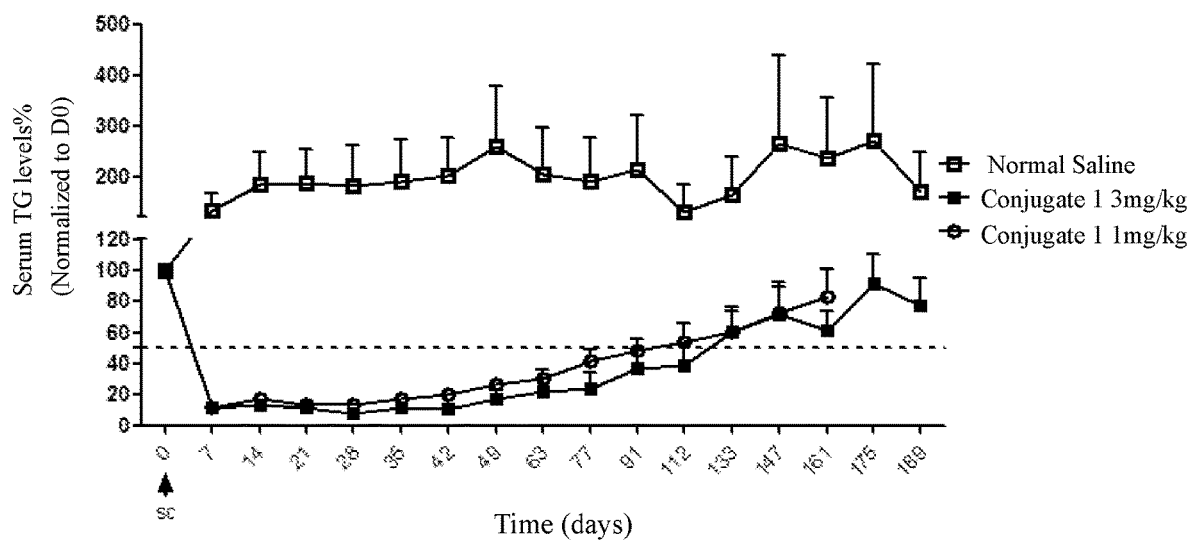

The measured results are shown in FIGS. 3A and 3B.

As can be seen from FIGS. 3A and 3B, conjugate 1 shows the effect of significantly reducing the contents of TG and CHO in mouse serum over a period of up to 189 days, indicating that this conjugate could stably and effectively inhibit the expression of APOC3 gene over a long period of time.

Experimental Example 3-2

This experimental example investigated the effects of conjugate 2 on the contents of total cholesterol (CHO) and triglyceride (TG) in serum of human APOC3 transgenic mice.

Detection was performed according to the same method as that in Experimental Example 3-1, except that 8 mice for each group, the conjugate to be administered was conjugate 2; five groups of doses (0.1, 0.3, 1, 3 and 9 mg/kg) were individually administered; the dosage volume remained unchanged and the concentration of conjugate solutions was adjusted; the test continued until day 112 after administration. The results are shown in FIGS. 4A and 4B.

Figure 4A:
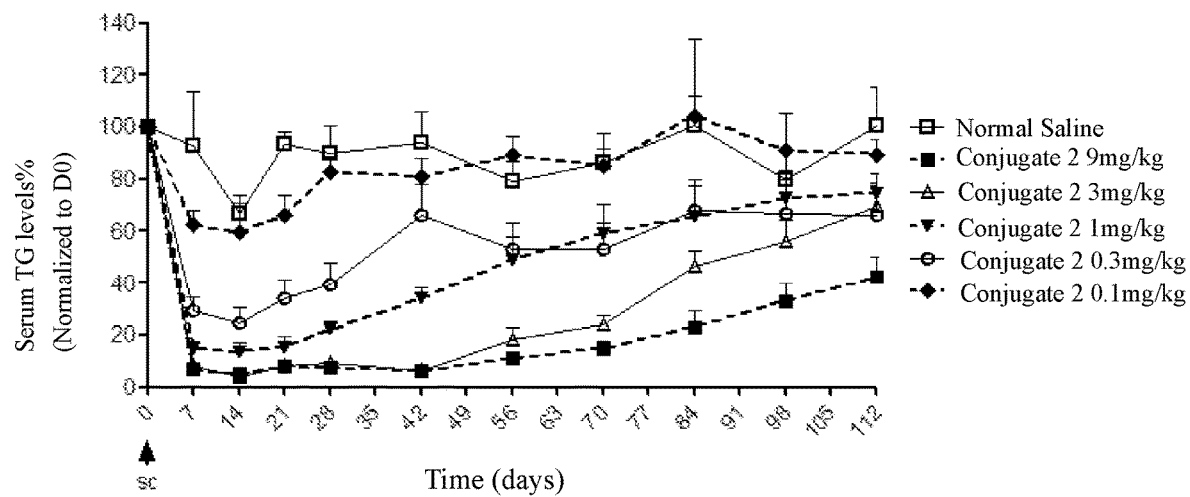
FIGS. 4A and 4B show the inhibition rate of conjugate 2 at different doses on blood lipid, indicated by total cholesterol (CHO) and triglyceride (TG) in serum.
Figure 4B:
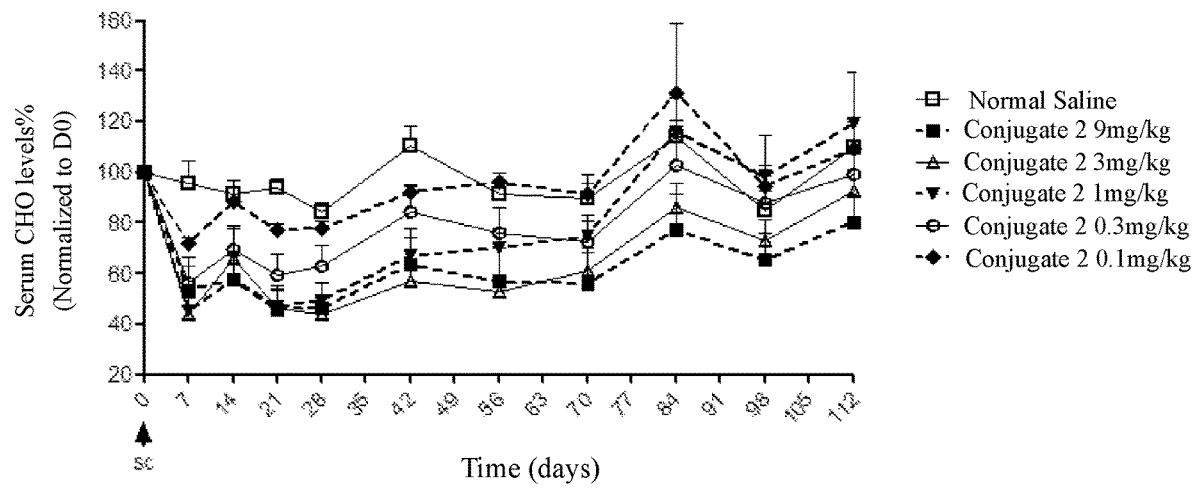
Figure 5A:
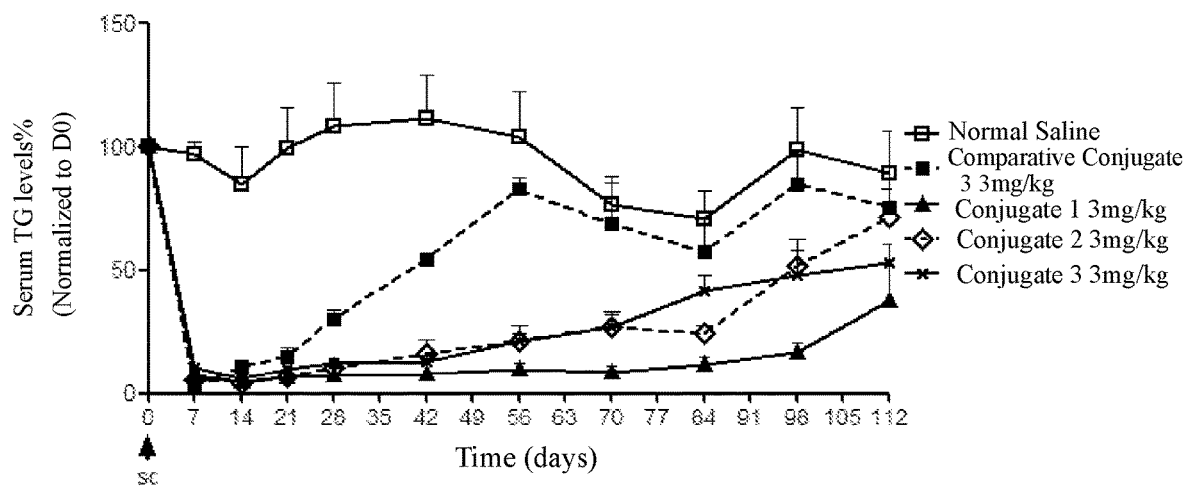
FIGS. 5A, 5B, 5C and 5D show the inhibition rate of conjugates 1-3 at different doses on blood lipid, indicated by total cholesterol (CHO) and triglyceride (TG) in serum.
Figure 5B:
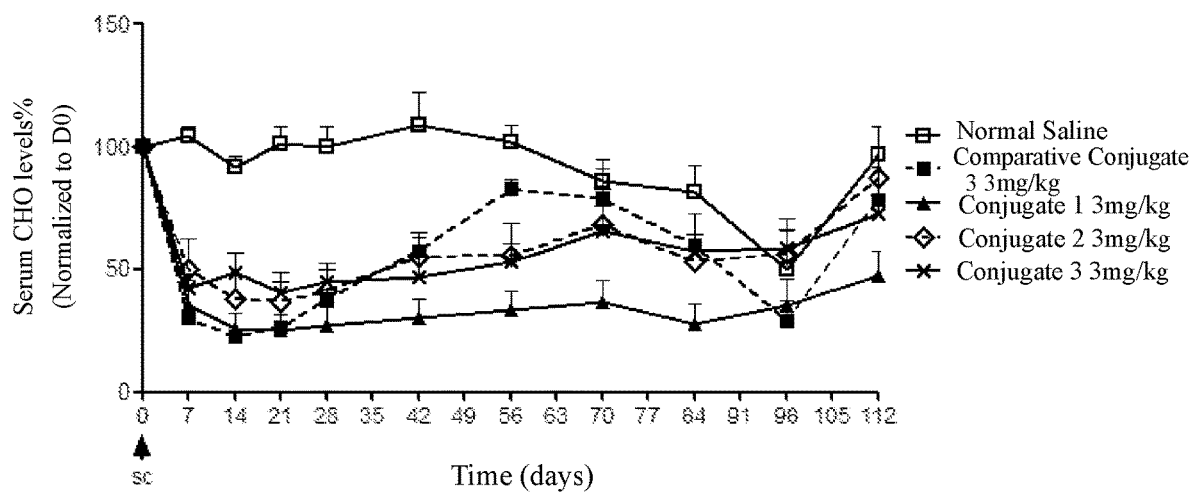
Figure 5C:
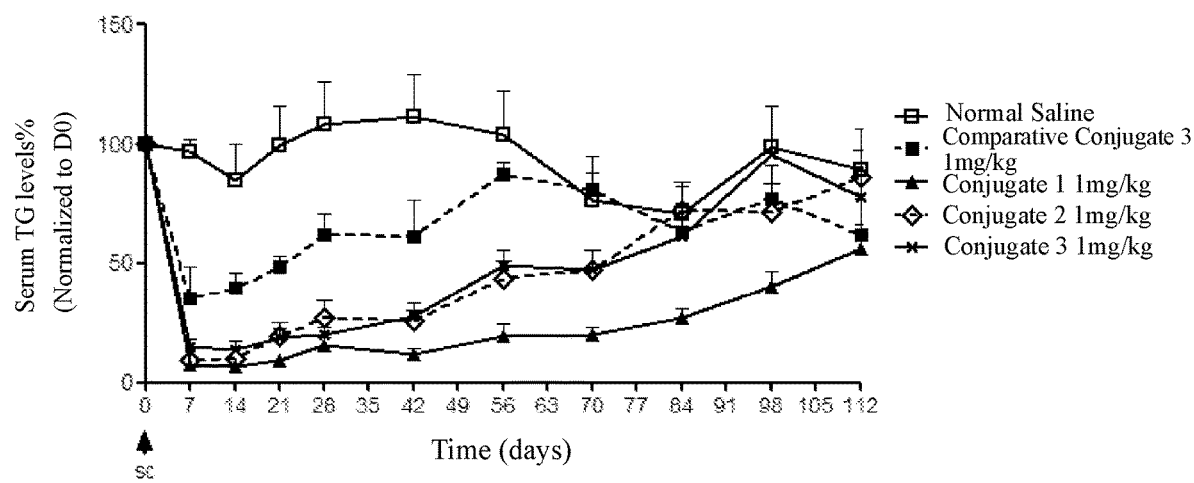
Figure 5D:
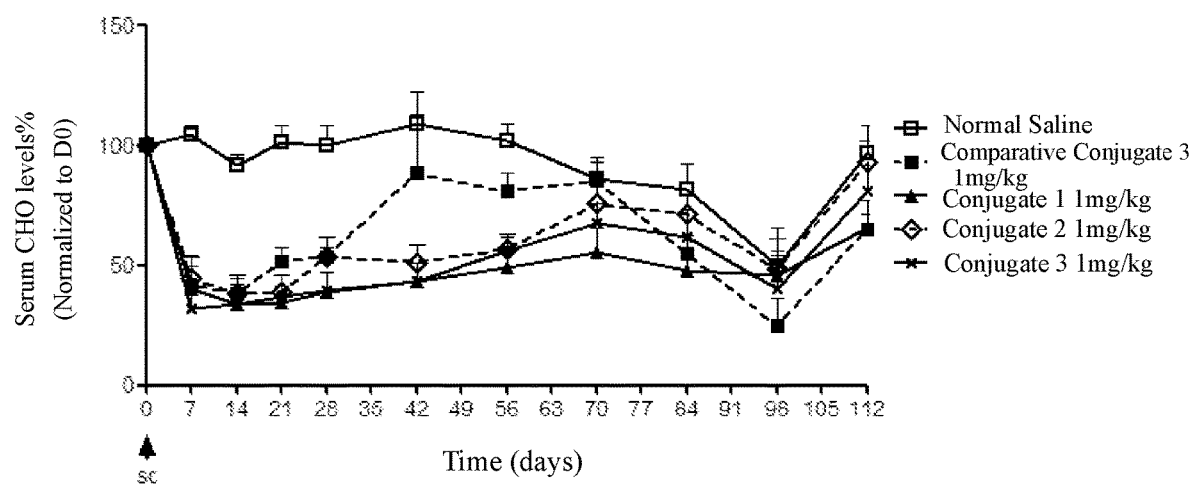

As can be seen from the results of FIGS. 4A and 4B, conjugate 2 significantly reduces the levels of TG and CHO in transgenic mice over a period of up to 112 days, and this reduction effect shows significant dose-dependent effect.

Experimental Example 3-3

This experimental example compared the effects of conjugates 1-3 on the contents of total cholesterol (CHO) and triglyceride (TG) in serum of human APOC3 transgenic mice.

The contents of total cholesterol (CHO) and triglyceride (TG) in mouse serum were measured using the same method as that in Experimental Example 3-1, except that 6 mice for each group, conjugates 1, 2 and 3 and comparative conjugate 3 were individually administered; two groups of doses (1 mg/kg and 3 mg/kg) were administered for each conjugate; the dosage volume remained unchanged and the concentration of conjugate solutions was adjusted; the test continued until day 112 after administration. The results are shown in FIGS. 5A-5D.

As can be seen from the results of FIGS. 5A-5D, the conjugates 1-3 of the present disclosure at different doses show the effect of continuously reducing the blood lipid level in the transgenic mice over a period of up to 112 days, and this reduction effect as a whole was superior to that of comparative conjugate 3.

The above results show that the conjugates of the present disclosure can effectively reduce the expression amount of APOC3 mRNA in liver, reduce the contents of total cholesterol and triglyceride in blood, can be used to prevent and/or treat dyslipidemia, and thus has good application prospect in clinics.

Some embodiments of the present disclosure are described in detail above, but the present disclosure is not limited to the specific details of the above-described embodiments. Various simple variations to the technical solution of the present disclosure can be made within the scope of the technical concept of the present disclosure, and these simple variations are within the scope of the present disclosure. It is to be noted that each of the specific technical features described in the above embodiments can be combined in any suitable manner as long as no contradiction is caused. In order to avoid unnecessary repetition, the various possible combination manners are no longer described in the present disclosure.

In addition, the various different embodiments of the present disclosure may also be carried out in any combination as long as it does not contravene the idea of the present disclosure, which should also be regarded as the disclosure of the present disclosure.

The invention claimed is:

1. A siRNA conjugate, which has the structure represented by Formula (1):

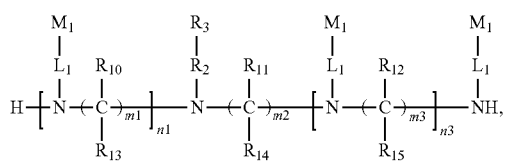

Formula (1)

wherein, n1 is an integer of 1-2, n3 is an integer of 0-1, and n1+n3=2-3;

m1, m2, and m3 are independently an integer of 2-10;

each of $R_{10}$, $R_{11}$, $R_{12}$, $R_{13}$, $R_{14}$ and $R_{15}$ is independently H, or selected from the group consisting of $C_1$-$C_{10}$ alkyl, $C_1$-$C_{10}$ haloalkyl, and $C_1$-$C_{10}$ alkoxy;

$R_3$ is a group having the structure represented by Formula A59:

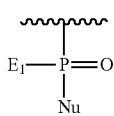

(A59)

wherein $E_1$ is OH, SH or $BH_2$, and Nu is a siRNA;

in said siRNA, each nucleotide is independently a modified or unmodified nucleotide; the siRNA comprises a sense strand and an antisense strand; the sense strand comprises a nucleotide sequence 1, and the antisense strand comprises a nucleotide sequence 2; said nucleotide sequence 1 and nucleotide sequence 2 are at least partly reverse complementary to form a double-stranded region, wherein the nucleotide sequence 1 has the same length as the nucleotide sequence represented by SEQ ID NO: 1 with no more than 3 nucleotide differences, and the nucleotide sequence 2 has the same length as the nucleotide sequence represented by SEQ ID NO:2 with no more than 3 nucleotide differences:

(SEQ ID NO: 1)
5'-CAAUAAAGCUGGACAAGAZ-3';

(SEQ ID NO: 2)
5'-Z'UCUUGUCCAGCUUUAUUG-3';

wherein, Z is A and Z' is U, and the nucleotide sequence 1 comprises a nucleotide $Z_A$ at the corresponding position of Z, the nucleotide sequence 2 comprises a nucleotide Z'B at the corresponding position of Z', wherein $Z'_B$ is the first nucleotide at 5' terminal of the antisense strand;

$R_2$ is a linear alkylene of 1 to 20 carbon atoms in length, wherein one or more carbon atoms are optionally replaced with one or more groups selected from the group consisting of: C(O), NH, O, S, CH=N, $S(O)_2$, $C_2$-$C_{10}$ alkeylene, $C_2$-$C_{10}$ alkynylene, $C_6$-$C_{10}$ arylene, $C_3$-$C_{18}$ heterocyclylene, or $C_5$-$C_{10}$ heteroarylene, and wherein $R_2$ is optionally substituted by any one or more groups selected from the group consisting of: $C_1$-$C_{10}$ alkyl, $C_6$-$C_{10}$ aryl, $C_5$-$C_{10}$ heteroaryl, $C_1$-$C_{10}$ haloalkyl, —O$C_1$-$C_{10}$ alkyl, —O$C_1$-$C_{10}$ alkylphenyl, —$C_1$-$C_{10}$ alkyl-OH, —O$C_1$-$C_{10}$ haloalkyl, —S$C_1$-$C_{10}$ alkyl, —S$C_1$-$C_{10}$ alkylphenyl, —$C_1$-$C_{10}$ alkyl-SH, haloalkyl, halo, —OH, —SH, —NH$_2$, —$C_1$-$C_{10}$ alkyl-NH$_2$, —N($C_1$-$C_{10}$ alkyl)($C_1$-$C_{10}$ alkyl), —NH($C_1$-$C_{10}$ alkyl), cyano, nitro, —CO$_2$H, —C(O)O($C_1$-$C_{10}$ alkyl), —CON($C_1$-$C_{10}$ alkyl)($C_1$-$C_{10}$ alkyl), —CONH($C_1$-$C_{10}$ alkyl), —CONH$_2$, —NHC(O)($C_1$-$C_{10}$ alkyl), —NHC(O)(phenyl), —N($C_1$-$C_{10}$ alkyl)C(O)($C_1$-$C_{10}$ alkyl), —N($C_1$-$C_{10}$ alkyl)C(O)(phenyl), —C(O)$C_1$-$C_{10}$ alkyl, —C(O)$C_1$-$C_{10}$ alkylphenyl, —C(O)$C_1$-$C_{10}$ haloalkyl, —OC(O)$C_1$-$C_{10}$ alkyl, —SO$_2$($C_1$-$C_{10}$ alkyl), —SO$_2$(phenyl), —S$_{02}$($C_1$-$C_{10}$ haloalkyl), —SO$_2$NH$_2$, —SO$_2$NH($C_1$-$C_{10}$ alkyl), —SO$_2$NH(phenyl), —NHSO$_2$($C_1$-$C_{10}$ alkyl), —NHSO$_2$(phenyl), and —NHSO$_2$($C_1$-$C_{10}$ haloalkyl);

each $L_1$ is a linear alkylene of 1 to 70 carbon atoms in length, wherein one or more carbon atoms are optionally replaced with one or more groups selected from the group consisting of: C(O), NH, O, S, CH=N, S(O)$_2$, $C_2$-$C_{10}$ alkeylene, $C_2$-$C_{10}$ alkynylene, $C_6$-$C_{10}$ arylene, $C_3$-$C_{18}$ heterocyclylene, and $C_5$-$C_{10}$ heteroarylene; and wherein $L_1$ is optionally substituted by any one or more groups selected from the group consisting of: $C_1$-$C_{10}$ alkyl, $C_6$-$C_{10}$ aryl, $C_5$-$C_{10}$ heteroaryl, haloalkyl, —O$C_1$-$C_{10}$ alkyl, —O$C_1$-$C_{10}$ alkylphenyl, alkyl-OH, —O$C_1$-$C_{10}$ haloalkyl, —S$C_1$-$C_{10}$ alkyl, —S$C_1$-$C_{10}$ alkylphenyl, alkyl-SH, —S$C_1$-$C_{10}$ haloalkyl, halo, —OH, —SH, —NH$_2$, —$C_1$-$C_{10}$ alkyl-NH$_2$, alkyl)($C_1$-$C_{10}$ alkyl), —NH($C_1$-$C_{10}$ alkyl), cyano, nitro, —CO$_2$H, —C(O)O($C_1$-$C_{10}$ alkyl), —CON($C_1$-$C_{10}$ alkyl)($C_1$-$C_{10}$ alkyl), —CONH($C_1$-$C_{10}$ alkyl), —CONH$_2$, —NHC(O)($C_1$-$C_{10}$ alkyl), —NHC(O)(phenyl), alkyl)C(O)($C_1$-$C_{10}$ alkyl), —N($C_1$-$C_{10}$ alkyl)C(0)(phenyl), —C(O)$C_1$-$C_{10}$ alkyl, —C(O)$C_1$-$C_{10}$ alkylphenyl, —C(O)$C_1$-$C_{10}$ haloalkyl, —OC(O)$C_1$-$C_{10}$ alkyl, —S$_{02}$($C_1$-$C_{10}$ alkyl), —S$_{02}$(phenyl), —S$_{02}$($C_1$-$C_{10}$ haloalkyl), —SO$_2$NH$_2$, —SO$_2$NH($C_1$-$C_{10}$ alkyl), —SO$_2$NH(phenyl), —NHSO$_2$($C_1$-$C_{10}$ alkyl), —NHSO$_2$(phenyl), and —NHSO$_2$($C_1$-$C_{10}$ haloalkyl);

∿∿∿ represents a site where a group is attached to the rest of the molecule; and M1 represents a targeting group, wherein each of the targeting groups is independently a ligand having affinity to asialoglycoprotein receptors on the surface of mammalian hepatocytes.

2. The siRNA conjugate according to claim 1, wherein each L1 is independently selected from connection combinations of one or more of the groups having Formulae A1-A26:

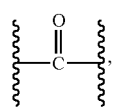
(A1)

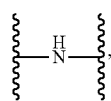
(A2)

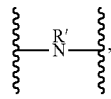
(A3)

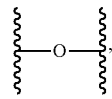
(A4)

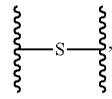
(A5)

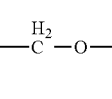
(A6)

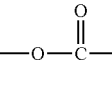
(A7)

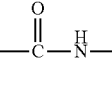
(A8)

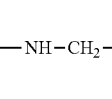
(A9)

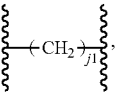
(A10)

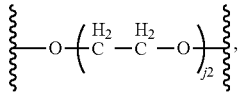
(A11)

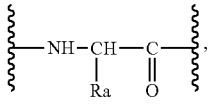
(A12)

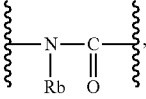
(A13)

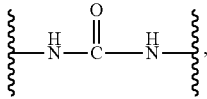
(A14)

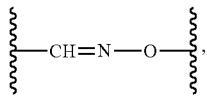
(A15)

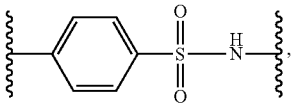
(A16)

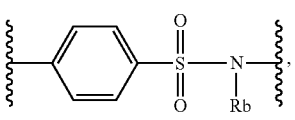
(A17)

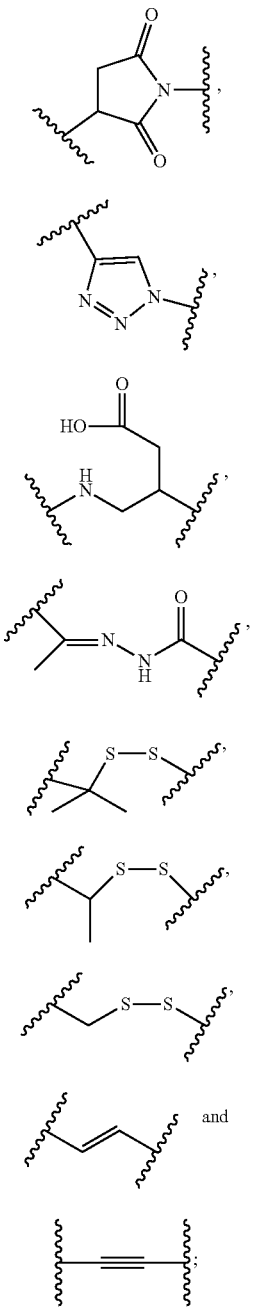
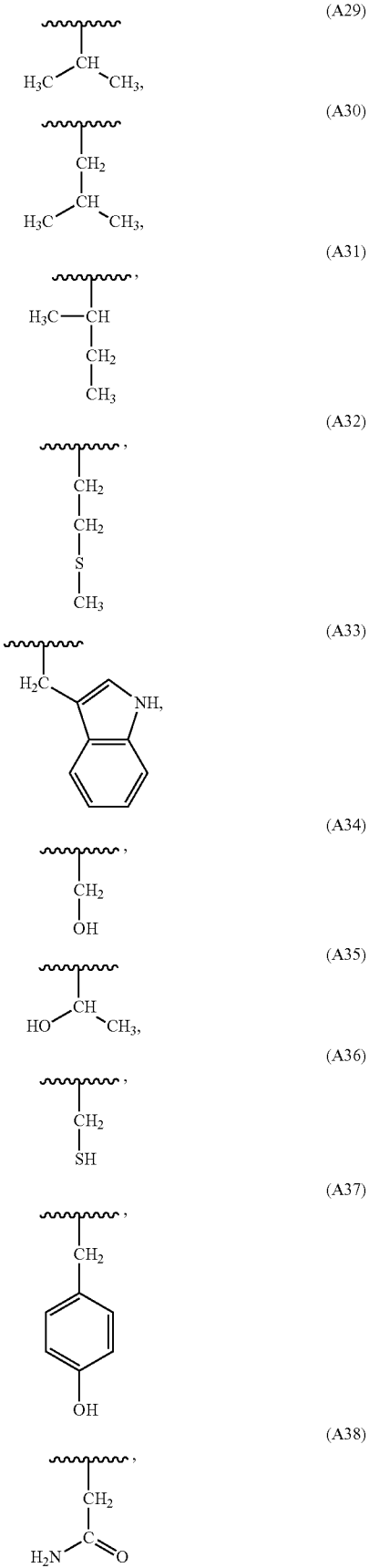
wherein, j1 is an integer of 1-20; j2 is an integer of 1-20; R' is a $C_1$-$C_{10}$ alkyl;
Ra is selected from the group consisting of Formulae A27-A45 and any combination thereof:

(A39) 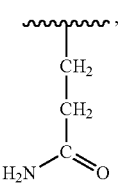

(A40) 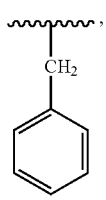

(A41) 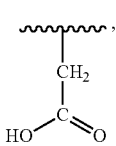

(A42) 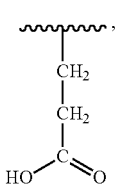

(A43) 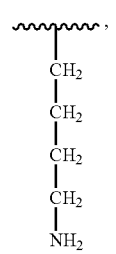

(A44) 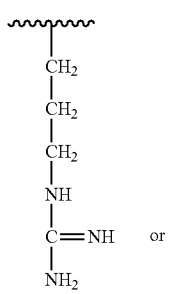

(A45) 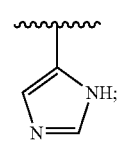

Rb is a $C_1$-$C_{10}$ alkyl.

3. The siRNA conjugate according to claim 2, wherein $L_1$ is selected from connection combinations of one or more of A1, A4, A5, A6, A8, A10, A11, A13; or $L_1$ is selected from connection combinations of at least two of A1, A4, A8, A10, and A11.

4. The siRNA conjugate according to claim 1, wherein $L_1$ is 3 to 25 atoms in length.

5. The siRNA conjugate according to claim 4, wherein $L_1$ is 4 to 15 atoms in length.

6. The siRNA conjugate according to claim 1, wherein m1, m2 and m3 are each independently an integer of 2-5, or wherein m1 =m2=m3.

7. The siRNA conjugate according to claim 1, wherein each of the targeting group is independently selected from the group consisting of D-mannopyranose, L-mannopyranose, D-arabinose, D-xylofuranose, L-xylofuranose, D-glucose, L-glucose, D-galactose, L-galactose, α-D-mannofuranose, β-D-mannofuranose, α-D-mannopyranose, β-D-mannopyranose, α-D-glucopyranose, β-D-glucopyranose, α-D-glucofuranose, β-D-glucofuranose, α-D-fructofuranose, α-D-fructopyranose, α-D-galactopyranose, β-D-galactopyranose, α-D-galactofuranose, β-D-galactofuranose, glucosamine, sialic acid, galactosamine, N-acetylgalactosamine, N-trifluoroacetylgalactosamine, N-propionylgalactosamine, N-n-butyrylgalactosamine, N-isobutyrylgalactosamine, 2-amino-3-O—[(R)-1-carboxyethyl]-2-deoxy-β-D-glucopyranose, 2-deoxy-2-methylamino-L-glucopyranose, 4,6-dideoxy-4-formamido-2,3-di-O-methyl-D-mannopyranose, 2-deoxy-2-sulfoamino-D-glucopyranose, N-glycolyl-a-neuraminic acid, 5-thio-β-D-glucopyranose, methyl 2,3,4-tris-O-acetyl-1-thio-6-O-trityl-α-D-glucopyranoside, 4-thio-β-D-galactopyranose, ethyl 3,4,6,7-tetra-O-acetyl-2-deoxy-1,5-dithio-α-D-glucoheptopyranoside, 2,5-anhydro-D-allononitrile, ribose, D-ribose, D-4-thioribose, L-ribose, and L-4-thioribose.

8. The siRNA conjugate according to claim 1, wherein $R_2$ comprises both a site linking to the N atom on the nitrogenous backbone and a site linking to the P atom in $R_3$; and wherein in $R_2$, the site linking to the N atom on the nitrogenous backbone forms an amide bond with the N atom, and the site linking to the P in $R_3$ forms a phosphoester bond with the P or wherein $R_2$ is selected from B5, B6, B5' or B6':

(B5) 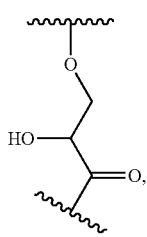

(B6) 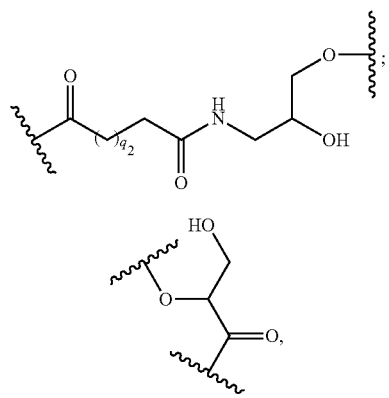
(B5′) 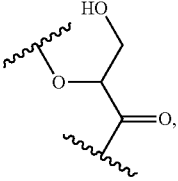
(B6′) 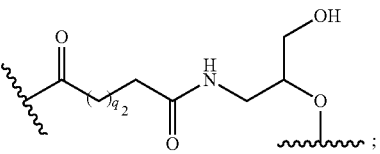
wherein ~~~ represents the site where a group is covalently linked, and $q_2$ is an integer of 1-10.
9. The siRNA conjugate according to claim 1, wherein the conjugate has the structure represented by Formula (3), (4), (5), (6), (7), (8), (9), (10), (11), (12), (13), (14), (15), (16), (17), (18), (19), (20), (21) or (22):
Formula (3)
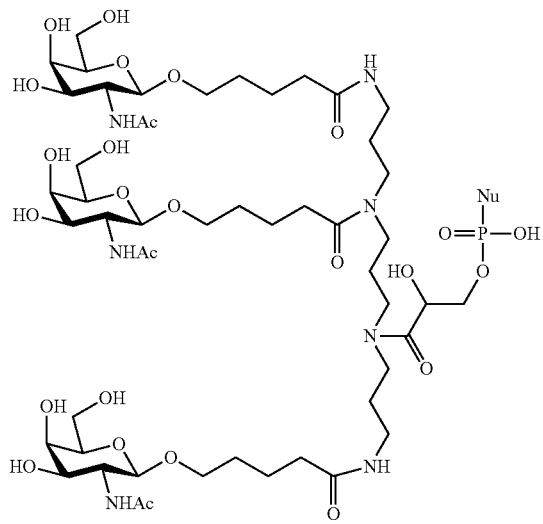
Formula (4)
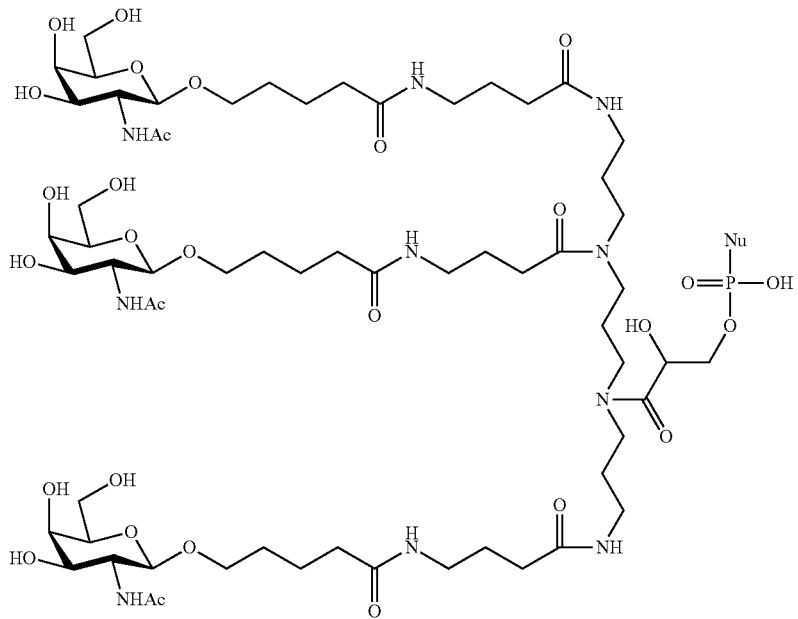

Formula (5)
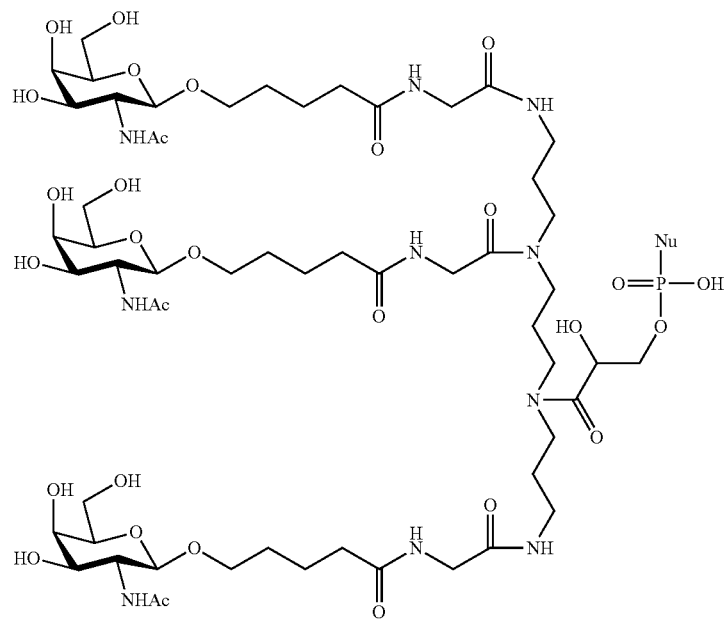
Formula (6)
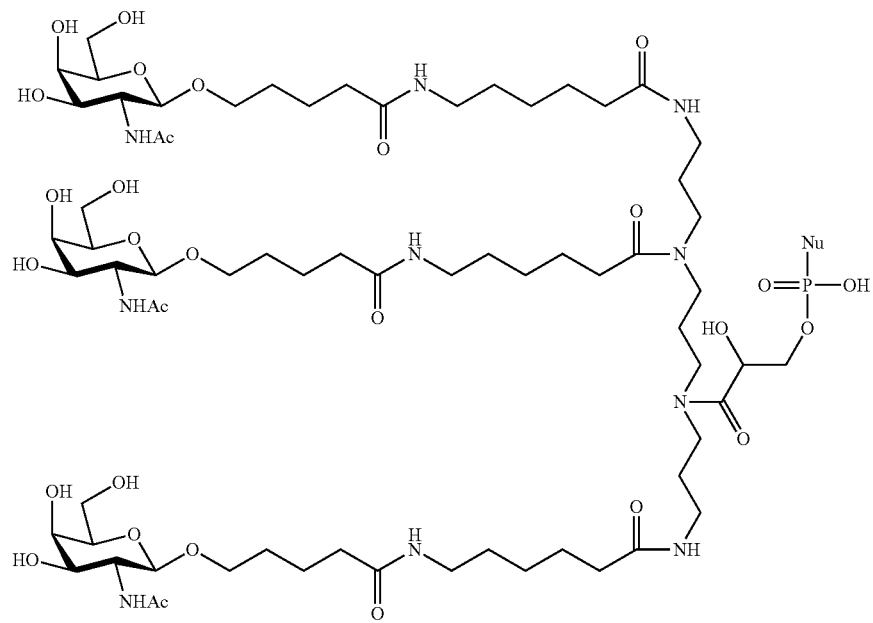

Formula (7)
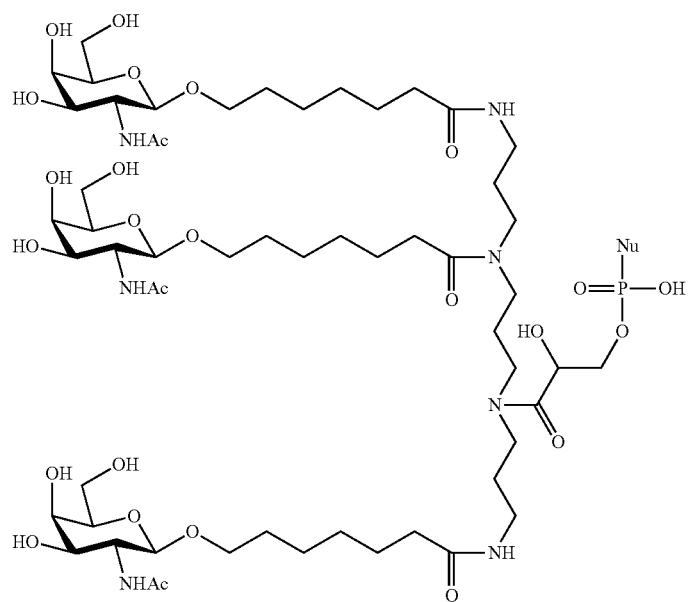
Formula (8)
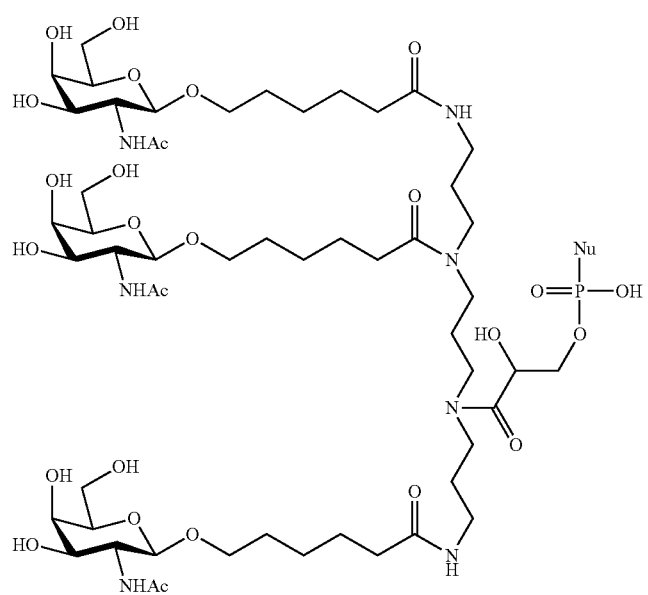

Formula (9)
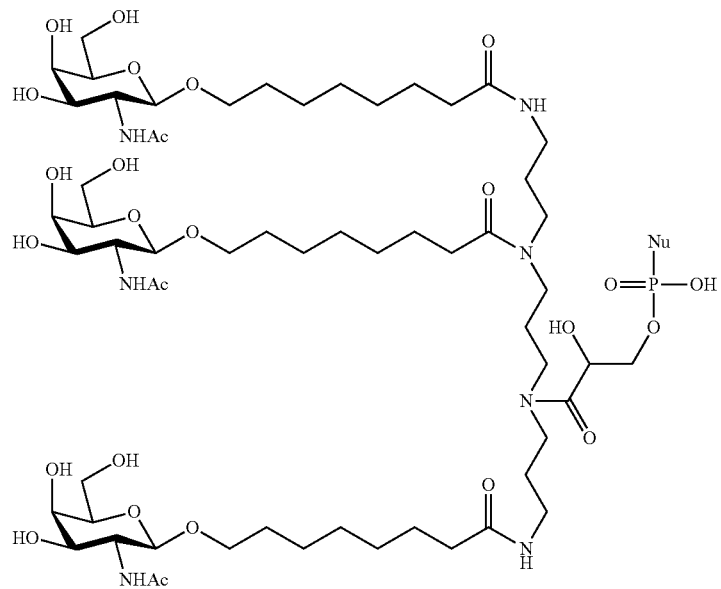
Formula (10)
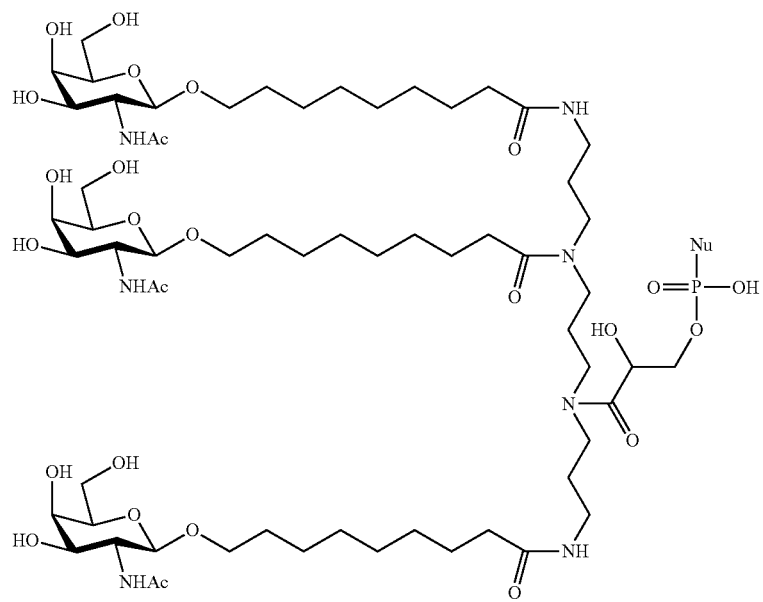

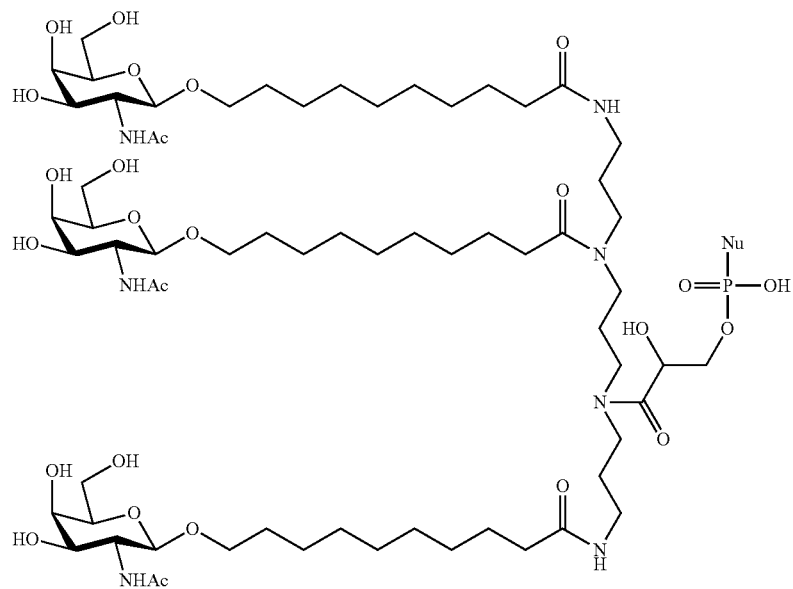
Formula (11)
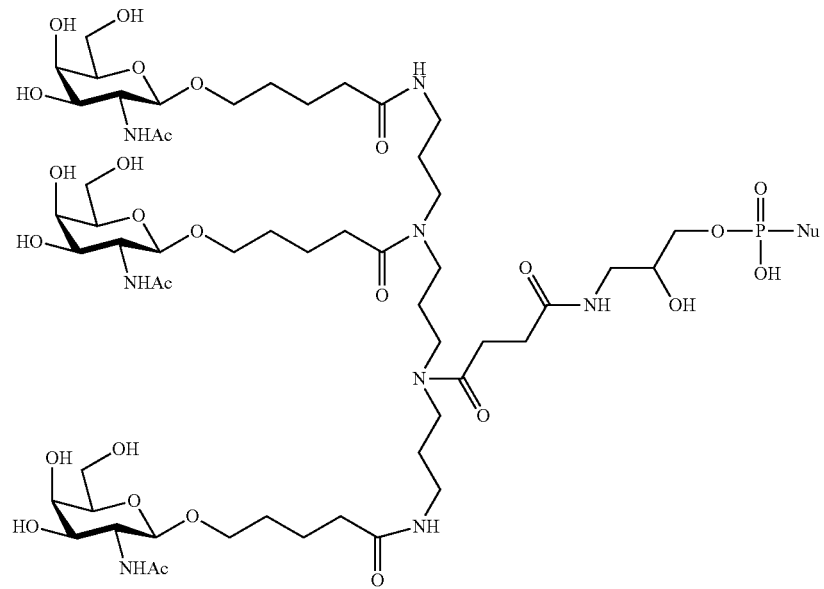
Formula (12)

Formula (13)
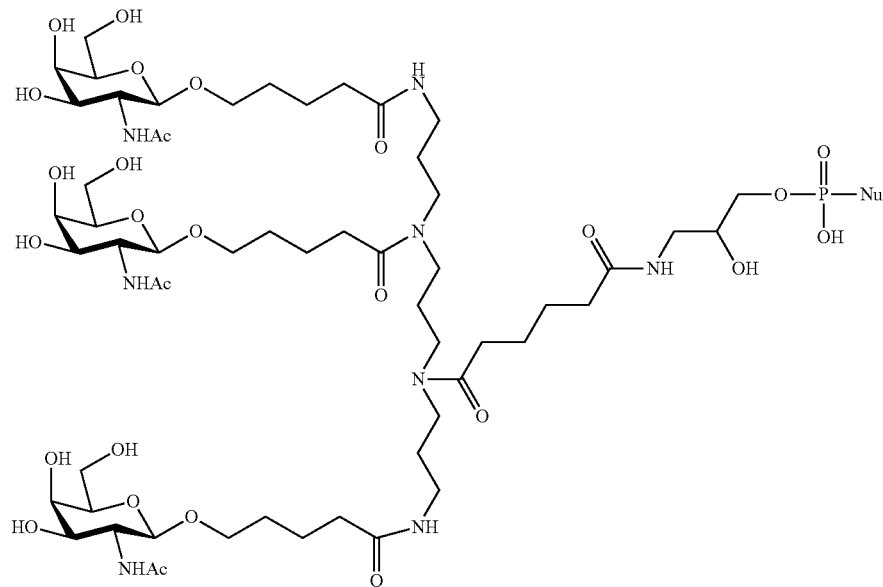
Formula (14)
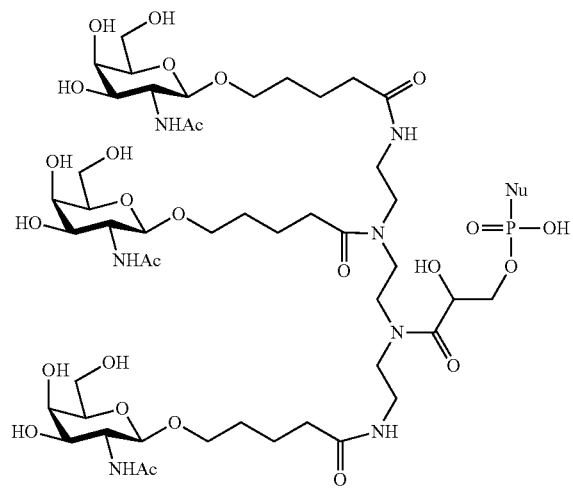
Formula (15)
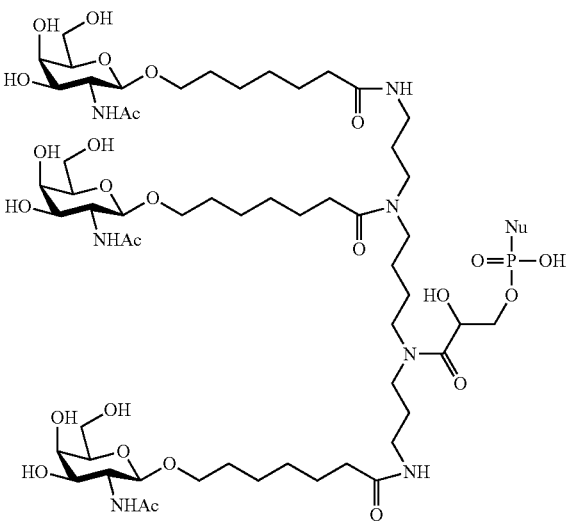

249
Formula (16)
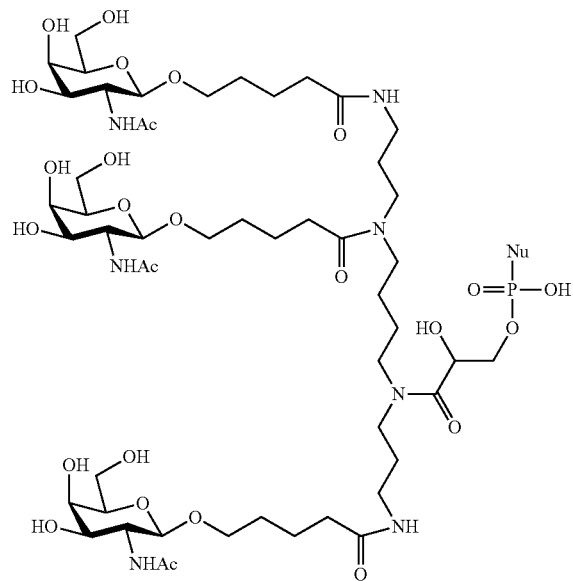
250
-continued
Formula (17)
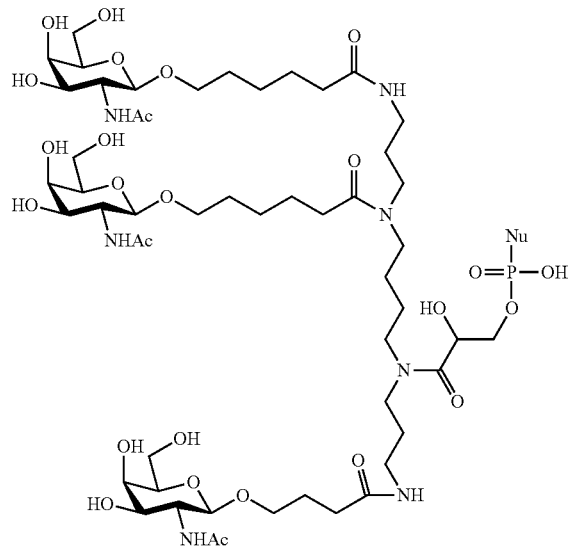
Formula (18)
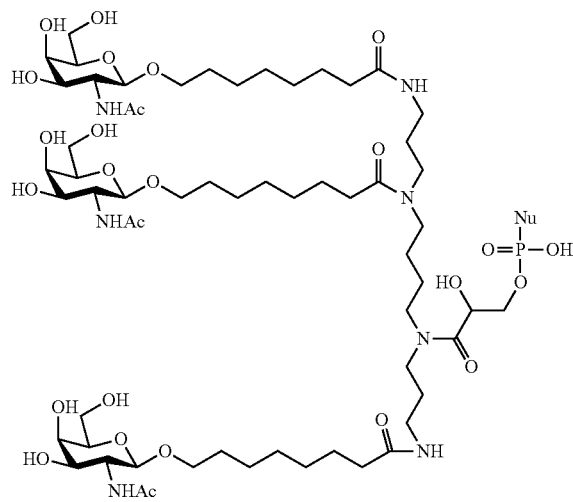
Formula (19)
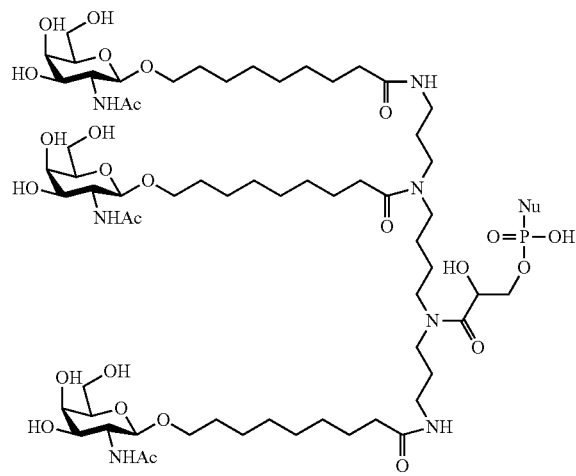

Formula (20)

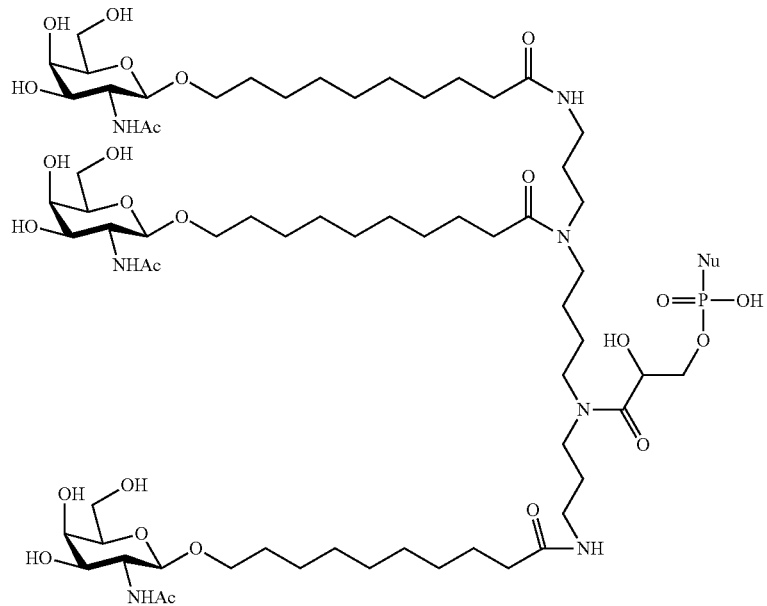

Formula (21)

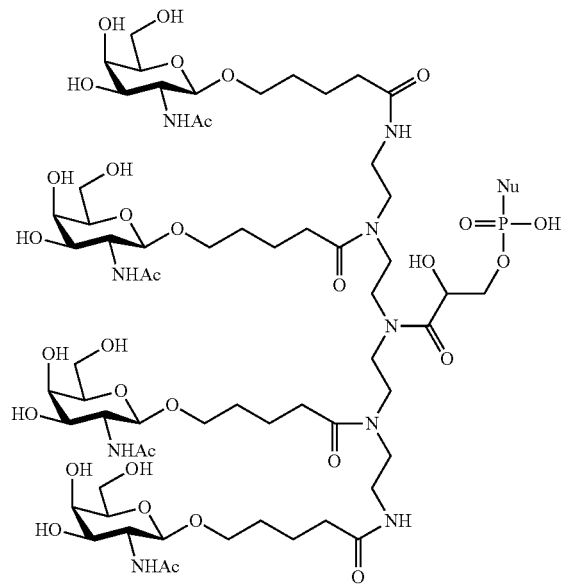

Formula (22)

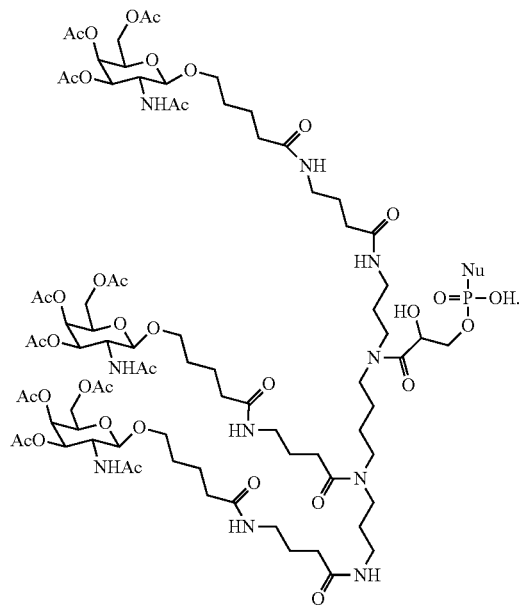

10. The siRNA conjugate according to claim 1, wherein the P atom in the Formula A59 is linked to 3' terminal of the sense strand of the siRNA.

11. The siRNA conjugate according to claim 1, wherein the nucleotide difference between the nucleotide sequence 2 and the nucleotide sequence represented by SEQ ID NO:2 includes the difference at the position of Z'B, wherein Z'B is selected from A, C or G.

12. The siRNA conjugate according to claim 1, wherein the sense strand further comprises a nucleotide sequence 3, the antisense strand further comprises a nucleotide sequence 4, and the nucleotide sequence 3 and the nucleotide sequence 4 each independently have a length of 1 to 4 nucleotides; the nucleotide sequence 3 is linked to the 5' terminal of the nucleotide sequence 1, the nucleotide sequence 4 is linked to the 3' terminal of the nucleotide sequence 2, and the nucleotide sequence 3 and the nucleotide sequence 4 have the same length and are substantially reverse complementary or completely reverse complementary; said "substantially reverse complementary" means that there is no more than 1 base mispairing between two nucleotide sequences; said "completely reverse complementary" means that there is no mispairing between two nucleotide sequences;

wherein the nucleotide sequence 3 and the nucleotide sequence 4 both have a length of one nucleotide, and the base of the nucleotide sequence 3 is C;

or the nucleotide sequence 3 and the nucleotide sequence 4 both have a length of 2 nucleotides, and in the direction from 5' terminal to 3' terminal, the bases of the nucleotide sequence 3 are sequentially C and C;

or, the nucleotide sequence 3 and the nucleotide sequence 4 both have a length of 3 nucleotides, and in the direction from 5' terminal to 3' terminal, the bases of nucleotide sequence 3 are sequentially U, C and C;

or, the nucleotide sequence 3 and the nucleotide sequence 4 both have a length of 4 nucleotides, and in the direction from 5' terminal to 3' terminal, the bases of nucleotide sequence 3 are sequentially C, U, C and C.

13. The siRNA conjugate according to claim 1, wherein the siRNA further comprises a nucleotide sequence 5; the nucleotide sequence 5 has a length of 1 to 3 nucleotides, and is linked to the 3'terminal of the antisense strand, thereby forming a 3' overhang terminal of the antisense strand.

14. The siRNA conjugate according to claim 13, wherein the nucleotide sequence 5 has a length 2 nucleotides, and in the direction from 5' terminal to 3' terminal, the nucleotide sequence 5 is 2 continuous thymine deoxyribonucleotides, 2 continuous uridine ribonucleotides, or 2 nucleotides complementary to the target mRNA.

15. The siRNA conjugate according to claim 1, wherein the sense strand comprises the nucleotide sequence represented by SEQ ID NO:60, and the antisense strand comprises the nucleotide sequence represented by SEQ ID NO:3:

```
                                         (SEQ ID NO: 60)
5'-CAAUAAAGCUGGACAAGAZ_A-3';

(SEQ ID NO: 3)
5'-Z'_BUCUUGUCCAGCUUUAUUGGGAG-3';
``` or, the sense strand comprises the nucleotide sequence represented by SEQ ID NO:4, and the antisense strand comprises the nucleotide sequence represented by SEQ ID NO:5:

```
                                          (SEQ ID NO: 4)
5'-CCCAAUAAAGCUGGACAAGAZ_A-3';

(SEQ ID NO: 5)
5'-Z'_BUCUUGUCCAGCUUUAUUGGGAG-3';
``` wherein $Z'_B$ is the first nucleotide at the 5'terminal of the antisense strand, $Z_A$ is selected from A, U, G or C, and $Z'_B$ is a nucleotide complementary to $Z_A$.

16. The siRNA conjugate according to claim 1, wherein the siRNA is siAP1 or siAP2:

```
siAP1
sense strand:
                                          (SEQ ID NO: 6)
5'-CAAUAAAGCUGGACAAGAA-3';

antisense strand:
                                          (SEQ ID NO: 7)
5'-UUCUUGUCCAGCUUUAUUGGG-3';

siAP2
sense strand:
                                          (SEQ ID NO: 8)
5'-CCCAAUAAAGCUGGACAAGAA-3';

antisense strand:
                                          (SEQ ID NO: 9)
5'-UUCUUGUCCAGCUUUAUUGGGAG-3'.
```

17. The siRNA conjugate according to claim 1, wherein each nucleotide in the sense strand and the antisense strand is independently a fluoro modified nucleotide or a non-fluoro modified nucleotide, the fluoro modified nucleotide refers to a nucleotide formed by replacing 2'-hydroxy of the ribose group with fluoro, and the non-fluoro modified nucleotide refers to a nucleotide formed by replacing 2'-hydroxy of the ribose group with a non-fluoro group, or a nucleotide analogue, wherein the fluoro modified nucleotide is present in the nucleotide sequence 1 and the nucleotide sequence 2; and in the direction from 5' terminal to 3' terminal, the nucleotides at positions 7, 8, 9 of the nucleotide sequence 1 are fluoro modified nucleotides; and in the direction from 5'terminal to 3'terminal, the nucleotides at positions 2, 6, 14 and 16 of the nucleotide sequence 2 are fluoro modified nucleotides.

18. The siRNA conjugate according to claim 17, wherein each non-fluoro modified nucleotide is a methoxy modified nucleotide, and the methoxy modified nucleotide refers to a nucleotide formed by replacing 2'-hydroxy of the ribose group with a methoxy group.

19. The siRNA conjugate according to claim 1, wherein in the direction from 5' terminal to 3' terminal, the nucleotides at positions 5, 7, 8 and 9 of the nucleotide sequence 1 in the sense strand of the siRNA are fluoro modified nucleotides, and the nucleotides at the other positions in the sense strand of the siRNA are methoxy modified nucleotides; and in the direction from 5' terminal to 3' terminal, the nucleotides at positions 2, 6, 8, 9, 14 and 16 of the nucleotide sequence 2 in the sense strand of the siRNA are fluoro modified nucleotides, and the nucleotides at the other positions in the sense strand of siRNA are methoxy modified nucleotides;

or, in the direction from 5' terminal to 3' terminal, the nucleotides at positions 7, 8 and 9 of the nucleotide sequence 1 in the sense strand of the siRNA are fluoro modified nucleotides, and the nucleotides at the other positions in the sense strand of the siRNA are methoxy modified nucleotides; and in the direction from 5' terminal to 3' terminal, the nucleotides at positions 2, 6, 14 and 16 of the nucleotide sequence 2 in the antisense strand of the siRNA are fluoro modified nucleotides, and the nucleotides at the other positions in the antisense strand of the siRNA are methoxy modified nucleotides.

20. The siRNA conjugate according to claim 1, wherein the siRNA is any one of siAP1-M1, siAP2-M1, siAP1-M2, and siAP2-M2:

```
siAP1-M1
sense strand:
                                         (SEQ ID NO: 10)
5'-CmAmAmUmAfAmAfGfCfUmGmGmAmCmAmAmGmAmAm-3' antisense strand:
                                         (SEQ ID NO: 11)
5'-UmUfCmUmUmGfUmCfCfAmGmCmUmUfUmAfUmUmGmGmGm-3' siAP2-M1
sense strand:
                                         (SEQ ID NO: 12)
5'-CmCmCmAmAmUmAfAmAfGfCfUmGmGmAmCmAmAmGmAmAm-3' antisense strand:
                                         (SEQ ID NO: 13)
5'-UmUfCmUmUmGfUmCfCfAmGmCmUmUfUmAfUmUmGmGmGmAmGm-3' siAP1-M2
sense strand:
                                         (SEQ ID NO: 14)
5'-CmAmAmUmAmAmAfGfCfUmGmGmAmCmAmAmGmAmAm-3'
``` antisense strand:

(SEQ ID NO: 15)
5'-UmUfCmUmUmGfUmCmCmAmGmCmUmUfUmAfUmUmGmGmGm-3' siAP2-M2
sense strand:

(SEQ ID NO: 16)
5'-CmCmCmAmAmUmAmAmAfGfCfUmGmGmAmCmAmAmGmAmAm-3' antisense strand:

(SEQ ID NO: 17)
5'-mUfCmUmUmGfUmCmCmAmGmCmUmUfUmAfUmUmGmGmAmGm-3', wherein C, G, U, and A represent the base composition of the nucleotides; m represents that the nucleotide adjacent to the left side of the letter m is a methoxy modified nucleotide; and f represents that the nucleotide adjacent to the left side of the letter f is a fluoro modified nucleotide.

21. The siRNA conjugate according to claim 1, wherein in the siRNA, at least one phosphate group is a phosphorothioate group, and the phosphorothioate linkage is present at at least one of the following positions:

the position between the first and second nucleotides at 5' terminal of the sense strand;

the position between the second and third nucleotides at 5' terminal of the sense strand;

the position between the first and second nucleotides at 3' terminal of the sense strand;

the position between the second and third nucleotides at 3' terminal of the sense strand;

the position between the first and second nucleotides at 5' terminal of the antisense strand;

the position between the second and third nucleotides at 5' terminal of the antisense strand;

the position between the first and second nucleotides at 3' terminal of the antisense strand; and the position between the second and third nucleotides at 3' terminal of the antisense strand.

22. The siRNA conjugate according to claim 1, wherein the siRNA is any one of siAP1-M1S, siAP2-M1S, siAP1-M2S, and siAP2-M2S:

siAP1-M1S
sense strand:

(SEQ ID NO: 18)
5'-CmsAmsAmUmAfAmAfGfCfUmGmGmAmCmAmAmGmAmAm-3' antisense strand:

(SEQ ID NO: 19)
5'-UmsUfsCmUmUmGfUmCfCfAmGmCmUmUfUmAfUmUmGmsGmsGm-3' siAP2-M1S
sense strand:

(SEQ ID NO: 20)
5'-CmsCmsCmAmAmUmAfAmAfGfCfUmGmGmAmCmAmAmGmAmAm-3' antisense strand:

(SEQ ID NO: 21)
5'-UmsUfsCmUmUmGfUmCfCfAmGmCmUmUfUmAfUmUmGmGmsAmsGm-3' siAP1-M2S
sense strand:

(SEQ ID NO: 22)
5'-CmsAmsAmUmAmAmAfGfCfUmGmGmAmCmAmAmGmAmAm-3' antisense strand:

(SEQ ID NO: 23)
5'-UmsUfsCmUmUmGfUmCmCmAmGmCmUmUfUmAfUmUmGmsGmsGm-3' siAP2-M2S
sense strand:

(SEQ ID NO: 24)
5'-CmsCmsCmAmAmUmAmAmAfGfCfUmGmGmAmCmAmAmGmAmAm-3' antisense strand:

(SEQ ID NO: 25)
5'-UmsUfsCmUmUmGfUmCmCmAmGmCmUmUfUmAfUmUmGmGmsAmsGm-3', wherein C, G, U, and A represent the base composition of the nucleotides; m represents that the nucleotide adjacent to the left side of the letter m is a methoxy modified nucleotide; f represents that the nucleotide adjacent to the left side of the letter f is a fluoro modified nucleotide; and s represents that the linkage between the two nucleotides adjacent to both sides of the letter s is a phosphorothioate linkage.

23. The siRNA conjugate according to claim 1, wherein the 5'-terminal nucleotide in the antisense strand is a 5'-phosphate nucleotide or a 5'-phosphate analogue modified nucleotide.

24. The siRNA conjugate according to claim 1, wherein the siRNA is any one of siAP1-M1P1, siAP2-M1P1, siAP1-M2P1, siAP2-M2P1, siAP1-M1SP1, siAP2-M1SP1, siAP1-M2SP1, and siAP2-M2SP1:

siAP1-M1P1
sense strand:

(SEQ ID NO: 10)
5'-CmAmAmUmAfAmAfGfCfUmGmGmAmCmAmAmGmAmAm-3' antisense strand:

(SEQ ID NO: 26)
5'-P1-UmUfCmUmUmGfUmCfCfAmGmCmUmUfUmAfUmUmGmGmGm-3' siAP2-M1P1
sense strand:

(SEQ ID NO: 12)
5'-CmCmCmAmAmUmAfAmAfGfCfUmGmGmAmCmAmAmGmAmAm-3' antisense strand:

(SEQ ID NO: 27)
5'-P1-UmUfCmUmUmGfUmCfCfAmGmCmUmUfUmAfUmUmGmGmGmAmGm-3' siAP1-M2P1
sense strand:

(SEQ ID NO: 14)
5'-CmAmAmUmAmAmAfGfCfUmGmGmAmCmAmAmGmAmAm-3' antisense strand:

(SEQ ID NO: 28)
5'-P1-UmUfCmUmUmGfUmCmCmAmGmCmUmUfUmAfUmUmGmGmGm-3' siAP2-M2P1
sense strand:

(SEQ ID NO: 16)
5'-CmCmCmAmAmUmAmAmAfGfCfUmGmGmAmCmAmAmGmAmAm-3' antisense strand:

(SEQ ID NO: 29)
5'-P1-UmUfCmUmUmGfUmCmCmAmGmCmUmUfUmAfUmUmGmGmGmAmGm-3' siAP1-M1SP1
sense strand:
(SEQ ID NO: 18)
5'-CmsAmsAmUmAfAmAfGfCfUmGmGmAmCmAmAmGmAmAm-3' antisense strand:
(SEQ ID NO: 30)
5'-P1-UmsUfsCmUmUmGfUmCfCfAmGmCmUmUfUmAfUmUmGmsGmsGm-3' siAP2-M1SP1
sense strand:
(SEQ ID NO: 20)
5'-CmsCmsCmAmAmUmAfAmAfGfCfUmGmGmAmCmAmAmGmAmAm-3' antisense strand:
(SEQ ID NO: 31)
5'-P1-UmsUfsCmUmUmGfUmCfCfAmGmCmUmUfUmAfUmUmGmGmsAmsGm-3' siAP1-M2SP1
sense strand:
(SEQ ID NO: 22)
5'-CmsAmsAmUmAmAfGfCfUmGmGmAmCmAmAmGmAmAm-3' antisense strand:
(SEQ ID NO: 32)
5'-P1-UmsUfsCmUmUmGfUmCmCmAmGmCmUmUfUmAfUmUmGmsGmsGm-3' siAP2-M2SP1
sense strand:
(SEQ ID NO: 24)
5'-CmsCmsCmAmAmUmAmAfGfCfUmGmGmAmCmAmAmGmAmAm-3' antisense strand:
(SEQ ID NO: 33)
5'-P1-UmsUfsCmUmUmGfUmCmCmAmGmCmUmUfUmAfUmUmGmGmsAmsGm-3', wherein C, G, U, and A represent the base composition of the nucleotides; m represents that the nucleotide adjacent to the left side of the letter m is a methoxy modified nucleotide; f represents that the nucleotide adjacent to the left side of the letter f is a fluoro modified nucleotide; s represents that a phosphorothioate linkage is present between the two nucleotides adjacent to both sides of the letter s; P1 represents that the nucleotide adjacent to the right side of the letter P1 is a 5'-phosphate nucleotide or a 5'-phosphate analogue modified nucleotide.

25. A method for treating dyslipidemia, wherein the method comprises administering an effective amount of the siRNA conjugate according to claim 1 to a subject suffering from dyslipidemia.

26. A method for inhibiting the expression of APOC3 gene in hepatocytes, wherein the method comprises contacting an effective amount of the siRNA conjugate according to claim 1 with the hepatocytes.

\* \* \* \* \*

UNITED STATES PATENT AND TRADEMARK OFFICE
CERTIFICATE OF CORRECTION

PATENT NO. : 11,660,347 B2
APPLICATION NO. : 16/758532
DATED : May 30, 2023
INVENTOR(S) : Hongyan Zhang, Shan Gao and Daiwu Kang Page 1 of 7

It is certified that error appears in the above-identified patent and that said Letters Patent is hereby corrected as shown below:

In the Specification

Column 45, Lines 11-14:
"heteroaryl, $C_1$-$C_{10}$ haloalkyl, —$OC_1$-$C_{10}$ alkyl, alkylphenyl, —$C_1$-$C_{10}$ alkyl-OH, haloalkyl, —$SC_1$-$C_{10}$ alkyl, alkylphenyl, —$C_1$-$C_{10}$ alkyl-SH, haloalkyl, halo, —OH, —SH, —$NH_2$, alkyl-$NH_2$, —$N(C_1$-$C_{10}$ alkyl)($C_1$-$C_{10}$ alkyl), —NH"
Should read:
-- heteroaryl, $C_1$-$C_{10}$ haloalkyl, -$OC_1$-$C_{10}$ alkyl, -$OC_1$-$C_{10}$ alkylphenyl, -$C_1$-$C_{10}$ alkyl-OH, -$OC_1$-$C_{10}$ haloalkyl, -$SC_1$-$C_{10}$ alkyl, -$SC_1$-$C_{10}$ alkylphenyl, -$C_1$-$C_{10}$ alkyl-SH, -$SC_1$-$C_{10}$ haloalkyl, halo, -OH, -SH, -$NH_2$, -$C_1$-$C_{10}$ alkyl-$NH_2$, -$N(C_1$-$C_{10}$ alkyl)($C_1$-$C_{10}$ alkyl), -NH --

Column 45, Line 36:
"alkylphenyl, alkyl-SH, —$SC_1$-$C_{10}$ haloalkyl, halo, —OH,"
Should read:
-- alkylphenyl, -$C_1$-$C_{10}$ alkyl-SH, -$SC_1$-$C_{10}$ haloalkyl, halo, -OH, --

Column 45, Line 41:
"$C_{10}$ alkyl), —NHC(O)(phenyl), alkyl)C(O)($C_1$-$C_{10}$ alkyl),"
Should read:
-- $C_{10}$ alkyl), -NHC(O)(phenyl), -$N(C_1$-$C_{10}$ alkyl)C(O)($C_1$-$C_{10}$ alkyl), --

Signed and Sealed this
Twenty-fourth Day of September, 2024

Katherine Kelly Vidal
*Director of the United States Patent and Trademark Office*

CERTIFICATE OF CORRECTION (continued)
U.S. Pat. No. 11,660,347 B2

Column 64, Formula (17):

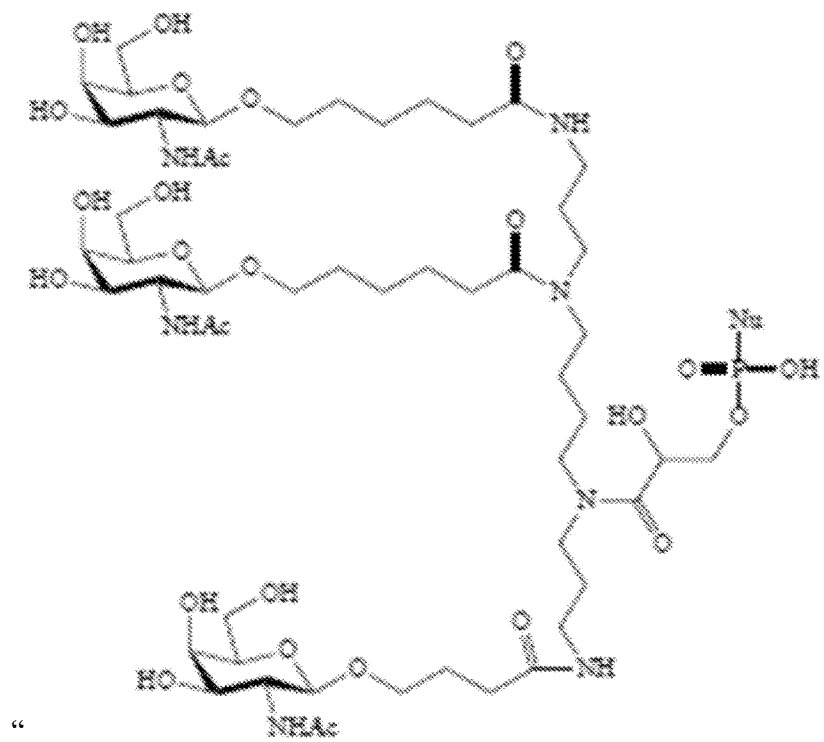

"                                                                      "

Should read:

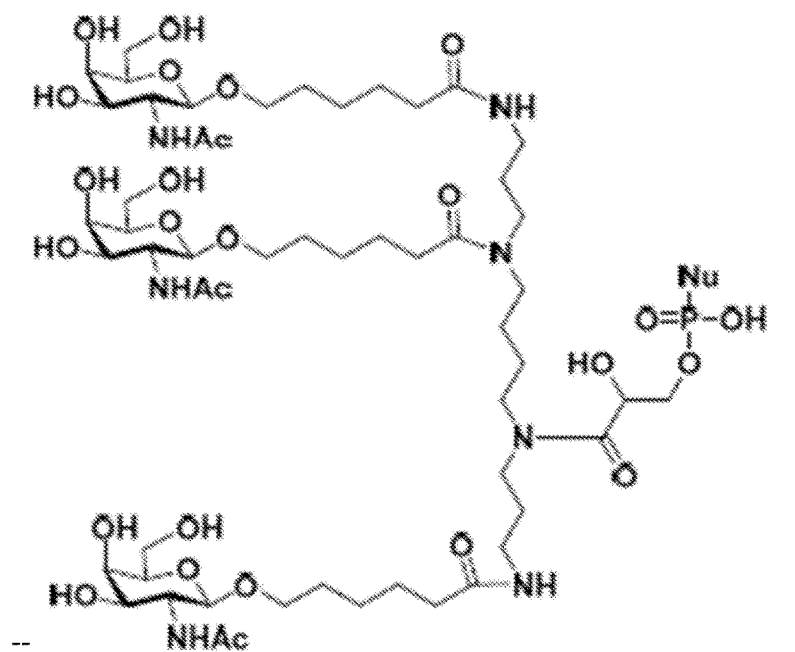

--                                                                     --

Column 78, Line 45:
"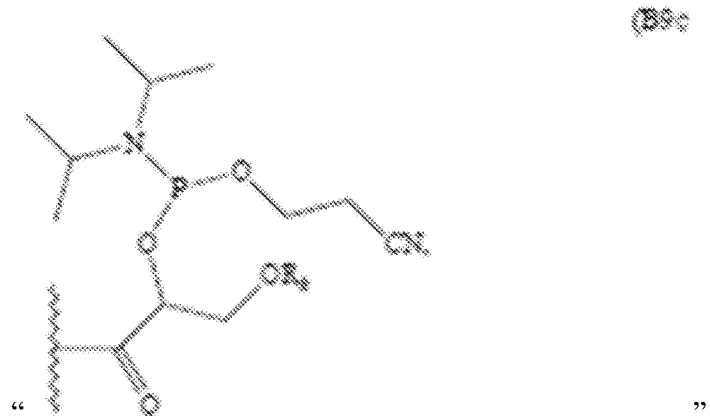"
Should read:
--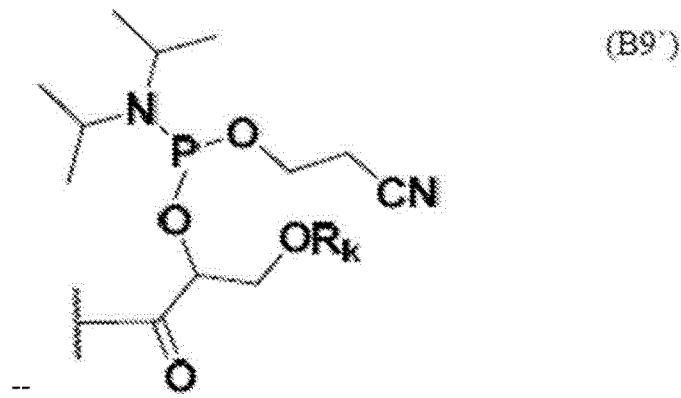--
Column 78, Line 56:
"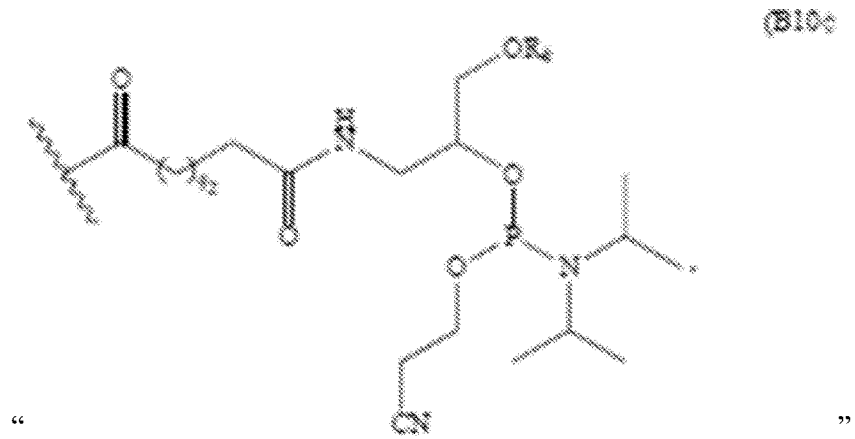"

Should read:
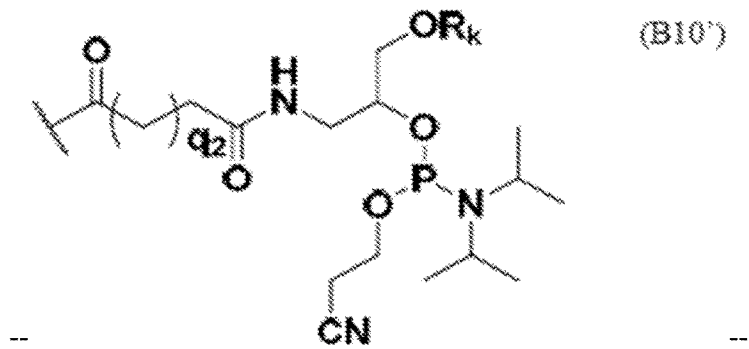
Column 79, Line 27:
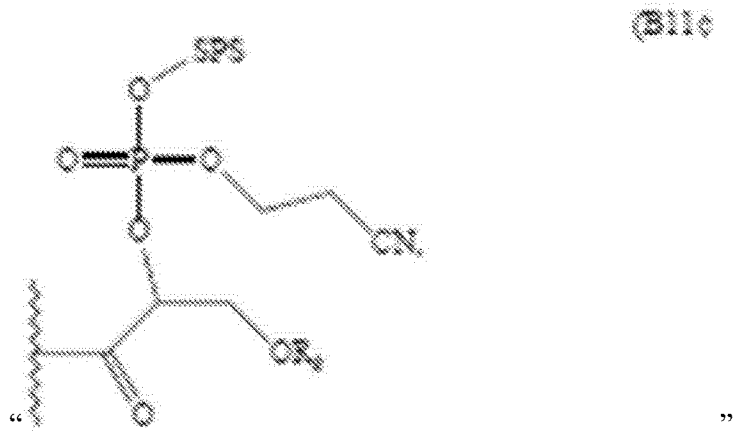
Should read:
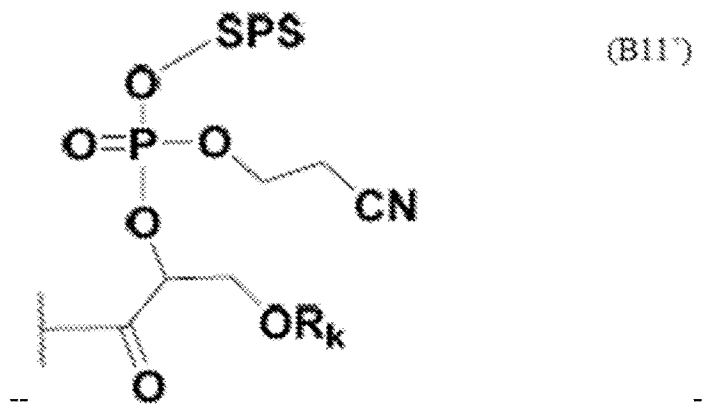

Column 79, Line 39:

"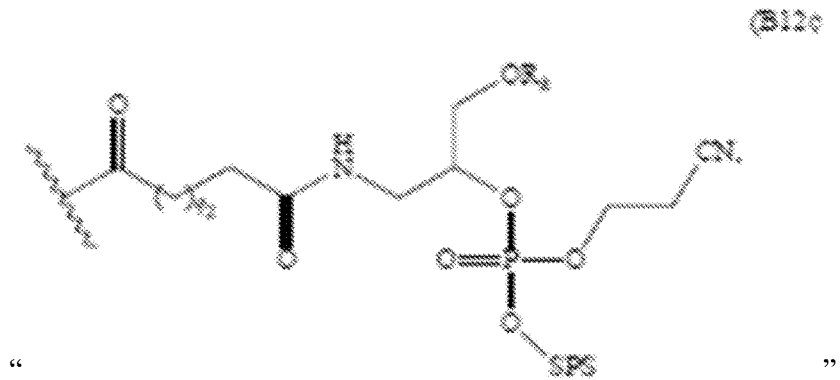"

Should read:

-- 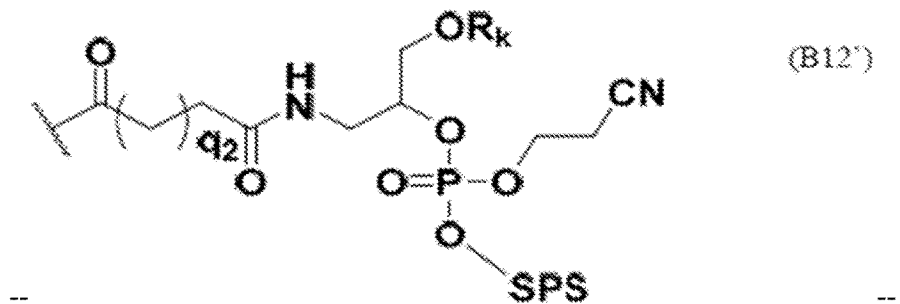 --

Column 205, Line 30:
"test group/the expression amount of (3-actin mRNA in the"
Should read:
-- test group/the expression amount of (β-actin mRNA in the --

In the Claims

Column 231, Line 5:
"—SC$_1$-C$_{10}$ alkylphenyl, —C$_1$-C$_{10}$ alkyl-SH, haloalkyl,"
Should read:
-- -SC$_1$-C$_{10}$ alkylphenyl, -C$_1$-C$_{10}$ alkyl-SH, -SC$_1$-C$_{10}$ haloalkyl --

Column 231, Line 14:
"(phenyl), —S$_{02}$(C$_1$-C$_{10}$ haloalkyl), —SO$_2$NH$_2$,"
Should read:
-- (phenyl), -SO$_2$(C$_1$-C$_{10}$ haloalkyl), -SO$_2$NH$_2$,--

Column 231, Lines 26-38:
"alkyl, C6-C10 aryl, C5-C10 heteroaryl, haloalkyl, —OC1-C10 alkyl, —OC1-C10 alkylphenyl, alkyl-OH, —OC1-C10 haloalkyl, —SC1-C10 alkyl, —SC1-C10 alkylphenyl, alkyl-SH, —SC1-C10 haloalkyl, halo, —OH, —SH, —NH2, —C1-C10 alkyl-NH2, alkyl)(C1-C10 alkyl), —NH(C1-C10 alkyl), cyano, nitro, —CO2H, —C(O)O(C1-C10 alkyl), —CON(C1-C10 alkyl)(C1-C10 alkyl), —CONH(C1-C10 alkyl), —CONH2,—NHC(O)(C1-C10 alkyl), —NHC(O)(phenyl), alkyl)C(O)(C1-C10 alkyl), —N(C1-C10 alkyl)C(0)(phenyl), —C(O)C1-C10 alkyl, —C(O)C1-C10 alkylphenyl, —C(O)C1-C10 haloalkyl, —OC(O)C1-C10 alkyl, —S02(C1-C10 alkyl), —S02(phenyl), —S02(C1-C10 haloalkyl), —SO2NH2,"
Should read:
-- alkyl, C6-C10 aryl, C5-C10 heteroaryl, C1-C10 haloalkyl, -OC1-C10 alkyl, -OC1-C10 alkylphenyl, -C1-C10 alkyl-OH, -OC1-C10 haloalkyl, -SC1-C10 alkyl, -SC1-C10 alkylphenyl, -C1-C10 alkyl-SH, -SC1-C10 haloalkyl, halo, -OH, -SH, -NH$_2$, -C1-C10 alkyl-NH$_2$, -N(C1-C10 alkyl)(C1-C10 alkyl), -NH(C1-C10 alkyl), cyano, nitro, -CO$_2$H, -C(O)O(C1-C10 alkyl), -CON(C1-C10 alkyl)(C1-C10 alkyl), -CONH(C1-C10 alkyl), -CONH$_2$, -NHC(O)(C1-C10 alkyl), -NHC(O)(phenyl), -N(C1-C10 alkyl)C(O)(C1-C10 alkyl), -N(C1-C10 alkyl)C(O)(phenyl), -C(O)C1-C10 alkyl, -C(O)C1-C10 alkylphenyl, -C(O)C1-C10 haloalkyl, -OC(O)C1-C10 alkyl, -SO$_2$(C1-C10 alkyl), -SO$_2$(phenyl), -SO$_2$C1-C10 haloalkyl), -SO$_2$NH$_2$, --

Column 250, Formula 17:

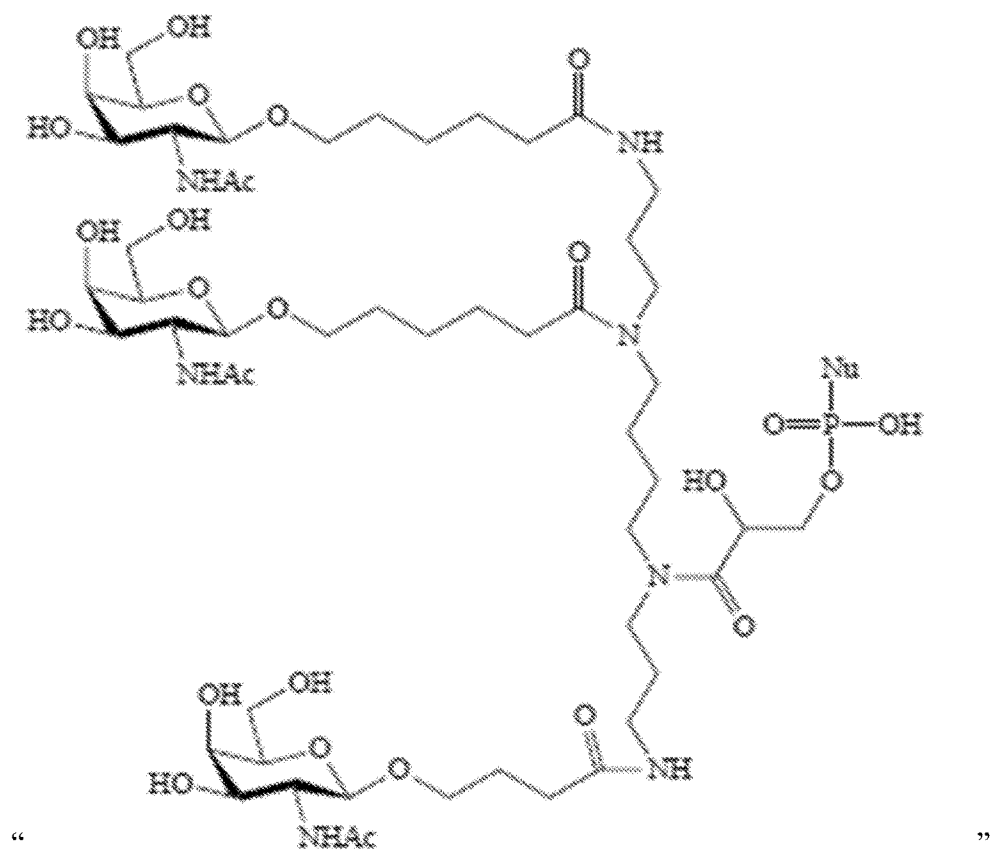

"                                                                                              "

CERTIFICATE OF CORRECTION (continued)
U.S. Pat. No. 11,660,347 B2

Should read:

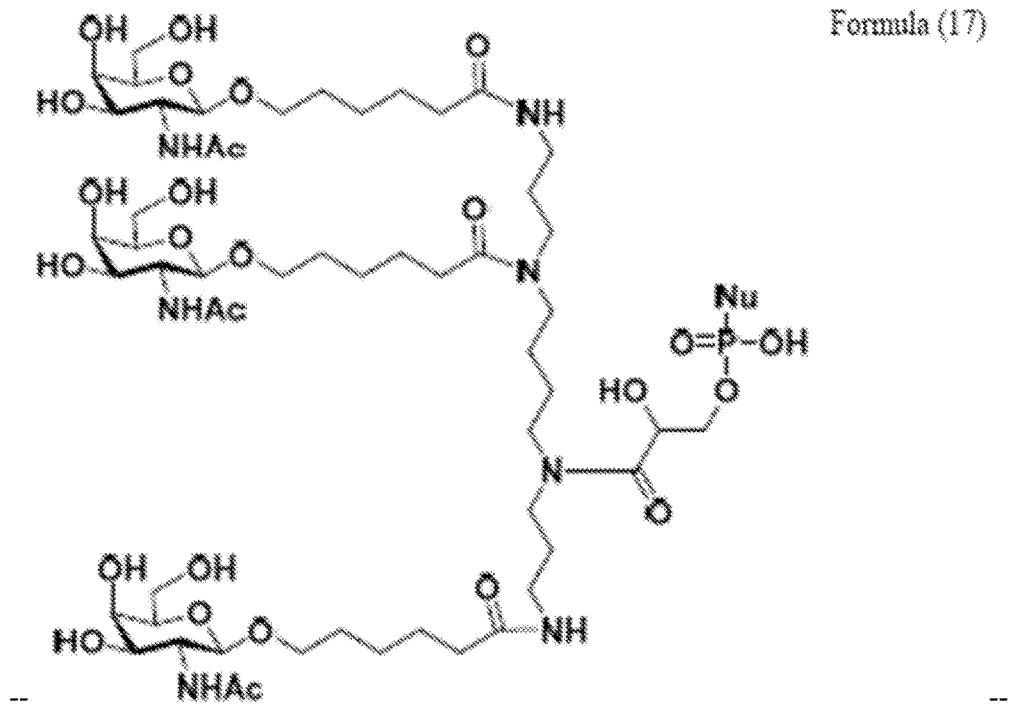

Formula (17)